US011534461B2

(12) United States Patent
Chapuis et al.

(10) Patent No.: US 11,534,461 B2
(45) Date of Patent: Dec. 27, 2022

(54) HIGH AFFINITY MERKEL CELL POLYOMAVIRUS T ANTIGEN-SPECIFIC TCRS AND USES THEREOF

(71) Applicants: FRED HUTCHINSON CANCER CENTER, Seattle, WA (US); UNIVERSITY OF WASHINGTON, Seattle, WA (US)

(72) Inventors: Aude G. Chapuis, Seattle, WA (US); Paul T. Nghiem, Redmond, WA (US); Megan S. McAfee, Seattle, WA (US); Natalie J. Miller, Seattle, WA (US); Kelly Garneski Paulson, Shoreline, WA (US); David Martin Koelle, Seattle, WA (US); Thomas M. Schmitt, Seattle, WA (US); Candice Church, Seattle, WA (US)

(73) Assignees: FRED HUTCHINSON CANCER CENTER, Seattle, WA (US); UNIVERSITY OF WASHINGTON, Seattle, WA (US)

( * ) Notice: Subject to any disclaimer, the term of this patent is extended or adjusted under 35 U.S.C. 154(b) by 155 days.

(21) Appl. No.: 16/348,378

(22) PCT Filed: Nov. 14, 2017

(86) PCT No.: PCT/US2017/061645
§ 371 (c)(1),
(2) Date: May 8, 2019

(87) PCT Pub. No.: WO2018/090057
PCT Pub. Date: May 17, 2018

(65) Prior Publication Data
US 2020/0030378 A1 Jan. 30, 2020

Related U.S. Application Data

(60) Provisional application No. 62/421,902, filed on Nov. 14, 2016, provisional application No. 62/480,247, filed on Mar. 31, 2017.

(51) Int. Cl.
| | | |
|---|---|---|
| A61K 35/17 | (2015.01) | |
| C07K 14/725 | (2006.01) | |
| C07K 16/28 | (2006.01) | |
| A61K 38/00 | (2006.01) | |

(52) U.S. Cl.
CPC .......... *A61K 35/17* (2013.01); *C07K 14/7051* (2013.01); *C07K 16/2818* (2013.01); *C07K 16/2827* (2013.01); *A61K 38/00* (2013.01); *C07K 2317/21* (2013.01); *C07K 2317/24* (2013.01); *C07K 2317/76* (2013.01)

(58) Field of Classification Search
CPC .... A61K 35/17; A61K 38/00; C07K 14/7051; C07K 2317/21; C07K 2317/24; C07K 2317/76
See application file for complete search history.

(56) References Cited

U.S. PATENT DOCUMENTS

| 5,283,173 | A | 2/1994 | Fields et al. |
|---|---|---|---|
| 5,468,614 | A | 11/1995 | Fields et al. |
| 9,228,007 | B1 | 1/2016 | Kitchen et al. |
| 2003/0219463 | A1 | 11/2003 | Falkenburg et al. |
| 2004/0087025 | A1 | 5/2004 | June et al. |
| 2011/0189141 | A1 | 8/2011 | Kieback et al. |
| 2011/0243972 | A1 | 10/2011 | Jaffee |
| 2014/0315735 | A1 | 10/2014 | Sugiyama |
| 2015/0337369 | A1 | 11/2015 | Davis et al. |
| 2016/0280755 | A1 | 9/2016 | Smith et al. |

FOREIGN PATENT DOCUMENTS

| WO | 97/09433 | 3/1997 |
|---|---|---|
| WO | 2012/038055 A1 | 3/2012 |
| WO | 2013/166321 A1 | 11/2013 |

OTHER PUBLICATIONS

Afanasiev et al. Merkel Polyomavirus-Specific T Cells Fluctuate with Merkel Cell Carcinoma Burden and Express Therapeutically Targetable PD-1 and Tim-3 Exhaustion Markers. Clin Cancer Res; 19(19) Oct. 1, 2013 (Year: 2013).*
Chapuis et al. Regression of Metastatic Merkel Cell Carcinoma Following Transfer of Polyomavirus-Specific T Cells and Therapies Capable of Reinducing HLA Class-I. Cancer Immunol Res; 2(1) Jan. 2014 (Year: 2014).*
Rosati et al. Overview of methodologies for T-cell receptor repertoire analysis. BMC Biotechnology (2017) 17:61 (Year: 2017).*
Fischer et al. Predicting antigen specificity of single T cells based on TCR CDR3 regions. Molecular Systems Biology 16: e9416 | 2020 (Year: 2020).*
Afanasiev et al., "Merkel Polyomavirus-Specific T Cells Fluctuate with Merkel Cell Carcinoma Burden and Express Therapeutically Targetable PD-1 and Tim-3 Exhaustion Markers," *Clin. Cancer Res.* *19*(19):5351-5360, Oct. 1, 2013.
Altschul et al., "Gapped BLAST and PSI-BLAST: a new generation of protein database search programs," *Nucleic Acids Research* *25*(17):3389-3402, 1997.
Bolotin et al., "MiXCR: software for comprehensive adaptive immunity profiling," *Nature Methods* *12*(5):380-381, May 2015.
Chapuis et al., "Abstract LB-136: IL-21-derived melanoma-reactive CTL combined with anti-CTLA4 persist, acquire central memory characteristics, and mediate tumor regression in patients with metastatic melanoma," *Cancer Research* *72*(8 Suppl.), Apr. 2012. (4 pages).

(Continued)

*Primary Examiner* — Amy E Juedes
*Assistant Examiner* — Brian Hartnett
(74) *Attorney, Agent, or Firm* — Seed IP Law Group LLP

(57) ABSTRACT

The present disclosure provides binding proteins and TCRs with high affinity and specificity against Merkel cell polyomavirus T antigen epitopes or peptides, T cells expressing such high affinity Merkel cell polyomavirus T antigen specific TCRs, nucleic acids encoding the same, and compositions for use in treating Merkel cell carcinoma.

37 Claims, 35 Drawing Sheets

Specification includes a Sequence Listing.

(56) References Cited

OTHER PUBLICATIONS

Chapuis et al., "Transferred melanoma-specific CD8+ T cells persist, mediate tumor regression, and acquire central memory phenotype," *PNAS* 109(12):4592-4597, Mar. 20, 2012.
Chapuis et al., "Transferred WT1-reactive CD8+ T cells can mediate antileukemic activity and persist in post-transplant patients," *Sci. Transl. Med.* 5(174), Feb. 27, 2013. (25 pages).
Chen et al., "Serological evidence of Merkel cell polyomavirus primary infections in childhood," *Journal of Clinical Virology* 50:125-129, 2011.
Choi et al., "High Avidity Antigen-Specific CTL Identified by CD8-Independent Tetramer Staining," *The Journal of Immunology* 171:5116-5123, 2003.
Dossett et al., "Adoptive Immunotherapy of Disseminated Leukemia With TCR-transduced, CD8+ T Cells Expressing a Known Endogenous TCR," *Molecular Therapy* 17(4):742-749, Apr. 2009.
Extended European Search Report, dated Jul. 20, 2020, for European Application No. 17870477.1. (11 pages).
Feng et al., "Clonal Integration of a Polyomavims in Human Merkel Cell Carcinoma," *Science* 379:1096-1100, Feb. 22, 2008.
Garneski et al., "Does a new polyomavims contribute to Merkel cell carcinoma?" *Genome Biology* 9(6):228.1-228.4, 2008.
Goh et al., "Mutational landscape of MCPyV-positive and MCPyV-negative Merkel cell carcinomas with implications for immunotherapy," *Oncotarget* 7(3):3403-3415, Dec. 7, 2015.
Gonzalez-Vela et al., "Shared Oncogenic Pathways Implicated in Both Virus-Positive and UV-Induced Merkel Cell Carcinomas," *Journal of Investigative Dermatology* 137:197-206, 2017.
Green et al., "Mitochondria and Apoptosis," *Science* 281:1309-1312, Aug. 28, 1998.
Han et al., "Linking T-cell receptor sequence to functional phenotype at the single-cell level," *Nat. Biotechnol.* 32(7):684-692, Jul. 2014. (23 pages).
Heath et al., "Clinical characteristics of Merkel cell carcinoma at diagnosis in 195 patients: the "AEIOU" features," *J Am. Acad. Dermatol.* 58(3): 375-381, Mar. 2008. (14 pages).
Ho et al., "In vitro methods for generating CD8+ T-cell clones for immunotherapy from the naïve repertoire," *Journal of Immunological Methods* 310:40-52, 2006.
Hodgson, "Merkel Cell Carcinoma: Changing Incidence Trends," *Journal of Surgical Oncology* 89:1-4, 2005.
Houben et al., "Merkel Cell Polyomavims-Infected Merkel Cell Carcinoma Cells Require Expression of Viral T Antigens," *Journal of Virology* 84(14):7064-7072, Jul. 2010.
Hurley et al., Accession No. M97704, Mar. 4, 2000. (2 pages).
Iyer et al., "Merkel Cell Polyomavims-Specific CD8+ and CD4+ T-cell Responses Identified in Merkel Cell Carcinomas and Blood" *Clin. Cancer Res.* 17(21):6671-6680, Nov. 1, 2011.
Iyer et al., "Single-fraction radiation therapy in patients with metastatic Merkel cell carcinoma," *Cancer Medicine* 4(8):1161-1170, 2015.
Kaufman et al., "Avelumab in patients with chemotherapy-refractory metastatic Merkel cell carcinoma: a multicentre, single-group, open-label, phase 2 trial," *Lancet Oncol.* 17(10):1374-1385, Oct. 2016. (24 pages).
Kim et al., "High Cleavage Efficiency of a 2A Peptide Derived from Porcine Teschovirus-1 in Human Cell Lines, Zebrafish and Mice," *PLoS ONE* 6(4):e18556, Apr. 2011. (8 pages).
Kim et al., "Immune epitope database analysis resource," *Nucleic Acids Research* 40:W525-W530, May 18, 2012.
Kuball et al., "Facilitating matched pairing and expression of TCR chains introduced into human T cells," *Blood* 109(6):2331-2338, Mar. 15, 2007. (17 pages).
Laugel et al., "Different T Cell Receptor Affinity Thresholds and CD8 Coreceptor Dependence Govern Cytotoxic T Lymphocyte Activation and Tetramer Binding Properties," *The Journal of Biological Chemistry* 282(33):23799-23810, Aug. 17, 2007. (13 pages).
Leen et al., "Improving T Cell Therapy for Cancer," *Annu. Rev. Immunol.* 25:243-265, 2007. (26 pages).

Lemos et al., "Merkel Cell Carcinoma: More Deaths but Still No. Pathway to Blame," *Journal of Investigative Dermatology* 127:2100-2103, 2007.
Lyngaa et al., "T-cell Responses to Oncogenic Merkel Cell Polyomavirus Proteins Distinguish Patients with Merkel Cell Carcinoma from Healthy Donors," *Clin. Cancer Res.* 20(7):1768-1778, Apr. 1, 2014.
Lyngaa, et al., "Using Merkel cell polyomavirus specific TCR gene therapy for treatment of Merkel cell carcinoma," *European Journal of Immunology* 46(Supp. 1):128, 2016. (2 pages) (Abstract Only).
Ma et al., "Merkel Cell Carcinoma in Immunosuppressed Patients," *Cancers* 6:1328-1350, Jun. 27, 2014.
Masella et al., "PANDAseq: PAired-eND Assembler for Illumina sequences," *BMC Bioinformatics* 13(31), Feb. 14, 2012. (7 pages).
Miller et al., "Tumor-Infiltrating Merkel Cell Polyomavirus-Specific T Cells Are Diverse and Associated with Improved Patient Survival," *Cancer Immunol. Res.* 5(2):137-147, 2017. (12 page) (Published Online Jan. 16, 2017).
Nghiem et al., "PD-1 Blockade with Pembrolizumab in Advanced Merkel-Cell Carcinoma," *The New England Journal of Medicine* 374(26):2542-2552, Jun. 30, 2016.
Pallan, "Investigating T cell immunity against the oncogenic Merkel cell polyomavirus," A thesis submitted to the University of Birmingham for the degree of Doctor of Philosophy (PhD), Sep. 2016. (268 pages).
Pastrana et al., "Quantitation of Human Seroresponsiveness to Merkel Cell Polyomavirus," *PLoS Pathogens* 5(9):e1000578, 11 pages, Sep. 11, 2009. (11 pages).
Paulson et al., "Antibodies to Merkel Cell Polyomavirus T Antigen Oncoproteins Reflect Tumor Burden in Merkel Cell Carcinoma Patients," *Cancer Res.* 70(21):8388-8397, Nov. 1, 2010. (11 pages).
Paulson et al., "Array-CGH Reveals Recurrent Genomic Changes in Merkel Cell Carcinoma Including Amplification of L-Myc," *Journal of Investigative Dermatology* 129:1547-1555, 2009. (published online Nov. 20, 2008).
Paulson et al., "Systemic Immune Suppression Predicts Diminished Merkel Cell Carcinoma-Specific Survival Independent of Stage," *Journal of Investigative Dermatology* 133:642-646, 2013. (Published online Nov. 29, 2012).
Paulson et al., "Transcriptome-Wide Studies of Merkel Cell Carcinoma and Validation of Intratumoral CD8+ Lymphocyte Invasion As an Independent Predictor of Survival," *Journal of Clinical Oncology* 29(12):1539-1546, Apr. 20, 2011.
Robbins et al., "Tumor Regression in Patients With Metastatic Synovial Cell Sarcoma and Melanoma Using Genetically Engineered Lymphocytes Reactive With NY-ESO-1," *Journal of Clinical Oncology* 29(7):917-924, Mar. 1, 2011.
Robins et al., "Comprehensive assessment of T-cell receptor β-chain diversity in αβ T cells," *Blood* 114(19):4099-4107, Nov. 5, 2009.
Robins et al., "Overlap and Effective Size of the Human CD8+ T Cell Receptor Repertoire," *Sci. Transl. Med.* 2:47ra64, Sep. 1, 2010. (9 pages).
Robins et al., "Ultra-sensitive detection of rare T cell clones," *J. Immunol. Methods*. 375(0):14-19, Jan. 31, 2012. (9 pages).
Rodig et al., "Improved detection suggests all Merkel cell carcinomas harbor Merkel polyomavirus," *J. Clin. Invest.* 122(12):4645-4653, Dec. 2012. (10 pages).
Scatchard, "The Attractions of Proteins for Small Molecules and Ions," *Annals New York Academy of Sciences* 51:660-672, May 1949.
Schmitt et al., "T Cell Receptor Gene Therapy for Cancer," *Human Gene Therapy* 20:1240-1248, Nov. 2009.
Scholten et al., "Codon modification of T cell receptors allows enhanced functional expression in transgenic human T cells," *Clinical Immunology* 119:135-145, 2006. (Published Online Feb. 2, 2006).
Shuda et al., "Human Merkel cell polyomavirus infection I. MCV T antigen expression in Merkel cell carcinoma, lymphoid tissues and lymphoid tumors," *Int. J. Cancer* 125:1243-1249, 2009. (Published Online Apr. 14, 2009).
Shuda et al., "T antigen mutations are a human tumor-specific signature for Merkel cell polyomavirus," *PNAS* 105(42):16272-16277, Oct. 21, 2008.

(56) References Cited

OTHER PUBLICATIONS

Stone et al., "Role of T cell receptor affinity in the efficacy and specificity of adoptive T cell therapies," *Frontiers in Immunology* 4(244), Aug. 2013. (16 pages).
Stromnes et al., "Re-adapting T cells for cancer therapy: from mouse models to clinical trials," *Immunol. Rev.* 257(1):145-164, Jan. 2014. (34 pages).
Sun et al., Accession No. AB977861, Jul. 30, 2015. (1 page).
Till et al., "Adoptive immunotherapy for indolent non-Hodgkin lymphoma and mantle cell lymphoma using genetically modified autologous CD20-specific T cells," *Blood* 112(6):2261-2271, Sep. 15, 2008. (25 pages).
Torikai et al., "A foundation for universal T-cell based immunotherapy: T cells engineered to express a CD19-specific chimeric-antigen-receptor and eliminate expression of endogenous TCR," *Blood* 119(24):5697-5705, Jun. 14, 2012.
Torikai et al., "Genetic editing of HLA expression in hematopoietic stem cells to broaden their human application," *Scientific Reports* 6:21757, Feb. 23, 2016. (11 pages).
Torikai et al., "Toward eliminating HLA class I expression to generate universal cells from allogeneic donors," *Blood* 122(8):1341-1349, Aug. 22, 2013.
Tumeh et al., "PD-1 blockade induces responses by inhibiting adaptive immune resistance," *Nature* 575(7528):568-571, Nov. 27, 2014. (24 pages).
Vandeven et al., "Rationale for immune-based therapies in Merkel polyomavirus-positive and -negative Merkel cell carcinomas," *Immunotherapy* 8(8):907-921, 2016. (Published Online Jul. 6, 2016).
Wang et al., "Optimizing Adoptive Polyclonal T Cell Immunotherapy of Lymphomas, Using a Chimeric T Cell Receptor Possessing CD28 and CD137 Costimulatory Domains," *Human Gene Therapy* 18:712-725, Aug. 2007. (16 pages).
Warren et al., "Exhaustive T-cell repertoire sequencing of human peripheral blood samples reveals signatures of antigen selection and a directly measured repertoire size of at least 1 million clonotypes," *Genome Research* 21:790-797, 2011. (9 pages) (Published Online Feb. 24, 2011).
Webb et al., "Functional and Structural Characteristics of NY-ESO-1-related HLA A2-restricted Epitopes and the Design of a Novel Immunogenic Analogue," *The Journal of Biological Chemistry* 279(22):23438-23446, May 28, 2004. (10 pages).
Wilson, "Analyzing Biomolecular Interactions" *Science* 295:2103-2105, Mar. 15, 2002.
Wolff et al., "Monoclonal Antibody Homodimers: Enhanced Antitumor Activity in Nude Mice," *Cancer Research* 53:2560-2565, Jun. 1, 1993. (7 pages).
Zoete et al., "Structure-based, rational design of T cell receptors," *Frontiers in Immunology* 4(268), Sep. 2013. (19 pages).
Chapuis et al., "Regression of Metastatic Merkel Cell Carcinoma Following Transfer of Polyomavirus-Specific T Cells and Therapies Capable of Reinducing HLA Class-I," *Cancer Immunol. Res.* 2(1):27-36, 2014. (11 pages).
Chapuis et al., "Tracking the Fate and Origin of Clinically Relevant Adoptively Transferred CD8+ T cells In Vivo," *Sci. Immunol.* 2(8), 2017. (20 pages).
International Search Report and Written Opinion, dated Feb. 20, 2018, for International Application No. PCT/US2017/061645, 9 pages.
Kuball et al., "Cooperation of Human Tumor-Reactive CD4+ and CD8+ T Cells after Redirection of Their Specificity by a High-Affinity p53A2.1-Specific TCR," *Immunity* 22:117-129, 2005.
Chapuis, "Harnessing the therapeutic potential of native and TCR gene-modified T cells," *Illumina Immuno-Oncology Symposium*, Mar. 14, 2017. (68 pages; pp. 20-32).
Chothia et al., "The outline structure of the T-cell αβ receptor," *The EMBO Journal* 7(12):3745-3755, 1988.
Jores et al., "Resolution of hypervariable regions in T-cell receptor β chains by a modified Wu-Kabat index of amino acid diversity," *Proc. Natl. Acad. Sci. USA* 87:9138-9142, Dec. 1990.

Lefranc et al., "IMGT unique numbering for immunoglobulin and T cell receptor variable domains and Ig superfamily V-like domains," *Developmental and Comparative Immunology* 27:55-77, 2003.
Penix et al., "Two Essential Regulatory Elements in the Human Interferon γ Promoter Confer Activation Specific Expression in T Cells," *The Journal of Experimental Medicine* 178:1483-1496, Nov. 1993.
Thompson et al., "cis-Acting Sequences Required for Inducible Interleukin-2 Enhancer Function Bind a Novel Ets-Related Protein, Elf-1," *Molecular and Cellular Biology* 12(3):1043-1053, Mar. 1992.
Todd et al., "Transcription of the Interleukin 4 Gene Is Regulated by Multiple Promoter Elements," *J. Exp. Med.* 177:1663-1674, Jun. 1993.
Afanasiev et al., "Vascular E-selectin expression correlates with CD8 lymphocyte infiltration and improved outcome in Merkel cell carcinoma," *J. Invest. Dermatol.* 133(8)2065-2073, Aug. 2013, (17 pages).
Allen et al., "Merkel Cell Carcinoma: Prognosis and Treatment of Patients From a Single Institution," Journal of Clinical Oncology 23(10):2300-2309, Apr. 1, 2005.
Chen et al., "Limit-Dilution Assay and Clonal Expansion of All T Cells Capable of Proliferation," *Journal of Immunological Methods* 52:307-322, 1982.
Clinicaltrials.Gov, "Viral Oncoprotein Targeted Autologous T Cell Therapy for Merkel Cell Carcinoma," ClinicalTrials.gov Identifier: NCT0175 845 8, Jan. 1, 2013, URL= https://clinicaltrials.gov/ct2/show/NCT0175 845 8, download date May 2, 2022, (9 pages).
Derby et al., "High-Avidity CTL Exploit Two Complementary Mechanisms to Provide Better Protection Against Viral Infection Than Low-Avidity CTL," *The Jounal of Immunology* 166:1690-1697, 2001,(9 pages).
Draper et al., "Targeting of HPV-16+ epithelial cancer cells by TCRgene engineered T cells directed against E6," Clin. Cancer Res. 21 (19):4431-4439, Oct. 1, 2015 (23 pages).
Dutoit et al., "Heterogeneous T-Cell Response to MAGE-A10254-262: High Avidity-specific Cytolytic T Lymphocytes Show Superior Antitumor Activity," *Cancer Research* 61:5850-5856, Aug. 1, 2001.
Houben et al., "An intact retinoblastoma protein-binding site in Merkel cell polyomavirus large T antigen is required for promoting growth of Merkel cell carcinoma cells," *International Journal of Cancer* 130:847-856, 2012.
Iyer et al., "Response rate and durability of chemotherapy for metastatic Merkel cell carcinoma among 62 patients," *Journal of Clinical Oncology* 32(15 suppl):9091, May 20, 2014, (4 pages).
Johnson et al., "Gene therapy with human and mouse T-cell receptors mediates cancer regression and targets normal tissues expressing cognate antigen," *Blood* 114(3):535-546, Jul. 16, 2009. (13 pages).
Koelle et al., "Antigenic Specificities of Human CD4+ T-Cell Clones Recovered from Recurrent Genital Herpes Simplex Virus Type 2 Lesions," *Journal of Virology* 68(5):2803-2810, May 1994,.
Lemos et al., "Pathologic nodal evaluation improves prognostic accuracy in Merkel cell carcinoma: Analysis of 5,823 cases as the basis of the first consensus staging system for this cancer," *J. Am. Acad. Dermatol.* 55(5):751-761, Nov. 2010, (20 pages).
Li et al., "Determinants of public T cell responses," *Cell Research* 22(1):33-42, Jan. 2012.
Messaoudi et al., "Direct Link Between mhc Polymorphism, T Cell Avidity, and Diversity in Immune Defense," *Science* 295(5599):1797-1800. Nov. 29, 2002, (5 pages).
Miller et al., "Emerging and Mechanism-Based Therapies for Recurrent or Metastatic Merkel Cell Carcinoma," *Curr. Treat. Options Oncol.* 14(2):249-263, Jun. 2013, (16 pages).
Nauerth et al., "TCR-ligand kofr-rate predicts protective capacity of antigen-specific CD8+ T cells for adoptive transfer," Sci. Transl. Med 5(192): 192ra87, Jul. 3, 2013, (21 pages).
Paulson et al., "CD8+ Lymphocyte Intratumoral Infiltration as a Stage-Independent Predictor of Merkel Cell Carcinoma Survival: A Population-Based Study," Am. J. Clin. Pathol. 142(4):452-458, Oct. 2014, (13 pages).

(56) References Cited

OTHER PUBLICATIONS

Paulson et al., "Downregulation of MHC-I expression is prevalent but reversible in Merkel cell carcinoma," *Cancer Immunol. Res.* 2(11): 1071-1079, Nov. 2014, (16 pages).

Peng et al., "Epigenetic silencing of $T_H1$-type chemokines shapes tumour immunity and immunotherapy," *Nature* 527:249-253, Nov. 12, 2015, (16 pages).

Santamaria-Barria et al., "Merkel Cell Carcinoma: 30-Year Experience from a Single Institution," *Ann. Surg. Oncol.* 20:1365-1373, 2013.

Sihto et al., "Tumor-infiltrating lymphocytes and outcome in Merkel cell carcinoma, a virus-associated cancer," *OncoImmunology* 1420-1421, Nov. 2012.

Tarantola et al., "Prognostic factors in Merkel cell carcinoma: Analysis of 240 cases," *J. Am. Acad. Dermatol.* 68(3):425-432, Mar. 2013.

Wang et al., "T-cell receptor aP diversity inversely correlates with pathogen-specific antibody levels in human cytomegalovirus infection," *Sci. Transl. Med.* 4(128): 128ra42, Apr. 4, 2012. (21 pages).

Zeh III et al., "High Avidity CTLs for Two Self-Antigens Demonstrate Superior In Vitro and In Vivo Antitumor Efficacy," *The Journal of Immunology* 7 52:989-994, 1999, (7 pages).

\* cited by examiner

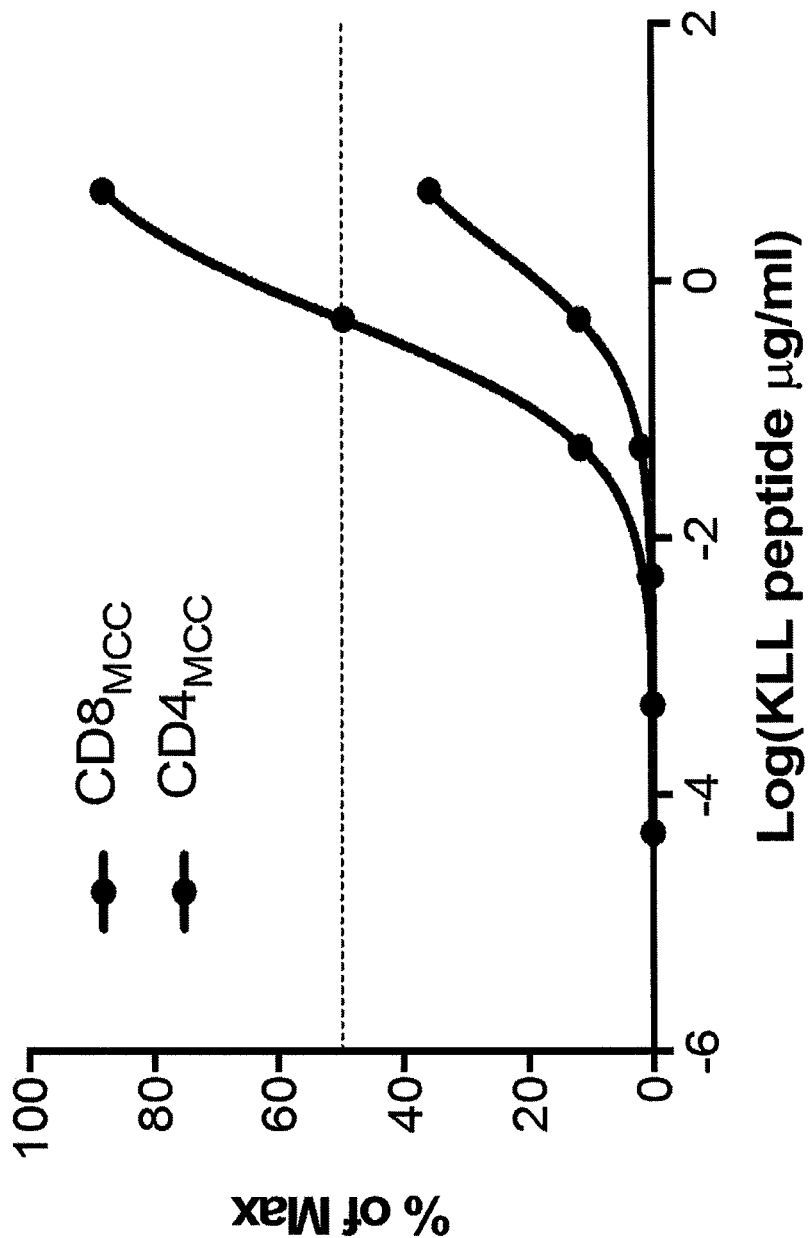

HIGH AFFINITY MERKEL CELL POLYOMAVIRUS T ANTIGEN-SPECIFIC TCRS AND USES THEREOF

STATEMENT OF GOVERNMENT INTEREST

This invention was made with government support under CA176841, CA162522, CA192475 and CA139052, awarded by the National Institutes of Health. The government has certain rights in the invention.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 360056_448USPC_SEQUENCE_LISTING.txt. The text file is 151 KB, was created on Oct. 14, 2019, and is being submitted electronically via EFS-Web.

BACKGROUND

Adoptive transfer of tumor-specific T-cells is an appealing strategy to eliminate existing tumors and requires the establishment of a robust population of antigen-specific T cells in vivo to eliminate existing tumor and prevent recurrences (Stromnes et al., *Immunol. Rev.* 257:145, 2014). Although transfer of tumor-specific CD8+ cytotoxic T lymphocytes (CTLs) is safe and can mediate direct anti-tumor activity in select patients (Chapuis et al., *Cancer Res.* 72:LB-136, 2012; Chapuis et al., *Sci. Transl. Med.* 5:174ra127, 2013; Chapuis et al., *Proc. Nat'l. Acad. Sci. U.S.A.* 109:4592, 2012), the variability in the avidity of the CTLs isolated from each patient or donor limits the anti-tumor efficacy in clinical trials (Chapuis et al., 2013). Since TCR affinity is an important determinant of CTL avidity (Zoete et al., *Frontiers Immunol.* 4:268, 2013), strategies have been developed to redirect the antigen specificity of donor or patient T cells using high affinity TCRα/β genes isolated from a well-characterized T cell clone specific for a tumor-specific antigen (Stromnes et al., *Immunol. Rev.* 257:145, 2014; Robbins et al., *J. Clin. Oncol.* 29:917, 2011). Such high affinity self/tumor-reactive T cells are rare since T cells that express self/tumor-reactive TCRs are subject to central and peripheral tolerance (Stone and Kranz, *Frontiers Immunol.* 4:244, 2013), with relative TCR affinities varying widely between donors and patients. Therefore, many matched donors and patients must be screened to identify a sufficiently high-affinity antigen-specific T cell clone from which a TCRα/β gene therapy construct can be generated (see, e.g., Ho et al., *J. Immunol. Methods* 310:40, 2006).

Merkel cell carcinoma (MCC) is a rare, aggressive skin cancer with a reported incidence that has quadrupled since 1986 (Hodgson, *J. Surg. Oncol.* 89:1, 2005). There are currently over 2,000 new cases diagnosed each year in the United States (see Lemos and Nghiem, *J. Invest. Dermatol.* 127:2100, 2007), which is projected to almost double by the year 2025 (projected from Surveillance, Epidemiology, and End Results (SEER) Registry 18 data accessed January 2017, which is a program of the National Cancer Institute; see seer.cancer.gov). An increased risk of MCC has been linked with immunosuppression related to UV radiation, viral infections, organ transplantation, and chronic lymphocytic leukemia (Paulson et al., *J. Invest. Dermatol.* 129: 1547, 2009; Goh et al., *Oncotarget* 7:3403, 2016; Feng et al., *Science* 319:1096, 2008). While MCC is more frequently observed in immunocompromised or elderly populations, more than 90% of patients with MCC do not appear to be observably immune compromised (Heath et al., *J. Am. Acad. Dermatol.* 58:375, 2008). Nonetheless, MCC is more lethal than melanoma with a reported 40% mortality rate (Heath et al., 2008), and MCC has a very poor prognosis once metastasized with a reported 5-year relative survival for patients having stage IV metastatic disease of only 18% (Lemos and Nghiem, 2007). To date there is no established effective treatment for MCC patients. There are ongoing clinical trials using immune-modulation, such as immune checkpoint blocking antibodies (see Nghiem et al., *N. Engl. J. Med.* 374:2542, 2016; Kaufman et al., *Lancet* 17:1374, 2016) that result in only a 30% to 60% response rate, or targeted delivery of interleukin (IL)-2 (see www.immomec.eu)

Merkel cell polyomavirus (MCPyV) has been found to be associated with 80% of MCC cases (Garneski et al., *Genome Biol.* 9:228, 2008; Rodig et al., *J. Clin. Invest.* 122:4645, 2012), while the rest appear to be associated with UV-light exposure (Goh et al., 2016; González-Vela et al., *J. Invest. Dermatol.* 137:197, 2017). Like other polyomaviruses, MCPyV contains two early genes that encode the large T antigen (LTA) and the small T antigen (STA), which are regarded as oncoproteins. LTA and STA share 78 amino acids at the amino-terminus and their expression appears to be necessary for the maintenance of MCC (Houben et al., *J. Virol.* 84:7064, 2010). The transforming activity of LTA appears to be related to a tumor-specific truncation mutation that eliminates the helicase domain (Shuda et al., *Proc. Nat'l. Acad. Sci. USA* 105:16272, 2008). Serologic studies have shown that anti-MCPyV antibodies are present in up to 88% of adults and more than 40% of children younger than 5 years (Pastrana et al., *PLoS Pathogens* 5:e1000578, 2009; Chen et al., *J. Clin. Virol.* 50:125, 2011), which indicates that MCPyV infection is common. But, antibodies against LTA and STA are largely restricted to patients with MCC and titers correlate with tumor burden (Paulson et al., *Cancer Res.* 70:8388, 2010). Many unique T cell epitopes in the MCPyV T proteins have been identified (Iyer et al., *Clin. Cancer Res.* 17:6671, 2011; Afanasiev et al., *Clin. Cancer Res.* 19:5351, 2013; Lyngaa et al., *Clin. Cancer Res.* 20:1768, 2014). Intratumoral CD8 T cell infiltration (also known as tumor infiltrating lymphocytes or TILs) has been has been correlated with increased survival of MCC patients, but only about a quarter of such patients have such immunity (Paulson et al., *J. Clin. Oncol.* 29:1539, 2011; Paulson et al., *J. Invest. Dermatol.* 133:642, 2013).

There is a clear need for alternative highly antigen-specific TCR immunotherapies directed against Merkel cell carcinoma. Presently disclosed embodiments address these needs and provide other related advantages.

BRIEF DESCRIPTION OF THE DRAWINGS

FIGS. 12A-12F show that a patient-derived class I MCPyV T antigen-specific TCR (MCC1) can activate CD4 T cells. (A) CD8 T cells were successfully transduced with codon-optimized MCC-specific TCR (MCC1). KLL peptide-Tetramer sorted cells were sorted and expanded in culture for two weeks using a REP protocol in which a second expansion occurs with autologous irradiated PBMs and remained tetramer positive. CD8+ T cells transduced with KLL-specific TCR (MCC1) (B) specifically kill in a 4 hour chromium release assay, (C) indicating that the MCPyV KLL-epitope is naturally processed and presented at levels high enough to trigger T cell function. Transduced CD8+ T cells readily proliferate over 72 hours (D) and make effector cytokines (E) in response to stimulation with peptide loaded HLA-A*02:01 K562 cells. CD4+ T cells transduced with MCC1 TCR have a reduced sensitivity to engage cytokine secretion (F), but the maximum percentage of transduced cells that secrete effector cytokines IFNγ, IL-2 and TNF at saturating levels of peptide (5 µg/mL) is similar between CD4+ and CD8+ T cells.

DETAILED DESCRIPTION

Figure 1:
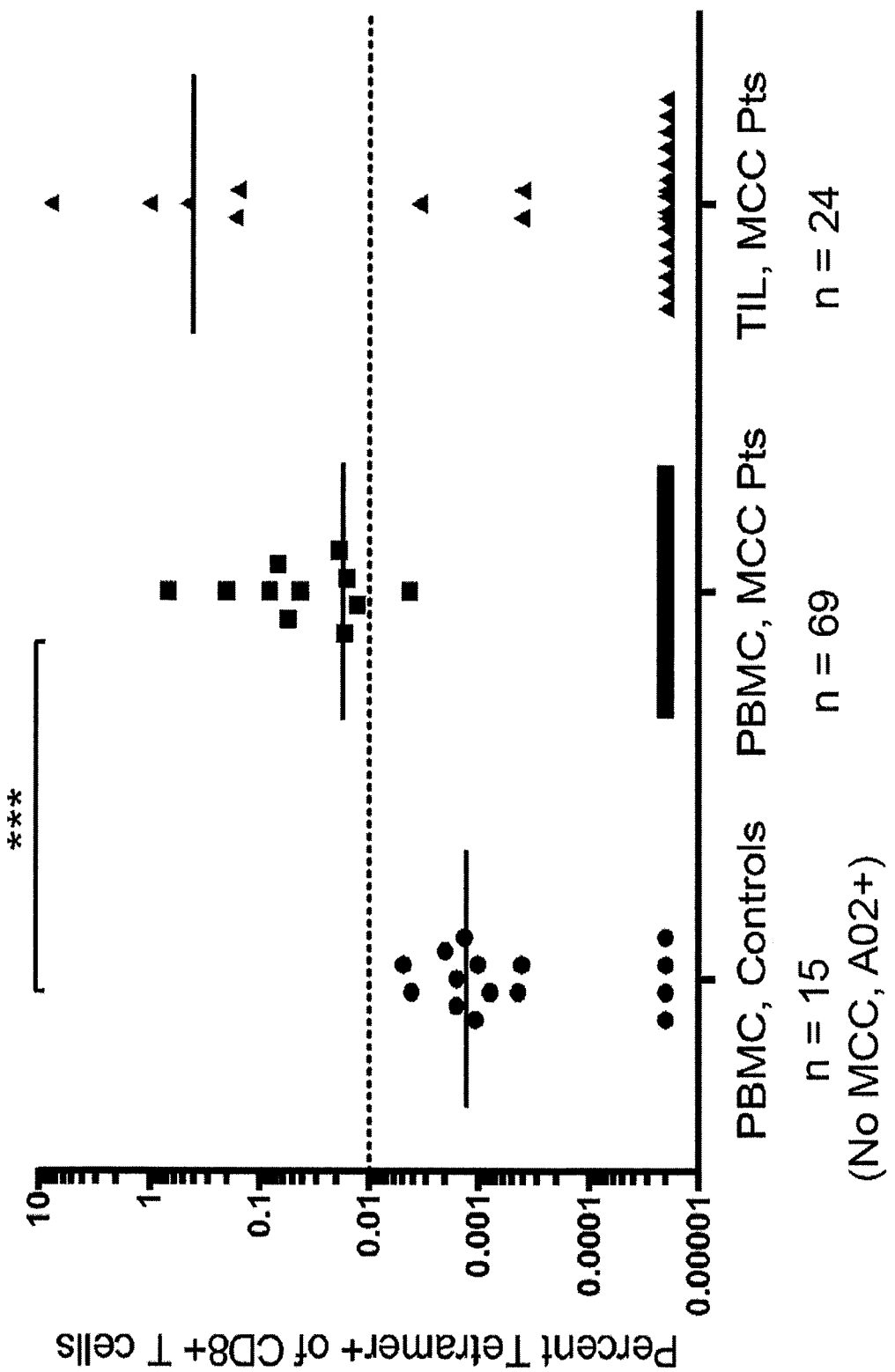
FIG. 1 shows the frequency of KLL tetramer+ CD8+ T cells in PBMC and TIL from MCC patients and controls. MCPyV-specific T-cell frequencies among HLA-A*02+ patients (n=69 for PBMC, 24 for TIL) or PBMC from control subjects (n=15). PBMC acquired when patients had evidence of disease was used in all analyses. Mean for each group is depicted, with dashed line at threshold for credible responses. The mean frequency of tetramer+ CD8+ cells was significantly different between MCC patient PBMC and control subjects (p=0.0004 by Mann Whitney test) but not significantly different between MCC patient TIL and control PBMC (p=0.11).

In one aspect, the present disclosure provides T cell receptors (TCRs) having high affinity for Merkel Cell Polyomavirus (MCPyV) T antigen peptides associated with a major histocompatibility complex (MHC) (e.g., human leukocyte antigen, HLA) for use in, for example, adoptive immunotherapy to treat Merkel cell cancer (MCC).

By way of background, tumor antigens can be generally categorized as oncofetal (e.g., expressed in fetal tissues only and cancerous somatic cells), oncoviral (e.g., encoded by tumorigenic transforming viruses), overexpressed/accumulated (e.g., expressed by both normal and neoplastic tissue, with the level of expression highly elevated in neoplasia), cancer-testis (e.g., expressed only in adult reproductive tissues, such as testis and placenta, and cancer cells), lineage-restricted (e.g., expressed largely by a single cancer histotype), mutated (e.g., expressed by cancer cells only due to genetic mutation or alteration in transcription), post-translationally altered (e.g., tumor-associated alterations in glycosylation, etc.), or idiotypic (e.g., highly polymorphic genes where a tumor cell expresses a specific "clonotype," such as in B cell, T cell lymphoma/leukemia resulting from clonal aberrancies).

By way of further background, Merkel cells are found in the epidermis and serve as touch cells by relaying touch-related information, such as texture and pressure, to the brain. While they are present in human skin at varying levels according to body site, they are at highest density on the fingertips and lips/face where touch sensation is most acute. In addition, they produce certain hormones and are sometimes referred to as neuroendocrine cells, although the reasons they produce certain hormones is unknown. Merkel cell carcinoma (MCC) is a rare, but highly aggressive, cutaneous neuroendocrine carcinoma, associated with the Merkel cell polyomavirus (MCPyV) in 80% of cases (Goh et al., 2016). The incidence of MCC is dramatically elevated in immunosuppressed patients (Ma and Brewer, *Cancers* 6:1328, 2014).

In virus-positive MCCs, the presumptive tumor antigens are non-self-proteins encoded in the viral genome (Paulson et aL., 2010). An identified HLA-A*02:01 restricted MCPyV epitope is KLLEIAPNC (SEQ ID NO:17) (MCC/KLL) (Lyngaa et al., 2014), which has been associated with improved survival in patients. Therefore, MCPyV was targeted for immunotherapy due to its limited on target/off tissue toxicity therapeutic profile due to the targeting of a viral antigen only present in diseased tissue (Vandeven and Nghiem, *Immunotherapy* 8:907, 2016). One approach was to clonally expand the number of autologous MCPyV-specific T cells to promote a therapeutic effect in patients who control disease, but this was limited due to the insufficient numbers of MCPyV-specific T cells obtained (about 0.25% to 14% of the total dose needed, data not shown). Another drawback to this approach is that the avidity of the MCPyV-specific T cells obtained ranged over 3 orders of magnitude from one patient to another. In addition, this approach was limited by the fact that MCPyV-specific T cells could not be identified or grown in 86% of patients screened (n=69) (data not shown). Finally, even if cells could be clonally expanded, current procedures take more than about 2 months to generate the cells of interest.

An advantage of the instant disclosure is to provide a high affinity binding protein or TCR specific for Merkel cell polyomavirus (MCPyV) T antigen (TA) epitopes present on TA peptides or TA protein fragments, wherein a cell engineered to express such a binding protein or TCR is capable of binding to a TA-peptide:HLA complex and provide a therapeutic effect, optionally wherein the binding protein or TCR has high enough avidity to bind independent of CD8. In addition, such TCRs may optionally be capable of more efficiently associating with a CD3 protein as compared to endogenous TCRs.

A method to quickly and simultaneously screen and rank T cell clonotypes (based on affinity) from a large cohort of HLA matched donors in a short time (about 6-8 weeks) was used to enrich for cells with high-affinity TCRs specific for a Merkel cell polyomavirus T antigen by using limiting concentrations of a Merkel cell polyomavirus T antigen-specific pMHC multimers. The TCRβ repertoire was analyzed for frequency and coupled with bioinformatics to accurately identify TCR α-chain and β-chain pairs.

The compositions and methods described herein will in certain embodiments have therapeutic utility for the treatment of diseases and conditions associated with a Merkel cell polyomavirus T antigen. Such diseases include various forms of hyperproliferative disorders, such as cancer. Non-limiting examples of these and related uses are described herein and include in vitro, ex vivo and in vivo stimulation of Merkel cell polyomavirus T antigen-specific T cell responses, such as by the use of genetically engineered T cells expressing an enhanced affinity TCR specific for a Merkel cell polyomavirus T antigen epitope or peptide.

Prior to setting forth this disclosure in more detail, it may be helpful to an understanding thereof to provide definitions of certain terms to be used herein. Additional definitions are set forth throughout this disclosure.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means±20% of the indicated range, value, or structure, unless otherwise indicated. It should be understood that the terms "a" and "an" as used herein refer to "one or more" of the enumerated components. The use of the alternative (e.g., "or") should be understood to mean either one, both, or any combination thereof of the alternatives. As used herein, the terms "include," "have" and "comprise" are used synonymously, which terms and variants thereof are intended to be construed as non-limiting.

In addition, it should be understood that the individual compounds, or groups of compounds, derived from the various combinations of the structures and substituents described herein, are disclosed by the present application to the same extent as if each compound or group of compounds was set forth individually. Thus, selection of particular structures or particular substituents is within the scope of the present disclosure.

The term "consisting essentially of" limits the scope of a claim to the specified materials or steps, or to those that do not materially affect the basic characteristics of a claimed invention. For example, a protein domain, region, or module (e.g., a binding domain, hinge region, linker module) or a protein (which may have one or more domains, regions, or modules) "consists essentially of" a particular amino acid sequence when the amino acid sequence of a domain, region, module, or protein includes extensions, deletions, mutations, or a combination thereof (e.g., amino acids at the amino- or carboxy-terminus or between domains) that, in combination, contribute to at most 20% (e.g., at most 15%, 10%, 8%, 6%, 5%, 4%, 3%, 2% or 1%) of the length of a domain, region, module, or protein and do not substantially affect (i.e., do not reduce the activity by more than 50%, such as no more than 40%, 30%, 25%, 20%, 15%, 10%, 5%, or 1%) the activity of the domain(s), region(s), module(s), or protein (e.g., the target binding affinity of a binding protein).

"Merkel cell carcinoma" or "MCC" or "neuroendocrine carcinoma of the skin," as used herein, refers to hyperproliferative or uncontrolled growth of cells in the skin that share some characteristics with normal Merkel cells of the skin, which may be infected with a Merkel cell polyomavirus (MCPyV) or have a high somatic mutation burden (e.g., due to exposure to UV light) in one of more genes including RB1, TP53, chromatin modification pathway genes (e.g., ASXL1, MLL2, MLL3), JNK pathway genese (e.g, MAP3K1, TRAF7), and DNA-damage pathway (e.g., ATM, MSH2, BRCA1). The MCC arising from infection with MCPyV may also be referred to as "MCPyV-positive MCC" and MCC arising from a high somatic mutation burden may also be referred to as "MCPyV-negative MCC."

As used herein, an "immune system cell" means any cell of the immune system that originates from a hematopoietic stem cell in the bone marrow, which gives rise to two major lineages, a myeloid progenitor cell (which give rise to myeloid cells such as monocytes, macrophages, dendritic cells, meagakaryocytes and granulocytes) and a lymphoid progenitor cell (which give rise to lymphoid cells such as T cells, B cells and natural killer (NK) cells). Exemplary immune system cells include a CD4+ T cell, a CD8+ T cell, a CD4− CD8− double negative T cell, a γδ T cell, a regulatory T cell, a natural killer cell, and a dendritic cell. Macrophages and dendritic cells may be referred to as "antigen presenting cells" or "APCs," which are specialized cells that can activate T cells when a major histocompatibility complex (MHC) receptor on the surface of the APC complexed with a peptide interacts with a TCR on the surface of a T cell.

"Major histocompatibility complex" (MHC) refers to glycoproteins that deliver peptide antigens to a cell surface. MHC class I molecules are heterodimers having a membrane spanning a chain (with three a domains) and a non-covalently associated β2 microglobulin. MHC class II molecules are composed of two transmembrane glycoproteins, α and β, both of which span the membrane. Each chain has two domains. MHC class I molecules deliver peptides originating in the cytosol to the cell surface, where a peptide:MHC complex is recognized by CD8$^+$ T cells. MHC class II molecules deliver peptides originating in the vesicular system to the cell surface, where they are recognized by CD4$^+$ T cells. Human MHC is referred to as human leukocyte antigen (HLA).

A "T cell" is an immune system cell that matures in the thymus and produces T cell receptors (TCRs). T cells can be naïve (not exposed to antigen; increased expression of CD62L, CCR7, CD28, CD3, CD127, and CD45RA, and decreased expression of CD45RO as compared to $T_{CM}$), memory T cells ($T_M$) (antigen-experienced and long-lived), and effector cells (antigen-experienced, cytotoxic). $T_M$ can be further divided into subsets of central memory T cells ($T_{CM}$, increased expression of CD62L, CCR7, CD28, CD127, CD45RO, and CD95, and decreased expression of CD54RA as compared to naïve T cells) and effector memory T cells ($T_{EM}$, decreased expression of CD62L, CCR7, CD28, CD45RA, and increased expression of CD127 as compared to naïve T cells or $T_{cm}$). Effector T cells ($T_E$) refers to antigen-experienced CD8+ cytotoxic T lymphocytes that have decreased expression of CD62L, CCR7, CD28, and are positive for granzyme and perforin as compared to $T_{CM}$. Other exemplary T cells include regulatory T cells, such as CD4+ CD25+ (Foxp3+) regulatory T cells and Treg17 cells, as well as Tr1, Th3, CD8+CD28−, and Qa-1 restricted T cells.

"T cell receptor" (TCR) refers to an immunoglobulin superfamily member (having a variable binding domain, a constant domain, a transmembrane region, and a short cytoplasmic tail; see, e.g., Janeway et al., *Immunobiology: The Immune System in Health and Disease*, 3$^{rd}$ Ed., Current Biology Publications, p. 4:33, 1997) capable of specifically binding to an antigen peptide bound to a MHC receptor. A TCR can be found on the surface of a cell or in soluble form and generally is comprised of a heterodimer having α and β chains (also known as TCRα and TCRβ, respectively), or γ and δ chains (also known as TCRγ and TCRδ, respectively). Like immunoglobulins, the extracellular portion of TCR chains (e.g., α-chain, β-chain) contain two immunoglobulin domains, a variable domain (e.g., α-chain variable domain or V$_α$, β-chain variable domain or V$_β$; typically amino acids 1 to 116 based on Kabat numbering Kabat et al., "Sequences of Proteins of Immunological Interest, US Dept. Health and Human Services, Public Health Service National Institutes of Health, 1991, 5$^{th}$ ed.) at the N-terminus, and one constant domain (e.g., α-chain constant domain or C$_α$, typically amino acids 117 to 259 based on Kabat, β-chain constant domain or C$_β$, typically amino acids 117 to 295 based on Kabat) adjacent to the cell membrane. Also like immunoglobulins, the variable domains contain complementary determining regions (CDRs) separated by framework regions (FRs) (see, e.g., Jores et al., *Proc. Nat'l Acad. Sci. U.S.A.* 87:9138, 1990; Chothia et al., *EMBO J.* 7:3745, 1988; see also Lefranc et al., *Dev. Comp. Immunol.* 27:55, 2003). In certain embodiments, a TCR is found on the surface of T cells (or T lymphocytes) and associates with the CD3 complex. The source of a TCR as used in the present disclosure may be from various animal species, such as a human, mouse, rat, rabbit or other mammal.

"CD3" is known in the art as a multi-protein complex of six chains (see, Abbas and Lichtman, 2003; Janeway et al., p 172 and 178, 1999). In mammals, the complex comprises a CD3γ chain, a CD3δ chain, two CD3ε chains, and a homodimer of CD3ζ chains. The CD3γ, CD3δ, and CD3ε chains are highly related cell surface proteins of the immunoglobulin superfamily containing a single immunoglobulin domain. The transmembrane regions of the CD3γ, CD3δ, and CD3ε chains are negatively charged, which is a characteristic that allows these chains to associate with the positively charged T cell receptor chains. The intracellular tails of the CD3γ, CD3δ, and CD3ε chains each contain a single conserved motif known as an immunoreceptor tyrosine-based activation motif or ITAM, whereas each CD3ζ chain has three. Without wishing to be bound by theory, it is believed the ITAMs are important for the signaling capacity of a TCR complex. CD3 as used in the present disclosure may be from various animal species, including human, mouse, rat, or other mammals.

As used herein, "TCR complex" refers to a complex formed by the association of CD3 with TCR. For example, a TCR complex can be composed of a CD3γ chain, a CD3δ chain, two CD3ε chains, a homodimer of CD3ζ chains, a TCRα chain, and a TCRβ chain. Alternatively, a TCR complex can be composed of a CD3γ chain, a CD3δ chain, two CD3ε chains, a homodimer of CD3ζ chains, a TCRγ chain, and a TCRδ chain.

A "component of a TCR complex," as used herein, refers to a TCR chain (i.e., TCRα, TCRβ, TCRγ or TCRδ), a CD3 chain (i.e., CD3γ, CD3δ, CD3ε or CD3ζ), or a complex formed by two or more TCR chains or CD3 chains (e.g., a complex of TCRα and TCRβ, a complex of TCRγ and TCRδ, a complex of CD3ε and CD3δ, a complex of CD3γ and CD3ε, or a sub-TCR complex of TCRα, TCRβ, CD3γ, CD3δ, and two CD3ε chains).

A "binding domain" (also referred to as a "binding region" or "binding moiety"), as used herein, refers to a molecule or portion thereof (e.g., peptide, oligopeptide, polypeptide, protein) that possesses the ability to specifically and non-covalently associate, unite, or combine with a target (e.g., Merkel cell polyomavirus T antigen, Merkel cell polyomavirus T antigen peptide:MHC complex). A binding domain includes any naturally occurring, synthetic, semisynthetic, or recombinantly produced binding partner for a biological molecule, a molecular complex (i.e., complex comprising two or more biological molecules), or other target of interest. Exemplary binding domains include single chain immunoglobulin variable regions (e.g., scTCR, scFv), receptor ectodomains, ligands (e.g., cytokines, chemokines), or synthetic polypeptides selected for their specific ability to bind to a biological molecule, a molecular complex or other target of interest.

As used herein, "specifically binds" or "specific for" refers to an association or union of a binding protein (e.g., TCR receptor) or a binding domain (or fusion protein thereof) to a target molecule with an affinity or K$_a$ (i.e., an equilibrium association constant of a particular binding interaction with units of 1/M) equal to or greater than 10$^5$ M$^{-1}$ (which equals the ratio of the on-rate [k$_{on}$] to the off-rate [k$_{off}$] for this association reaction), while not significantly associating or uniting with any other molecules or components in a sample. Binding proteins or binding domains (or fusion proteins thereof) may be classified as "high affinity" binding proteins or binding domains (or fusion proteins thereof) or as "low affinity" binding proteins or binding domains (or fusion proteins thereof). "High affinity" binding proteins or binding domains refer to those binding proteins or binding domains having a K$_a$ of at least 10$^7$ M$^{-1}$, at least 10$^8$ M$^{-1}$, at least 10$^9$ M$^{-1}$, at least 10$^{10}$ M$^{-1}$, at least 10$^{11}$ M$^{-1}$, at least 10$^{12}$ M$^{-1}$, or at least 10$^{13}$ M$^{-1}$. "Low affinity" binding proteins or binding domains refer to those binding proteins or binding domains having a K$_a$ of up to 10$^7$ M$^{-1}$, up to 10$^6$ M$^{-1}$, up to 10$^5$ M$^{-1}$. Alternatively, affinity may be defined as an equilibrium dissociation constant (K$_d$) of a particular binding interaction with units of M (e.g., 10$^{-5}$ M to 10$^{-13}$ M).

In certain embodiments, a receptor or binding domain may have "enhanced affinity," which refers to selected or engineered receptors or binding domains with stronger binding to a target antigen than a wild type (or parent) binding domain. For example, enhanced affinity may be due to a K$_a$ (equilibrium association constant) for the target antigen that is higher than the wild type binding domain, due to a K$_d$ (dissociation constant) for the target antigen that is less than that of the wild type binding domain, due to an off-rate (k$_{off}$) for the target antigen that is less than that of the wild type binding domain, or a combination thereof. In certain embodiments, enhanced affinity TCRs may be codon optimized to enhance expression in a particular host cell, such as T cells (Scholten et al., *Clin. Immunol.* 119:135, 2006).

A variety of assays are known for identifying binding domains of the present disclosure that specifically bind a particular target, as well as determining binding domain or fusion protein affinities, such as Western blot, ELISA, analytical ultracentrifugation, spectroscopy and surface plasmon resonance (Biacore®) analysis (see, e.g., Scatchard et al., *Ann. N.Y. Acad. Sci.* 51:660, 1949; Wilson, *Science*

295:2103, 2002; Wolff et al., *Cancer Res.* 53:2560, 1993; and U.S. Pat. Nos. 5,283,173, 5,468,614, or the equivalent).

The term "Merkel cell polyomavirus T antigen-specific binding protein" or "MCPyV-T antigen-specific binding protein" refers to a protein or polypeptide that specifically binds to a Merkel cell polyomavirus T antigen epitope, peptide or T antigen fragment. In some embodiments, a protein or polypeptide specifically binds to a Merkel cell polyomavirus T antigen epitope or T antigen peptide thereof, such as a Merkel cell polyomavirus T antigen epitope peptide complexed with an WIC or HLA molecule, e.g., on a cell surface, with at or at least about an avidity or affinity sufficient to elicit an immune response. In certain embodiments, a Merkel cell polyomavirus T antigen epitope-specific binding protein binds a Merkel cell polyomavirus T antigen-derived peptide:HLA complex (or MCPyV-T antigen-derived peptide:MHC complex) with a $K_d$ of less than about $10^{-8}$ M, less than about $10^{-9}$ M, less than about $10^{-10}$ M, less than about $10^{-11}$ M, less than about $10^{-12}$ M, or less than about $10^{-13}$ M, or with an affinity that is about the same as, at least about the same as, or is greater than at or about the affinity exhibited by an exemplary MCPyV-T antigen-specific binding protein provided herein, such as any of the MCPyV-T antigen-specific TCRs provided herein, for example, as measured by the same assay. In certain embodiments, a MCPyV-T antigen-specific binding protein comprises a MCPyV-T antigen-specific immunoglobulin superfamily binding protein or binding portion thereof.

Assays for assessing affinity or apparent affinity or relative affinity are known. In certain examples, apparent affinity for a TCR is measured by assessing binding to various concentrations of tetramers, for example, by flow cytometry using labeled tetramers. In some examples, apparent $K_D$ of a TCR is measured using 2-fold dilutions of labeled tetramers at a range of concentrations, followed by determination of binding curves by non-linear regression, apparent $K_D$ being determined as the concentration of ligand that yielded half-maximal binding.

The term "Merkel cell polyomavirus T antigen-specific binding domain" or "Merkel cell polyomavirus T antigen-specific binding fragment" refer to a domain or portion of a Merkel cell polyomavirus T antigen-specific binding protein responsible for the specific Merkel cell polyomavirus T antigen binding. A Merkel cell polyomavirus T antigen-specific binding domain alone (i.e., without any other portion of a Merkel cell polyomavirus T antigen-specific binding protein) can be soluble and can bind to a Merkel cell polyomavirus T antigen epitope or peptide with a $K_d$ of less than about $10^{-8}$ M, less than about $10^{-9}$ M, less than about $10^{-10}$ M, less than about $10^{-11}$ M, less than about $10^{-12}$ M, or less than about $10^{-13}$ M. Exemplary Merkel cell polyomavirus T antigen-specific binding domains include Merkel cell polyomavirus T antigen-specific scTCR (e.g., single chain αβTCR proteins such as Vα-L-Vβ, Vβ-L-Vα, Vα-Cα-L-Vα, or Vα-L-Vβ-Cβ, wherein Vα and Vβ are TCRα and β variable domains respectively, Cα and Cβ are TCRα and β constant domains, respectively, and L is a linker) and scFv fragments as described herein, which can be derived from an anti-Merkel cell polyomavirus T antigen TCR or antibody.

Principles of antigen processing by antigen presenting cells (APC) (such as dendritic cells, macrophages, lymphocytes or other cell types), and of antigen presentation by APC to T cells, including major histocompatibility complex (MHC)-restricted presentation between immunocompatible (e.g., sharing at least one allelic form of an MHC gene that is relevant for antigen presentation) APC and T cells, are well established (see, e.g., Murphy, Janeway's Immunobiology ($8^{th}$ Ed.) 2011 Garland Science, NY; chapters 6, 9 and 16). For example, processed antigen peptides originating in the cytosol (e.g., tumor antigen, intrcellular pathogen) are generally from about 7 amino acids to about 11 amino acids in length and will associate with class I MHC molecules, whereas peptides processed in the vesicular system (e.g., bacterial, viral) will vary in length from about 10 amino acids to about 25 amino acids and associate with class II MHC molecules.

"Merkel cell polyomavirus T antigen" or "Merkel cell polyomavirus T antigen peptide" refer to a naturally or synthetically produced portion of a Merkel cell polyomavirus T antigen protein ranging in length from about 7 amino acids to about 15 amino acids, which can form a complex with a MHC (e.g., HLA) molecule and such a complex can bind with a TCR specific for a Merkel cell polyomavirus T antigen peptide:MHC (e.g., HLA) complex.

A "linker" refers to an amino acid sequence that connects two proteins, polypeptides, peptides, domains, regions, or motifs and may provide a spacer function compatible with interaction of the two sub-binding domains so that the resulting polypeptide retains a specific binding affinity (e.g., scTCR) to a target molecule or retains signaling activity (e.g., TCR complex). In certain embodiments, a linker is comprised of about two to about 35 amino acids, for instance, or about four to about 20 amino acids or about eight to about 15 amino acids or about 15 to about 25 amino acids. Exemplary linkers include Gycine-Serine (Gly-Ser) linkers, such as those provided in SEQ ID NO:27 and 28.

"Junction amino acids" or "junction amino acid residues" refer to one or more (e.g., about 2-10) amino acid residues between two adjacent motifs, regions or domains of a polypeptide, such as between a binding domain and an adjacent constant domain or between a TCR chain and an adjacent self-cleaving peptide. Junction amino acids may result from the construct design of a fusion protein (e.g., amino acid residues resulting from the use of a restriction enzyme site during the construction of a nucleic acid molecule encoding a fusion protein).

An "altered domain" or "altered protein" refers to a motif, region, domain, peptide, polypeptide, or protein with a non-identical sequence identity to a wild type motif, region, domain, peptide, polypeptide, or protein (e.g., a wild type TCRα chain, TCRβ chain, TCRα constant domain, TCRβ constant domain) of at least 85% (e.g., 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%).

As used herein, "nucleic acid" or "nucleic acid molecule" refers to any of deoxyribonucleic acid (DNA), ribonucleic acid (RNA), oligonucleotides, fragments generated, for example, by the polymerase chain reaction (PCR) or by in vitro translation, and fragments generated by any of ligation, scission, endonuclease action, or exonuclease action. In certain embodiments, the nucleic acids of the present disclosure are produced by PCR. Nucleic acids may be composed of monomers that are naturally occurring nucleotides (such as deoxyribonucleotides and ribonucleotides), analogs of naturally occurring nucleotides (e.g., α-enantiomeric forms of naturally-occurring nucleotides), or a combination of both. Modified nucleotides can have modifications in or replacement of sugar moieties, or pyrimidine or purine base moieties. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. Nucleic acid molecules can be either single stranded or double stranded.

The term "isolated" means that the material is removed from its original environment (e.g., the natural environment if it is naturally occurring). For example, a naturally occurring nucleic acid or polypeptide present in a living animal is not isolated, but the same nucleic acid or polypeptide, separated from some or all of the co-existing materials in the natural system, is isolated. Such nucleic acid could be part of a vector and/or such nucleic acid or polypeptide could be part of a composition (e.g., a cell lysate), and still be isolated in that such vector or composition is not part of the natural environment for the nucleic acid or polypeptide. The term "gene" means the segment of DNA involved in producing a polypeptide chain; it includes regions preceding and following the coding region "leader and trailer" as well as intervening sequences (introns) between individual coding segments (exons).

As used herein, the term "genetically engineered" refers to a cell, microorganism, nucleic acid molecule, or vector that has been recombinantly created by human intervention—that is, modified by introduction of a heterologous nucleic acid molecule, or refers to a cell or microorganism that has been altered such that expression of an endogenous nucleic acid molecule or gene is controlled, deregulated or constitutive. Human generated genetic alterations may include, for example, modifications that introduce nucleic acid molecules (which may include an expression control element, such as a promoter) that encode one or more proteins or enzymes, or other nucleic acid molecule additions, deletions, substitutions, or other functional disruption of or addition to a cell's genetic material. Exemplary modifications include those in coding regions or functional fragments thereof of heterologous or homologous polypeptides from a reference or parent molecule.

As used herein, "mutation" refers to a change in the sequence of a nucleic acid molecule or polypeptide molecule as compared to a reference or wild-type nucleic acid molecule or polypeptide molecule, respectively. A mutation can result in several different types of change in sequence, including substitution, insertion or deletion of nucleotide(s) or amino acid(s). In certain embodiments, a mutation is a substitution of one or three codons or amino acids, a deletion of one to about 5 codons or amino acids, or a combination thereof.

A "conservative substitution" is recognized in the art as a substitution of one amino acid for another amino acid that has similar properties. Exemplary conservative substitutions are well known in the art (see, e.g., WO 97/09433 at page 10; Lehninger, Biochemistry, $2^{nd}$ Edition; Worth Publishers, Inc. NY, N.Y., pp. 71-77, 1975; Lewin, Genes IV, Oxford University Press, NY and Cell Press, Cambridge, Mass., p. 8, 1990).

The term "construct" refers to any polynucleotide that contains a recombinantly engineered nucleic acid molecule. A construct may be present in a vector (e.g., a bacterial vector, a viral vector) or may be integrated into a genome. A "vector" is a nucleic acid molecule that is capable of transporting another nucleic acid molecule. Vectors may be, for example, plasmids, cosmids, viruses, a RNA vector or a linear or circular DNA or RNA molecule that may include chromosomal, non-chromosomal, semi-synthetic or synthetic nucleic acid molecules. Exemplary vectors are those capable of autonomous replication (episomal vector) or expression of nucleic acid molecules to which they are linked (expression vectors).

Viral vectors include retrovirus, adenovirus, parvovirus (e.g., adeno-associated viruses), coronavirus, negative strand RNA viruses such as ortho-myxovirus (e.g., influenza virus), rhabdovirus (e.g., rabies and vesicular stomatitis virus), paramyxovirus (e.g., measles and Sendai), positive strand RNA viruses such as picornavirus and alphavirus, and double-stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields et al., Eds., Lippincott-Raven Publishers, Philadelphia, 1996).

"Lentiviral vector," as used herein, means HIV-based lentiviral vectors for gene delivery, which can be integrative or non-integrative, have relatively large packaging capacity, and can transduce a range of different cell types. Lentiviral vectors are usually generated following transient transfection of three (packaging, envelope and transfer) or more plasmids into producer cells. Like HIV, lentiviral vectors enter the target cell through the interaction of viral surface glycoproteins with receptors on the cell surface. On entry, the viral RNA undergoes reverse transcription, which is mediated by the viral reverse transcriptase complex. The product of reverse transcription is a double-stranded linear viral DNA, which is the substrate for viral integration into the DNA of infected cells.

The term "operably-linked" refers to the association of two or more nucleic acid molecules on a single nucleic acid fragment so that the function of one is affected by the other. For example, a promoter is operably-linked with a coding sequence when it is capable of affecting the expression of that coding sequence (i.e., the coding sequence is under the transcriptional control of the promoter). "Unlinked" means that the associated genetic elements are not closely associated with one another and the function of one does not affect the other.

As used herein, "expression vector" refers to a DNA construct containing a nucleic acid molecule that is operably-linked to a suitable control sequence capable of effecting the expression of the nucleic acid molecule in a suitable host. Such control sequences include a promoter to effect transcription, an optional operator sequence to control such transcription, a sequence encoding suitable mRNA ribosome binding sites, and sequences which control termination of transcription and translation. The vector may be a plasmid, a phage particle, a virus, or simply a potential genomic insert. Once transformed into a suitable host, the vector may replicate and function independently of the host genome, or may, in some instances, integrate into the genome itself. In the present specification, "plasmid," "expression plasmid," "virus" and "vector" are often used interchangeably.

The term "expression", as used herein, refers to the process by which a polypeptide is produced based on the encoding sequence of a nucleic acid molecule, such as a gene. The process may include transcription, post-transcriptional control, post-transcriptional modification, translation, post-translational control, post-translational modification, or any combination thereof.

The term "introduced" in the context of inserting a nucleic acid molecule into a cell, means "transfection", or "transformation" or "transduction" and includes reference to the incorporation of a nucleic acid molecule into a eukaryotic or prokaryotic cell wherein the nucleic acid molecule may be incorporated into the genome of a cell (e.g., chromosome, plasmid, plastid, or mitochondrial DNA), converted into an autonomous replicon, or transiently expressed (e.g., transfected mRNA).

As used herein, "heterologous" or "exogenous" nucleic acid molecule, construct or sequence refers to a nucleic acid molecule or portion of a nucleic acid molecule that is not native to a host cell, but may be homologous to a nucleic acid molecule or portion of a nucleic acid molecule from the host cell. The source of the heterologous or exogenous nucleic acid molecule, construct or sequence may be from a different genus or species. In certain embodiments, a heterologous or exogenous nucleic acid molecule is added (i.e., not endogenous or native) to a host cell or host genome by, for example, conjugation, transformation, transfection, electroporation, or the like, wherein the added molecule may integrate into the host genome or exist as extra-chromosomal genetic material (e.g., as a plasmid or other form of self-replicating vector), and may be present in multiple copies. In addition, "heterologous" refers to a non-native enzyme, protein or other activity encoded by an exogenous nucleic acid molecule introduced into the host cell, even if the host cell encodes a homologous protein or activity.

As described herein, more than one heterologous or exogenous nucleic acid molecule can be introduced into a host cell as separate nucleic acid molecules, as a plurality of individually controlled genes, as a polycistronic nucleic acid molecule, as a single nucleic acid molecule encoding a fusion protein, or any combination thereof. For example, as disclosed herein, a host cell can be modified to express two or more heterologous or exogenous nucleic acid molecules encoding desired TCR specific for a Merkel cell polyomavirus T antigen peptide (e.g., TCRα and TCRβ). When two or more exogenous nucleic acid molecules are introduced into a host cell, it is understood that the two or more exogenous nucleic acid molecules can be introduced as a single nucleic acid molecule (e.g., on a single vector), on separate vectors, integrated into the host chromosome at a single site or multiple sites, or any combination thereof. The number of referenced heterologous nucleic acid molecules or protein activities refers to the number of encoding nucleic acid molecules or the number of protein activities, not the number of separate nucleic acid molecules introduced into a host cell.

As used herein, the term "endogenous" or "native" refers to a gene, protein, or activity that is normally present in a host cell. Moreover, a gene, protein or activity that is mutated, overexpressed, shuffled, duplicated or otherwise altered as compared to a parent gene, protein or activity is still considered to be endogenous or native to that particular host cell. For example, an endogenous control sequence from a first gene (e.g., promoter, translational attenuation sequences) may be used to alter or regulate expression of a second native gene or nucleic acid molecule, wherein the expression or regulation of the second native gene or nucleic acid molecule differs from normal expression or regulation in a parent cell.

The term "homologous" or "homolog" refers to a molecule or activity found in or derived from a host cell, species or strain. For example, a heterologous or exogenous nucleic acid molecule may be homologous to a native host cell gene, and may optionally have an altered expression level, a different sequence, an altered activity, or any combination thereof.

"Sequence identity," as used herein, refers to the percentage of amino acid residues in one sequence that are identical with the amino acid residues in another reference polypeptide sequence after aligning the sequences and introducing gaps, if necessary, to achieve the maximum percent sequence identity, and not considering any conservative substitutions as part of the sequence identity. The percentage sequence identity values can be generated using the NCBI BLAST2.0 software as defined by Altschul et al. (1997) "Gapped BLAST and PSI-BLAST: a new generation of protein database search programs", Nucleic Acids Res. 25:3389-3402, with the parameters set to default values.

As used herein, a "hematopoietic progenitor cell" is a cell that can be derived from hematopoietic stem cells or fetal tissue and is capable of further differentiation into mature cells types (e.g., immune system cells). Exemplary hematopoietic progenitor cells include those with a $CD24^{Lo}$ $Lin^-$ $CD117^+$ phenotype or those found in the thymus (referred to as progenitor thymocytes).

As used herein, the term "host" refers to a cell (e.g., T cell) or microorganism targeted for genetic modification with a heterologous or exogenous nucleic acid molecule to produce a polypeptide of interest (e.g., high or enhanced affinity anti-Merkel cell polyomavirus T antigen TCR).

As used herein, "hyperproliferative disorder" refers to excessive growth or proliferation as compared to a normal or undiseased cell. Exemplary hyperproliferative disorders include tumors, cancers, neoplastic tissue, carcinoma, sarcoma, malignant cells, pre-malignant cells, as well as non-neoplastic or non-malignant hyperproliferative disorders (e.g., adenoma, fibroma, lipoma, leiomyoma, hemangioma, fibrosis, restenosis, as well as autoimmune diseases such as rheumatoid arthritis, osteoarthritis, psoriasis, inflammatory bowel disease, or the like).

Binding Proteins Specific for Merkel Cell Polyomavirus T Antigen Peptides

Ideal targets for immunotherapy are immunogenic proteins with high expression in malignant tissues and limited-to-absent expression in normal tissues. As noted herein, Merkel cell polyomavirus (MCPyV) T antigen characteristics render it a good target for immunotherapy, including MCPyV having limited on target/off tissue toxicity due to the targeting of a viral antigen only present in diseased tissue (Vandeven and Nghiem, 2016).

Conservative substitutions of amino acids are well known and may occur naturally or may be introduced when the binding protein or TCR is genetically engineered. Amino acid substitutions, deletions, and additions may be introduced into a protein using mutagenesis methods known in the art (see, e.g., Sambrook et al., *Molecular Cloning: A Laboratory Manual,* 3d ed., Cold Spring Harbor Laboratory Press, NY, 2001). Oligonucleotide-directed site-specific (or segment specific) mutagenesis procedures may be employed to provide an altered polynucleotide that has particular codons altered according to the substitution, deletion, or insertion desired. Alternatively, random or saturation mutagenesis techniques, such as alanine scanning mutagenesis, error prone polymerase chain reaction mutagenesis, and oligonucleotide-directed mutagenesis may be used to prepare immunogen polypeptide variants (see, e.g., Sambrook et al., supra).

A variety of criteria can be used to determine whether an amino acid that is substituted at a particular position in a peptide or polypeptide is conservative (or similar). For example, a similar amino acid or a conservative amino acid substitution is one in which an amino acid residue is replaced with an amino acid residue having a similar side chain. Similar amino acids may be included in the following categories: amino acids with basic side chains (e.g., lysine, arginine, histidine); amino acids with acidic side chains (e.g., aspartic acid, glutamic acid); amino acids with uncharged polar side chains (e.g., glycine, asparagine, glutamine, serine, threonine, tyrosine, cysteine, histidine); amino acids with nonpolar side chains (e.g., alanine, valine, leucine, isoleucine, proline, phenylalanine, methionine, tryptophan); amino acids with beta-branched side chains (e.g., threonine, valine, isoleucine), and amino acids with aromatic side chains (e.g., tyrosine, phenylalanine, tryptophan). Proline, which is considered more difficult to classify, shares properties with amino acids that have aliphatic side chains (e.g., leucine, valine, isoleucine, and alanine). In certain circumstances, substitution of glutamine for glutamic acid or asparagine for aspartic acid may be considered a similar substitution in that glutamine and asparagine are amide derivatives of glutamic acid and aspartic acid, respectively. As understood in the art "similarity" between two polypeptides is determined by comparing the amino acid sequence and conserved amino acid substitutes thereto of the polypeptide to the sequence of a second polypeptide (e.g., using GENEWORKS, Align, the BLAST algorithm, or other algorithms described herein and practiced in the art).

Species (or variants) of a particular binding protein or high affinity T cell receptors (TCRs) specific for Merkel cell polyomavirus T antigen epitopes or peptides may include a protein that has at least 85%, 90%, 95%, or 99% amino acid sequence identity to any of the exemplary amino acid sequences disclosed herein (e.g., SEQ ID NOS:1-4, 13, 14 and 38-354), provided that (a) at least three or four of the CDRs have no mutations, (b) the CDRs that do have mutations have only up to two amino acid substitutions, up to a contiguous five amino acid deletion, or a combination thereof, and (c) the binding protein retains its ability to bind to a Merkel cell polyomavirus T antigen peptide:HLA complex with a $K_d$ less than or equal to about $10^{-8}$M.

In any of the aforementioned embodiments, the present disclosure provides a high affinity T cell receptor (TCR), comprising an α-chain and a β-chain, wherein the TCR binds to Merkel cell polyomavirus T antigen peptide:HLA-A*201 complex on a cell surface, optionally independent or in the absence of CD8. In certain embodiments, a $V_β$ chain comprises or is derived from a TRBV10-2, TRBV19, TRBV30, TRBV9, or TRBV28 gene. In further embodiments, a $V_α$ chain comprises or is derived from a TRAV12-1, TRAV38-1, TRAV34, TRAV16, or TRAV5 allele. In particular embodiments, a binding protein comprises (a) a $V_β$ chain comprised of or derived from a TRBV10-2 gene and a $V_α$ chain comprised of or derived from a TRAV12-1 gene; (b) a $V_β$ chain comprised of or derived from a TRBV10-2 gene and a $V_α$ chain comprised of or derived from a TRAV38-1 gene; (c) a $V_β$ chain comprised of or derived from a TRBV19 gene and a $V_α$ chain comprised of or derived from a TRAV12-1 gene; (d) a $V_β$ chain comprised of or derived from a TRBV19 gene and a $V_α$ chain comprised of or derived from a TRAV38-1 gene; (e) a $V_β$ chain comprised of or derived from a TRBV30 gene and a $V_α$ chain comprised of or derived from a TRAV38-1 or 34 gene; (f) a $V_β$ chain comprised of or derived from a TRBV28 gene and a $V_α$ chain comprised of or derived from a TRAV16 gene; or (g) a $V_β$ chain comprised of or derived from a TRBV9 gene and a $V_α$ chain comprised of or derived from a TRAV5 gene.

In certain embodiments, this disclosure provides a binding protein comprising administering to a subject having or at risk of having Merkel cell carcinoma a therapeutically effective amount of a host cell comprising a heterologous nucleic acid molecule encoding a binding protein comprising (a) a T cell receptor (TCR) α-chain variable ($V_α$) domain having a CDR3 amino acid sequence of any one of SEQ ID NOS:13 and 38-62, and a TCR β-chain variable ($V_β$) domain; or (b) a $V_α$ domain of (a) and a $V_β$ domain having a CDR3 amino acid sequence of any one of SEQ ID NOS:14 and 63-354. In further embodiments, this disclosure provides a binding protein comprising administering to a subject having or at risk of having Merkel cell carcinoma a therapeutically effective amount of a host cell comprising a heterologous nucleic acid molecule encoding a binding protein comprising (a) a T cell receptor (TCR) α-chain variable ($V_α$) domain having a CDR3 amino acid sequence of any one of SEQ ID NOS:13, 44 and 355-366, and a TCR β-chain variable ($V_β$) domain; or (b) a $V_α$ domain of (a) and a $V_β$ domain having a CDR3 amino acid sequence of any one of SEQ ID NOS:14, 69 and 365-374. In still further embodiments, the binding protein is capable of specifically binding to (a) a Merkel cell polyomavirus T antigen peptide:human leukocyte antigen (HLA) complex on a cell surface independent of CD8 or in the absence of CD8, (b) a KLLEIAPNC (SEQ ID NO:17):HLA complex or a KLLEIAPNA (SEQ ID NO:37):HLA complex with a $K_d$ less than or equal to about $10^{-8}$M, or both. In yet further embodiments, a binding protein comprises a $V_α$ domain that is at least about 90% identical to an amino acid sequence of SEQ ID NO:1, and comprises a $V_β$ domain that is at least about 90% identical to an amino acid sequence of SEQ ID NO:3, provided that (a) at least three or four of the CDRs have no change in sequence, wherein the CDRs that do have sequence changes have only up to two amino acid substitutions, up to a contiguous five amino acid deletion, or a combination thereof, and (b) the binding protein remains capable of specifically binding to a Merkel cell polyomavirus T antigen peptide:HLA cell surface complex independent, or in the absence of, CD8.

In certain embodiments, a $V_α$ domain comprises or consists of the amino acid sequence of SEQ ID NO:1, a $V_β$ domain comprises or consists of the amino acid sequence of SEQ ID NO:3, or a $V_α$ domain comprises or consists of the amino acid sequence of SEQ ID NO:1 and a $V_β$ domain comprises or consists of the amino acid sequence of SEQ ID NO:3. Such constructs may further comprise a constant domain, such as an α-chain constant domain having at least 90% sequence identity to, comprising or consisting of an amino acid sequence of SEQ ID NO:2, a β-chain constant domain having at least 90% sequence identity to, comprising, or consisting of an amino acid sequence of SEQ ID NO:4, or both.

In certain embodiments, any of the aforementioned Merkel cell polyomavirus T antigen specific binding proteins are each a T cell receptor (TCR), a chimeric antigen receptor or an antigen-binding fragment of a TCR, any of which can be chimeric, humanized or human. In further embodiments, an antigen-binding fragment of the TCR comprises a single chain TCR (scTCR) or a chimeric antigen receptor (CAR). In certain embodiments, a Merkel cell polyomavirus T antigen specific binding protein is a TCR.

In any of the aforementioned embodiments, the present disclosure provides a Merkel cell polyomavirus T antigen specific binding protein wherein a $V_α$ domain comprises or consists of an α-chain constant domain having an amino acid sequence as disclosed herein, a $V_β$ domain comprises or consists of a β-chain constant domain having an amino acid sequence as disclosed herein, or any combination thereof. In certain embodiments, there is provided a composition comprising a Merkel cell polyomavirus T antigen peptide-specific binding protein or high affinity TCR according to any one of the aforementioned embodiments and a pharmaceutically acceptable carrier, diluent, or excipient.

Methods useful for isolating and purifying genetically engineered soluble TCR, by way of example, may include obtaining supernatants from suitable host cell/vector systems that secrete the genetically engineered soluble TCR into culture media and then concentrating the media using a commercially available filter. Following concentration, the concentrate may be applied to a single suitable purification matrix or to a series of suitable matrices, such as an affinity matrix or an ion exchange resin. One or more reverse phase HPLC steps may be employed to further purify a recombinant polypeptide. These purification methods may also be employed when isolating an immunogen from its natural environment. Methods for large scale production of one or more of the isolated/genetically engineered soluble TCR described herein include batch cell culture, which is monitored and controlled to maintain appropriate culture conditions. Purification of the soluble TCR may be performed according to methods described herein and known in the art and that comport with laws and guidelines of domestic and foreign regulatory agencies.

In certain embodiments, nucleic acid molecules encoding an immunoglobulin superfamily binding protein or high affinity TCR specific for Merkel cell polyomavirus T antigen are used to transfect/transduce a host cell (e.g., T cells) for use in adoptive transfer therapy. Advances in TCR sequencing have been described (e.g., Robins et al., *Blood* 114:4099, 2009; Robins et al., *Sci. Translat. Med.* 2:47ra64, 2010; Robins et al., (September 10) *J. Imm. Meth. Epub ahead of print*, 2011; Warren et al., *Genome Res.* 21:790, 2011) and may be employed in the course of practicing the embodiments according to the present disclosure. Similarly, methods for transfecting/transducing T cells with desired nucleic acids have been described (e.g., U.S. Patent Application Pub. No. US 2004/0087025) as have adoptive transfer procedures using T cells of desired antigen-specificity (e.g., Schmitt et al., *Hum. Gen.* 20:1240, 2009; Dossett et al., *Mol. Ther.* 17:742, 2009; Till et al., *Blood* 112:2261, 2008; Wang et al., *Hum. Gene Ther.* 18:712, 2007; Kuball et al., *Blood* 109:2331, 2007; US 2011/0243972; US 2011/0189141; Leen et al., *Ann. Rev. Immunol.* 25:243, 2007), such that adaptation of these methodologies to the presently disclosed embodiments is contemplated, based on the teachings herein, including those directed to high affinity TCRs specific for Merkel cell polyomavirus T antigen peptides complexed with an HLA receptor.

Merkel cell polyomavirus T antigen-specific binding proteins or domains, as described herein, may be functionally characterized according to methodologies used for assaying T cell activity, including determination of T cell binding, activation or induction and also including determination of T cell responses that are antigen-specific. Examples include determination of T cell proliferation, T cell cytokine release, antigen-specific T cell stimulation, MHC restricted T cell stimulation, CTL activity (e.g., by detecting $^{51}$Cr release from pre-loaded target cells), changes in T cell phenotypic marker expression, and other measures of T-cell functions. Procedures for performing these and similar assays are may be found, for example, in Lefkovits (*Immunology Methods Manual: The Comprehensive Sourcebook of Techniques*, 1998). See, also, *Current Protocols in Immunology*; Weir, *Handbook of Experimental Immunology*, Blackwell Scientific, Boston, Mass. (1986); Mishell and Shigii (eds.) *Selected Methods in Cellular Immunology*, Freeman Publishing, San Francisco, Calif. (1979); Green and Reed, *Science* 281:1309 (1998) and references cited therein.

"MHC-peptide tetramer staining" refers to an assay used to detect antigen-specific T cells, which features a tetramer of MHC molecules, each comprising an identical peptide having an amino acid sequence that is cognate (e.g., identical or related to) at least one antigen (e.g., Merkel cell polyomavirus T antigen), wherein the complex is capable of binding T cell receptors specific for the cognate antigen. Each of the MHC molecules may be tagged with a biotin molecule. Biotinylated MHC/peptides are tetramerized by the addition of streptavidin, which can be fluorescently labeled. The tetramer may be detected by flow cytometry via the fluorescent label. In certain embodiments, an MHC-peptide tetramer assay is used to detect or select enhanced affinity TCRs of the instant disclosure.

Levels of cytokines may be determined according to methods described herein and practiced in the art, including for example, ELISA, ELISPOT, intracellular cytokine staining, and flow cytometry and combinations thereof (e.g., intracellular cytokine staining and flow cytometry). Immune cell proliferation and clonal expansion resulting from an antigen-specific elicitation or stimulation of an immune response may be determined by isolating lymphocytes, such as circulating lymphocytes in samples of peripheral blood cells or cells from lymph nodes, stimulating the cells with antigen, and measuring cytokine production, cell proliferation and/or cell viability, such as by incorporation of tritiated thymidine or non-radioactive assays, such as MTT assays and the like. The effect of an immunogen described herein on the balance between a Th1 immune response and a Th2 immune response may be examined, for example, by determining levels of Th1 cytokines, such as IFN-γ, IL-12, IL-2, and TNF-β, and Type 2 cytokines, such as IL-4, IL-5, IL-9, IL-10, and IL-13.

Polynucleotides Encoding Binding Proteins Specific for Merkel Cell Polyomavirus T Antigen Isolated or genetically engineered nucleic acid molecules encoding binding protein (e.g., immunoglobulin superfamily binding protein) or high affinity T cell receptor (TCR) specific for Merkel cell polyomavirus T antigen as described herein may be produced and prepared according to various methods and techniques of the molecular biology or polypeptide purification arts. Construction of an expression vector that is used for genetically engineering a binding protein or high affinity engineered TCR specific for a Merkel cell polyomavirus T antigen peptide of interest can be accomplished by using any suitable molecular biology engineering techniques known in the art, including the use of restriction endonuclease digestion, ligation, transformation, plasmid purification, and DNA sequencing as described in, for example, Sambrook et al. (1989 and 2001 editions; *Molecular Cloning: A Laboratory Manual*, Cold Spring Harbor Laboratory Press, NY) and Ausubel et al. (Current Protocols in Molecular Biology, 2003). To obtain efficient transcription and translation, a polynucleotide in each genetically engineered expression construct includes at least one appropriate expression control sequence (also called a regulatory sequence), such as a leader sequence and particularly a promoter operably (i.e., operatively) linked to the nucleotide sequence encoding the immunogen.

Certain embodiments relate to nucleic acids that encode the polypeptides contemplated herein, for instance, binding proteins or high affinity TCRs specific for Merkel cell polyomavirus T antigen. As one of skill in the art will recognize, a nucleic acid may refer to a single- or a double-stranded DNA, cDNA or RNA in any form, and may include a positive and a negative strand of the nucleic acid which complement each other, including anti-sense DNA, cDNA and RNA. Also included are siRNA, microRNA, RNA—DNA hybrids, ribozymes, and other various naturally occurring or synthetic forms of DNA or RNA.

In any of the aforementioned embodiments, a polynucleotide encoding a binding protein of the instant disclosure is codon optimized for efficient expression in a target host cell.

Techniques for recombinant (i.e., engineered) DNA, peptide and oligonucleotide synthesis, immunoassays, tissue culture, transformation (e.g., electroporation, lipofection), enzymatic reactions, purification and related techniques and procedures may be generally performed as described in various general and more specific references in microbiology, molecular biology, biochemistry, molecular genetics, cell biology, virology and immunology as cited and discussed throughout the present specification. See, e.g., Sambrook et al., *Molecular Cloning: A Laboratory Manual,* 3d ed., Cold Spring Harbor Laboratory Press, Cold Spring Harbor, N.Y.; *Current Protocols in Molecular Biology* (John Wiley and Sons, updated July 2008); *Short Protocols in Molecular Biology: A Compendium of Methods from Current Protocols in Molecular Biology,* Greene Pub. Associates and Wiley-Interscience; Glover, *DNA Cloning: A Practical Approach,* vol. I & II (IRL Press, Oxford Univ. Press USA, 1985); *Current Protocols in Immunology* (Edited by: John E. Coligan, Ada M. Kruisbeek, David H. Margulies, Ethan M. Shevach, Warren Strober 2001 John Wiley & Sons, NY, N.Y.); *Real-Time PCR: Current Technology and Applications,* Edited by Julie Logan, Kirstin Edwards and Nick Saunders, 2009, Caister Academic Press, Norfolk, UK; Anand, *Techniques for the Analysis of Complex Genomes,* (Academic Press, New York, 1992); Guthrie and Fink, *Guide to Yeast Genetics and Molecular Biology* (Academic Press, New York, 1991); *Oligonucleotide Synthesis* (N. Gait, Ed., 1984); *Nucleic Acid Hybridization* (B. Hames & S. Higgins, Eds., 1985); *Transcription and Translation* (B. Hames & S. Higgins, Eds., 1984); *Animal Cell Culture* (R. Freshney, Ed., 1986); Perbal, *A Practical Guide to Molecular Cloning* (1984); *Next-Generation Genome Sequencing* (Janitz, 2008 Wiley-VCH); *PCR Protocols (Methods in Molecular Biology)* (Park, Ed., 3rd Edition, 2010 Humana Press); *Immobilized Cells And Enzymes* (IRL Press, 1986); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); Harlow and Lane, *Antibodies,* (Cold Spring Harbor Laboratory Press, Cold Spring Harbor, N.Y., 1998); *Immunochemical Methods In Cell And Molecular Biology* (Mayer and Walker, eds., Academic Press, London, 1987); *Handbook Of Experimental Immunology,* Volumes I-IV (D. M. Weir and C C Blackwell, eds., 1986); Roitt, *Essential Immunology,* 6th Edition, (Blackwell Scientific Publications, Oxford, 1988); *Embryonic Stem Cells: Methods and Protocols* (Methods in Molecular Biology) (Kurstad Turksen, Ed., 2002); *Embryonic Stem Cell Protocols: Volume I: Isolation and Characterization* (Methods in Molecular Biology) (Kurstad Turksen, Ed., 2006); *Embryonic Stem Cell Protocols: Volume II: Differentiation Models* (Methods in Molecular Biology) (Kurstad Turksen, Ed., 2006); *Human Embryonic Stem Cell Protocols* (Methods in Molecular Biology) (Kursad Turksen Ed., 2006); *Mesenchymal Stem Cells: Methods and Protocols* (Methods in Molecular Biology) (Darwin J. Prockop, Donald G. Phinney, and Bruce A. Bunnell Eds., 2008); *Hematopoietic Stem Cell Protocols* (Methods in Molecular Medicine) (Christopher A. Klug, and Craig T. Jordan Eds., 2001); *Hematopoietic Stem Cell Protocols* (Methods in Molecular Biology) (Kevin D. Bunting Ed., 2008) *Neural Stem Cells: Methods and Protocols* (Methods in Molecular Biology) (Leslie P. Weiner Ed., 2008).

In certain embodiments, the instant disclosure provides a host cell comprising a polynucleotide encoding a $V_\alpha$ domain that is at least about 80% identical to the polynucleotide sequence of any one of SEQ ID NOS:5, 6, and 375-384, and a polynucleotide encoding a $V_\beta$ domain that is at least about 80% identical to the polynucleotide sequence of any one of SEQ ID NOS:9, 10, and 385-394. In further embodiments, a host cell comprising a polynucleotide encoding a $V_\alpha$ domain comprising or consisting of the polynucleotide sequence of any one of SEQ ID NOS:5, 6, and 375-384, a polynucleotide encoding a $V_\beta$ domain comprising or consisting of the polynucleotide sequence of any one of SEQ ID NOS:9, 10, and 385-394, or a combination thereof. In still further embodiments, a $V_\beta$ domain encoding polynucleotide comprises a nucleotide sequence encoding a β-chain constant domain that is at least about 80% identical to the polynucleotide sequence of any one of SEQ ID NOS:11, 12, 415 and 416, an α-chain constant domain that is at least about 80% identical to the polynucleotide sequence of SEQ ID NO:7 or 8, or combination thereof. In further embodiments, the polynucleotide encoding a TCR $V_\alpha$ domain comprises or consists of the polynucleotide of any one of SEQ ID NOS:6 and 395-404, the polynucleotide encoding a $V_\beta$ domain comprises or consists of the polynucleotide sequence of any one of SEQ ID NOS:10 and 405-414, the polynucleotide encoding an α-chain constant domain comprises or consists of the polynucleotide sequence of SEQ ID NO:8, and the polynucleotide encoding a β-chain constant domain comprises or consists of the polynucleotide sequence of any one of SEQ ID NOS:12, 415 and 416.

In any of the embodiments described herein, a binding protein-encoding polynucleotide can further comprise a polynucleotide that encodes a self-cleaving polypeptide, wherein the polynucleotide encoding the self-cleaving polypeptide is located between, for example, a polynucleotide encoding a $V_\alpha$ chain and a polynucleotide encoding a $V_\beta$ chain. When the binding protein encoding polynucleotides, and self-cleaving polypeptide are expressed by a host cell, the binding protein will be present on the host cell surface as separate molecules that can associate or form a complex (e.g., TCR). In certain embodiments, a self-cleaving polypeptide comprises a 2A peptide from porcine teschovirus-1 (P2A; SEQ ID NO:25, encoded by the polynucleotide of SEQ ID NO:18 or 19), *Thosea asigna* virus (T2A; SEQ ID NO:24, encoded by the polynucleotide of SEQ ID NO:20), equine rhinitis A virus (E2A; SEQ ID NO:23, encoded by the polynucleotide of SEQ ID NO:21), or foot-and-mouth disease virus (F2A; SEQ ID NO:26, encoded by the polynucleotide of SEQ ID NO:22). Further exemplary nucleic acid and amino acid sequences the 2A peptides are set forth in, for example, Kim et al. (*PLOS One* 6:e18556, 2011, which 2A nucleic acid and amino acid sequences are incorporated herein by reference in their entirety). In certain embodiments, a polynucleotide encoding a self-cleaving peptide is disposed between the TCR α-chain encoding polynucleotide and the TCR β-chain encoding polynucleotide.

Certain embodiments include nucleic acid molecules contained in a vector. One of skill in the art can readily ascertain suitable vectors for use with certain embodiments disclosed herein. An exemplary vector may comprise a nucleic acid molecule capable of transporting another nucleic acid molecule to which it has been linked, or which is capable of replication in a host organism. Some examples of vectors include plasmids, viral vectors, cosmids, and others. Some vectors may be capable of autonomous replication in a host cell into which they are introduced (e.g. bacterial vectors having a bacterial origin of replication and episomal mammalian vectors), whereas other vectors may be integrated into the genome of a host cell or promote integration of the polynucleotide insert upon introduction into the host cell and thereby replicate along with the host genome (e.g., lentiviral vector)). Additionally, some vectors are capable of directing the expression of genes to which they are operatively linked (these vectors may be referred to as "expression vectors"). According to related embodiments, it is further understood that, if one or more agents (e.g., polynucleotides encoding binding proteins or high affinity TCRs specific for Merkel cell polyomavirus T antigen, or variants thereof, as described herein) is co-administered to a subject, that each agent may reside in separate or the same vectors, and multiple vectors (each containing a different agent the same agent) may be introduced to a cell or cell population or administered to a subject.

In certain embodiments, nucleic acid molecules encoding binding proteins or high affinity TCRs specific for a Merkel cell polyomavirus T antigen epitope or peptide, may be operatively linked to certain elements of a vector. For example, polynucleotide sequences that are needed to effect the expression and processing of coding sequences to which they are ligated may be operatively linked. Expression control sequences may include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequences); sequences that enhance protein stability; and possibly sequences that enhance protein secretion. Expression control sequences may be operatively linked if they are contiguous with the gene of interest and expression control sequences that act in trans or at a distance to control the gene of interest. In certain embodiments, polynucleotides encoding binding proteins of the instant disclosure are contained in an expression vector that is a viral vector, such as a lentiviral vector or a γ-retroviral vector.

In particular embodiments, a genetically engineered expression vector is delivered into an appropriate cell, for example, a T cell or an antigen-presenting cell, i.e., a cell that displays a peptide/MHC complex on its cell surface (e.g., a dendritic cell) and lacks CD8. In certain embodiments, the host cell is a hematopoietic progenitor cell or a human immune system cell. For example, the immune system cell can be a CD4+ T cell, a CD8+ T cell, a CD4−CD8− double negative T cell, a γδ T cell, a natural killer cell, a dendritic cell, or any combination thereof. In certain embodiments, wherein a T cell is the host, the T cell can be naïve, a central memory T cell, an effector memory T cell, or any combination thereof. A genetically engineered expression vector of this disclosure may also include, for example, lymphoid tissue-specific transcriptional regulatory elements (TREs), such as a B lymphocyte, T lymphocyte, or dendritic cell specific TREs. Lymphoid tissue specific TREs are known in the art (see, e.g., Thompson et al., *Mol. Cell. Biol.* 12:1043, 1992); Todd et al., *J. Exp. Med.* 177:1663, 1993); Penix et al., *J. Exp. Med.* 178:1483, 1993).

In certain embodiments, a host cell may optionally already possess or be modified to include other genetic modifications that confer desired properties related or unrelated to biosynthesis of the heterologous or exogenous protein (e.g., inclusion of a detectable marker; deleted, altered or truncated endogenous TCR; increased co-stimulatory factor expression). For example, in any of the embodiments provided herein, a host cell can be a "universal donor" cell that is modified to reduce or eliminate expression of one or more endogenous genes involved in an immune response. For example, a T cell may be modified to reduce or eliminate expression of one or more polypeptides selected from PD-1, LAG-3, CTLA4, TIGIT, TIM3, an HLA complex component, or a TCR or TCR complex component.

Without wishing to be bound by theory, certain endogenously expressed immune cell proteins may be recognized as foreign by an allogeneic host that receives the modified immune cells, which may result in elimination of the modified immune cells (e.g., an HLA allele), or may downregulate the immune activity of the modified immune cells (e.g., PD-1, LAG-3, CTLA4, TIGIT), or may interfere with the binding activity of a heterologously expressed binding protein of the present disclosure (e.g., an endogenous TCR that binds to a non-tumor-associated antigen and interferes with the antigen-specific receptor of the modified immune cell specifically binding to a tumor-associated antigen). Accordingly, decreasing or eliminating expression or activity of such endogenous genes or proteins can improve the activity, tolerance, and persistence of the modified immune cells in an allogeneic host setting, and can allow universal administration of the cells (e.g., to any recipient regardless of HLA type).

In certain embodiments, a host cell (e.g., modified immune cell) of this disclosure comprises a chromosomal gene knockout of one or more genes encoding a PD-1, LAG-3, CTLA4, TIM3, TIGIT, an HLA complex component (e.g., a gene that encodes an α1 macroglobulin, an α2 macroglobulin, an α3 macroglobulin, a β1 microglobulin, or a β2 microglobulin), a TCR component (e.g., a gene that encodes a TCR variable region or a TCR constant region) (see, e.g., Torikai et al., *Nature Sci. Rep.* 6:21757 (2016); Torikai et al., *Blood* 119(24):5697 (2012); and Torikai et al., *Blood* 122(8):1341 (2013); the gene editing techniques, compositions, and adoptive cell therapies of which are incorporated herein by reference in their entirety). For example, in some embodiments, a chromosomal gene knockout is produced using a CRISPR/Cas9 system, and may involve transfection of the modified immune cell with a lentivirus (e.g., pLentiCRISPRv2; Torikai et al., *Blood* (2016)) expressing a CRISPR/Cas9 system targeting PD-1, LAG-3, CTLA4, an HLA component, or a TCR component, or any combination thereof. Primers useful for designing a lentivirus that expresses a CRISPR/Cas9 system for inhibiting an endogenously expressed immune cell protein include for example, primer pairs comprising forward and reverse primers having the nucleotide sequences set forth in SEQ ID NOS:29 and 30, 31 and 32, 33 and 34, and 35 and 36. In other embodiments, a chromosomal gene knockout is generated using a homing endonuclease that have been modified with the modular DNA binding domains of TALENs to make a fusion protein known as megaTALs. MegaTALS can be utilized not only to knock-out genes but also to introduce (knock-in) heterologous or exogenous polynucleotides when used in combination with an exogenous donor template encoding a polynucleotide of interest, such as a TCRα chain, TCRβ chain or both, wherein the TCR produced by the cell is specific for a Merkel cell polyomavirus T antigen peptide.

In certain embodiments, a host cell is a human hematopoietic progenitor cell transduced with a heterologous or exogenous nucleic acid molecule encoding a TCRα chain, TCRβ chain or both, wherein the TCR produced by the cell is specific for a Merkel cell polyomavirus T antigen peptide.

In any of the embodiments described herein, a host cell may comprise a polynucleotide, which may optionally be delivered by a vector or carried on a vector, that encodes a polynucleotide construct as set forth in any one or more of the polynucleotides of SEQ ID NOS:417-426.

In addition to vectors, certain embodiments relate to host cells that comprise the vectors that are presently disclosed. One of skill in the art readily understands that many suitable host cells are available in the art. A host cell may include any individual cell or cell culture which may receive a vector or the incorporation of nucleic acids and/or proteins, as well as any progeny cells. The term also encompasses progeny of the host cell, whether genetically or phenotypically the same or different. Suitable host cells may depend on the vector and may include mammalian cells, animal cells, human cells, simian cells, insect cells, yeast cells, and bacterial cells. These cells may be induced to incorporate the vector or other material by use of a viral vector, transformation via calcium phosphate precipitation, DEAE-dextran, electroporation, microinjection, or other methods. See, for example, Sambrook et al., *Molecular Cloning: A Laboratory Manual* 2d ed. (Cold Spring Harbor Laboratory, 1989).

Methods of Treatment

In certain aspects, the instant disclosure is directed to methods for treating a hyperproliferative disorder or a condition characterized by Merkel cell polyomavirus T antigen expression by administering to a human subject in need thereof a composition comprising a binding protein or high affinity TCR specific for Merkel cell polyomavirus T antigen according to any the aforementioned binding proteins or TCRs.

The presence of a hyperproliferative disorder or malignant condition in a subject refers to the presence of dysplastic, cancerous and/or transformed cells in the subject, including, for example neoplastic, tumor, non-contact inhibited or oncogenically transformed cells, or the like (e.g., Merkel cell carcinoma). In certain embodiments, there are provided methods for treating a Merkel cell carcinoma.

As understood by a person skilled in the medical art, the terms, "treat" and "treatment," refer to medical management of a disease, disorder, or condition of a subject (i.e., patient, host, who may be a human or non-human animal) (see, e.g., Stedman's Medical Dictionary). In general, an appropriate dose and treatment regimen provide one or more of a binding protein or high affinity TCR specific for a Merkel cell polyomavirus T antigen epitope or peptide, or a host cell expressing such a binding protein or high affinity TCR, and optionally in combination with an adjunctive therapy (e.g., a cytokine such as IL-2, IL-15, IL-21, or any combination thereof; chemotherapy such as interferon-beta (IFN-β), radiation therapy such as localized radiation therapy), in an amount sufficient to provide therapeutic or prophylactic benefit. Therapeutic or prophylactic benefit resulting from therapeutic treatment or prophylactic or preventative methods include, for example an improved clinical outcome, wherein the object is to prevent or retard or otherwise reduce (e.g., decrease in a statistically significant manner relative to an untreated control) an undesired physiological change or disorder, or to prevent, retard or otherwise reduce the expansion or severity of such a disease or disorder. Beneficial or desired clinical results from treating a subject include abatement, lessening, or alleviation of symptoms that result from or are associated the disease or disorder to be treated; decreased occurrence of symptoms; improved quality of life; longer disease-free status (i.e., decreasing the likelihood or the propensity that a subject will present symptoms on the basis of which a diagnosis of a disease is made); diminishment of extent of disease; stabilized (i.e., not worsening) state of disease; delay or slowing of disease progression; amelioration or palliation of the disease state; and remission (whether partial or total), whether detectable or undetectable; or overall survival.

"Treatment" can also mean prolonging survival when compared to expected survival if a subject were not receiving treatment. Subjects in need of the methods and compositions described herein include those who already have the disease or disorder, as well as subjects prone to have or at risk of developing the disease or disorder. Subjects in need of prophylactic treatment include subjects in whom the disease, condition, or disorder is to be prevented (i.e., decreasing the likelihood of occurrence or recurrence of the disease or disorder). The clinical benefit provided by the compositions (and preparations comprising the compositions) and methods described herein can be evaluated by design and execution of in vitro assays, preclinical studies, and clinical studies in subjects to whom administration of the compositions is intended to benefit, as described in the examples.

Cells expressing a binding protein or high affinity TCR specific for a Merkel cell polyomavirus T antigen epitope or peptide as described herein may be administered to a subject in a pharmaceutically or physiologically acceptable or suitable excipient or carrier. Pharmaceutically acceptable excipients are biologically compatible vehicles, e.g., physiological saline, which are described in greater detail herein, that are suitable for administration to a human or other non-human mammalian subject.

A therapeutically effective dose is an amount of host cells (expressing a binding protein or high affinity TCR specific for a Merkel cell polyomavirus T antigen epitope or peptide) used in adoptive transfer that is capable of producing a clinically desirable result (i.e., a sufficient amount to induce or enhance a specific T cell immune response against cells expressing a Merkel cell polyomavirus T antigen (e.g., a cytotoxic T cell (CTL) response in vivo or cell lysis in vitro in the presence of the specific Merkel cell polyomavirus T antigen epitope or peptide) in a statistically significant manner) in a treated human or non-human mammal. As is well known in the medical arts, the dosage for any one patient depends upon many factors, including the patient's size, weight, body surface area, age, the particular therapy to be administered, sex, time and route of administration, general health, and other drugs being administered concurrently. Doses will vary, but a preferred dose for administration of a host cell comprising a recombinant expression vector as described herein is about $10^7$ cells/m$^2$, about $5 \times 10^7$ cells/m$^2$, about $10^8$ cells/m$^2$, about $5 \times 10^8$ cells/m$^2$, about $10^9$ cells/m$^2$, about $5 \times 10^9$ cells/m$^2$, about $10^{10}$ cells/m$^2$, about $5 \times 10^{10}$ cells/m$^2$, or about $10^{11}$ cells/m$^2$.

Pharmaceutical compositions may be administered in a manner appropriate to the disease or condition to be treated (or prevented) as determined by persons skilled in the medical art. An appropriate dose and a suitable duration and frequency of administration of the compositions will be determined by such factors as the health condition of the patient, size of the patient (i.e., weight, mass, or body area), the type and severity of the patient's disease, the particular form of the active ingredient, and the method of administration. In general, an appropriate dose and treatment regimen provide the composition(s) in an amount sufficient to provide therapeutic and/or prophylactic benefit (such as described herein, including an improved clinical outcome, such as more frequent complete or partial remissions, or longer disease-free and/or overall survival, or a lessening of symptom severity). For prophylactic use, a dose should be sufficient to prevent, delay the onset of, or diminish the severity of a disease associated with disease or disorder. Prophylactic benefit of the immunogenic compositions administered according to the methods described herein can be determined by performing pre-clinical (including in vitro and in vivo animal studies) and clinical studies and analyzing data obtained therefrom by appropriate statistical, biological, and clinical methods and techniques, all of which can readily be practiced by a person skilled in the art.

A condition associated with Merkel cell polyomavirus T antigen expression includes any disorder or condition in which cellular or molecular events lead to hyperproliferative disorder, such as Merkel cell carcinoma (MCC). A subject having such a disorder or condition would benefit from treatment with a composition or method of the presently described embodiments. Some conditions associated with Merkel cell polyomavirus T antigen expression may include acute as well as chronic or recurrent disorders and diseases, such as those pathological conditions that predispose a subject to MCC.

Certain methods of treatment or prevention contemplated herein include administering a host cell (which may be autologous, allogeneic or syngeneic) comprising a desired nucleic acid molecule as described herein that is stably integrated into the chromosome of the cell. For example, such a cellular composition may be generated ex vivo using autologous, allogeneic or syngeneic immune system cells (e.g., T cells, antigen-presenting cells, natural killer cells) in order to administer a Merkel cell polyomavirus T antigen-targeted T-cell composition to a subject as an adoptive immunotherapy.

As used herein, administration of a composition or therapy or combination therapies thereof refers to delivering the same to a subject, regardless of the route or mode of delivery. Administration may be effected continuously or intermittently, and parenterally. Administration may be for treating a subject already confirmed as having a recognized condition, disease or disease state, or for treating a subject susceptible to or at risk of developing such a condition, disease or disease state. Co-administration with an adjunctive therapy may include simultaneous and/or sequential delivery of multiple agents in any order and on any dosing schedule (e.g., Merkel cell polyomavirus T antigen specific recombinant (i.e., engineered) host cells with one or more cytokines, such as IL-2; immunosuppressive therapy such as a chemotherapy (e.g., IFN-β, etoposide, carboplatin), radiation therapy (e.g., localized), surgical excision, Mohs micrographic surgery, immune modulators (e.g., immune modulators, such as immune checkpoint inhibitors, including antibodies specific for PD-1, PD-L1, CTLA-4), or any combination thereof), or a treatment that upregulates MHC Class I, such as localized radiation (e.g., single fraction irradiation is well accepted as a treatment for metastatic MCC palliation or single fraction radiation therapy targeting 8Gy is used on a single MCC lesion; see, e.g., Iyer et al., Cancer Med. 4:1161, 2015), one or more Th1-type cytokines (e.g., IFN-β, IFN-γr any combination thereof.

In still further embodiments, the subject being treated may further receive other immunosuppressive therapy, such as calcineurin inhibitors, corticosteroids, microtubule inhibitors, low dose of a mycophenolic acid prodrug, or any combination thereof. In yet further embodiments, a subject being treated has received a non-myeloablative or a myeloablative cellular immunotherapy transplant, wherein the treatment may be administered at least two to at least three months after the non-myeloablative or myeloablative cell transplant.

In certain embodiments, a plurality of doses of a genetically engineered host cell as described herein is administered to the subject, which may be administered at intervals between administrations of about two to about four weeks. In further embodiments, a cytokine is administered sequentially, provided that the subject was administered the genetically engineered host cell at least three or four times before cytokine administration. In certain embodiments, the cytokine is administered subcutaneously (e.g., IL-2, IL-15, IL-21). In still further embodiments, the subject being treated is further receiving immunosuppressive therapy, such as calcineurin inhibitors, corticosteroids, microtubule inhibitors, low dose of a mycophenolic acid prodrug, or any combination thereof. In yet further embodiments, the subject being treated has received a non-myeloablative or a myeloablative hematopoietic cell transplant, wherein the treatment may be administered at least two to at least three months after the non-myeloablative hematopoietic cell transplant.

In some embodiments, compositions and host cells as described herein are administered with chemotherapeutic agents or immune modulators (e.g., immunosuppressants, or inhibitors of immunosuppression components, such as immune checkpoint inhibitors). Immune checkpoint inhibitors include inhibitors of CTLA-4, A2AR, B7-H3, B7-H4, BTLA, HVEM, GALS, IDO, KIR, LAG-3, PD-1, PD-L1, PD-L2, Tim-3, VISTA, TIGIT, LAIR1, CD160, 2B4, TGFR beta, CEACAM-1, CEACAM-3, CEACAM-5, CD244, or any combination thereof. An inhibitor of an immune checkpoint molecule can be an antibody or antigen binding fragment thereof, a fusion protein, a small molecule, an RNAi molecule, (e.g., siRNA, shRNA, or miRNA), a ribozyme, an aptamer, or an antisense oligonucleotide. A chemotherapeutic can be a B-Raf inhibitor, a MEK inhibitor, a VEGF inhibitor, a VEGFR inhibitor, a tyrosine kinase inhibitor, an anti-mitotic agent, or any combination thereof.

In any of the embodiments herein, a method of treating a subject having or at risk of having Merkel cell carcinoma, comprising administering to human subject having or at risk of having Merkel cell carcinoma a composition comprising a binding protein specific for a Merkel cell polyomavirus T antigen peptide as disclosed herein, and a therapeutically effective amount of an inhibitor of an immunosuppression component, such as an immune checkpoint inhibitor. In some embodiments, an immune checkpoint inhibitor is an inhibitor of CTLA-4, A2AR, B7-H3, B7-H4, BTLA, HVEM, GALS, IDO, KIR, LAG-3, PD-1, PD-L1, PD-L2, Tim-3, VISTA, TIGIT, LAIR1, CD160, 2B4, TGFR beta, CEACAM-1, CEACAM-3, CEACAM-5, CD244, or any combination thereof. In further embodiments, the instant disclosure provides a method of treating a subject having or at risk of having Merkel cell carcinoma, comprising administering to human subject having or at risk of having Merkel cell carcinoma a composition comprising (a) a binding protein specific for a Merkel cell polyomavirus T antigen peptide as disclosed herein, (b) a therapeutically effective amount of an inhibitor of an immunosuppression component, such as an immune checkpoint inhibitor, and (c) an upregulator of MHC Class I molecules, such as localized radiation (e.g., single fraction irradiation), IFN-β, IFN-γ, or a combination thereof.

Accordingly, in certain embodiments, this disclosure provides methods of treating a subject having or at risk of having Merkel cell carcinoma, comprising administering to a subject having or at risk of having Merkel cell carcinoma a therapeutically effective amount of a host cell comprising a heterologous nucleic acid molecule encoding a binding protein comprising (a) a T cell receptor (TCR) α-chain variable ($V_\alpha$) domain having a CDR3 amino acid sequence of any one of SEQ ID NOS:13, 44 and 355-366, and a TCR β-chain variable ($V_\beta$) domain; or (b) a $V_\alpha$ domain of (a) and a $V_\beta$ domain having a CDR3 amino acid sequence of any one of SEQ ID NOS:14, 69 and 365-374; and a therapeutically effective amount of an inhibitor of an immunosuppression component, such as an immune checkpoint inhibitor. In some embodiments, an immune checkpoint inhibitor is an inhibitor of CTLA-4, A2AR, B7-H3, B7-H4, BTLA, HVEM, GAL9, IDO, KIR, LAG-3, PD-1, PD-L1, PD-L2, Tim-3, VISTA, TIGIT, LAIR1, CD160, 2B4, TGFR beta, CEACAM-1, CEACAM-3, CEACAM-5, CD244, or any combination thereof. In some embodiments, an immune checkpoint inhibitor is selected from (a) an antibody specific for PD-1, such as pidilizumab, lambrolizumab, nivolumab, or pembrolizumab; (b) an antibody specific for PD-L1, such as avelumab, BMS-936559 (also known as MDX-1105), durvalumab, or atezolizumab; or (c) an antibody specific for CTLA4, such as tremelimumab or ipilimumab. In any of these methods, the treatment may further comprise an upregulator of MHC Class I molecules, such as localized radiation (e.g., single fraction irradiation), IFN-β, IFN-γ, or a combination thereof.

In further embodiments, this disclosure provides methods of treating a subject having or at risk of having Merkel cell carcinoma, comprising administering to a subject having or at risk of having Merkel cell carcinoma a therapeutically effective amount of a host cell comprising a heterologous nucleic acid molecule encoding a binding protein comprises a $V_\alpha$ domain that is at least about 90% identical to an amino acid sequence of SEQ ID NO:1, and comprises a $V_\beta$ domain that is at least about 90% identical to an amino acid sequence of SEQ ID NO:3, provided that (a) at least three or four of the CDRs have no change in sequence, wherein the CDRs that do have sequence changes have only up to two amino acid substitutions, up to a contiguous five amino acid deletion, or a combination thereof, and (b) the binding protein remains capable of specifically binding to a Merkel cell polyomavirus T antigen peptide:HLA cell surface complex, optionally independent, or in the absence, of CD8; and a therapeutically effective amount of an inhibitor of an immunosuppression component, such as an immune checkpoint inhibitor. In some embodiments, an immune checkpoint inhibitor is an inhibitor of CTLA-4, A2AR, B7-H3, B7-H4, BTLA, HVEM, GAL9, IDO, KIR, LAG-3, PD-1, PD-L1, PD-L2, Tim-3, VISTA, TIGIT, LAIR1, CD160, 2B4, TGFR beta, CEACAM-1, CEACAM-3, CEACAM-5, CD244, or any combination thereof. In some embodiments, an immune checkpoint inhibitor is selected from (a) an antibody specific for PD-1, such as pidilizumab, lambrolizumab, nivolumab, or pembrolizumab; (b) an antibody specific for PD-L1, such as BMS-936559 (also known as MDX-1105), durvalumab, atezolizumab, or avelumab; or (c) an antibody specific for CTLA4, such as tremelimumab or ipilimumab.

Exemplary chemotherapeutic agents include alkylating agents (e.g., cisplatin, oxaliplatin, carboplatin, busulfan, nitrosoureas, nitrogen mustards such as bendamustine, uramustine, temozolomide), antimetabolites (e.g., aminopterin, methotrexate, mercaptopurine, fluorouracil, cytarabine, gemcitabine), taxanes (e.g., paclitaxel, nab-paclitaxel, docetaxel), anthracyclines (e.g., doxorubicin, daunorubicin, epirubicin, idaruicin, mitoxantrone, valrubicin), bleomycin, mytomycin, actinomycin, hydroxyurea, topoisomerase inhibitors (e.g., camptothecin, topotecan, irinotecan, etoposide, teniposide), monoclonal antibodies (e.g., ipilimumab, pembrolizumab, nivolumab, avelumab, alemtuzumab, bevacizumab, cetuximab, gemtuzumab, panitumumab, rituximab, tositumomab, trastuzumab), vinca alkaloids (e.g., vincristine, vinblastine, vindesine, vinorelbine), cyclophosphamide, prednisone, leucovorin, oxaliplatin, hyalurodinases, or any combination thereof. In certain embodiments, a chemotherapeutic is vemurafenib, dabrafenib, trametinib, cobimetinib, sunitinib, erlotinib, paclitaxel, docetaxel, or any combination thereof. In some embodiments, a patient is first treated with a chemotherapeutic agent that inhibits or destroys other immune cells followed by a pharmaceutical composition described herein. In some cases, chemotherapy may be avoided entirely.

An effective amount of a therapeutic or pharmaceutical composition refers to an amount sufficient, at dosages and for periods of time needed, to achieve the desired clinical results or beneficial treatment, as described herein. An effective amount may be delivered in one or more administrations. If the administration is to a subject already known or confirmed to have a disease or disease-state, the term "therapeutic amount" may be used in reference to treatment, whereas "prophylactically effective amount" may be used to describe administrating an effective amount to a subject that is susceptible or at risk of developing a disease or disease-state (e.g., recurrence) as a preventative course.

The level of a CTL immune response may be determined by any one of numerous immunological methods described herein and routinely practiced in the art. The level of a CTL immune response may be determined prior to and following administration of any one of the herein described Merkel cell polyomavirus T antigen-specific binding proteins expressed by, for example, a T cell. Cytotoxicity assays for determining CTL activity may be performed using any one of several techniques and methods routinely practiced in the art (see, e.g., Henkart et al., "Cytotoxic T-Lymphocytes" in *Fundamental Immunology*, Paul (ed.) (2003 Lippincott Williams & Wilkins, Philadelphia, Pa.), pages 1127-50, and references cited therein).

Antigen-specific T cell responses are typically determined by comparisons of observed T cell responses according to any of the herein described T cell functional parameters (e.g., proliferation, cytokine release, CTL activity, altered cell surface marker phenotype, etc.) that may be made between T cells that are exposed to a cognate antigen in an appropriate context (e.g., the antigen used to prime or activate the T cells, when presented by immunocompatible antigen-presenting cells) and T cells from the same source population that are exposed instead to a structurally distinct or irrelevant control antigen. A response to the cognate antigen that is greater, with statistical significance, than the response to the control antigen signifies antigen-specificity.

A biological sample may be obtained from a subject for determining the presence and level of an immune response to a Merkel cell polyomavirus T antigen-derived peptide as described herein. A "biological sample" as used herein may be a blood sample (from which serum or plasma may be prepared), biopsy specimen, body fluids (e.g., lung lavage, ascites, mucosal washings, synovial fluid), bone marrow, lymph nodes, tissue explant, organ culture, or any other tissue or cell preparation from the subject or a biological source. Biological samples may also be obtained from the subject prior to receiving any immunogenic composition, which biological sample is useful as a control for establishing baseline (i.e., pre-immunization) data.

The pharmaceutical compositions described herein may be presented in unit-dose or multi-dose containers, such as sealed ampoules or vials. Such containers may be frozen to preserve the stability of the formulation until. In certain embodiments, a unit dose comprises a genetically engineered host cell as described herein at a dose of about $10^7$ cells/m$^2$ to about $10^{11}$ cells/m$^2$. The development of suitable dosing and treatment regimens for using the particular compositions described herein in a variety of treatment regimens, including e.g., parenteral or intravenous administration or formulation.

If the subject composition is administered parenterally, the composition may also include sterile aqueous or oleaginous solution or suspension. Suitable non-toxic parenterally acceptable diluents or solvents include water, Ringer's solution, isotonic salt solution, 1,3-butanediol, ethanol, propylene glycol or polythethylene glycols in mixtures with water. Aqueous solutions or suspensions may further comprise one or more buffering agents, such as sodium acetate, sodium citrate, sodium borate or sodium tartrate. Of course, any material used in preparing any dosage unit formulation should be pharmaceutically pure and substantially non-toxic in the amounts employed. In addition, the active compounds may be incorporated into sustained-release preparation and formulations. Dosage unit form, as used herein, refers to physically discrete units suited as unitary dosages for the subject to be treated; each unit may contain a predetermined quantity of genetically engineered cells or active compound calculated to produce the desired therapeutic effect in association with an appropriate pharmaceutical carrier.

In general, an appropriate dosage and treatment regimen provides the active molecules or cells in an amount sufficient to provide therapeutic or prophylactic benefit. Such a response can be monitored by establishing an improved clinical outcome (e.g., more frequent remissions, complete or partial, or longer disease-free survival) in treated subjects as compared to non-treated subjects. Increases in preexisting immune responses to a tumor protein generally correlate with an improved clinical outcome. Such immune responses may generally be evaluated using standard proliferation, cytotoxicity or cytokine assays, which are routine in the art and may be performed using samples obtained from a subject before and after treatment.

EXAMPLES

Example 1

Materials and Methods

Human subjects and samples: This study was approved by the Fred Hutchinson Cancer Research Center (FHCRC) Institutional Review Board and conducted according to Declaration of Helsinki principles. Informed consent was received from all participants. Subjects were HLA class I typed via polymerase chain reaction (PCR) at Bloodworks Northwest (Seattle, Wash.). All samples were clinically annotated with long-term patient follow-up data. PBMC: Heparinized blood was obtained from MCC patients and peripheral blood mononuclear cells (PBMCs) were cryopreserved after routine Ficoll preparation at a dedicated specimen processing facility at FHCRC. Patient Tumors: When available, fresh MCC tumor material from core and/or punch biopsy samples were processed and TIL cultured for two weeks before analysis as described in Iyer et al., 2011. For excised tumors of larger volume (>1 cm$^3$), the remaining tissue was digested as described in Afanasiev et al., 2013, and single cell suspensions were cryopreserved.

T cell receptor β sequencing and analysis: Tetramer+ Cells: At least 2 million PBMC or TIL were stained with anti-CD8-PE antibody (Clone 3B5, Life Technologies), A*02/KLL-APC tetramer (Immune Monitoring Lab, FHCRC) and 7-AAD viability dye (BioLegend). Tetramer+, CD8$^{high}$ cells were sorted via FACSAriaII (BD) and flash frozen (average of 710 cells from PBMC (n=9), 5776 cells from TIL (n=5), range 350-8,000 and 1844-12799, respectively). Samples were submitted to Adaptive Biotechnologies (Seattle, Wash.) for genomic DNA extraction, TRB sequencing and normalization. All TRB sequences detected in ≥2 cells (estimated number of genomes ≥2) were categorized as tetramer+ clonotypes. Whole tumor sequencing: Primary tumors were used for analysis, except when patients presented with unknown primaries and nodal disease (n=2), primaries with limited material but abundant nodal disease available for analysis (n=1) or metastatic disease (n=1). Tumor samples consisted of molecular curls of 25 microns from formalin-fixed, paraffin embedded (FFPE) tissue blocks (n=10), nodal tumor digest frozen ex vivo (n=1) or flash frozen core biopsy of a metastatic lesion (n=1). Samples were submitted to Adaptive Biotechnologies as described above. Tetramer+ cell infiltration: KLL-specific clonotypes within tumors (n=12 tumors) were identified based on TCRβ CDR3 amino acid sequences from the tetramer-sorted samples. The frequency of all KLL-specific T cells within each tumor is reported as the cumulative percentage of productive sequencing reads of clonotypes detected in both the tetramer-sorted sample and the tumor.

Survival and recurrence analysis: Statistical analyses were performed on Stata software version 14.0 for Macintosh (StataCorp, College Station, Tex.) and Prism 6 for Mac OS X (Graph Pad Software, Inc). MCC-specific survival is defined as the interval from the diagnostic biopsy date to death by MCC. Recurrence-free survival was defined as the interval from the diagnostic biopsy date to the date of MCC recurrence, last follow up or death by MCC. Log-rank analysis was performed and a p-value of 0.05 was considered statistically significant. Kaplan-Meier survival curves were created to visualize MCC-specific survival and recurrence-free survival data; groupings of patients were based on percentage of tetramer+ T cells in the tumor (Higher=1.9-18%, n=9 versus Lower=0-0.14%, n=2) as well as number of T cell clonotypes (Many=5-108, n=7; versus Few=0-3, n=4) were selected a priori. Patients who were alive at the last time of follow-up were censored on their last day of follow-up and patients who died of unknown causes were censored on their day of death.

Creation of KLL-specific T cell clones: PBMC or lymphocytes from a tumor digest were stained and sorted as described above into T cell medium (TCM) containing RPMI, 8% human serum, 200 nM L-glutamine and 100 U/ml Penicillin-Streptomycin, and cloned at 0.25 to 3 cells per well with allogeneic irradiated feeders, IL-2 (Hemagen Diagnostics) and PHA (Remel) as described[29] with addition of 20 ng/mL rIL-15 (R&D Systems) after day 2. After 2 weeks, microcultures with visible growth were screened for specificity via tetramer; TCR variable beta chain (TCRVβ) expression was assessed by staining clones with fluorescent anti-TCRVβ antibodies (IOTest Beta Mark, Beckman Coulter). Wells selected for screening, expansion, and TCR analysis came from plates with <37% of cultures having visual growth, yielding a 95% chance of clonality per the Poisson distribution (Chen et al., *J. Immunol. Methods* 52:307, 1982). Cultures with tetramer+ cells, reactivity to peptide and dissimilar TCRVβ chains were further expanded with IL-2 and anti-CD3 clone OKT3 mAb (Miltenyi Biotec) as described in Iyer et al., 2011, plus 20 ng/mL rIL-15. Prior to harvesting RNA for TCR analysis, cultures were held at least 2 weeks to minimize persistent feeder cell-derived RNA. CD8-independent Tetramer Staining: Clones were stained with a HLA-A*02:01/KLL tetramer containing D227K/T228A mutations in HLA-A*02:01, using methods as above. These mutations abrogate HLA class I:CD8 binding to identify clones expressing TCRs with the ability to bind independent of CD8 stabilization and can indicate high TCR avidity (Choi et al., *J. Immunol.* 171:5116, 2003; Laugel et al., *J. Biol. Chem.* 282:23799, 2007).

TCR α & β sequencing of clones: Simultaneous sequencing of TCRα and TCRβ repertoires was performed as described in Han et al., *Nat. Biotechnol.* 32:684, 2014. Briefly, total RNA was isolated from clonally expanded populations using Qiagen RNeasy Plus, followed by One Step RT/PCR (Qiagen) primed with multiplexed TCR primers. This reaction was used as template with a second set of nested TCRα and TCRβ primers, followed by PCR to add barcoding and paired end primers. Templates were purified using AMPure (Agencourt Biosciences) then normalized prior to running on Illumina MiSeq v2-300. Pairs of 150 nucleotide sequences were merged into contigs using PandaSeq (Masella et al., *BMC Bioinformatics* 13:31, 2012). Merged sequences were then separated according to inline barcodes identifying the plate and well of origin, generating one file of derived sequences for each clone of interest. Files for each clone were processed with MiXCR (Bolotin et al., *Nat. Methods* 12:380, 2015) to identify and quantify clonotypes and assign VDJ allele usage. Cultures in which the dominant TCRβ nucleotide sequence was present at <97% of productive sequence reads were classified as possibly polyclonal and excluded from further analysis.

T cell functional assays: T cell clones were tested for specificity and functional avidity via cytokine release assays. Cytokine Release with Peptide-pulsed Targets: Secreted IFN-γ was measured after co-incubating $2\times10^4$ clonal KLL-specific T cells with $5\times10^4$ T2 cells (ATCC) plus antigenic peptide at $\log_{10}$ dilutions to final concentration from $10^{-6}$ to $10^{-12}$ molar in 200 µl TCM for 36 hours. Due to possible oxidation and dimerization of cysteine residues in the antigenic KLLEIAPNC (SEQ ID NO:17) peptide, the homolog KLLEIAPNA (SEQ ID NO:37) was used to allow for efficient HLA class I presentation; similar substitution has been shown to not alter recognition of HLA-peptide complex by TCRs raised against the native peptide (Webb et al., *J. Biol. Chem.* 279:23438, 2004). IFN-γ in cell culture supernatants was assayed by ELISA according to manufacturer's recommendations (Human IFN gamma ELISA Ready-SET-Go Kit, affymetrix). To estimate $EC_{50}$ (the amount of peptide leading to 50% of maximum IFN-γ secretion), IFN-γ secretion by each T cell clone was analyzed via nonlinear regression using Prism version 6.0 (GraphPad). In addition, IFN-γ release by KLL-specific clonotypes was measured after incubation with three MCPyV+, HLA-A*02+ MCC cell lines (WaGa and MKL-2 [gift of Dr. Becker, German Cancer Research Center], and MS-1 [gift of Dr. Shuda, University of Pittsburg]. Cell lines were early passage and authenticated with short tandem repeat analysis). Cell lines were stimulated with IFN-β (Betaseron, BayerHealthCare; 3,000 U/mL) for 24 hours to induce expression of HLA class I, followed by 24 hours of culture after IFN-β washout. A total of $2\times10^4$ clonal KLL-specific T cells were incubated with $5\times10^4$ cells from each MCC cell line, +/−IFN-β treatment, and incubated for 36 hours. Supernatants were assayed by ELISA as described above. Cytokine Release with Large T-Ag transfected Targets: T cell clones were incubated with antigen presenting cells transiently transfected with plasmids encoding HLA-A*02:01 and GFP-truncated Large T-Ag (tLTAg) fusion protein (pDEST103-GFP-tLTAg). pDEST103-GFP-tLTAg was created using Gateway recombination cloning technology (Gateway) to insert tLTAg from pCMV-MCV156 (Paulson et al., *Cancer Res.* 70:8388, 2010) into pDEST103-GFP. A total of $3\times10^4$ COS-7 cells (ATCC, CRL-1651) were plated in flat-bottom 96-well plates in DMEM+10% FBS, 200 nM L-glutamine and 100 U/ml Penicillin-Streptomycin. After incubating for 24 hours, wells were transfected using FuGENE HD (Promega) at a 6:1 ratio of transfection reagent to DNA with 25 ng HLA-A*02:01 and limiting dilution of pDEST103-GFP-tLTAg (25-0.08 ng) plus irrelevant DNA (pcDNA-6/myc-His C, Gateway) to a total of 25 ng. 48 hours after transfection, $10^4$ viable KLL-specific T cells in TCM were added to target wells in duplicate. After 36 hours, supernatants were assayed by ELISA for IFN-γ secretion and $EC_{50}$ calculated as above. Transfected COS-7 cells were harvested at 48 and 72 hours post-transfection to quantitate transfection efficiency by flow cytometry.

Immunohistochemistry: FFPE embedded tumor tissue was stained and slides scored by a dermatopathologist who was blinded to patient characteristics. Samples were stained with anti-CD8 (Dako, clone 144B at 1:100) and intratumoral CD8+ T cells (completely surrounded by tumor without neighboring stroma) on a scale from 0 (absent CD8+ cells) to 5 (>732 intratumoral CD8+ cells/mm$^2$) as described by Paulson et. al., 2011. In addition, tumors were stained with anti-MHC class I[27] (MBL, clone EMR8-5) and CM2B4 to measure MCPyV T-antigen expression (Shuda et al., *Int. J. Cancer* 125:1243, 2009) (Santa Cruz, 1:50). Tumors were stained with anti-CD4 (Cell Marque clone SP35, 1:25) and anti-FoxP3 (eBiosciences clone FJK-16s, 1:25) and reported as the number of positive cells/mm$^2$.

T cell receptor clonality: Tetramer-sorted cells: Shannon entropy was calculated on the estimated number of genomes (≥2) of all productive TRB and normalized by dividing by the log 2 of unique productive sequences in each sample. Clonality was calculated as 1—normalized entropy. Tumors: Clonality was calculated in the same method, using all TRB sequences in the sample to calculate normalized entropy.

Example 2

Screening HLA-Matched MCC Patients for CD8+ T Cells Specific for the MCPyV KLL Epitope HLA-A*02 is a prevalent HLA-type present in approximately 55% of the MCC cohort examined (n=97 low-resolution HLA class I typed patients; HLA-A*02:01 is the dominant A02 allele). An A*02-restricted T cell response was detected in MCC patients to an epitope of the common T-Ag (amino acids 15-23; KLLEIAPNC; SEQ ID NO:17) in 14% of PBMC (10 of 69) and 21% of cultured tumor infiltrating lymphocytes (TILs) (5/24; TILs were expanded with mitogen/cytokine for 2 weeks (Iyer et al., 2011)) from HLA-A*02+ patients. No tetramer+ cells were detected in PBMC from healthy HLA-matched controls (FIG. 1). Among HLA-A*02+ patients, neither MCC-specific survival nor recurrence-free survival were significantly different between patients with or without detectable KLL-specific tetramer+ T cells (p=0.593 and p=0.643, data not shown). The detected KLL-specific T cells were likely primed by MCPyV due to the limited homology between the KLL epitope and the homologous region of other polyomaviruses known to infect humans (Table 1). Moreover, this epitope is predicted to bind to HLA-A*02 approximately 100× better than these homologous peptides ($IC_{50}$ for the KLL MCPyV peptide is 299 nM versus 6,950-25,799 nM for all other homologs as determined by the Immune Epitope Database (Kim et al., *Nucleic Acids Res.* 40:W525, 2012)).

TABLE 1

Homologs to MCPyV KLL-Epitope from other Polyomaviruses

| VIRUS | T-Ag AA # | | | | | | | | | $IC_{50}$ binding to HLA-A*02 (nM) |
|---|---|---|---|---|---|---|---|---|---|---|
| | 15 | 16 | 17 | 18 | 19 | 20 | 21 | 22 | 23 | |
| MCPyV | K | L | L | E | I | A | P | N | C | 299 |
| BKV | D | L | L | G | L | E | R | A | A | 19,316 |
| JCV | D | L | L | G | L | D | R | S | A | 19,439 |
| KIV | Q | L | L | C | L | D | M | S | C | 6,950 |
| WUV | Q | L | L | G | L | D | M | T | C | 7,444 |
| SV40 | D | L | L | G | L | E | R | S | A | 19,586 |
| HPyV6 | D | L | I | G | L | S | M | A | C | 19,258 |
| HPyV7 | E | L | I | G | L | N | M | A | C | 15,594 |
| TSV | D | L | L | Q | I | P | R | H | C | 25,799 |

Residues at positions 15, 18 and 20-22 (underlined) are highly divergent. While putative HLA 'anchor residues' 2 and 9 are conserved and may permit presentation of homologs by HLA-A*02, differences in TCR contact residues (middle of peptide) may be sufficient to reduce binding of homologs by MCPyV KLL-epitope (amino acids 15-23) specific T cells. Homologs are much less likely to bind to human HLA-A*0201, based on $IC_{50}$ values calculated via ANN using the online Immune Epitope Database Analysis Resource binding prediction tool.

Example 3

Characteristics of Patients with KLL-specific T Cells

Twelve patients had robust populations of KLL tetramer+ cells (>0.04% of CD8+ T cells) in their PBMC and/or cultured TIL. Patient demographics, relevant disease metrics, and frequency of tetramer+ populations are summarized in Table 2. All patients were Caucasian, with a median age of 65 (range 50-77). The patients presented at varying stages of disease. Some developed progressive disease and others showed no evidence of disease after definitive treatment during a median follow up period of 2.7 years (range 1.1-6.0) years.

TABLE 2

Characteristics of MCC Patients with A*02/KLL Tetramer+ T cells

| Pt ID | Stage at Dx | Gender | Primary Site | Survival Status | Recurrence | Age at Dx | Tetramer+ Samples | Tetramer+ % of CD8s |
|---|---|---|---|---|---|---|---|---|
| w678 | IIA | M | lower limb | alive | Local & Distant | 64 | PBMC | 0.08 |
| | | | | | | | TIL | <0.01* |
| w683 | IIA | M | lower limb | alive | LN & Distant | 66 | PBMC | 0.69 |
| w750 | IIA | F | buttock | deceased | LN & Distant | 58 | PBMC | 0.19 |
| w782 | IIIA | M | upper limb | deceased | Local & Distant | 74 | PBMC | 0.05 |
| w830 | IIIA | M | head & neck | deceased | Local & Distant | 58 | PBMC | 0.20 |
| w851 | IIIB | F | unknown | alive (NED) | No | 77 | PBMC | <0.01* |
| | | | | | | | TIL | 0.16 |
| w871 | IA | M | buttock | alive (NED) | No | 53 | PBMC | <0.01* |
| | | | | | | | TIL | 0.17 |
| w876 | IIIB | M | unknown | alive (NED) | No | 50 | PBMC | 0.08 |
| | | | | | | | TIL | 7.98 |
| w878 | IV | F | unknown | deceased | N/A | 54 | PBMC | 0.06 |
| | | | | | | | TIL | <0.01* |
| w1045 | IIIA | F | head & neck | deceased | Distant | 70 | PBMC | 0.02 |
| w1051 | IIIB | M | unknown | alive (NED) | No | 70 | PBMC | <0.01* |
| | | | | | | | TIL | 0.43 |
| z1116 | IIIB | M | unknown | alive | Distant | 67 | PBMC | 0.2 |
| | | | | | | | TIL | 1.04 |

Abbreviations: MCC, Merkel cell carcinoma; Pt, patient; Dx, diagnosis; NED, no evidence of disease; LN, lymph node; TIL, tumor infiltrating lymphocytes; M, male; F, female.

*Denotes samples that had insufficient tetramer+ T cells for further analysis. TIL samples were unavailable for 5 of the 12 patients.

Example 4

Sequencing of KLL Tetramer+ T Cells

Figure 2:
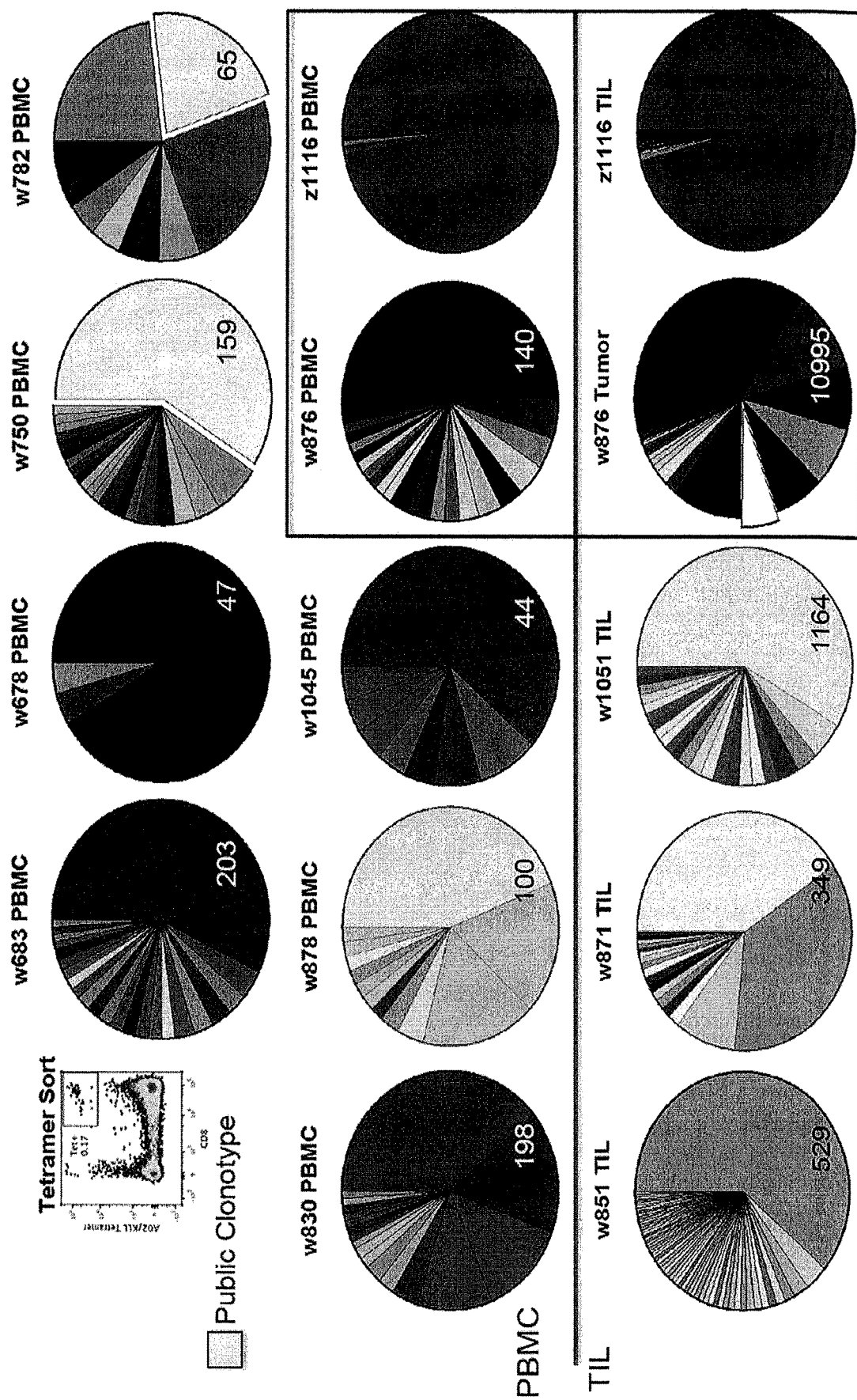
FIG. 2 shows the TRB CDR3 clonotype diversity among KLL tetramer+ CD8+ cells from PBMC and TIL of 12 patients. KLL tetramer+ CD8+ T cells were sorted by flow cytometry (a representative plot is shown) and the CDR3 region from TRB was sequenced. All productive TRB clonotypes with an estimated number of genomes≥2 within each sample are indicated in proportion to their prevalence with a pie chart, with the total number of T cells sequenced indicated at bottom right in each pie. Patients are identified by unique "w" or "z" number. Among 397 total TRB clonotypes, only one shared clonotype was detected among two patients (Public TCR, highlighted in yellow). Paired tumor and PBMC samples were available for two patients (boxed).

The complementarity determining region 3 (CDR3) region of TRB of KLL tetramer-sorted cells from PBMC (n=9) and/or TIL (n=5) from 12 patients were sequenced (FIG. 2 and Table 4). Out of 397 unique TRB sequences, only one public TCRβ clonotype was detected and shared between two patients. This clonotype dominated the KLL-specific repertoire of these patients (59.1 or 21.5% of KLL-specific TRB sequencing reads). Complete TCRβ sequence results for each patient, in order of decreasing frequency, are in Table 3.

TABLE 3

List of all TCRβ Clonotypes Resolved from HLA-A*02 01/KLL-tetramer sorted T cells, Annotated by Patient

| CDR3 | TCRBV allele | TCRBJ allele | CDR3 | TCRBV allele | TCRBJ allele |
|---|---|---|---|---|---|
| w678 | | | w782 cont'd | | |
| CAIRQFDANTGELFF (SEQ ID NO: 68) | TCRBV10-03*01 | TCRBJ02-02*01 | CASSPPSSGNTIYF (SEQ ID NO: 134) | TCRBV18-01*01 | TCRBJ01-03*01 |
| CASSIIAGSSYNEQFF (SEQ ID NO: 69) | TCRBV19-01 | TCRBJ02-01*01 | CASSVRVQQRKNIQYF (SEQ ID NO: 135) | TCRBV21-01*01 | TCRBJ02-04*01 |
| CASSSGNPSTDTQYF (SEQ ID NO: 14) | TCRBV10-02*01 | TCRBJ02-03*01 | CAIRTLDMNTGELFF (SEQ ID NO: 136) | TCRBV10-03*01 | TCRBJ02-02*01 |
| CASSGGLLHVLDEQYF (SEQ ID NO: 95) | TCRBV21-01*01 | TCRBJ02-07*01 | CSARPGQGAYNSPLHF (SEQ ID NO: 137) | TCRBV20 | TCRBJ01-06*01 |
| CATTWRRYYEQYF (SEQ ID NO: 96) | TCRBV06-07*01 | TCRBJ02-07*01 | CASSLYREETQYF (SEQ ID NO: 138) | TCRBV07-07*01 | TCRBJ02-05*01 |
| w683 | | | w830 | | |
| CASRSQNYYGYTF* (SEQ ID NO: 67) | TCRBV06-05*01 | TCRBJ01-02*01 | CASSIMLYSNQPQHF (SEQ ID NO: 64) | TCRBV19-01 | TCRBJ01-05*01 |
| CASSILLVPIATNEKLFF (SEQ ID NO: 97) | TCRBV19-01 | TCRBJ01-04*01 | CAIRARDQNTGELFF (SEQ ID NO: 66) | TCRBV10-03*01 | TCRBJ02-02*01 |
| CASRSQNYYGYTF* (SEQ ID NO: 67) | TCRBV06-06 | TCRBJ01-02*01 | CASSILGASNQPQHF* (SEQ ID NO: 65) | TCRBV19-01 | TCRBJ01-05*01 |
| CASRSQNYYGYTF* (SEQ ID NO: 67) | TCRBV06-01*01 | TCRBJ01-02*01 | CASSLAGFRFF (SEQ ID NO: 63) | TCRBV12 | TCRBJ02-01*01 |
| CASRSQNYYGYTF* (SEQ ID NO: 67) | TCRBV06 | TCRBJ01-02*01 | CASSLTGLAGTDTQYF (SEQ ID NO: 139) | TCRBV07-03*01 | TCRBJ02-03*01 |
| CASRSQNYYGYTF* (SEQ ID NO: 67) | TCRBV06 | TCRBJ01-02*01 | CAIRKQDQNTGELFF (SEQ ID NO: 140) | TCRBV10-03*01 | TCRBJ02-02*01 |
| CASSRALATARKNIQYF (SEQ ID NO: 98) | TCRBV21-01*01 | TCRBJ02-04*01 | CASSFPGAGSNTGELFF (SEQ ID NO: 141) | TCRBV28-01*01 | TCRBJ02-02*01 |
| CASSLSMLQQRKNIQYF (SEQ ID NO: 99) | TCRBV21-01*01 | TCRBJ02-04*01 | CASSLVIATQIRTEAFF (SEQ ID NO: 142) | TCRBV21-01*01 | TCRBJ01-01*01 |
| CASRSQNYYGYTF* (SEQ ID NO: 67) | TCRBV06-08*01 | TCRBJ01-02*01 | CASSILGASNQPQHF* (SEQ ID NO: 65) | TCRBV19-01 | TCRBJ01-05*01 |
| CASRSQNYYGYTF* (SEQ ID NO: 67) | TCRBV06-09*01 | TCRBJ01-02*01 | CASRGLLAQQSRANVLTF (SEQ ID NO: 143) | TCRBV21-01*01 | TCRBJ02-06*01 |
| CASRSQNYYGYTF* (SEQ ID NO: 67) | TCRBV06-07*01 | TCRBJ01-02*01 | CASRHWLLQHARNTIYF (SEQ ID NO: 144) | TCRBV21-01*01 | TCRBJ01-03*01 |
| CASRSQNYYGYTF* (SEQ ID NO: 67) | TCRBV06-04 | TCRBJ01-02*01 | CASSNPQRIAQSRANVLTF (SEQ ID NO: 145) | TCRBV10-01 | TCRBJ02-06*01 |
| CASRSQNYYGYTF* (SEQ ID NO: 67) | TCRBV06 | TCRBJ01-02*01 | CPGSRYGSEQSRANVLTF (SEQ ID NO: 146) | TCRBV22-01*01 | TCRBJ02-06*01 |
| CASSSQNYYGYTF (SEQ ID NO: 100) | TCRBV06-05*01 | TCRBJ01-02*01 | CASSILLYSNQPQHF (SEQ ID NO: 147) | TCRBV19-01 | TCRBJ01-05*01 |
| CASSVALLQHARNTIYF (SEQ ID NO: 101) | TCRBV21-01*01 | TCRBJ01-03*01 | CASSWSVLQHARNTIYF (SEQ ID NO: 148) | TCRBV21-01*01 | TCRBJ01-03*01 |
| CASRAKLATLRTEAFF (SEQ ID NO: 102) | TCRBV21-01*01 | TCRBJ01-01*01 | CASSLGWGDTEAFF (SEQ ID NO: 149) | TCRBV12 | TCRBJ01-01*01 |
| CASRSQNYYGYTF* (SEQ ID NO: 67) | TCRBV10-03*01 | TCRBJ01-02*01 | CASSLTGLAGTDTQYF (SEQ ID NO: 150) | TCRBV07-03*01- | TCRBJ02-03*01 |
| CASRSQNYYGYTF* (SEQ ID NO: 67) | TCRBV06 | TCRBJ01-02*01 | w851 | | |
| CASRSQNYYGYTF* (SEQ ID NO: 67) | TCRBV06 | TCRBJ01-02*01 | | | |
| CASKTGGREKLFF (SEQ ID NO: 103) | TCRBV28-01*01 | TCRBJ01-04*01 | CASSILSNSYNEQFF (SEQ ID NO: 151) | TCRBV19-01 | TCRBJ02-01*01 |
| CASKKLDRPAPNSPLHF (SEQ ID NO: 104) | TCRBV03 | TCRBJ01-06*01 | CASRRAPGGGLYNEQFF (SEQ ID NO: 152) | TCRBV03 | TCRBJ02-01*01 |
| CASSEFLRGADYGYTF (SEQ ID NO: 105) | TCRBV25-01*01 | TCRBJ01-02*01 | CAIRTLDMNTGELFF (SEQ ID NO: 153) | TCRBV10-03*01 | TCRBJ02-02*01 |
| CASSLVGGRDEQYF (SEQ ID NO: 106) | TCRBV09-01 | TCRBJ02-07*01 | CASSLSRGLLNGYTF (SEQ ID NO: 154) | TCRBV27-01*01 | TCRBJ01-02*01 |
| w750 | | | CASSLVGGRDGYTF (SEQ ID NO: 155) | TCRBV12 | TCRBJ01-02*01 |
| | | | CASSQFWAGGIYEQYF (SEQ ID NO: 156) | TCRBV03 | TCRBJ02-07*01 |

TABLE 3-continued

List of all TCRβ Clonotypes Resolved from HLA-A*02 01/KLL-tetramer sorted T cells, Annotated by Patient

| CDR3 | TCRBV allele | TCRBJ allele | CDR3 | TCRBV allele | TCRBJ allele |
|---|---|---|---|---|---|
| CAIRDSNTGELFF (SEQ ID NO: 107) | TCRBV10-03*01 | TCRBJ02-02*01 | CASSQVGETQYF (SEQ ID NO: 157) | TCRBV04-01*01 | TCRBJ02-05*01 |
| CSARDLLAGTNTGELFF (SEQ ID NO: 108) | TCRBV20 | TCRBJ02-02*01 | CASSYQGEEETQYF (SEQ ID NO: 158) | TCRBV06-05*01 | TCRBJ02-05*01 |
| CAIRLADQNTGELFF (SEQ ID NO: 109) | TCRBV10-03*01 | TCRBJ02-02*01 | CATSSDRGGLQETQYF (SEQ ID NO: 159) | TCRBV15-01*01 | TCRBJ02-05*01 |
| CASRDIGSGPQHF (SEQ ID NO: 110) | TCRBV10-02*01 | TCRBJ01-05*01 | CASRHNVLQHARNTIYF (SEQ ID NO: 160) | TCRBV21-01*01 | TCRBJ01-03*01 |
| CASRDQNTGELFF (SEQ ID NO: 111) | TCRBV10-03*01 | TCRBJ02-02*01 | CASSGRLQQSRANVLTF (SEQ ID NO: 161) | TCRBV21-01*01 | TCRBJ02-06*01 |
| CAIRIRDQNTGELFF (SEQ ID NO: 112) | TCRBV10-03*01 | TCRBJ02-02*01 | CASSYPYGGGQNEQFF (SEQ ID NO: 162) | TCRBV06-05*01 | TCRBJ02-01*01 |
| CASRTIFATVMQDTQYF (SEQ ID NO: 113) | TCRBV21-01*01 | TCRBJ02-03*01 | CARGPTGGYTF (SEQ ID NO: 163) | TCRBV02-01*01 | TCRBJ01-02*01 |
| CAIRTRDQNTGELFF (SEQ ID NO: 114) | TCRBV10-03*01 | TCRBJ02-02*01 | CASSPRAGVDYGYTF (SEQ ID NO: 164) | TCRBV18-01*01 | TCRBJ01-02*01 |
| CASSRLQQRKNIQYF (SEQ ID NO: 115) | TCRBV21-01*01 | TCRBJ02-04*01 | CASSLVRDSYNEQFF (SEQ ID NO: 165) | TCRBV07-02*01 | TCRBJ02-01*01 |
| CASSIMVYSYNEKLFF (SEQ ID NO: 116) | TCRBV19-01 | TCRBJ01-01*01 | CASSGGRVNEKLFF (SEQ ID NO: 166) | TCRBV19-01 | TCRBJ01-04*01 |
| CAIREGDQNTGELFF (SEQ ID NO: 117) | TCRBV10-03*01 | TCRBJ02-02*01 | CASSLGGNTGELFF (SEQ ID NO: 167) | TCRBV27-01*01 | TCRBJ02-02*01 |
| CASSDFNPSTDTQYF (SEQ ID NO: 118) | TCRBV06-01*01 | TCRBJ02-03*01 | CASSEWGGTQPQHF (SEQ ID NO: 168) | TCRBV06-01*01 | TCRBJ01-05*01 |
| CASSRGSVSDEQYF (SEQ ID NO: 119) | TCRBV19-01 | TCRBJ02-07*01 | CATSGTGRWETQYF (SEQ ID NO: 169) | TCRBV15-01*01 | TCRBJ02-05*01 |
| CASSDRDLYGYTF (SEQ ID NO: 120) | TCRBV19-01 | TCRBJ01-02*01 | CASSLARGPGNTIYF (SEQ ID NO: 170) | TCRBV07-06*01 | TCRBJ01-03*01 |
| CASSIAAGDAYGYTF (SEQ ID NO: 121) | TCRBV19-01 | TCRBJ01-02*01 | CASRITMGQPQHF (SEQ ID NO: 171) | TCRBV19-01 | TCRBJ01-05*01 |
| CASSPRGDTEAFF (SEQ ID NO: 122) | TCRBV10-01 | TCRBJ01-01*01 | CASSDRVAGNEQFF (SEQ ID NO: 172) | TCRBV06-05*01 | TCRBJ02-01*01 |
| CASSFGSEQYF (SEQ ID NO: 123) | TCRBV05-04*01 | TCRBJ02-07*01 | CASSLTSGVTEAFF (SEQ ID NO: 173) | TCRBV07-09 | TCRBJ01-01*01 |
| CASSWELTNEQYF (SEQ ID NO: 124) | TCRBV05-04*01 | TCRBJ02-07*01 | CASSLSPELHGYTF (SEQ ID NO: 174) | TCRBV27-01*01 | TCRBJ01-02*01 |
| CASNRGSTQSRANVLTF (SEQ ID NO: 124) | TCRBV05-02*01 | TCRBJ02-06*01 | CATSRDSGGLDGDTQYF (SEQ ID NO: 175) | TCRBV15-01*01 | TCRBJ02-03*01 |
| CASSWRVQPQHF (SEQ ID NO: 125) | TCRBV28-01*01 | TCRBJ01-05*01 | CASSPGEWGSETQYF (SEQ ID NO: 176) | TCRBV03 | TCRBJ02-05*01 |
| CASSQSIADNYGYTF (SEQ ID NO: 126) | TCRBV16-01 | TCRBJ01-02*01 | CASSFGGGANEQFF (SEQ ID NO: 177) | TCRBV13-01*01 | TCRBJ02-01*01 |
| CASSLSGQPQHF (SEQ ID NO: 127) | TCRBV27-01*01 | TCRBJ01-05*01 | CASTPGGLPKNIQYF (SEQ ID NO: 178) | TCRBV11-01*01 | TCRBJ02-04*01 |
| | | | CASSATGTGDLEQFF (SEQ ID NO: 179) | TCRBV07-02*01 | TCRBJ02-01*01 |
| W782 | | | CASSWGYDSYNEQFF (SEQ ID NO: 180) | TCRBV05-06*01 | TCRBJ02-01*01 |
| CASSILGYSNQPQHF (SEQ ID NO: 128) | TCRBV19-01 | TCRBJ01-05*01 | CASSQETGEGNSPLHF (SEQ ID NO: 181) | TCRBV04-02*01 | TCRBJ01-06*01 |
| CAIRDSNTGELFF (SEQ ID NO: 129) | TCRBV10-03*01 | TCRBJ02-02*01 | CASRLTDRGRVGEKLFF (SEQ ID NO: 182) | TCRBV07-09 | TCRBJ01-04*01 |
| CAIRAGDSNTGELFF (SEQ ID NO: 130) | TCRBV10-03*01 | TCRBJ02-02*01 | CASSILSNSYNEQFF (SEQ ID NO: 183) | TCRBV19-01 | TCRBJ02-01*01 |
| CASREGAAYNEQFF** (SEQ ID NO: 131) | TCRBV06-01*01 | TCRBJ02-01*01 | CASSAGTAAGNTIYF (SEQ ID NO: 184) | TCRBV07-06*01 | TCRBJ01-03*01 |
| CASREGAAYNEQFF** (SEQ ID NO: 132) | TCRBV06 | TCRBJ02-01*01 | CASSGVKRSHKSRANVLTF (SEQ ID NO: 185) | TCRBV10-01 | TCRBJ02-06*01 |
| CATSDPLAASYEQYF (SEQ ID NO: 133) | TCRBV24 | TCRBJ02-07*01 | CASSGYHDGFSEQFF (SEQ ID NO: 186) | TCRBV06-01*01 | TCRBJ02-07*01 |
| w851 cont'd | | | w876 (PBMC) cont'd | | |
| CASSLQGAGQPQHF (SEQ ID NO: 187) | TCRBV19-01 | TCRBJ01-05*01 | CASRGDIGYRKTYGYTF (SEQ ID NO: 234) | TCRBV21-01*01 | TCRBJ01-02*01 |
| CADGRGDEQYF (SEQ ID NO: 188) | TCRBV02-01*01 | TCRBJ02-07*01 | CASSILSSSNQPQHF (SEQ ID NO: 235) | TCRBV19-01 | TCRBJ01-05*01 |
| CASSPVGGDQPQHF (SEQ ID NO: 189) | TCRBV07-09 | TCRBJ01-05*01 | CASTLGNPSTDTQYF (SEQ ID NO: 236) | TCRBV06-06 | TCRBJ02-03*01 |
| CASSIGRTYYGYTF (SEQ ID NO: 190) | TCRBV19-01 | TCRBJ01-02*01 | CASSSGTSGGLNYNEQFF (SEQ ID NO: 91) | TCRBV13-01*01 | TCRBJ02-01*01 |
| CAYGAGGPNTEAFF (SEQ ID NO: 191) | TCRBV05-08*01 | TCRBJ01-01*01 | CASSSGTSGGLTYNEQFF (SEQ ID NO: 86) | TCRBV13-01*01 | TCRBJ02-01*01 |
| CASNIYSQPQHF (SEQ ID NO: 192) | TCRBV19-01 | TCRBJ01-05*01 | CASSTLSGTHNEQFF (SEQ ID NO: 81) | TCRBV19-01 | TCRBJ02-01*01 |

TABLE 3-continued

List of all TCRβ3 Clonotypes Resolved from HLA-A*02 01/KLL-tetramer sorted T cells, Annotated by Patient

| CDR3 | TCRBV allele | TCRBJ allele | CDR3 | TCRBV allele | TCRBJ allele |
|---|---|---|---|---|---|
| CASSLEGDTEAFF (SEQ ID NO: 193) | TCRBV05-05*01 | TCRBJ01-01*01 | CASSAEVTNHQSRANVLTF (SEQ ID NO: 237) | TCRBV19-01 | TCRBJ02-06*01 |
| CASSETDRGLAYEQYV (SEQ ID NO: 194) | TCRBV06-01*01 | TCRBJ02-07*01 | CASSDTPDLNTEAFF* (SEQ ID NO: 74) | TCRBV06 | TCRBJ01-01*01 |
| CSARDRVGNTIYF (SEQ ID NO: 195) | TCRBV20 | TCRBJ01-03*01 | CASSYSTGVPEKLFF (SEQ ID NO: 238) | TCRBV06-05*01 | TCRBJ01-04*01 |
| CASSYFPGVEAFF (SEQ ID NO: 196) | TCRBV06-05*01 | TCRBJ01-01*01 | | | |
| CASSEGQGNSPLHF (SEQ ID NO: 197) | TCRBV09-01 | TCRBJ01-06*01 | w876 (TIL) | | |
| CASQTGFYNEQFF (SEQ ID NO: 198) | TCRBV06-05*01 | TCRBJ02-01*01 | CASSVLNTGELFF* (SEQ ID NO: 73) | TCRBV10-02*01 | TCRBJ02-02*01 |
| CASKTSGFPDTQYF (SEQ ID NO: 199) | TCRBV02-01*01 | TCRBJ02-03*01 | CAIRAGASYNEQFF* (SEQ ID NO: 70) | TCRBV28-01*01 | TCRBJ02-01*01 |
| CASSLSRGDSNQPQHF (SEQ ID NO: 200) | TCRBV27-01*01 | TCRBJ01-05*01 | CASRGQNTGELFF* (SEQ ID NO: 71) | TCRBV10-03*01 | TCRBJ02-02*01 |
| CASRESNTEAFF (SEQ ID NO: 201) | TCRBV27-01*01 | TCRBJ01-01*01 | CAIHEGDSNTGELFF* (SEQ ID NO: 77) | TCRBV10-03*01 | TCRBJ02-02*01 |
| CASSEGQSYEQYF (SEQ ID NO: 202) | TCRBV05-06*01 | TCRBJ02-07*01 | CAISARDQNTGELFF* (SEQ ID NO: 75) | TCRBV10-03*01 | TCRBJ02-02*01 |
| CASSSGTPSTDTQYF (SEQ ID NO: 204) | TCRBV06-06 | TCRBJ02-03*01 | CAIRRQDQNTGELFF* (SEQ ID NO: 76) | TCRBV10-03*01 | TCRBJ02-02*01 |
| CASRPDIPLGETQYF (SEQ ID NO: 205) | TCRBV06-05*01 | TCRBJ02-05*01 | CAIRGQDQNTGELFF* (SEQ ID NO: 239) | TCRBV10-03*01 | TCRBJ02-02*01 |
| CASSILSNSYNEQFF (SEQ ID NO: 206) | TCRBV19-01 | TCRBJ02-01*01 | CATRDINTGELFF* (SEQ ID NO: 94) | TCRBV10-03*01 | TCRBJ02-02*01 |
| CASKKLDRPAPNSPLHF (SEQ ID NO: 207) | TCRBV03 | TCRBJ01-06*01 | CASSQLRTGDEYEQYF (SEQ ID NO: 90) | TCRBV16-01 | TCRBJ02-07*01 |
| CASRRAPGGGLYNEQFS (SEQ ID NO: 208) | TCRBV03 | TCRBJ02 | CASSDTPDLNTEAFF* (SEQ ID NO: 74) | TCRBV06-01*01 | TCRBJ01-01*01 |
| CASSYQGEEETQYF (SEQ ID NO: 209) | TCRBV06 | TCRBJ02-05*01 | CASSFGSGTKDTQYF* (SEQ ID NO: 83) | TCRBV12 | TCRBJ02-03*01 |
| w871 | | | CASSSRTKAYEQYF (SEQ ID NO: 240) | TCRBV13-01*01 | TCRBJ02-07*01 |
| | | | CASSLIAGLSYEQYF (SEQ ID NO: 241) | TCRBV07-08*01 | TCRBJ02-07*01 |
| CASSSGTPSTDTQYF (SEQ ID NO: 210) | TCRBV06-06 | TCRBJ02-03*01 | CASSLAGLAGTDTQYF (SEQ ID NO: 78) | TCRBV07-02*01 | TCRBJ02-03*01 |
| CAINNRDQNTGELFF (SEQ ID NO: 211) | TCRBV10-03*01 | TCRBJ02-02*01 | CASTLGNPSTDTQYF* (SEQ ID NO: 242) | TCRBV06-06 | TCRBJ02-03*01 |
| CASTQSNTGELFF (SEQ ID NO: 212) | TCRBV10-02*01 | TCRBJ02-02*01 | CASSGQNTGELFF* (SEQ ID NO: 84) | TCRBV10-02*01 | TCRBJ02-02*01 |
| CASSETPDMNTEAFF (SEQ ID NO: 213) | TCRBV06-01*01 | TCRBJ01-01*01 | CASSVEDYTGELFF* (SEQ ID NO: 72) | TCRBV09-01 | TCRBJ02-02*01 |
| CASSSGTPSTDTQYF* (SEQ ID NO: 214) | TCRBV06-05*01 | TCRBJ02-03*01 | CASSIQLFVRTEAFF* (SEQ ID NO: 243) | TCRBV19-01 | TCRBJ01-01*01 |
| CASSSGTPSTDTQYF* (SEQ ID NO: 215) | TCRBV06 | TCRBJ02-03*01 | CASRASNTYGYTF* (SEQ ID NO: 80) | TCRBV06-05*01 | TCRBJ01-02*01 |
| CASTDSNTGELFF (SEQ ID NO: 216) | TCRBV10-02*01 | TCRBJ02-02*01 | CASSIIAYSNQPQHF (SEQ ID NO: 244) | TCRBV19-01 | TCRBJ01-05*01 |
| CASSSGTPSTDTQYF* (SEQ ID NO: 217) | TCRBV06-05*01 | TCRBJ02-03*01 | CASRSQLAVLNEQFF (SEQ ID NO: 92) | TCRBV19-01 | TCRBJ02-01*01 |
| CASSSGTPSTDTQYF* (SEQ ID NO: 218) | TCRBV06-09*01 | TCRBJ02-03*01 | CASSTLSGTHNEQFF (SEQ ID NO: 81) | TCRBV19-01 | TCRBJ02-01*01 |
| CASSSGTPSTDTQYF* (SEQ ID NO: 219) | TCRBV06-09*01 | TCRBJ02-03*01 | CASSILSSSNQPQHF (SEQ ID NO: 245) | TCRBV19-01 | TCRBJ01-05*01 |
| CASSLGVAGGSSYNEQFF (SEQ ID NO: 220) | TCRBV13-01*01 | TCRBJ02-01*01 | CASSLAGDRYF (SEQ ID NO: 246) | TCRBV12 | TCRBJ01-06*01 |
| CASSYSTGVPEKLFF (SEQ ID NO: 221) | TCRBV06-05*01 | TCRBJ01-04*01 | CCASSFGTSGGTTYNEQFF (SEQ ID NO: 247) | TCRBV13-01*01 | TCRBJ02-01*01 |
| CASSWYLATHSDNEQFF (SEQ ID NO: 222) | TCRBV21-01*01 | TCRBJ02-01*01 | CASSPWDEQFF (SEQ ID NO: 85) | TCRBV12 | TCRBJ02-01*01 |
| CASTGGLADTQYF (SEQ ID NO: 223) | TCRBV19-01 | TCRBJ02-03*01 | CASRGGSSYNEQFF (SEQ ID NO: 93) | TCRBV28-01*01 | TCRBJ02-01*01 |
| CASSSCMDIYKSRANVLTF (SEQ ID NO: 224) | TCRBV18-01*01 | TCRBJ02-06*01 | CASSSGTSGGLTYNEQFF (SEQ ID NO: 86) | TCRBV13-01*01 | TCRBJ02-01*01 |
| CASRRTSGGRTDTQYF (SEQ ID NO: 225) | TCRBV06 | TCRBJ02-03*01 | CASSYQIGLSYEQYF* (SEQ ID NO: 88) | TCRBV06-06 | TCRBJ02-07*01 |
| CASSSGTPSTDTQYF* (SEQ ID NO: 226) | TCRBV06-08*01 | TCRBJ02-03*01 | CASSEFAGQETQYF (SEQ ID NO: 79) | TCRBV02-01*01 | TCRBJ02-05*01 |

TABLE 3-continued

List of all TCRfβ Clonotypes Resolved from HLA-A*02 01/KLL-tetramer sorted T cells, Annotated by Patient

| CDR3 | TCRBV allele | TCRBJ allele | CDR3 | TCRBV allele | TCRBJ allele |
|---|---|---|---|---|---|
| CASSSGTPSTDTQYF* (SEQ ID NO: 227) | TCRBV06-06 | TCRBJ02-03*01 | CASSSGTSGGLNYNEQFF (SEQ ID NO: 91) | TCRBV13-01*01 | TCRBJ02-01*01 |
|  |  |  | CASSVLNTGELFF* (SEQ ID NO: 73) | TCRBV10-02*01 | TCRBJ02-02*01 |
|  | w876 (PBMC) |  | CASSVLNTGELFF* (SEQ ID NO: 73) | TCRBV10-03*01 | TCRBJ02-02*01 |
| CASSVLNTGELFF* (SEQ ID NO: 73) | TCRBV10-02*01 | TCRBJ02-02*01 | CAIHEGDSNTGELFF* (SEQ ID NO: 77) | TCRBV10-03*01 | TCRBJ02-02*01 |
| CAIRRQDQNTGELFF (SEQ ID NO: 76) | TCRBV10-03*01 | TCRBJ02-02*01 | CASSDTPDLNTEAFF* (SEQ ID NO: 74) | TCRBV06 | TCRBJ01-01*01 |
| CAIHEGDSNTGELFF* (SEQ ID NO: 77) | TCRBV10-03*01 | TCRBJ02-02*01 | CAIRRQDQNTGELFF (SEQ ID NO: 76) | TCRBV10-03*01 | TCRBJ02-02*01 |
| CASRGQNTGELFF (SEQ ID NO: 71) | TCRBV10-03*01 | TCRBJ02-02*01 | CASRGQNTGELFF* (SEQ ID NO: 71) | TCRBV10 | TCRBJ02-02*01 |
| CASSQLRTGDEYEQYF (SEQ ID NO: 90) | TCRBV16-01 | TCRBJ02-07*01 | CAIRGQNTGELFF (SEQ ID NO: 248) | TCRBV10-03*01 | TCRBJ02-02*01 |
| CATRDINTGELFF* (SEQ ID NO: 94) | TCRBV10-03*01 | TCRBJ02-02*01 | CASRASNTYGYTF* (SEQ ID NO: 80) | TCRBV06-06 | TCRBJ01-02*01 |
| CAIRAGASYNEQFF (SEQ ID NO: 70) | TCRBV28-01*01 | TCRBJ02-01*01 | CASSSRTKAYEQYF* (SEQ ID NO: 87) | TCRBV13-01*01 | TCRBJ02-07*01 |
| CAISARDQNTGELFF (SEQ ID NO: 75) | TCRBV10-03*01 | TCRBJ02-02*01 | CASSDTPDLNTEAFF* (SEQ ID NO: 74) | TCRBV06-09*01 | TCRBJ01-01*01 |
| CASSFGSGTKDTQYF (SEQ ID NO: 83) | TCRBV12 | TCRBJ02-03*01 | CASSDTPDLNTEAFF* (SEQ ID NO: 74) | TCRBV06-08*01 | TCRBJ01-01*01 |
| CASRGSIATRYNEKLFF (SEQ ID NO: 228) | TCRBV21-01*01 | TCRBJ01-04*01 | CASSVEDYTGELFF* (SEQ ID NO: 72) | TCRBV09-01 | TCRBJ02-02*01 |
| CASSDTPDLNTEAFF* (SEQ ID NO: 74) | TCRBV06-01*01 | TCRBJ01-01*01 | CASTLGNPSTDTQYF* (SEQ ID NO: 249) | TCRBV06-05*01 | TCRBJ02-03*01 |
| CASSLAGLAGTDTQYF (SEQ ID NO: 78) | TCRBV07-02*01 | TCRBJ02-03*01 | CASRASNTYGYTF* (SEQ ID NO: 80) | TCRBV06 | TCRBJ01-02*01 |
| CASSSRTKAYEQYF (SEQ ID NO: 87) | TCRBV13-01*01 | TCRBJ02-07*01 | CASRTVVLHWHHQPQHF (SEQ ID NO: 250) | TCRBV21-01*01 | TCRBJ01-05*01 |
| CARTESRQSRANVLTF (SEQ ID NO: 229) | TCRBV07-05*01 | TCRBJ02-06*01 | CAIRTGSAYNEQFF (SEQ ID NO: 251) | TCRBV28-01*01 | TCRBJ02-01*01 |
| CASSVEDYTGELFF* (SEQ ID NO: 72) | TCRBV09-01 | TCRBJ02-02*01 | CAISARDQNTGELFF* (SEQ ID NO: 75) | TCRBV10-03*01 | TCRBJ02-02*01 |
| CASRDRREQFF (SEQ ID NO: 230) | TCRBV21-01*01 | TCRBJ02-01*01 | CASSDTPDLNTEAFF* (SEQ ID NO: 74) | TCRBV10-03*01 | TCRBJ01-01*01 |
| CASRRVLAYRKTYGYTF (SEQ ID NO: 231) | TCRBV21-01*01 | TCRBJ01-02*01 | CSALPVTGAFQETQYF (SEQ ID NO: 252) | TCRBV20 | TCRBJ02-05*01 |
| CASRRCIATHTHNSPLHF (SEQ ID NO: 232) | TCRBV21-01*01 | TCRBJ01-06*01 | CASSVLNTGELFF (SEQ ID NO: 73) | TCRBV10-01 | TCRBJ02-02*01 |
| CAISADNCIQSRANVLTF (SEQ ID NO: 233) | TCRBV10-03*01 | TCRBJ02-06*01 | CAIRGQDQNTGELFF* (SEQ ID NO: 253) | TCRBV10-03*01 | TCRBJ02-02*01 |
| CASSGQNTGELFF* (SEQ ID NO: 84) | TCRBV10-02*01 | TCRBJ02-02*01 | CASRASNTYGYTF* (SEQ ID NO: 80) | TCRBV06-01*01 | TCRBJ01-02*01 |
|  |  |  | w876 (TIL) cont'd |  |  |
| CASSVLNTGELFF* (SEQ ID NO: 73) | TCRBV10-02*01 | TCRBJ02-02*01 | CASRDINSGELFF (SEQ ID NO: 281) | TCRBV10-03*01 | TCRBJ02-02*01 |
| CARSVLNTGELFF (SEQ ID NO: 254) | TCRBV10-02*01 | TCRBJ02-02*01 | CASSVLNTGELFF* (SEQ ID NO: 73) | TCRBV10-03*01 | TCRBJ02-02*01 |
| CAIRRQDQNTGELFF* (SEQ ID NO: 76) | TCRBV06-01*01 | TCRBJ02-02*01 | CASTLGNPSTDTQYF* (SEQ ID NO: 282) | TCRBV10-03*01 | TCRBJ02-03*01 |
| CASSVLNTGELFF* (SEQ ID NO: 73) | TCRBV10-02*01 | TCRBJ02-02*01 | CACSVLNTGELFF (SEQ ID NO: 283) | TCRBV10-02*01 | TCRBJ02-02*01 |
| CAIHEGDSNTGELFF* (SEQ ID NO: 77) | TCRBV06-01*01 | TCRBJ02-02*01 | CAIHEGDSNTGELFF* (SEQ ID NO: 77) | TCRBV10-03*01 | TCRBJ02-02*01 |
| CASSVLNTGELFF* (SEQ ID NO: 73) | TCRBV03 | TCRBJ02-02*01 | CAIHEGDSNTGELFF* (SEQ ID NO: 77) | TCRBV10-03*01 | TCRBJ02-02*01 |
| CASSPTGAVSYEQYF (SEQ ID NO: 255) | TCRBV12 | TCRBJ02-07*01 | CAIRAGASYNEQFF* (SEQ ID NO: 70) | TCRBV28-01*01 | TCRBJ02-01*01 |
| CSARAPTGTGNTGELFF (SEQ ID NO: 256) | TCRBV20 | TCRBJ02-02*01 | CAIRAVASYNEQFF (SEQ ID NO: 284) | TCRBV28-01*01 | TCRBJ02-01*01 |
| CATRDINTGELFF* (SEQ ID NO: 94) | TCRBV10 | TCRBJ02-02*01 | CAIRGQDQNTGELFF* (SEQ ID NO: 285) | TCRBV10-03*01 | TCRBJ02-02*01 |
| CAIRRQDQNTGELFF* (SEQ ID NO: 76) | TCRBV10-02*01 | TCRBJ02-02*01 | CAIRRQDHNTGELFF (SEQ ID NO: 286) | TCRBV10-03*01 | TCRBJ02-02*01 |
| CAISARDQNTGELFF* (SEQ ID NO: 75) | TCRBV10-02*01 | TCRBJ02-02*01 | CAIRRQDQNNGELFF (SEQ ID NO: 287) | TCRBV10-03*01 | TCRBJ02-02*01 |
| CASRGQNTGELFF* (SEQ ID NO: 71) | TCRBV10-02*01 | TCRBJ02-02*01 | CASRASNTYGYTF* (SEQ ID NO: 80) | TCRBV10-03*01 | TCRBJ01-02*01 |
| CASRGQNTGELFF* (SEQ ID NO: 71) | unresolved | TCRBJ02-02*01 | CASRGQDQNTGELFF (SEQ ID NO: 288) | TCRBV10-03*01 | TCRBJ02-02*01 |

TABLE 3-continued

List of all TCRfβ Clonotypes Resolved from HLA-A*02 01/KLL-tetramer sorted T cells, Annotated by Patient

| CDR3 | TCRBV allele | TCRBJ allele | CDR3 | TCRBV allele | TCRBJ allele |
|---|---|---|---|---|---|
| CAIRGQDQNTGELFF* (SEQ ID NO: 257) | TCRBV10-02*01 | TCRBJ02-02*01 | CASSLIAGLSYEQYF* (SEQ ID NO: 289) | TCRBV07-04*01 | TCRBJ02-07*01 |
| CAIRRQDQNTGELFF* (SEQ ID NO: 76) | TCRBV06-06 | TCRBJ02-02*01 | CAIHEGDSNTGELFF* (SEQ ID NO: 77) | TCRBV06-06 | TCRBJ02-02*01 |
| CASSGQNTGELFF* (SEQ ID NO: 84) | TCRBV10-02*01 | TCRBJ02-02*01 | CASSQLRTGDEYEQYF* (SEQ ID NO: 90) | TCRBV16-01 | TCRBJ02-07*01 |
| CAIRGQDQNTGELFF* (SEQ ID NO: 258) | TCRBV06-01*01 | TCRBJ02-02*01 | CASSSRTKAYEQYF* (SEQ ID NO: 87) | TCRBV05-02*01 | TCRBJ02-07*01 |
| CASSSRTKAYEQYF* (SEQ ID NO: 87) | TCRBV02-01*01 | TCRBJ02-07*01 | CAIRRQDQNTGELFF* (SEQ ID NO: 76) | TCRBV06-05*01 | TCRBJ02-02*01 |
| CASSSRTKAYEQYF* (SEQ ID NO: 87) | TCRBV27-01*01 | TCRBJ02-07*01 | CAIRRQDQNTGELFF* (SEQ ID NO: 76) | un-resolved | TCRBJ02-02*01 |
| CASTLGNPSTDTQYF* (SEQ ID NO: 259) | TCRBV06-09*01 | TCRBJ02-03*01 | CAISARDQNTGELFF* (SEQ ID NO: 75) | TCRBV06-05*01 | TCRBJ02-02*01 |
| CATRDINTGELFF* (SEQ ID NO: 94) | TCRBV10-02*01 | TCRBJ02-02*01 | CAISARDQNTGELFF* (SEQ ID NO: 75) | TCRBV06 | TCRBJ02-02*01 |
| CASSDRPRIAQSRANVLTF (SEQ ID NO: 260) | TCRBV10-01 | TCRBJ02-06*01 | CAISDTPDLNTEAFF (SEQ ID NO: 290) | TCRBV06-01*01 | TCRBJ01-01*01 |
| CASRRCIATTARNTIYF (SEQ ID NO: 261) | TCRBV21-01*01 | TCRBJ01-03*01 | CANSSRTKAYEQYF (SEQ ID NO: 291) | TCRBV13-01*01 | TCRBJ02-07*01 |
| CASSESNTLVGFF (SEQ ID NO: 262) | TCRBV10-02*01 | TCRBJ02-01*01 | CASRASNTYGYTF* (SEQ ID NO: 80) | TCRBV06-08*01 | TCRBJ01-02*01 |
| CPGRRARKRTSRANVLTF (SEQ ID NO: 263) | TCRBV22-01*01 | TCRBJ02-06*01 | CASSDTPDLNTEAFF (SEQ ID NO: 74) | TCRBV03 | TCRBJ01-01*01 |
| CASSLFSVYTQFF (SEQ ID NO: 264) | TCRBV12-01*01 | TCRBJ02-01*01 | CASSDTPDLNTEAFF (SEQ ID NO: 74) | TCRBV06-01*01 | TCRBJ01-01*01 |
| CASSLGVSGGMTYNEQFF (SEQ ID NO: 265) | TCRBV13-01*01 | TCRBJ02-01*01 | CASSDTPDLNTEAFF (SEQ ID NO: 74) | TCRBV06-01*01 | TCRBJ01-01*01 |
| CPGSRLGSEQSRANVLTF (SEQ ID NO: 266) | TCRBV22-01*01 | TCRBJ02-06*01 | CASSDTPDLNTEAFF (SEQ ID NO: 74) | TCRBV06-01*01 | TCRBJ01-01*01 |
| CASSVLNTGELFF* (SEQ ID NO: 73) | TCRBV10-01 | TCRBJ02-02*01 | CASSFGSGTKDTQYF* (SEQ ID NO: 83) | TCRBV03 | TCRBJ02-03*01 |
| CASSVLNTGELFF* (SEQ ID NO: 73) | TCRBV10-02*01 | TCRBJ02-02*01 | CASSFGSGTKDTQYF* (SEQ ID NO: 83) | TCRBV03 | TCRBJ02-03*01 |
| CAIRGQDQNTGELFF* (SEQ ID NO: 267) | TCRBV06-05*01 | TCRBJ02-02*01 | CASSFGSGTKDTQYF* (SEQ ID NO: 83) | TCRBV07-04*01 | TCRBJ02-03*01 |
| CASSLAGLAGTDTQYF* (SEQ ID NO: 78) | TCRBV11-02*02 | TCRBJ02-03*01 | CASSFGSGTKDTQYF* (SEQ ID NO: 83) | TCRBV12 | TCRBJ02-03*01 |
| CASSVLNTGELFF* (SEQ ID NO: 73) | TCRBV06-06 | TCRBJ02-02*01 | CASSLAGLAGTDTQYF* (SEQ ID NO: 78) | TCRBV07-06*01 | TCRBJ02-03*01 |
| CAIHEGDSNTGELFF* (SEQ ID NO: 77) | TCRBV06-05*01 | TCRBJ02-02*01 | CASSLAGLAGTDTQYF* (SEQ ID NO: 78) | TCRBV07-03*01 | TCRBJ02-03*01 |
| CAIHEGDSNTGELFF* (SEQ ID NO: 77) | TCRBV10-02*01 | TCRBJ02-02*01 | CASSLIAGLSYEQYF* (SEQ ID NO: 292) | TCRBV11-02*02 | TCRBJ02-07*01 |
| CASRASNTYGYTF* (SEQ ID NO: 80) | TCRBV06-09*01 | TCRBJ01-02*01 | CASSLIAGLSYEQYF* (SEQ ID NO: 293) | TCRBV07-01*01 | TCRBJ02-07*01 |
| CASRASNTYGYTF* (SEQ ID NO: 80) | TCRBV06 | TCRBJ01-02*01 | CASSLIAGLSYEQYF* (SEQ ID NO: 294) | TCRBV07-06*01 | TCRBJ02-07*01 |
| CASRGQNTGELFF* (SEQ ID NO: 71) | TCRBV06-05*01 | TCRBJ02-02*01 | CASSQLRTGDEYEQYF* (SEQ ID NO: 90) | TCRBV13-01*01 | TCRBJ02-07*01 |
| CASRGQNTGELFF* (SEQ ID NO: 71) | TCRBV06-01*01 | TCRBJ02-02*01 | CASSSRTKAYEQYF* (SEQ ID NO: 87) | TCRBV03 | TCRBJ02-07*01 |
| CASRGQNTGELFF* (SEQ ID NO: 71) | TCRBV06-06 | TCRBJ02-02*01 | CASSSRTKAYEQYF* (SEQ ID NO: 87) | TCRBV03 | TCRBJ02-07*01 |
| CASSDTPDLNTEAFF* (SEQ ID NO: 74) | TCRBV06-01*01 | TCRBJ01-01*01 | CASSSRTKAYEQYF* (SEQ ID NO: 87) | TCRBV02-01*01 | TCRBJ02-07*01 |
| CCASSFGTSGGTTYNEQFF (SEQ ID NO: 268) | TCRBV13-01*01 | TCRBJ02-01*01 | CASSSRTKAYEQYF* (SEQ ID NO: 87) | TCRBV02-01*01 | TCRBJ02-07*01 |
| CASSIQLFVRTEAFF* (SEQ ID NO: 269) | TCRBV19-01 | TCRBJ01-01*01 | CASSSRTKAYEQYF* (SEQ ID NO: 87) | TCRBV13-01*01 | TCRBJ02-07*01 |
| CASSLAGLAGTDTQYF* (SEQ ID NO: 78) | TCRBV07-09 | TCRBJ02-03*01 | CASSSRTKAYEQYF* (SEQ ID NO: 87) | TCRBV13-01*01 | TCRBJ02-07*01 |
| CASSLIAGLSYEQYF* (SEQ ID NO: 270) | TCRBV07-03*01 | TCRBJ02-07*01 | CASSVEDYTGELFF* (SEQ ID NO: 72) | TCRBV10-02*01 | TCRBJ02-02*01 |
| CASSRYGQGWEQYF (SEQ ID NO: 271) | TCRBV27-01*01 | TCRBJ02-07*01 | CASSVLNTGELFF* (SEQ ID NO: 73) | TCRBV06-05*01 | TCRBJ02-02*01 |
| CASSSRTKAYEQYF* (SEQ ID NO: 87) | TCRBV13-01*01 | TCRBJ02-07*01 | CASSVLNTGELFF* (SEQ ID NO: 73) | TCRBV06-05*01 | TCRBJ02-02*01 |
| CASSSRTKAYEQYF* (SEQ ID NO: 87) | TCRBV13-01*01 | TCRBJ02-07*01 | CASSVLNTGELFF* (SEQ ID NO: 73) | TCRBV06-09*01 | TCRBJ02-02*01 |
| CASSVEDYTGELFF* (SEQ ID NO: 72) | TCRBV03 | TCRBJ02-02*01 | CASSVLNTGELFF* (SEQ ID NO: 73) | TCRBV10-02*01 | TCRBJ02-02*01 |
| CASSVLNTGELFF* (SEQ ID NO: 73) | TCRBV09-01 | TCRBJ02-02*01 | CASSVLNTGELFF* (SEQ ID NO: 73) | TCRBV10-02*01 | TCRBJ02-02*01 |

TABLE 3-continued

List of all TCRβ Clonotypes Resolved from HLA-A*02 01/KLL-tetramer sorted T cells, Annotated by Patient

| CDR3 | TCRBV allele | TCRBJ allele | CDR3 | TCRBV allele | TCRBJ allele |
|---|---|---|---|---|---|
| CASSVLNTGELFF* (SEQ ID NO: 73) | TCRBV06-01*01 | TCRBJ02-02*01 | CASSVLNTGELFF* (SEQ ID NO: 73) | TCRBV10-02*01 | TCRBJ02-02*01 |
| CASSVLNTGELFF* (SEQ ID NO: 73) | TCRBV06-01*01 | TCRBJ02-02*01 | CASSYQIGLSYEQYF* (SEQ ID NO: 88) | TCRBV06 | TCRBJ02-07*01 |
| CASSYQIGLSYEQYF* (SEQ ID NO: 88) | TCRBV06-05*01 | TCRBJ02-07*01 | CASTLGNPSTDTQYF* (SEQ ID NO: 295) | TCRBV06 | TCRBJ02-03*01 |
| CASREGYSNQPQHF (SEQ ID NO: 272) | TCRBV19-01 | TCRBJ01-05*01 | CATRDINTGELFF* (SEQ ID NO: 94) | TCRBV06-01*01 | TCRBJ02-02*01 |
| CASSGRDRGSEKLFF (SEQ ID NO: 273) | TCRBV19-01 | TCRBJ01-04*01 | | w878 | |
| CASSGQVATHARNTIYF (SEQ ID NO: 274) | TCRBV21-01*01 | TCRBJ01-03*01 | | | |
| CASSHGRLNEKLFF (SEQ ID NO: 275) | TCRBV13-01*01 | TCRBJ01-04*01 | CASRGGASYNEQFF (SEQ ID NO: 296) | TCRBV28-01*01 | TCRBJ02-01*01 |
| CATSHSTVGYGYTF (SEQ ID NO: 276) | TCRBV10-03*01 | TCRBJ01-02*01 | CASSILLFSGNTIYF (SEQ ID NO: 297) | TCRBV19-01 | TCRBJ01-03*01 |
| CASSFDSKGSNTGELFF (SEQ ID NO: 89) | TCRBV28-01*01 | TCRBJ02-02*01 | CAIRSRDQNTGELFF (SEQ ID NO: 298) | TCRBV10-03*01 | TCRBJ02-02*01 |
| CASSLIIGRDPYEQYF (SEQ ID NO: 277) | TCRBV07-09 | TCRBJ02-07*01 | CASSQDARRSGNTIYF (SEQ ID NO: 299) | TCRBV14-01*01 | TCRBJ01-03*01 |
| CASSLVPSGSPVSAGELFF (SEQ ID NO: 278) | TCRBV11-02*02 | TCRBJ02-02*01 | CASSIQEGYSEQYF (SEQ ID NO: 300) | TCRBV19-01 | TCRBJ02-07*01 |
| CASSLWVAGYEQYF (SEQ ID NO: 279) | TCRBV07-09 | TCRBJ02-01*01 | CASSPALATTSRANVLTF (SEQ ID NO: 301) | TCRBV21-01*01 | TCRBJ02-06*01 |
| CSARLANSYEQYF (SEQ ID NO: 280) | TCRBV20 | TCRBJ02-07*01 | CASRTSNTYGYTF (SEQ ID NO: 302) | TCRBV06-05*01 | TCRBJ01-02*01 |
| CAISARDQNTGELFF* (SEQ ID NO: 75) | TCRBV10-03*01 | TCRBJ02-02*01 | CAIRAADQNTGELFF (SEQ ID NO: 303) | TCRBV10-03*01 | TCRBJ02-02*01 |
| | w1045 | | CASRQFLATPSDNEQFF (SEQ ID NO: 304) | TCRBV21-01*01 | TCRBJ02-01*01 |
| CASRTGSSYNEQFF (SEQ ID NO: 308) | TCRBV28-01*01 | TCRBJ02-01*01 | CASSLLRTSQETQYF (SEQ ID NO: 305) | TCRBV12 | TCRBJ02-05*01 |
| CASSTGEPGVYGYTF (SEQ ID NO: 309) | TCRBV06-05*01 | TCRBJ01-02*01 | CASSIQEGYSEQYF (SEQ ID NO: 306) | TCRBV19-01 | TCRBJ02-05*01 |
| CASTPGAGLKNEQFF (SEQ ID NO: 310) | TCRBV06-05*01 | TCRBJ02-01*01 | YASSDKSLGGVDTGELFF (SEQ ID NO: 307) | TCRBV26-01*01 | TCRBJ01-03*01 |
| CASSTGEPGVYGYTF (SEQ ID NO: 311) | TCRBV06-01*01 | TCRBJ01-02*01 | | w1116 (PBMC) | |
| CASTTGEGYEQYF (SEQ ID NO: 312) | TCRBV06-05*01 | TCRBJ02-07*01 | CAIRTLDMNTGELFF (SEQ ID NO: 320) | TCRBV10-03*01 | TCRBJ02-02*01 |
| CASSSGASLLNEQFF (SEQ ID NO: 313) | TCRBV06-05*01 | TCRBJ02-01*01 | CASSLNIAHHSDNEQFF (SEQ ID NO: 321) | TCRBV21-01*01 | TCRBJ02-01*01 |
| | w1051 | | CASKRLAGEGTGELFF (SEQ ID NO: 322) | TCRBV06 | TCRBJ02-02*01 |
| | | | CAISTLDMNTGELFF (SEQ ID NO: 323) | TCRBV10-03*01 | TCRBJ02-02*01 |
| CSARTGYNEQFF (SEQ ID NO: 314) | TCRBV20 | TCRBJ02-01*01 | CAIRTLDMNTGELFF (SEQ ID NO: 324) | un-resolved | TCRBJ02-02*01 |
| CASILIAGGYNEQFF (SEQ ID NO: 315) | TCRBV02-01*01 | TCRBJ02-01*01 | CASSSSTEILWLHL (SEQ ID NO: 325) | TCRBV28-0101 | TCRBJ01-02*01 |
| CASILIAGAYNEQFF (SEQ ID NO: 316) | TCRBV02-01*01 | TCRBJ02-01*01 | | w1116 (TIL) | |
| CASSPEGSGGYTF (SEQ ID NO: 317) | TCRBV18-01*01 | TCRBJ01-02*01 | CAIRTLDMNTGELFF (SEQ ID NO: 326) | TCRBV10-03*01 | TCRBJ02-02*01 |
| CASRCLVLQQSRANVLTF (SEQ ID NO: 318) | TCRBV21-01*01 | TCRBJ02-06*01 | CASSGPDGDNEQFF (SEQ ID NO: 327) | TCRBV09-01 | TCRBJ02-01*01 |
| CASSADRGGWSGNQPQHF (SEQ ID NO: 319) | TCRBV12 | TCRBJ01-05*01 | CAIRTLDMNTGELFF* (SEQ ID NO: 328) | TCRBV10-03*01 | TCRBJ02-02*01 |
| | | | CASSYPDVYEQYF* (SEQ ID NO: 329) | TCRBV06 | TCRBJ02-07*01 |
| w1116 (TIL) (Cont.) | | | CAIRTLDMNTGELFF* (SEQ ID NO: 330) | TCRBV10-03*01 | TCRBJ02-02*01 |
| CASSETGTWDEQYF (SEQ ID NO: 343) | TCRBV10-02*01 | TCRBJ02-07*01 | CAIRIRDQNTGELFF (SEQ ID NO: 331) | TCRBV10-03*01 | TCRBJ02-02*01 |
| CAIRTLDMNTGELFF* (SEQ ID NO: 344) | TCRBV10-03*01 | TCRBJ02-02*01 | CAIRTLDMNTGELFF* (SEQ ID NO: 332) | TCRBV06-05*01 | TCRBJ02-02*01 |
| CAIRTLDMNTGELLF (SEQ ID NO: 345) | TCRBV10-03*01 | TCRBJ02-02*01 | CASSYPDVYEQYF* (SEQ ID NO: 333) | TCRBV06 | TCRBJ02-05*01 |
| CAIRTLDMNTGELFF* (SEQ ID NO: 346) | TCRBV06 | TCRBJ02-02*01 | CASSEGKTKSQSRANVLTF (SEQ ID NO: 334) | TCRBV19-01 | TCRBJ02-06*01 |
| CASSSSTESYGYTF (SEQ ID NO: 347) | TCRBV28-01*01 | TCRBJ01-02*01 | | | |
| CAIRTLDMNTGELFF* (SEQ ID NO: 348) | TCRBV06-01*01 | TCRBJ02-02*01 | CASSLGNTEAFF (SEQ ID NO: 335) | TCRBV11-02*02 | TCRBJ01-01*01 |

TABLE 3-continued

List of all TCRβ Clonotypes Resolved from HLA-A*02 01/KLL-tetramer sorted T cells, Annotated by Patient

| CDR3 | TCRBV allele | TCRBJ allele | CDR3 | TCRBV allele | TCRBJ allele |
|---|---|---|---|---|---|
| CASSGPDGDNEQFF (SEQ ID NO: 349) | TCRBV09-01 | TCRBJ02-01*01 | CASSLVSSGGEAFF (SEQ ID NO: 336) | TCRBV07-09 | TCRBJ01-01*01 |
| CASSERHLHARNTIYF (SEQ ID NO: 350) | TCRBV03 | TCRBJ01-03*01 | CAIRTLDMNTGDLFF (SEQ ID NO: 337) | TCRBV10-03*01 | TCRBJ02-02*01 |
| CASRSLIATLLDEQYF (SEQ ID NO: 351) | TCRBV21-01*01 | TCRBJ02-07*01 | CASKKLDRPAPNSPLHF (SEQ ID NO: 338) | TCRBV03 | TCRBJ01-06*01 |
| CASSSTLKSQSRANVLTF (SEQ ID NO: 352) | TCRBV19-01 | TCRBJ02-06*01 | CASSGPDGGNEQFF* (SEQ ID NO: 339) | TCRBV09-01 | TCRBJ02-01*01 |
| CAISEPSGAQHF (SEQ ID NO: 353) | TCRBV10-03*01 | TCRBJ01-05*01 | CASSGPDGGNEQFF* (SEQ ID NO: 340) | TCRBV09-01 | TCRBJ02-01*01 |
| CATSDPLAASYEQYF (SEQ ID NO: 354) | TCRBV24 | TCRBJ02-07*01 | CASSSQRKSYGYTF (SEQ ID NO: 341) | TCRBV28-01*01 | TCRBJ01-02*01 |
| | | | CASSSSRKSYGYTF (SEQ ID NO: 342) | TCRBV28-01*01 | TCRBJ01-02*01 |

*Denotes non-unique CDR3s within a patient, encoded by a unique TRB nucleotide sequence and/or unique TCRBV or TCRBJ.

Figure 6:
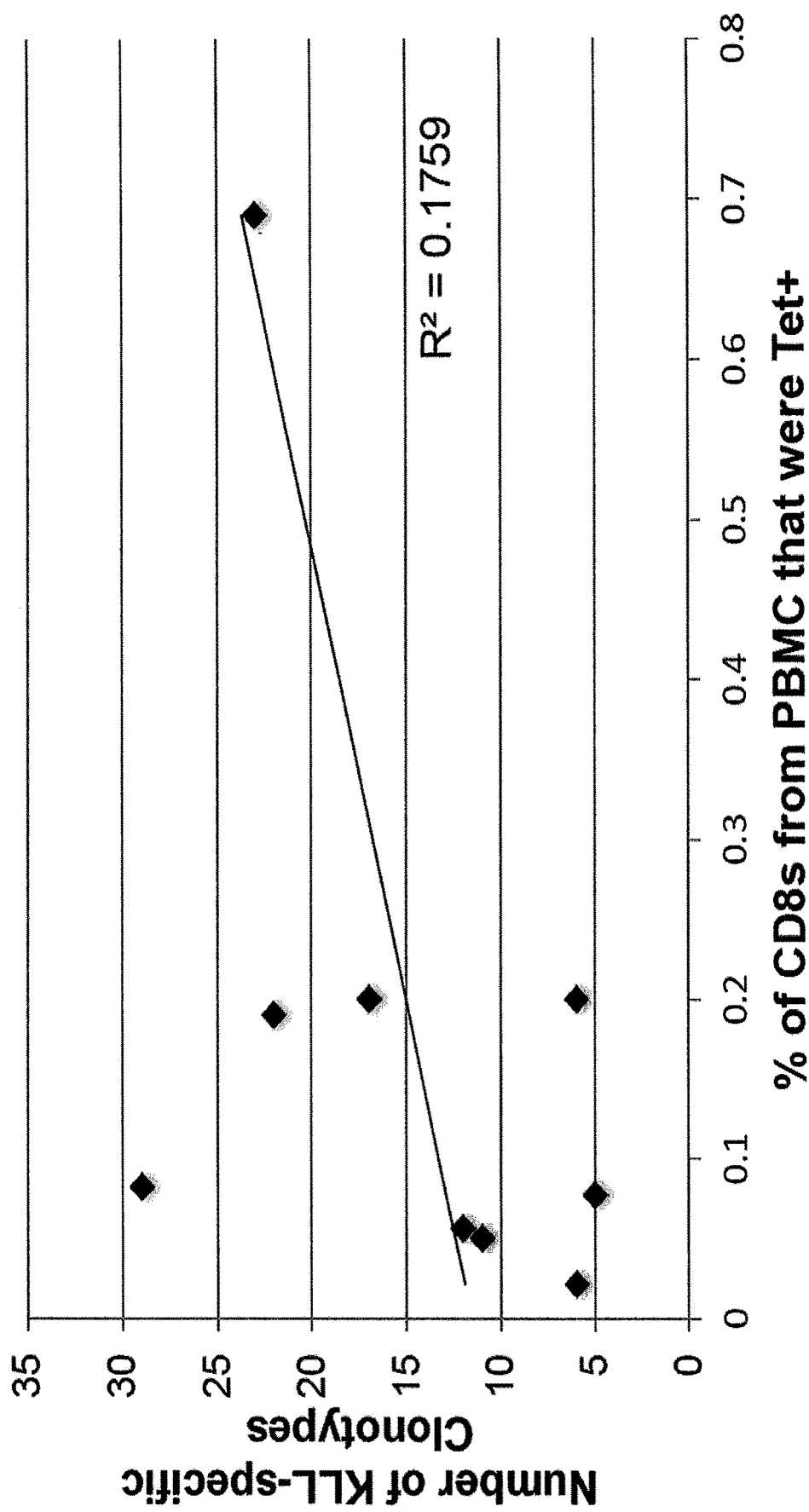
FIG. 6 shows KLL-specific TCR diversity in PBMC is not correlated with the magnitude of KLL-specific responses. Number of unique clonotypes (present at ≥2 estimated number of genomes in each sample) was plotted against % of CD8+ cells positive for KLL-tetramer staining. No significant correlation was found (r2=0.17).
Figure 7A:
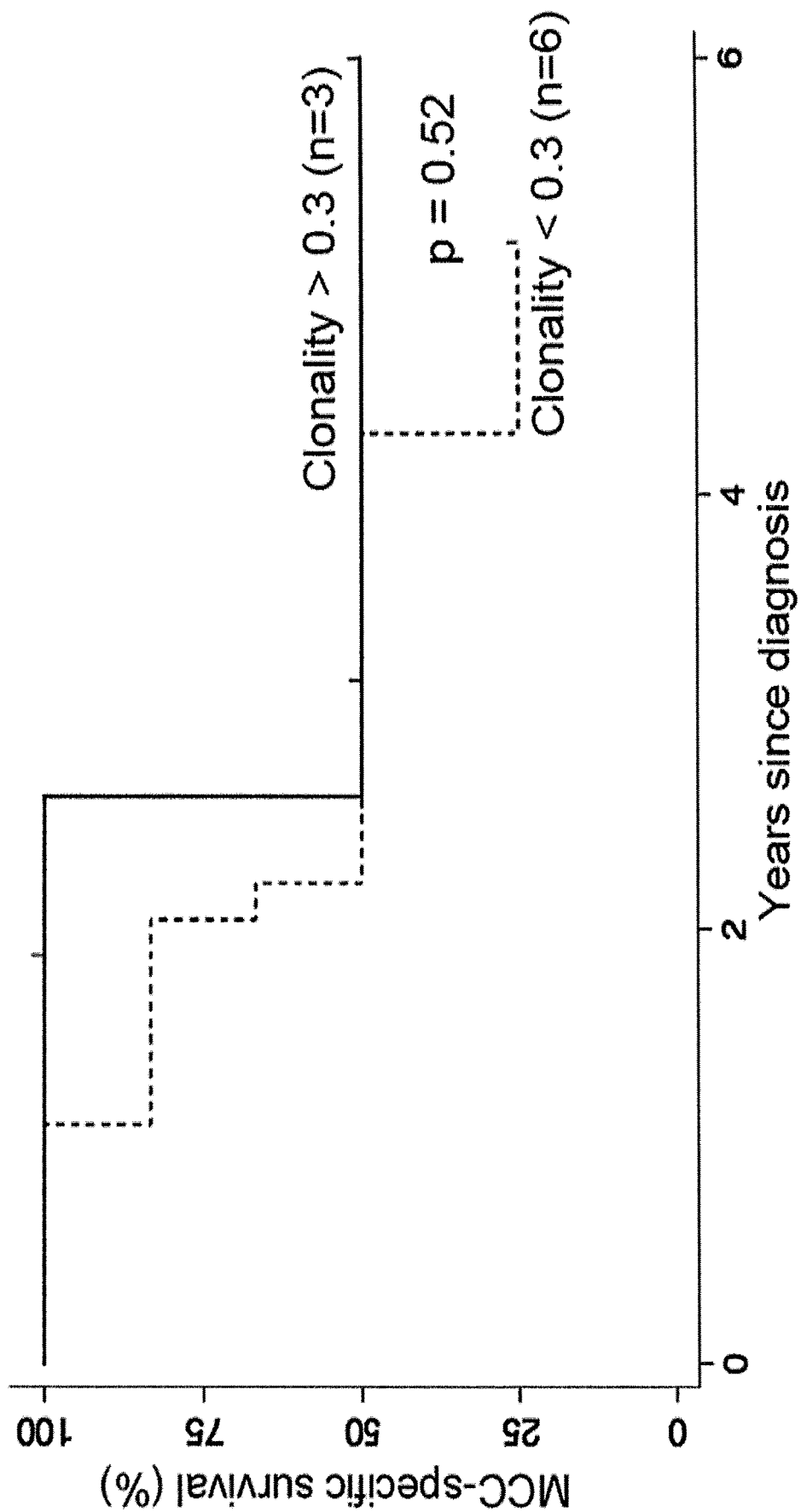
FIGS. 7A and 7B show clonality of KLL-specific T cell repertoire in PBMC of MCC patients does not correlate with disease outcome. Clonality of the KLL-specific repertoire from PBMC was calculated and patients were binned by high (>0.3, n=3) or low (<0.3, n=6) clonality. MCC-specific survival (A) or recurrence-free survival (B) between the two groups of patients were not significantly different by univariate analysis (p=0.52 or p=0.81 by log-rank test).
Figure 7B:
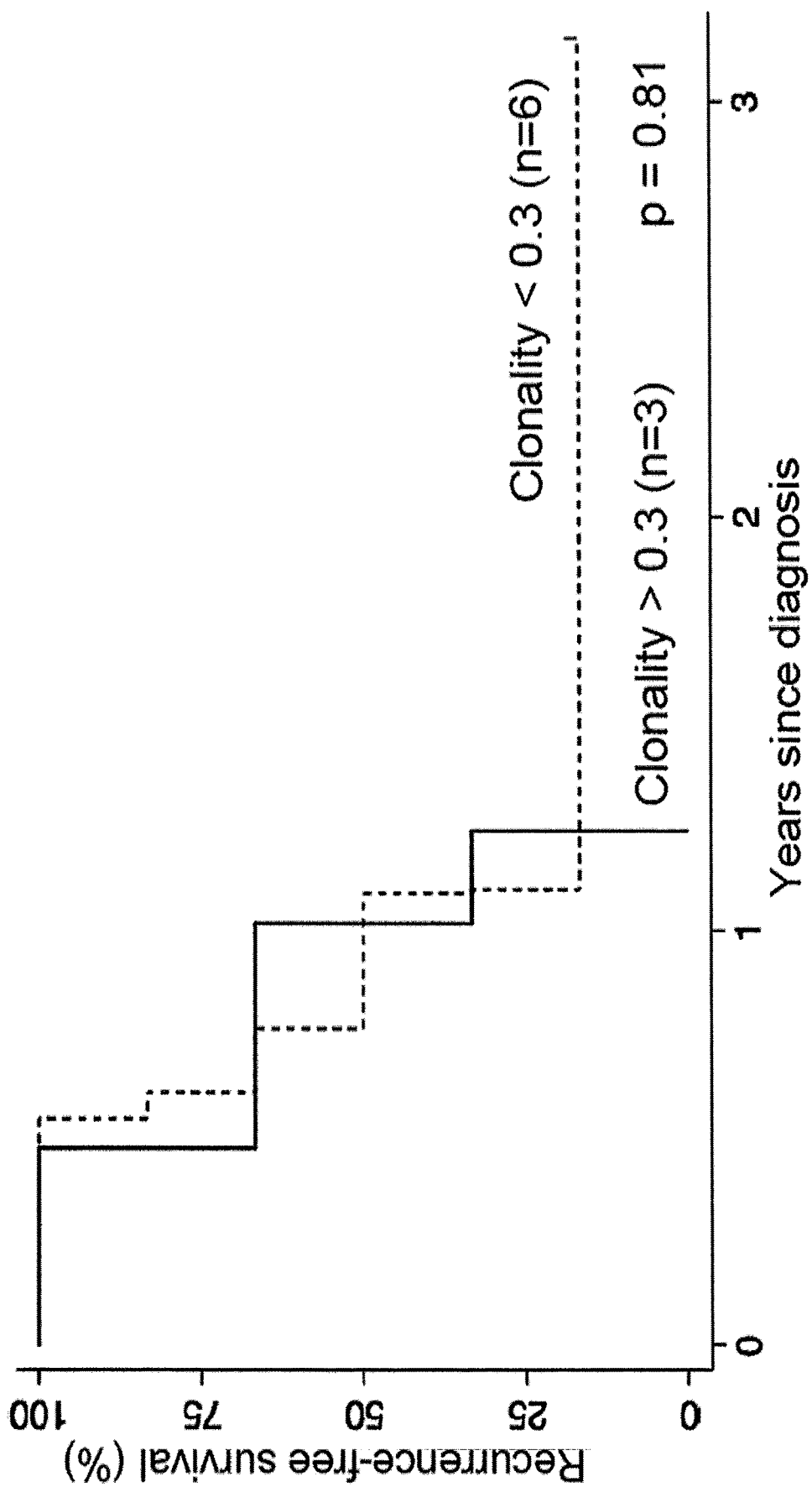

Paired KLL tetramer+ T cells from both PBMC and TIL were available for two patients (boxed). The diversity of the tetramer+ TRB repertoire varied greatly between patients. The overall TRB diversity in a sample was not correlated with the frequency of tetramer+ T cells among total CD8+ cells in PBMC (FIG. 6). The clonality of each tetramer+ sample from PBMC (range: 0-1 with a completely clonal sample=1; see Methods for details) was determined, which showed that there was no significant difference in MCC-specific survival or recurrence-free survival between patients with a less clonal (clonality<0.3, n=6) or more clonal (clonality>0.3, n=3) KLL-specific repertoire in their PBMC (FIG. 7, p=0.52 and p=0.81 by log-rank test).

Example 5

Assessment of T Cell Repertoire within Matched Tumor Samples

Figure 8A:
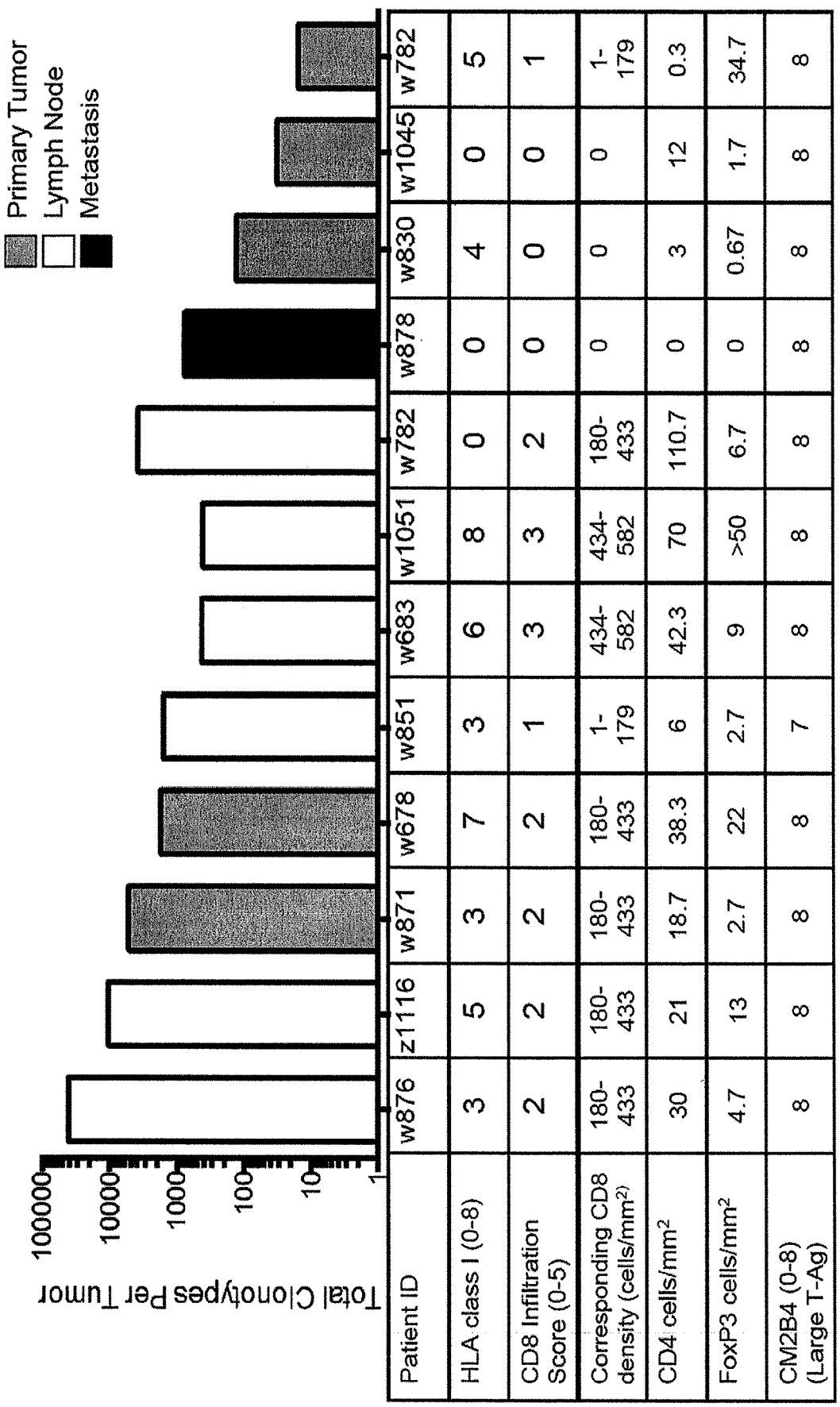
FIGS. 8A and 8B show T cell infiltrate of tumor samples characterized by TCR repertoire and IHC. (A) Tumors from 9 patients were analyzed for TCRβ repertoire and stained for HLA-I, CD8, CD4, and FoxP3. Due to low DNA yield from patient w782's primary tumor, the patient's nodal recurrence was also characterized. Tumor samples contained between 16 and 41,645 unique TCRs. Intratumoral CD8+ infiltration was categorized on a 0-5 scale as previously described (Paulson et al., 2011), with corresponding range of CD8+ cells/mm² below based on the scale from the same reference. CD4+ and FoxP3+ cells were scored directly as cells/mm². CD8+ cells infiltrated tumors more frequently than CD4+ or FoxP3+ cells in most tumors indicating that most TCRs are likely from CD8+ T cells. CM2B4 IHC (anti-MCPyV Large T Ag) was scored using the Allred system. Primary tumors=grey bars; lymph nodes=white; metastasis=black. (B) The density of T cells within each sample was normalized by dividing the number of T cells (per normalized sequencing) by the total amount of genomic DNA in each sample, per Adaptive Biotechnologies ImmunoSeq platform. Patients were separated a priori into those with many T cells (≥0.8 T cells/ng tumor DNA, n=7) or few T cells (<0.3 T cells/ng tumor DNA, n=3). There is no survival difference among patients based on their general immune infiltrate (p=0.59 by log-rank test).

Archival tumor samples were analyzed from 11 of 12 patients; tumor from w750 was unavailable. When possible, primary tumors were acquired (n=6). For four patients with an unknown primary who presented with nodal disease, lymph nodes were analyzed. Primary tumor from w878 had insufficient material for study and, therefore, a metastasis corresponding to the time of PBMC collection was analyzed. The primary tumor sample from w782 was small and, therefore, to ensure adequate sampling, a nodal tumor present at time of diagnosis from w782 was also analyzed. Tumors were assessed via immunohistochemistry (IHC) for viral status; HLA-I expression; and CD8+, CD4+ and FoxP3+ T cell infiltration (FIG. 8A). All patients were robustly positive for MCPyV Large T-Ag protein by IHC. CD8+ cells were more predominant than CD4+ or FoxP3+ T cells in the majority of samples. TRB CDR3 of all T cells in each tumor sample were sequenced and total unique TCRβ clonotypes/tumor were plotted in FIG. 8A (n=12, range=16-41,645 unique clonotypes/tumor).

Figure 8B:
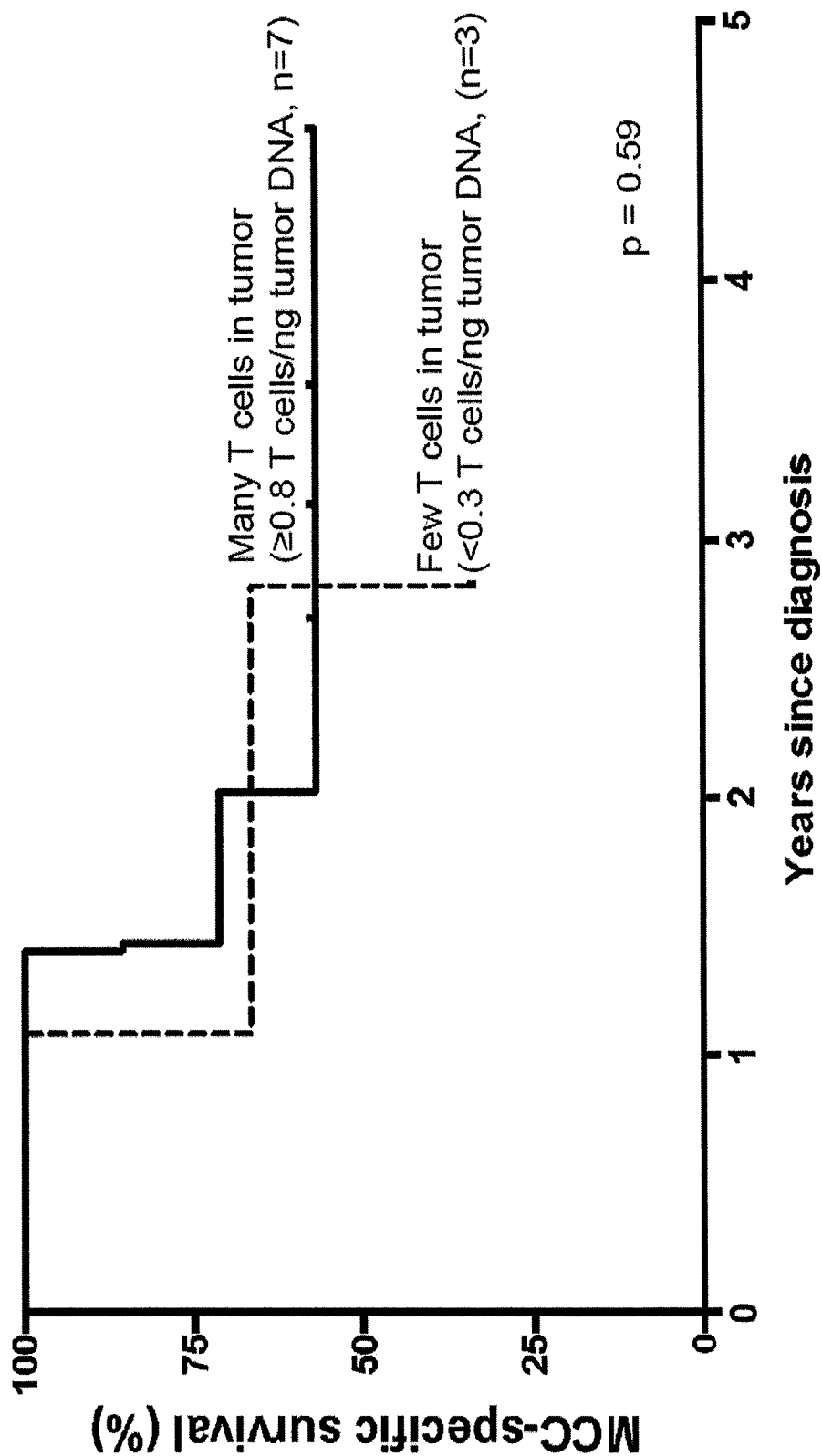
Figure 9A:
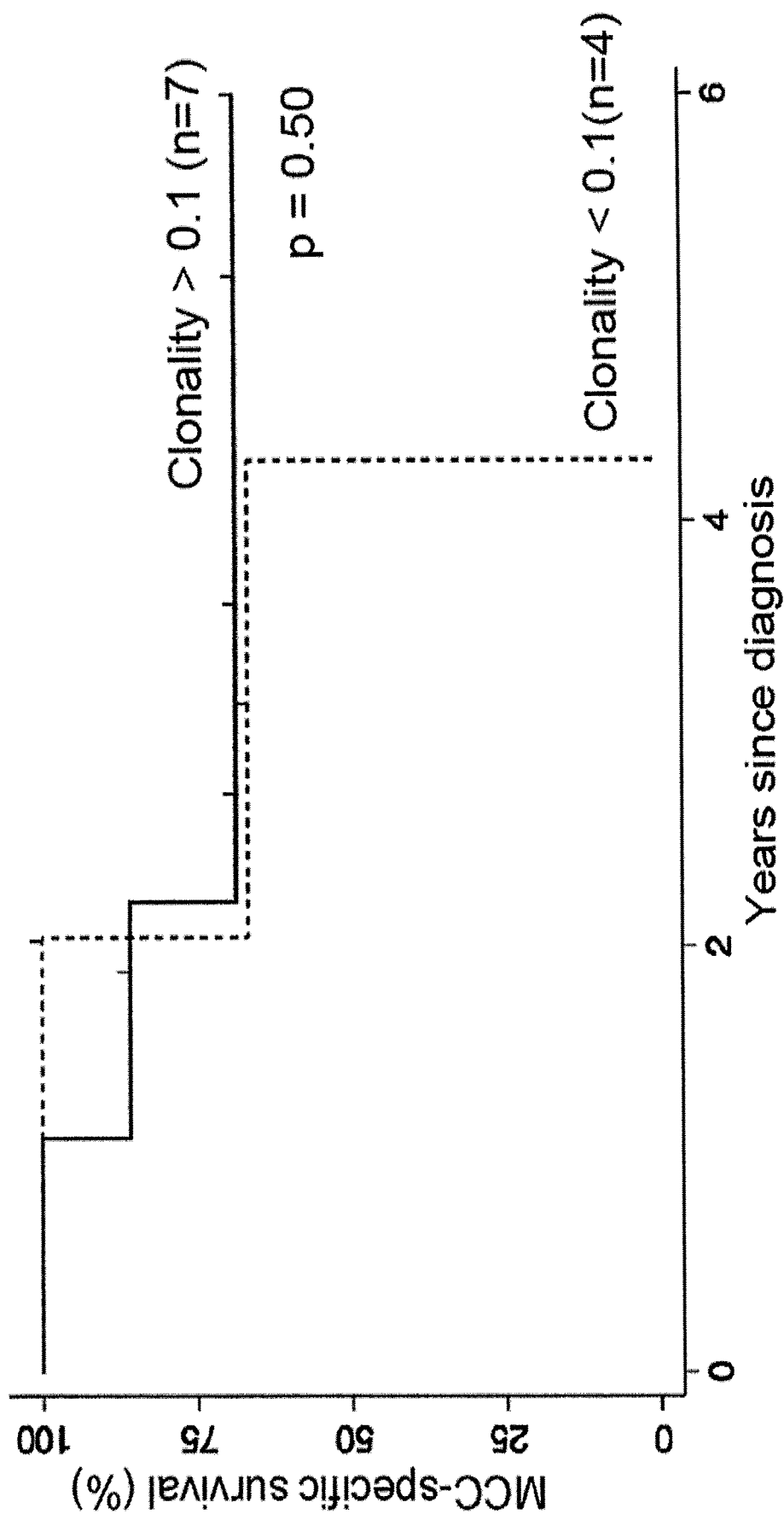
FIGS. 9A and 9B show clonality of T cell repertoire within tumors of MCC patients does not correlate with disease outcome. Patients were binned by whether their tumors had high (>0.1, n=7) or low (<0.1, n=4) clonality. (A) MCC-specific survival or (B) recurrence-free survival between the two groups of patients was not significantly different by univariate analysis (p=0.50 or p=0.64, respectively).
Figure 9B:
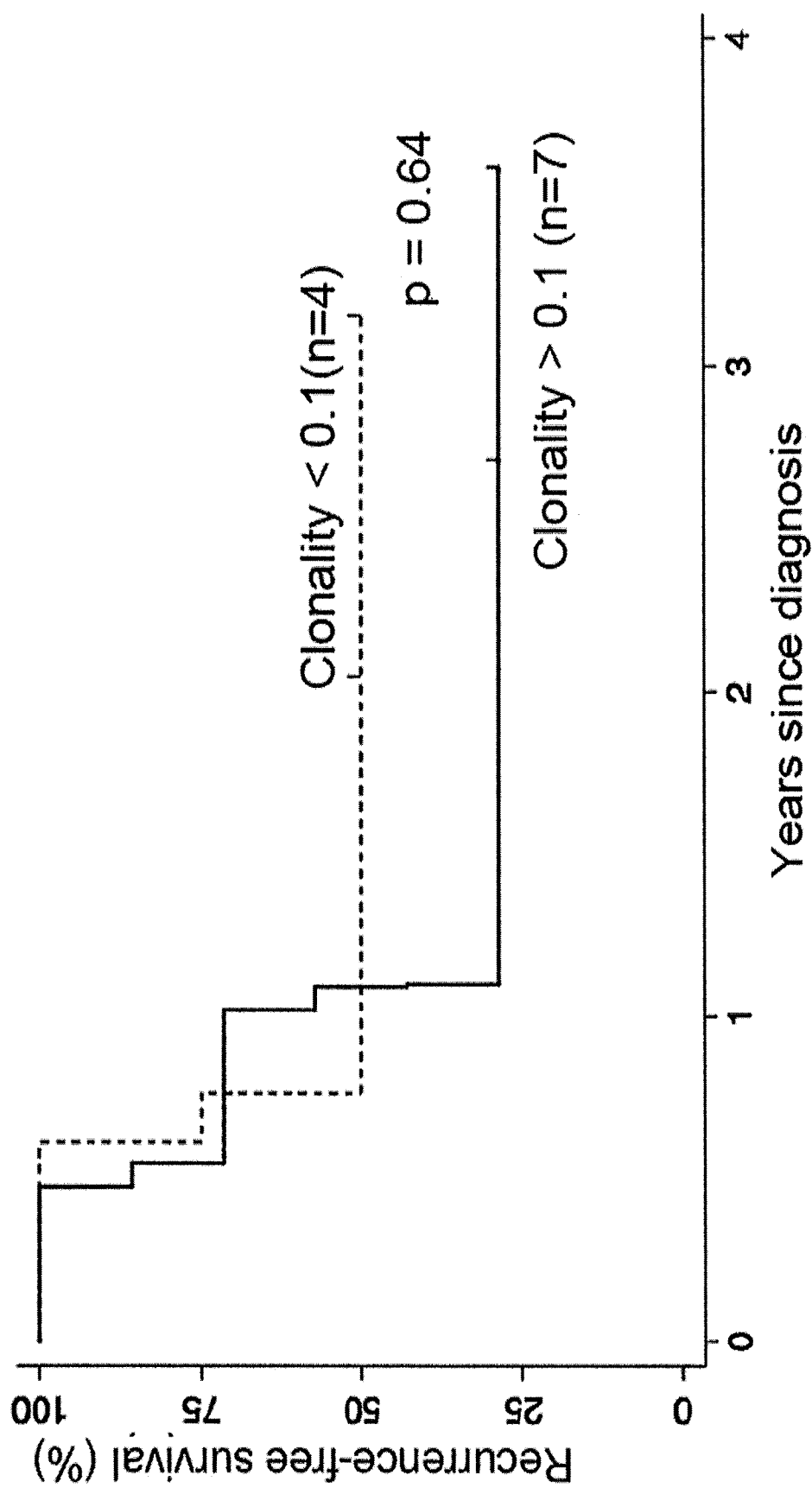

Whether having a greater number of total T cells was analyzed to determine if this was associated with a survival benefit. A priori, patients were binned by whether their tumors had many infiltrating T cells (TILs) (≥0.8 T cells/ng tumor DNA, n=7) or few T cells <0.3 T cells/ng tumor DNA, n=3); there was no detectable survival difference between these two groups of patients (FIG. 8B, p=0.59 by log-rank test). In addition, the TRB clonality of each tumor analyzed was calculated. Increased clonality of the immune infiltrate within tumors is thought to represent an enrichment of cancer antigen-specific T cells and has been associated with improved response to immunotherapy (Tumeh et al., Nature 515:568, 2014). There was no significant difference in MCC-specific survival or recurrence-free survival between patients with a less clonal repertoire in their tumors (clonality<0.1, n=7) versus those with a more clonal repertoire (clonality>0.1, n=4; FIGS. 9A and 9B, p=0.50 and p=0.64 by log-rank test).

Example 6

Assessment of Frequency of KLL-Specific TILs and MCC-Specific Survival

Figure 3A:
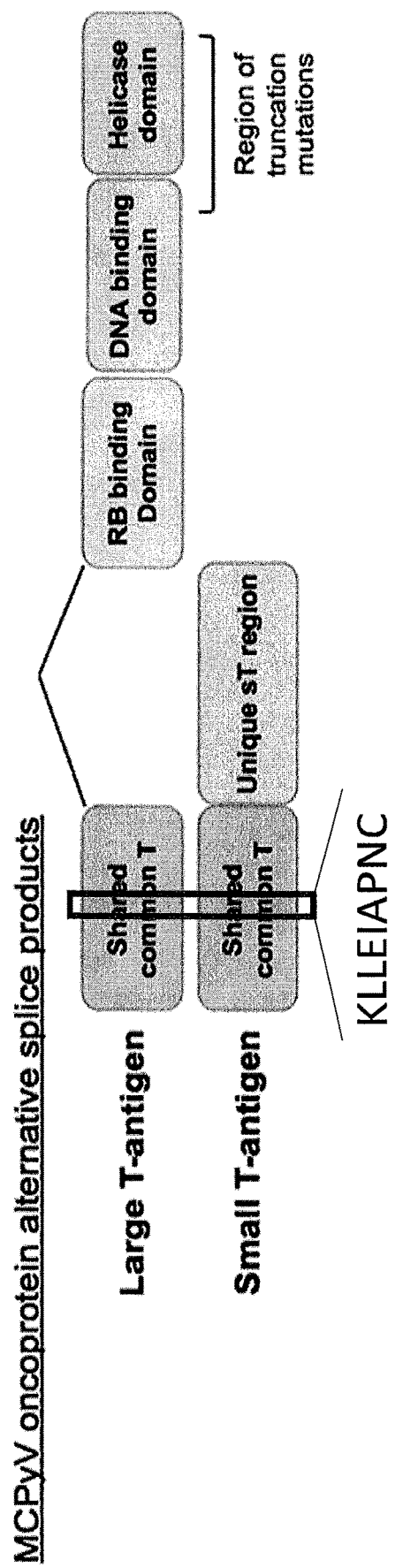
FIGS. 3A-3F show T antigen structure and that increased tumor infiltration of KLL-specific clonotypes are associated with improved MCC-specific survival. (A) A schematic of the different domains of the Merkel cell polyomavirus (MCPyV) large T antigen (LTA) and the small T antigen (STA). The location of the antigenic peptide found in both the LTA and STA-KLLEIAPNC (SEQ ID NO:17); referred to herein as the KLL peptide—which is bound with high avidity by the TCRs of this disclosure. (B) A wedge plot representing the total number of productive unique clonotypes/tumor plotted for each tumor on a log scale. Each tumor is identified by patient "w" or "z" number and type of tumor. Tumors from 11 of 12 patients were analyzed; no tumor could be acquired for patient w750. Primary tumor from w782 was small and LN was analyzed to ensure adequate sampling. KLL-specific clonotypes are depicted within each tumor with a width approximately proportional to their frequency within each tumor. More predominant clonotypes are located to the left for each tumor. The number of KLL-specific clonotypes out of the total number of unique clonotypes is tabulated at far right. Wedges for tumors from patients alive at time of sensor are in black, and wedges for tumors in grey are from patients who have died of MCC. (C) MCC-specific survival was significantly increased for patients who had higher (n=9) versus lower (n=2) percentage of KLL-specific T cells in tumor (1.9-18% versus 0-0.14%, p=0.0009 by log-rank test). (D) MCC-specific survival was increased for patients who had many (5-108, n=7) unique KLL-specific clonotypes in their tumors, compared to patients with few KLL-specific clonotypes (0-3, n=4, p=0.0051 by by log-rank test). (E) There was no significant difference in recurrence-free survival between patients with a higher versus lower frequency of KLL-specific T cells (patients binned as in FIG. 3C; p=0.4492 by log-rank analysis). (F) Patients who had many KLL-specific clonotypes (5-108, n=7) had a trend toward better recurrence-free survival compared to patients with intermediate or few tetramer+ clonotypes (0-3, n=4, p=0.1977 by log-rank test). LN=lymph node; UP=unknown primary; 1=primary lesion; Met=metastasis.
Figure 3B:
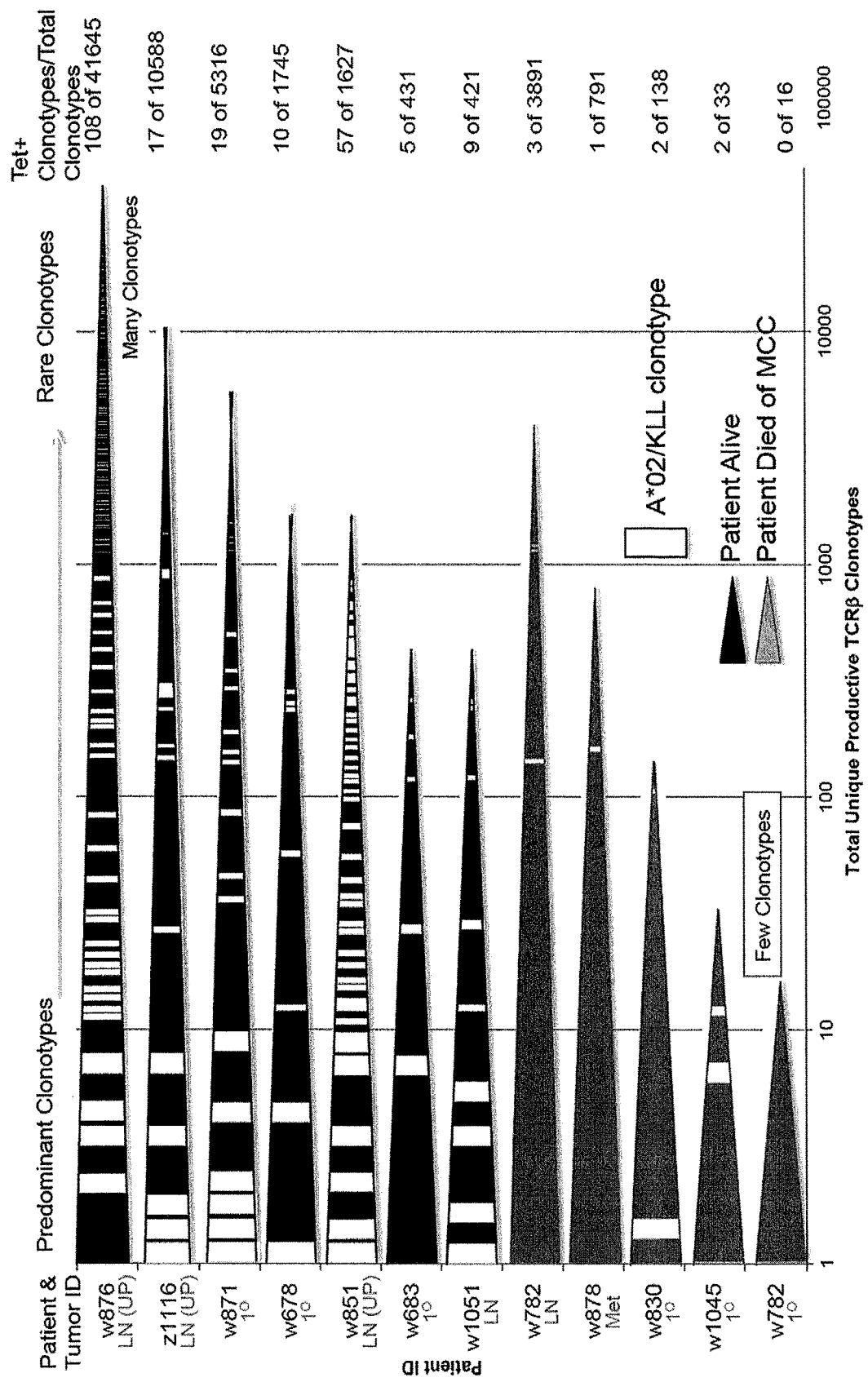
Figure 3C:
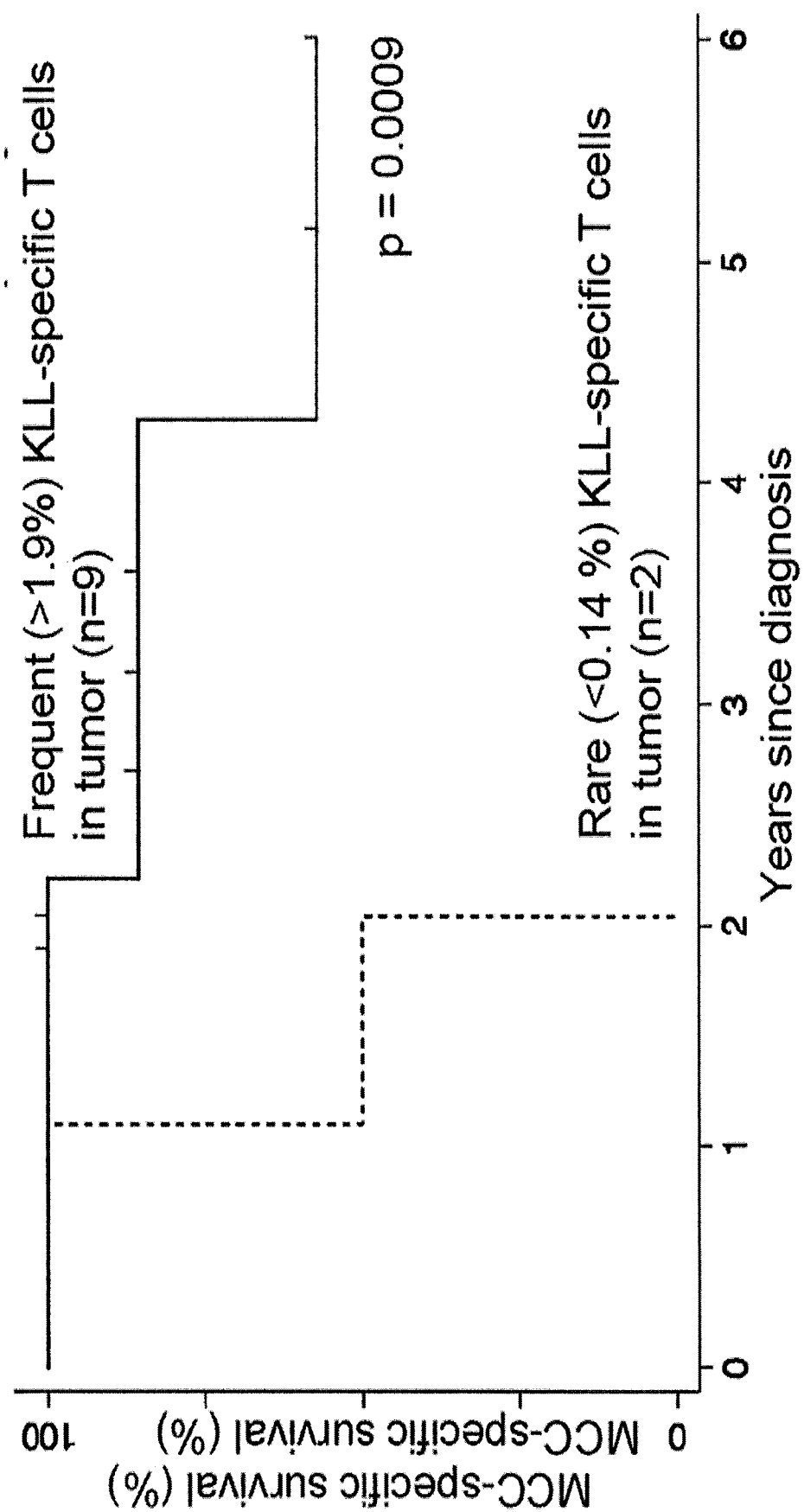
Figure 3D:
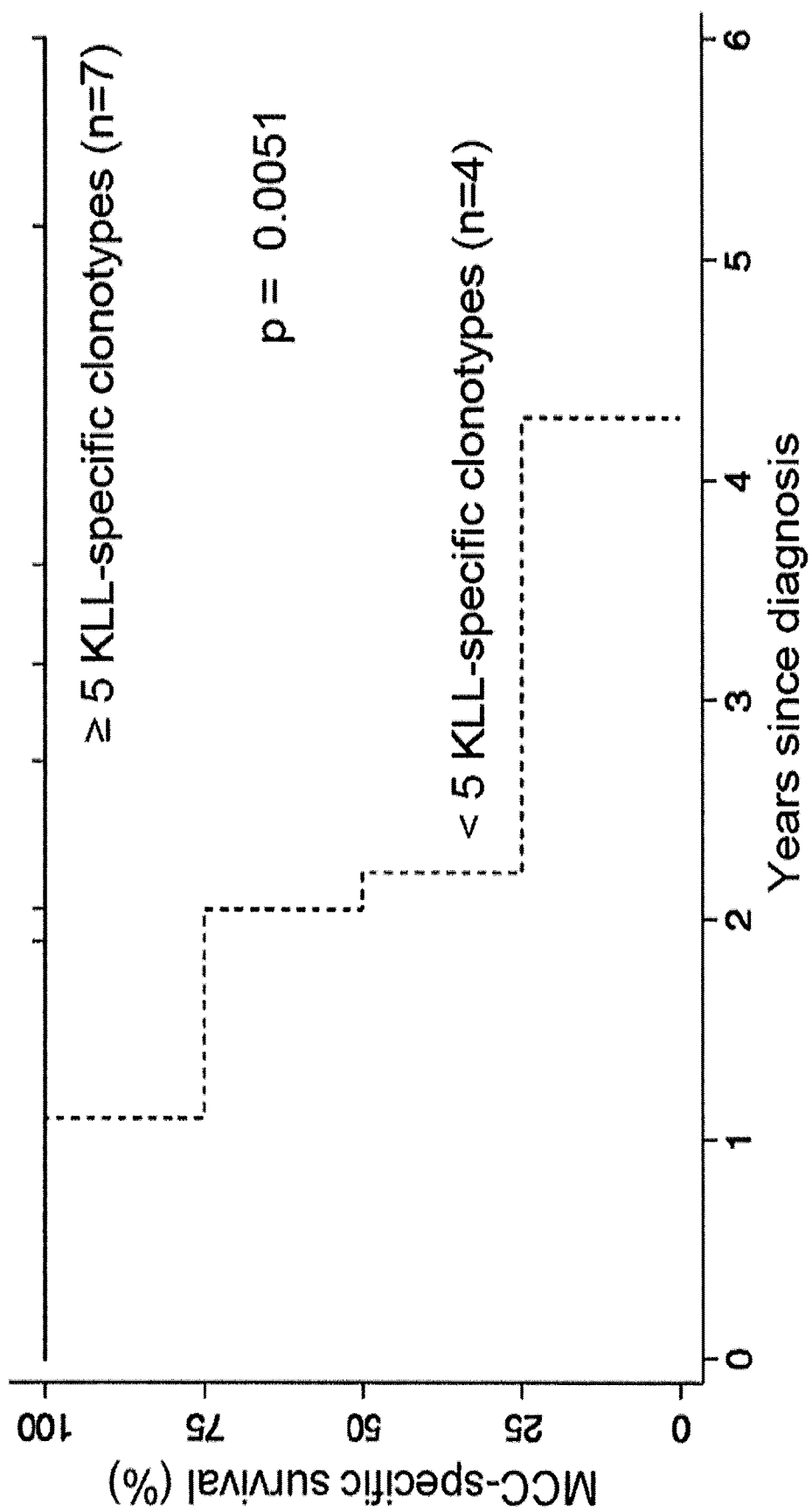
Figure 10A:
FIGS. 10A and 10B show the percentage and number of KLL Tetramer+ clonotypes amid tumors. (A) KLL-specific T cells constituted between 0-18% of the T cell repertoire of each tumor based on number of genomes sequenced. (B) Tumors contained between 0-108 unique KLL-specific clonotypes.
Figure 10B:
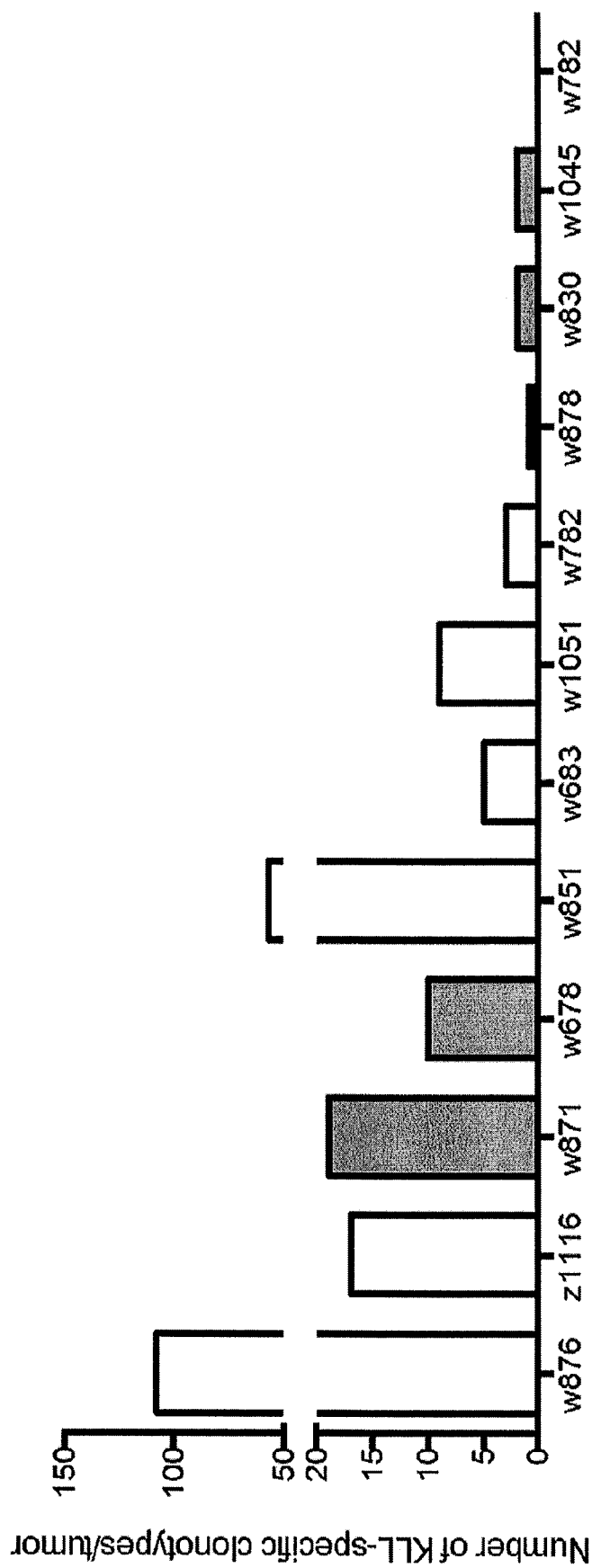

The frequency of KLL-specific T cells infiltrated MCC tumors was assessed next. KLL-specific clonotypes within tumors were identified by determining the intersection between TCRβ CDR3 amino acid sequences in the tetramer-sorted sample (from FIG. 2) and whole tumor samples from each patient. KLL-specific T cells constituted between 0-18% of the T cell repertoire of each tumor based on the total number of T cell genomes sequenced (n=12, mean 6.3%, s=5.8, FIG. 10A). Tumors contained between 0-108 unique KLL-specific TCRβ clonotypes (mean=19.4, s=32, FIG. 10B). The rank (based on frequency) of each KLL-specific clonotype within each tumor was plotted; individual clonotypes ranged between being the most prevalent clonotype to rare within each autologous tumor. KLL-specific clonotypes appeared to be more abundant (based on total percentage of all KLL-specific T cells in tumor) and predominant (based on percentage of individual KLL-specific clonotypes) in patients that were alive at last follow up (FIG. 3A). Patients were binned a priori based on percentage of tumor with KLL-specific T cells. MCC-specific survival was significantly increased for patients who had a higher (1.9-18%; n=7) versus lower (0-0.14%; n=2) percentage of KLL-associated T cells in tumor (FIG. 3C, p=0.0009 by log-rank test).

Figure 3E:
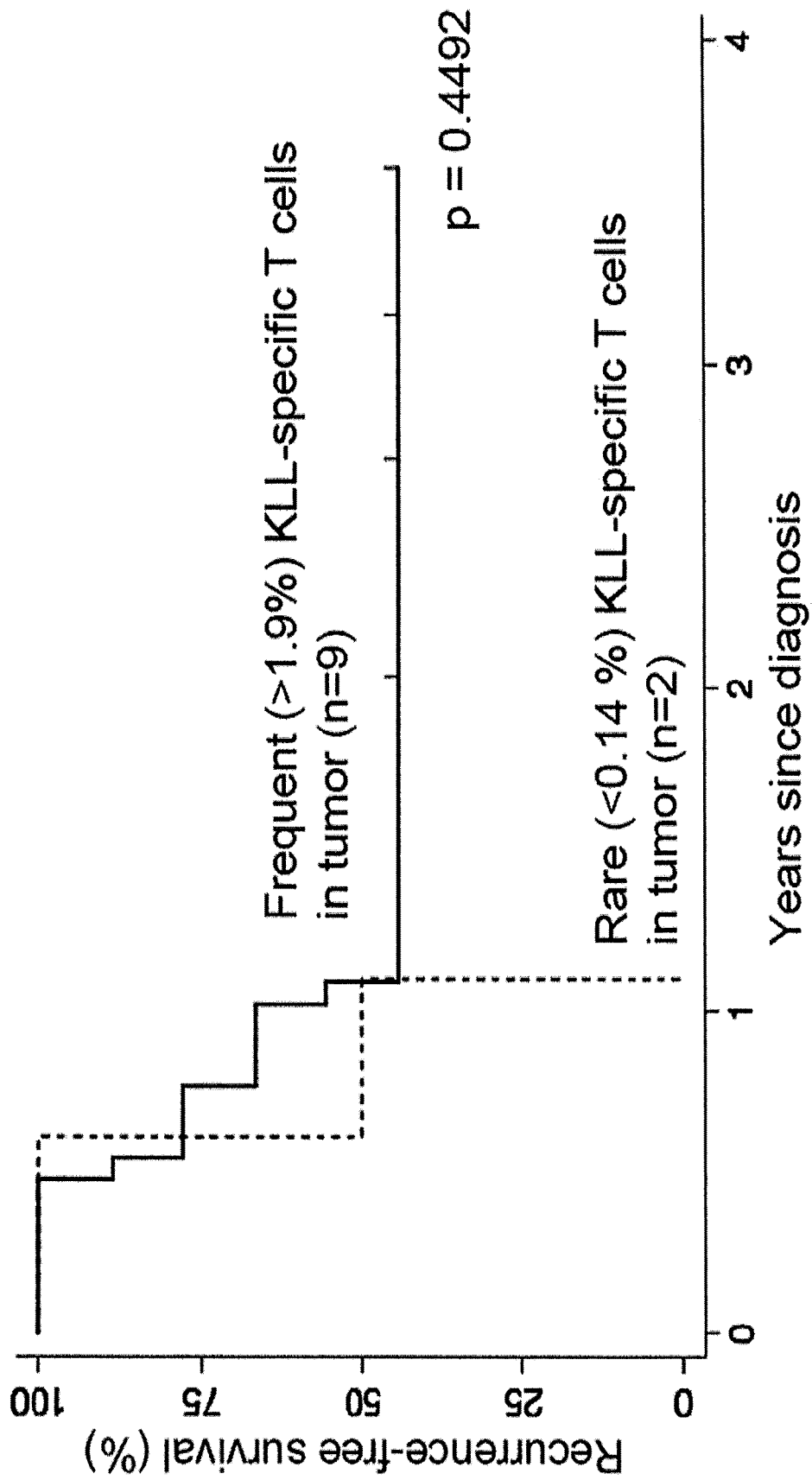
Figure 3F:
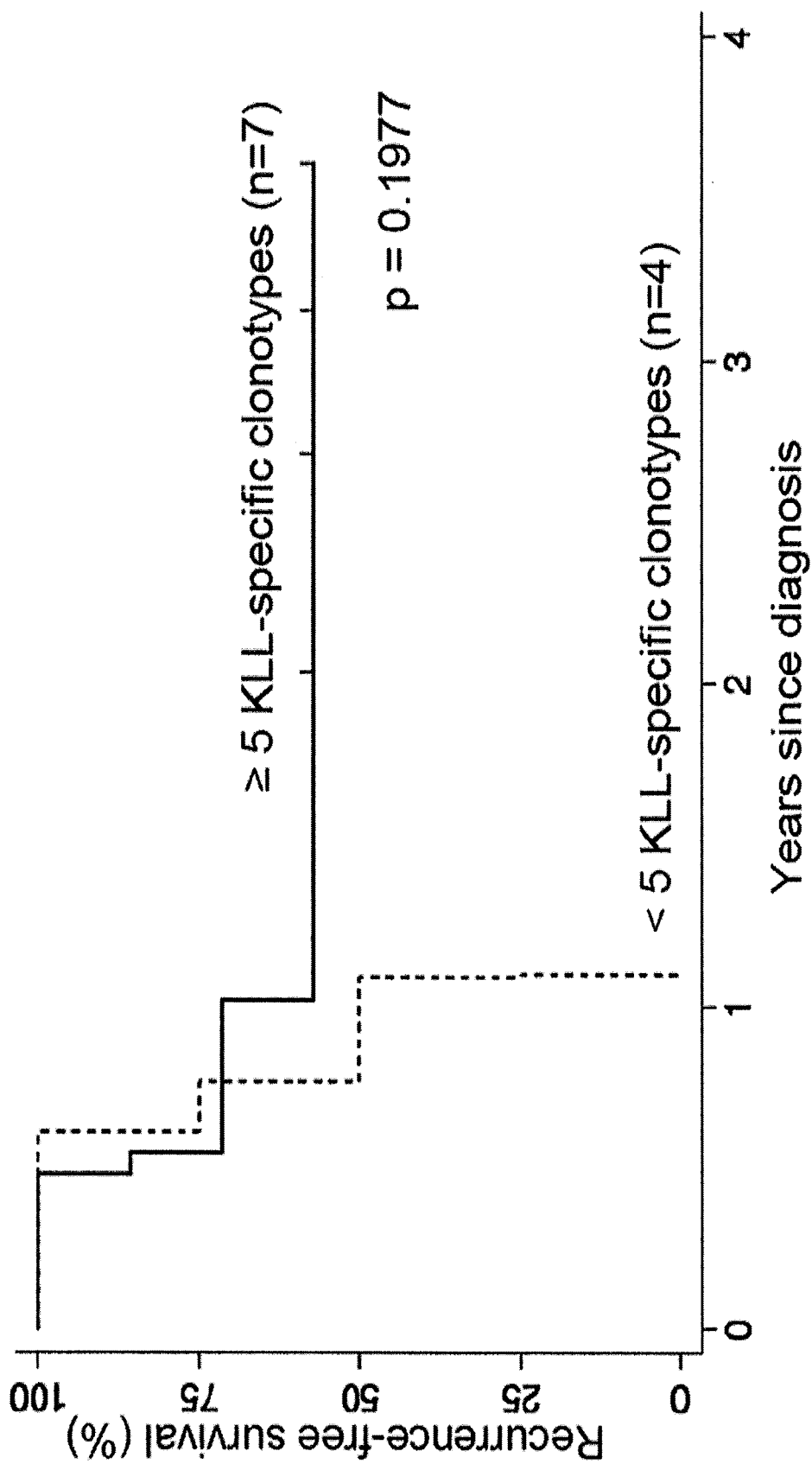

In addition, the number of unique KLL-specific TCRβ CDR3 clonotypes infiltrating tumors was measured to determine whether there was an association with survival. Indeed, there was a significant survival advantage among patients who had more (5-108, n=7) unique KLL-specific clonotypes in their tumors, compared to patients with few (0-3, n=4) KLL-specific clonotypes (FIG. 3C, p=0.0051). Next, the differences in frequency or diversity of KLL-specific T cell infiltration was assessed to determine whether these were associated with differences in recurrence-free survival. There was a trend for increased recurrence-free survival among patients with a higher versus lower frequency of KLL-specific T cells within tumors (FIG. 3E; p=0.4492), and among patients with more versus fewer KLL-specific clonotypes within tumors (FIG. 3F; p=0.1977).

Figure 4A:
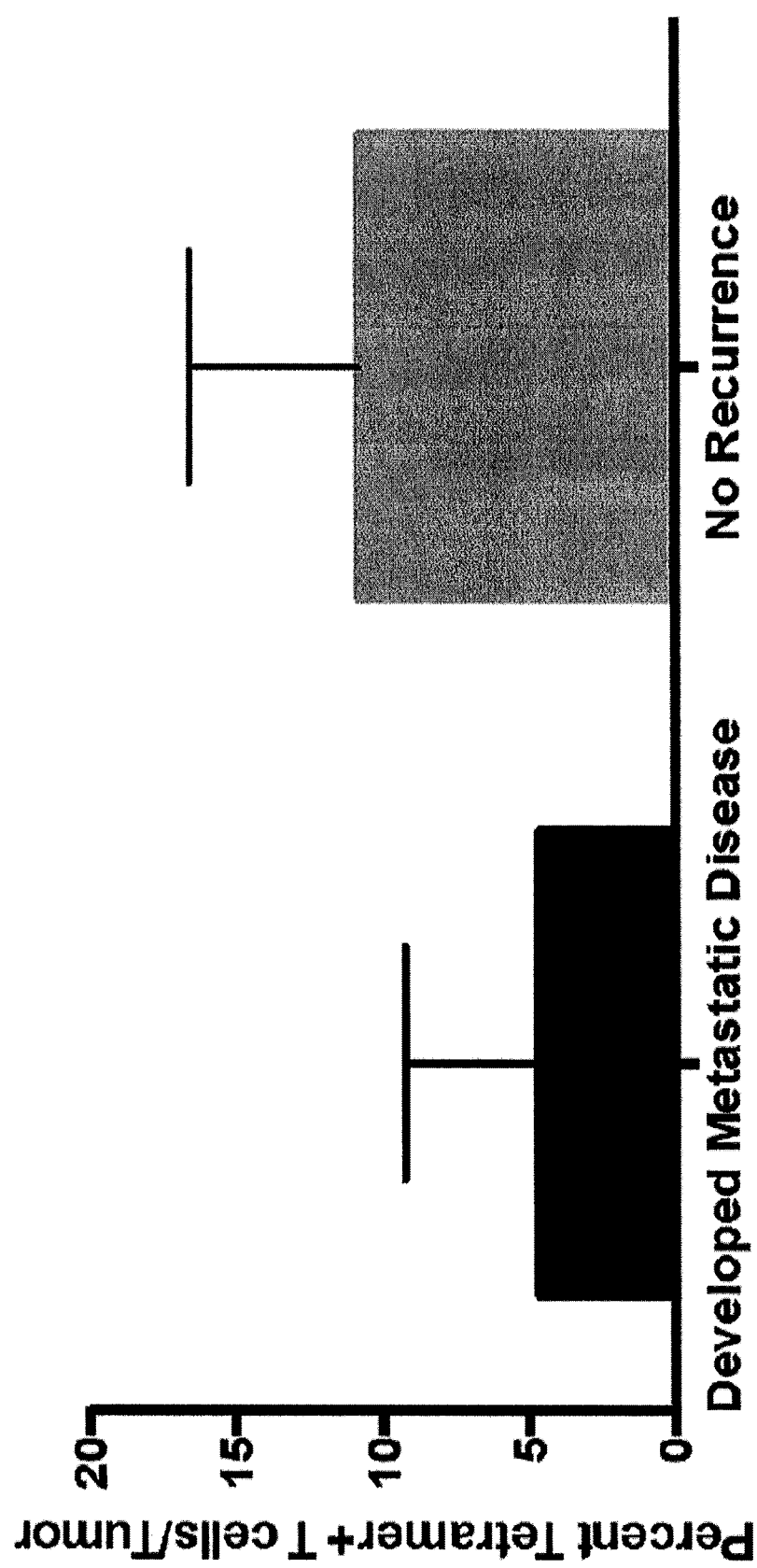
FIGS. 4A and 4B show patients without disease recurrence have a greater frequency and number of KLL-specific clonotypes in their tumors. Patients were grouped by whether they developed metastatic disease (n=7) or remained disease-free after definitive treatment of first presentation of disease (n=3). (A) The percentage of KLL-specific T cells was higher in patients without recurrence (range 4.3-18%) compared to those who developed metastatic disease (range 0-10.8%, p=0.11). (B) The number of KLL-specific clonotypes was significantly higher in patients without recurrence (median 38, range 9-108) compared to those who developed metastatic disease (median 2, range 0-17, p=0.02).
Figure 4B:
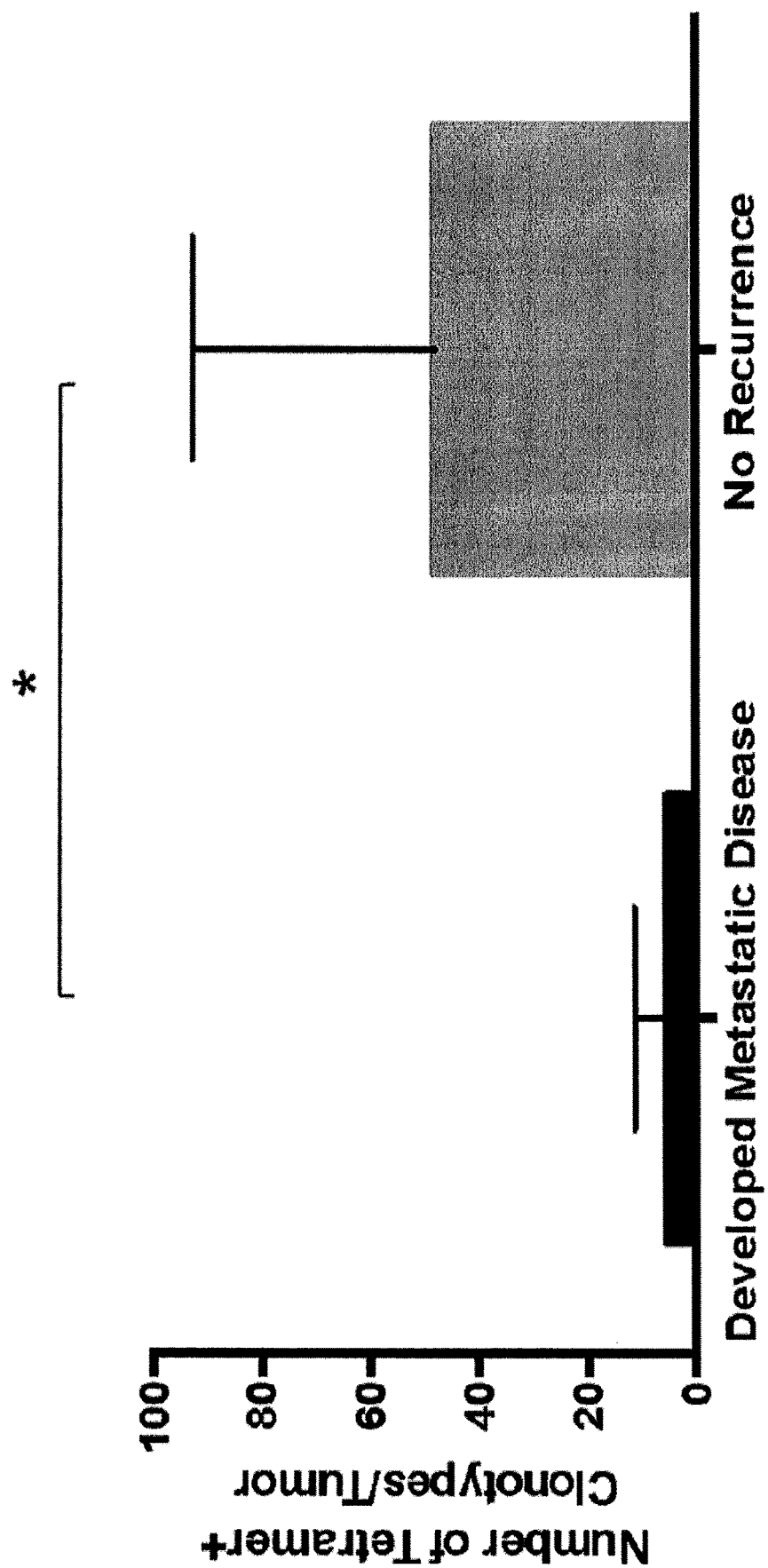
Figure 11:
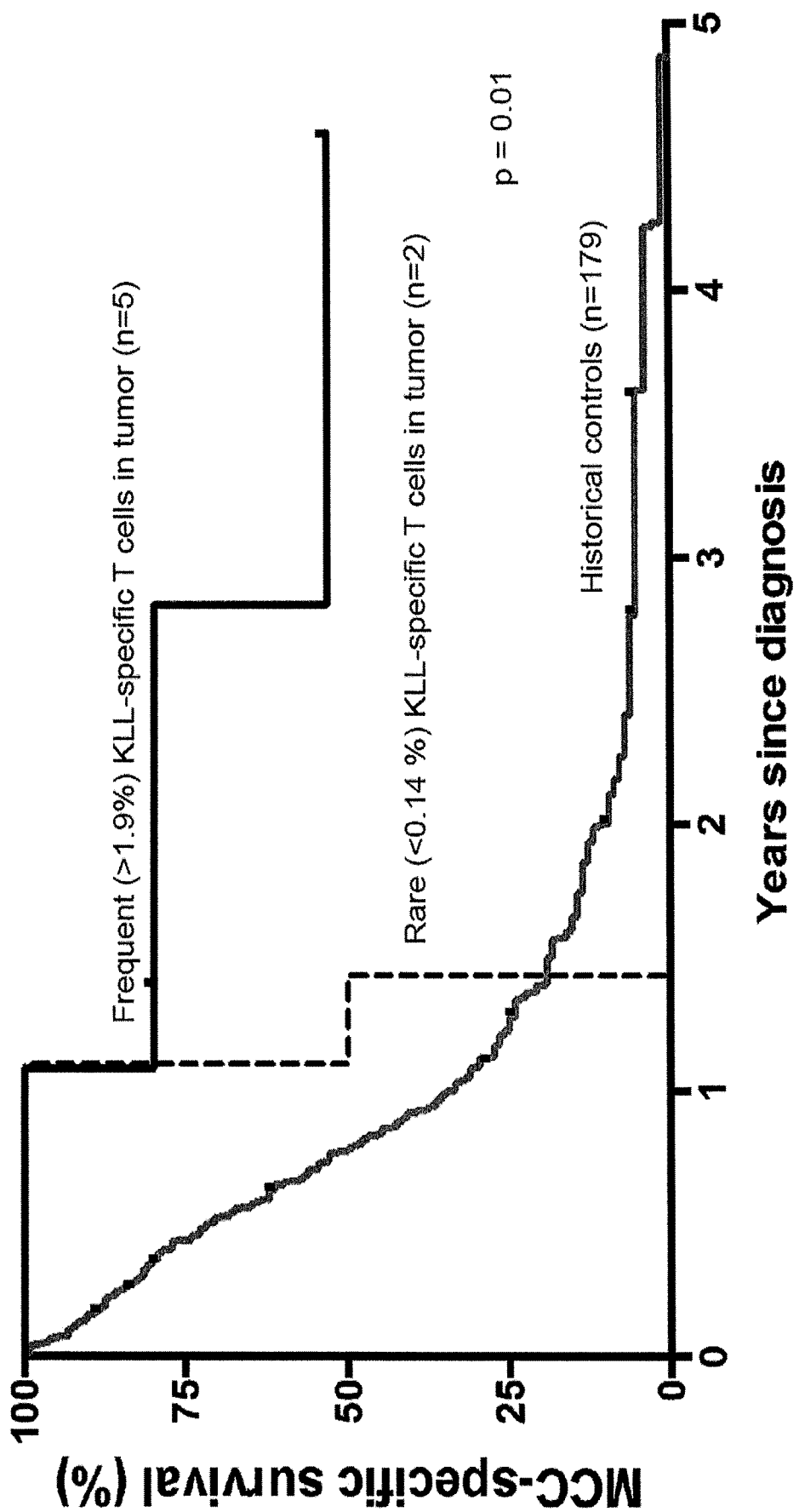
FIG. 11 shows patients with increased infiltration of KLL-specific T cells have increased survival after developing metastatic disease (p=0.15 by log-rank test), and is significant when compared to survival of a historical cohort of n=179 patients who developed metastatic disease and who were treated (p=0.01 by log-rank test).

When patients were separated into those who did and did not recur, the frequency of KLL-specific T cells was higher in tumors from patients without disease recurrence (median 10.4%) compared to patients who did recur (median of 3.2%, FIG. 4A, p=0.11). In addition, the diversity of unique KLL-specific clonotypes was significantly higher in patients who did not recur (median of 38 clonotypes) compared to patients who did recur (median of 2 clonotypes; FIG. 4B, p=0.02). Lastly, there was a trend toward increased survival after first metastasis in patients with more frequent (>1.9%) versus rare (<0.14%) KLL-specific cells within their tumors, and this difference is significant compared to a historical cohort of 179 patients (FIG. 11, p=0.01 by log-rank test).

Collectively, these data show that there is a significant survival advantage for patients for whom biopsies contain a higher relative percentage of KLL-specific T cells. Moreover, a diverse intratumoral infiltration of KLL-specific T cells is beneficial.

Example 7

TCRα/β Sequence Diversity Among KLL-specific CD8+ T Cell Clones

To gain insight into functional differences of unique KLL-specific TCRs, KLL-specific T cell clones were generated from MCC patients' PBMC (n=4) and/or ex vivo tumor digest (n=1) by sorting KLL-tetramer+ cells followed by limiting dilution cloning. Diversity of the TCRβ of several KLL-reactive clones per patient was studied with fluorescent anti-TCRVβ antibodies via flow cytometry, and clones encompassing the spectrum of TCRVβ usage were expanded for further study. The V, J and CDR3 sequences of both TCRα and β chains for 120 clones were determined and 71 monoclonal cultures were identified, 42 of which were comprised of distinct TCRs, recognizing the KLL epitope among 4 patients (Table 4). Among many private TCRα chains sequenced, one public TCRα chain using TRAV12-1*01 and encoding a CDR3 having the amino acid sequence of CVLNNNDMRF (SEQ ID NO:41) was found among clones from three of four patients.

TABLE 4

TCRα/β sequences of HLA-KLL tetramer + clones from four MCC patients

| Pt | Alpha Chain | | | Beta Chain | | | Functional Assays | | | |
| --- | --- | --- | --- | --- | --- | --- | --- | --- | --- | --- |
| | V gene | CDR3 region | J gene | V gene | CDR3 region | J gene | $EC_{50}$ (ng/mL peptide) | $EC_{50}$ (ng/uL DNA) | Recog. MS-1? | Mut Tet+? |
| w830 Clonotypes | | | | | | | | | | |
| 1 | TRAV2 4*01 | CAFNTDKLIF (SEQ ID NO: 38) | TRAJ34 *01 | TRBV12-4*01 | CASSLAGFRFF (SEQ ID NO: 63) | TRBJ2-1*01 | 4.6 0.4 | | No | Lower |
| 2 | TRAV3 8-1*01 | CALTSGSRLTF (SEQ ID NO: 39) | TRAJ27 *01 | TRBV19 *01 | CASSIMLYSNQPQHF (SEQ ID NO: 64) | TRBJ1-5*01 | 12 1.6 | 140 | No | Equal |
| 3 | TRAV3 8-1*01 | CAYPSTDKLIF (SEQ ID NO: 40) | TRAJ34 *01 | TRBV19 *01 | CASSILGASNQPQHF (SEQ ID NO: 65) | TRBJ1-5*01 | | 270 | | Equal |
| 4 | TRAV1 2-1*01 | CVLNNNDMRF (SEQ ID NO: 41) | TRAJ43 *01 | TRBV19 *01 | CASSILGASNQPQHF (SEQ ID NO: 65) | TRBJ1-5*01 | 1.1 | | No | Equal |
| 5 | TRAV1 2-1*01 | CVVNANDMRF (SEQ ID NO: 42) | TRAJ43 *01 | TRBV10-3*01 | CAIRARDQNTGELFF (SEQ ID NO: 66) | TRBJ2-2*01 | 5.1 0.89 | | No | Equal |
| w683 Clonotypes | | | | | | | | | | |
| 1 | TRAV1 2-1*01 | CVVALYSGGGA DGLTF (SEQ ID NO: 43) | TRAJ45 *01 | TRBV6-5*01 | CASRSQNYYGYTF (SEQ ID NO: 67) | TRBJ1-2*01 | 1.9 0.36 0.26 | | No | Lower |
| 2 | TRAV1 2-1*01 | CVLNNNDMRF (SEQ ID NO: 41) | TRAJ43 *01 | TRBV6-5*01 | CASRSQNYYGYTF (SEQ ID NO: 67) | TRBJ1-2*01 | 0.21 | | No | Lower |
| w678 Clonotypes | | | | | | | | | | |
| 1 | TRAV1 2-1*01 | CVLNNNDMRF (SEQ ID NO: 41) | TRAJ43 *01 | TRBV10-3*01 | CAIRQFDANTGELFF (SEQ ID NO: 68) | TRBJ2-2*01 | 0.43 0.50 0.47 | 0.32 | Yes | Equal |
| 1.5 | | UNKNOWN* | | TRBV10-3*01 | CAIRQFDANTGELFF (SEQ ID NO: 68) | TRBJ2-2*01 | 0.84 | | Yes | Equal |

TABLE 4-continued

TCRα/β sequences of HLA-KLL tetramer + clones from four MCC patients

| | Alpha Chain | | | Beta Chain | | | Functional Assays | | | |
|---|---|---|---|---|---|---|---|---|---|---|
| | | | | | | | EC$_{50}$ (ng/mL peptide) | EC$_{50}$ (ng/uL DNA) | Recog. MS-1? | Mut Tet+? |
| Pt | V gene | CDR3 region | J gene | V gene | CDR3 region | J gene | | | | |
| 2 | TRAV3 8-1*01 | CAFRVSHDMRF (SEQ ID NO: 44) | TRAJ43 *01 | TRBV19 *01 | CASSIIAGSSYNEQFF (SEQ ID NO: 69) | TRBJ2- 1*01 | 0.017 0.012 | | Yes | Lower |
| 3 | TRAV1 2-1*01 | CVVATYSGGGA DGLTF (SEQ ID NO: 13) | TRAJ45 *01 | TRBV19 *01 | CASSIIAGSSYNEQFF (SEQ ID NO: 69) | TRBJ2- 1*01 | 0.022 0.013 | 1.0 | Yes | Equal |
| 4 | TRAV1 2-1*01 | CVVATYSGGGA DGLTF (SEQ ID NO: 13) | TRAJ45 *01 | TRBV10- 2*01 | CASSSGNPSTDTQYF (SEQ ID NO: 14) | TRBJ2- 3*01 | 0.0094 0.028 | | Yes | Equal |
| 5 | TRAV3 8-1*01 | CAFRVSHDMRF (SEQ ID NO: 44) | TRAJ43 *01 | TRBV10- 2*01 | CASSSGNPSTDTQYF (SEQ ID NO: 14) | TRBJ2- 3*01 | 0.11 0.054 | | Yes | Lower |
| | UNKNOWN* | | | UNKNOWN* | | | 0.060 0.058 | | Yes | Equal |
| w876 Clonotypes | | | | | | | | | | |
| 1 | TRAV1 2-1*01 | CVVGEYSGGGA DGLTF (SEQ ID NO: 45) | TRAJ45 *01 | TRBV28 *01 | CAIRAGASYNEQFF (SEQ ID NO: 70) | TRBJ2- 1*01 | 0.31 | 5.6 | | Lower |
| 2 | TRAV1 2-1*01 | CVVTEYSGGGA DGLTF (SEQ ID NO: 46) | TRAJ45 *01 | TRBV10- 3*01 | CASRGQNTGELFF (SEQ ID NO: 71) | TRBJ2- 2*01 | 1.2 | | No | Lower |
| 3 | TRAV1 9*01 | CALGGGTFTSGT YKYIF (SEQ ID NO: 47) | TRAJ40 *01 | TRBV9* 02 | CASSVEDYTGELFF (SEQ ID NO: 72) | TRBJ2- 2*01 | 0.12 | 11 | No | Equal |
| 4 | TRAV1 2-1*01 | CVVYTGYSGGG ADGLTF (SEQ ID NO: 48) | TRAJ45 *01 | TRBV10- 2*01 | CASSVLNTGELFF (SEQ ID NO: 73) | TRBJ2- 2*01 | 0.31 | 14 | No | Equal |
| 5 | TRAV3 8-1*01 | CAYNQGGKLIF (SEQ ID NO: 49) | TRAJ23 *01 | TRBV10- 2*01 | CASSVLNTGELFF (SEQ ID NO: 73) | TRBJ2- 2*01 | 0.11 | | No | Equal |
| 6 | TRAV1 2-1*01 | CVVPLYSSASKIIF (SEQ ID NO: 50) | TRAJ3* 01 | TRBV6- 1*01 | CASSDTPDLNTEAFF (SEQ ID NO: 74) | TRBJ1- 1*01 | 0.015 0.035 | | No | Lower |
| 7 | TRAV1 2-1*01 | CVLNNNDRF (SEQ ID NO: 51) | TRAJ43 *01 | TRBV6- 1*01 | CASSDTPDLNTEAFF (SEQ ID NO: 74) | TRBJ1- 1*01 | 0.14 | 3.6 | No | Lower |
| 8 | TRAV1 2-1*01 | CVVYASKIIF (SEQ ID NO: 52) | TRAJ3* 01 | TRBV6- 1*01 | CASSDTPDLNTEAFF (SEQ ID NO: 74) | TRBJ1- 1*01 | | 4.2 | | Lower |
| 9 | TRAV1 2-1*01 | CVGNNNDMRF (SEQ ID NO: 53) | TRAJ43 *01 | TRBV10- 3*01 | CAISARDQNTGELFF (SEQ ID NO: 75) | TRBJ2- 2*01 | 0.12 0.24 | | No | Lower |
| 10 | TRAV1 2-1*01 | CVVYGSSNTGKL IF (SEQ ID NO: 54) | TRAJ37 *02 | TRBV10- 3*01 | CAIRRQDQNTGELFF (SEQ ID NO: 76) | TRBJ2- 2*01 | 0.70 | | No | Lower |
| 11 | TRAV1 2-1*01 | CVVYTGYSGGG ADGLTF (SEQ ID NO: 48) | TRAJ45 *01 | TRBV10- 3*01 | CAIHEGDSNTGELFF (SEQ ID NO: 77) | TRBJ2- 2*01 | | | | Equal |
| 12 | TRAV3 *01 | CAVRDNSGTYKY IF (SEQ ID NO: 55) | TRAJ40 *01 | TRBV7- 2*04 | CASSLAGLAGTDTQY F (SEQ ID NO: 78) | TRBJ2- 3*01 | | | | Lower |
| 13 | TRAV1 2-1*01 | CVVTDTSGGGA DGLTF (SEQ ID NO: 56) | TRAJ45 *01 | TRBV7- 2*04 | CASSLAGLAGTDTQY F (SEQ ID NO: 78) | TRBJ2- 3*01 | | 3.9 | | |
| 14 | TRAV1 2-1*01 | CVVPSAGKSTF (SEQ ID NO: 57) | TRAJ27 *01 | TRBV2* 03 | CASSEFAGQETQYF (SEQ ID NO: 79) | TRBJ2- 5*01 | | 5.4 | | Lower |

TABLE 4-continued

TCRα/β sequences of HLA-KLL tetramer + clones from four MCC patients

| | Alpha Chain | | | Beta Chain | | | Functional Assays | | | |
| --- | --- | --- | --- | --- | --- | --- | --- | --- | --- | --- |
| | | | | | | | $EC_{50}$ (ng/mL peptide) | $EC_{50}$ (ng/uL DNA) | Recog. MS-1? | Mut Tet+? |
| Pt | V gene | CDR3 region | J gene | V gene | CDR3 region | J gene | | | | |
| 15 | | UNKNOWN* | | TRBV6-5*01 | CASRASNTYGYTF (SEQ ID NO: 80) | TRBJ1-2*01 | | 80 | No | |
| 16 | TRAV38-1*01 | CAYNQGGKLIF (SEQ ID NO: 49) | TRAJ23*01 | TRBV19*01 | CASSTLSGTHNEQFF (SEQ ID NO: 81) | TRBJ2-1*01 | 0.12 | | No | Lower |
| 17 | TRAV12-1*01 | CVVYGSSNTGKLIF (SEQ ID NO: 54) | TRAJ37*02 | TRBV7-2*04 | CASSLAGLANNEQFF (SEQ ID NO: 82) | TRBJ2-1*01 | | | | Lower |
| 18 | TRAV14 | CAMREAQSGGYQKVTF (SEQ ID NO: 58) | TRAJ13*01 | TRBV12-4*01 | CASSFGSGTKDTQYF (SEQ ID NO: 83) | TRBJ2-3*01 | | | | Equal |
| 19 | TRAV12-1*01 | CVVYTGYSGGGADGLTF (SEQ ID NO: 48) | TRAJ45*01 | TRBV10-2*01 | CASSGQNTGELFF (SEQ ID NO: 84) | TRBJ2-2*01 | 0.92 | | No | Lower |
| 20 | TRAV10*01 | CVVSAGINGADGLTF (SEQ ID NO: 59) | TRAJ45*01 | TRBV12-4*01 | CASSPWDEQFF (SEQ ID NO: 85) | TRBJ2-1*01 | | | | Lower |
| 21 | TRAV3*01 | CAVRDNSGTYKYIF (SEQ ID NO: 55) | TRAJ40*01 | TRBV13*02 | CASSSGTSGGLTYNEQFF (SEQ ID NO: 86) | TRBJ2-1*01 | | | | |
| 22 | | UNKNOWN* | | TRBV13*02 | CASSSRTKAYEQYF (SEQ ID NO: 87) | TRBJ2-7*01 | | | | |
| 23 | TRAV12-3*01 | CAMSVAQGGSEKLVF (SEQ ID NO: 60) | TRAJ57*01 | TRBV6-6*01 | CASSYQIGLSYEQYF (SEQ ID NO: 88) | TRBJ2-7*01 | | | | |
| 24 | | UNKNOWN* | | TRBV28*01 | CASSFDSKGSNTGELFF (SEQ ID NO: 89) | TRBJ2-2*01 | | | | |
| 25 | TRAV27*01 | CAGDQGGSEKLVF (SEQ ID NO: 61) | TRAJ57*01 | TRBV16*01 | CASSQLRTGDEYEQYF (SEQ ID NO: 90) | TRBJ2-7*01 | | | | |
| 26 | TRAV12-1*01 | CVVYTGYSGGGADGLTF (SEQ ID NO: 48) | TRAJ45*01 | TRBV13*02 | CASSSGTSGGLNYNEQFF (SEQ ID NO: 91) | TRBJ2-1*01 | | | | |
| 27 | TRAV3*01 | CALTGYSTLTF (SEQ ID NO: 62) | TRAJ11*01 | TRBV19*01 | CASRSQLAVLNEQFF (SEQ ID NO: 92) | TRBJ2-1*01 | | | | |
| 28 | | UNKNOWN* | | TRBV28*01 | CASRGGSSYNEQFF (SEQ ID NO: 93) | TRBJ2-1*01 | | | | |
| 29 | TRAV12-1*01 | CVVPLYSSASKIIF (SEQ ID NO: 50) | TRAJ3*01 | TRBV10-2*01 | CASSVLNTGELFF (SEQ ID NO: 73) | TRBJ2-2*01 | 0.12 0.16 | 3.3 | No | Equal |
| 30 | | UNKNOWN* | | TRBV10-3*01 | CATRDINTGELFF (SEQ ID NO: 94) | TRBJ2-2*01 | | | | |
| 31 | | UNKNOWN* | | TRBV6-1*01 | CASSDTPDLNTEAFF (SEQ ID NO: 74) | TRBJ1-1*01 | | 24 | | |

*Certain TRA or TRB sequences were unresolved with next-generation sequencing.

Example 8

Functional Avidity of KLL-Specific Clones

Figure 5A:
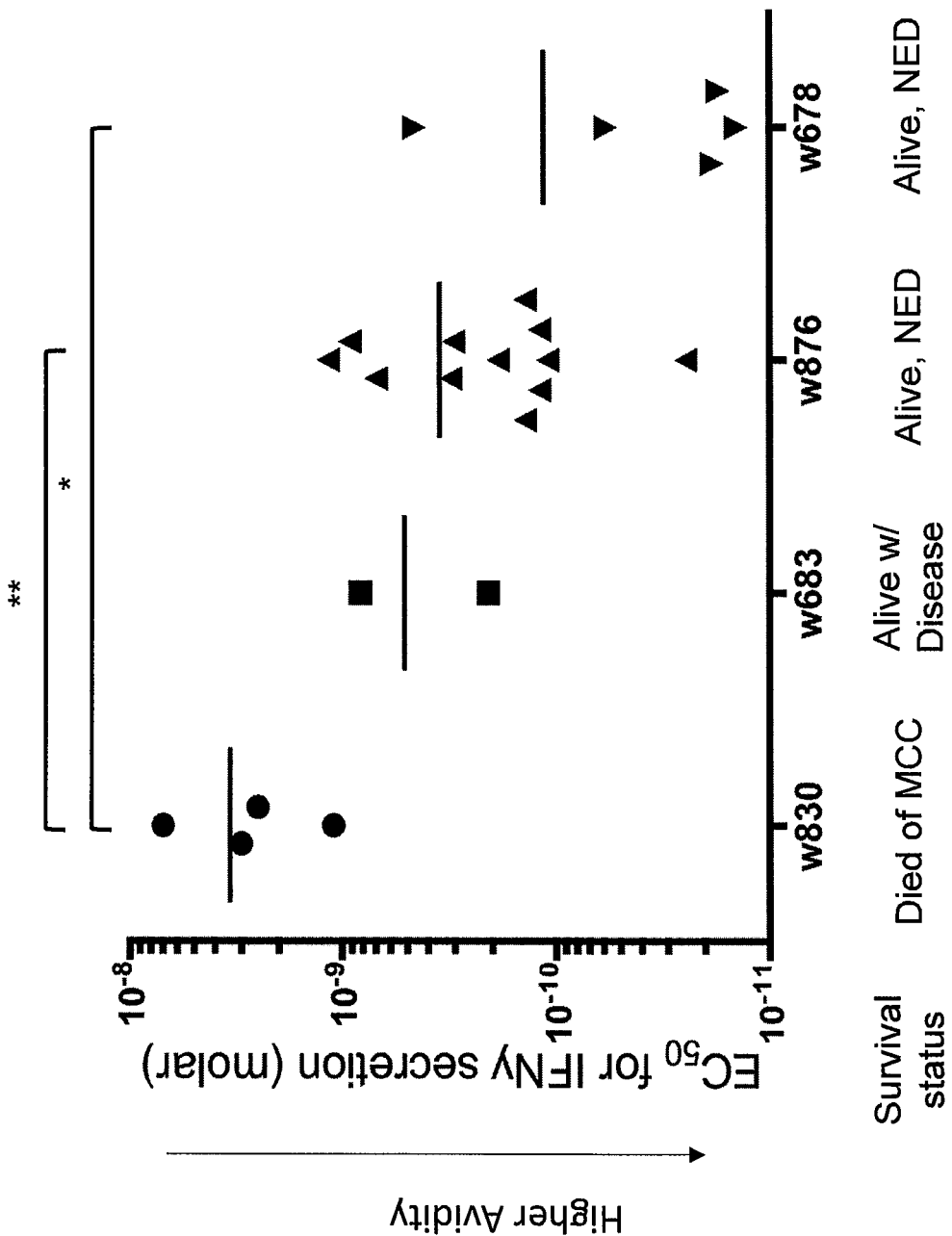
FIGS. 5A-5D show functional avidity results of 28 KLL-specific clonotypes from 4 patients. (A) $EC_{50}$ values for IFN-γ secretion by KLL-specific clones in response to peptide concentration or (B) concentration of tLT-Ag DNA transfected into Cos7 cells are plotted for each patient, with mean of all clones/patient depicted by the horizontal bar. For replicate experiments of clones with the same TCR, a single point representing the mean $EC_{50}$ is plotted. Clonotypes from the same patient generally had similar functional avidities; more avid clonotypes were detected among patients with better MCC-specific survival. Statistical comparisons were made between patients; *, p<0.05; **, p<0.01, Mann Whitney test; NED=no evidence of disease. The high avidity correlates with improved treatment outcomes. (C) Clonotypes from one patient respond to the MCPyV+, HLA-A02+ MCC cell line MS-1+/–IFN-γ treatment to upregulate HLA-I; responses of each clone to T2 cells+/– KLL peptide are shown for comparison. Mean of duplicates+SEM are shown after subtracting background IFN-γ secretion by T cells without targets; representative results from one of at least two separate experiments with each clone are shown. (D) Select clonotypes are able to bind a CD8-independent KLL-tetramer.
Figure 5B:
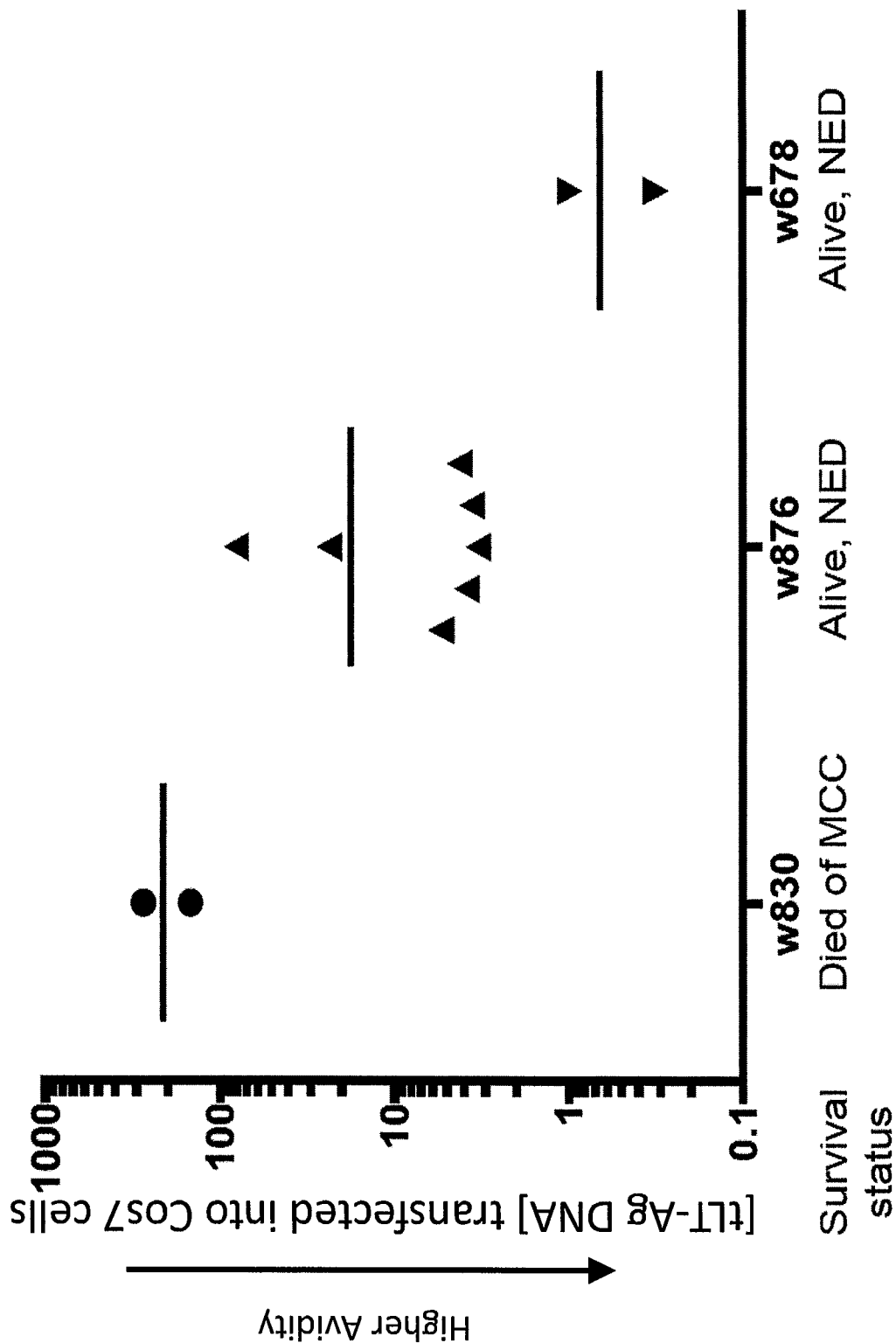
Figure 5C:
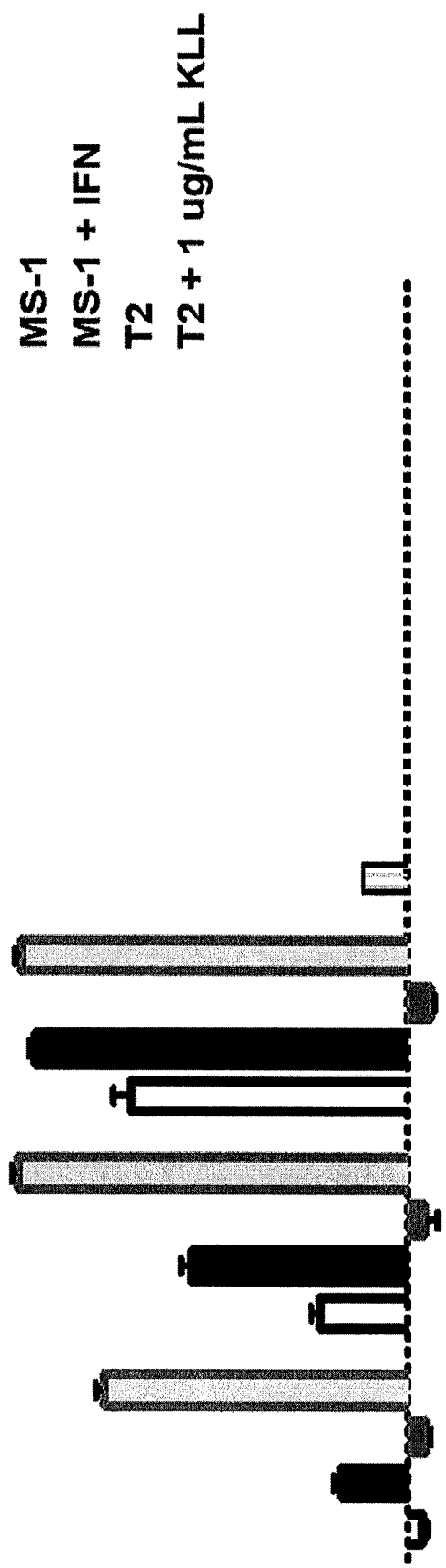
Figure 5D:
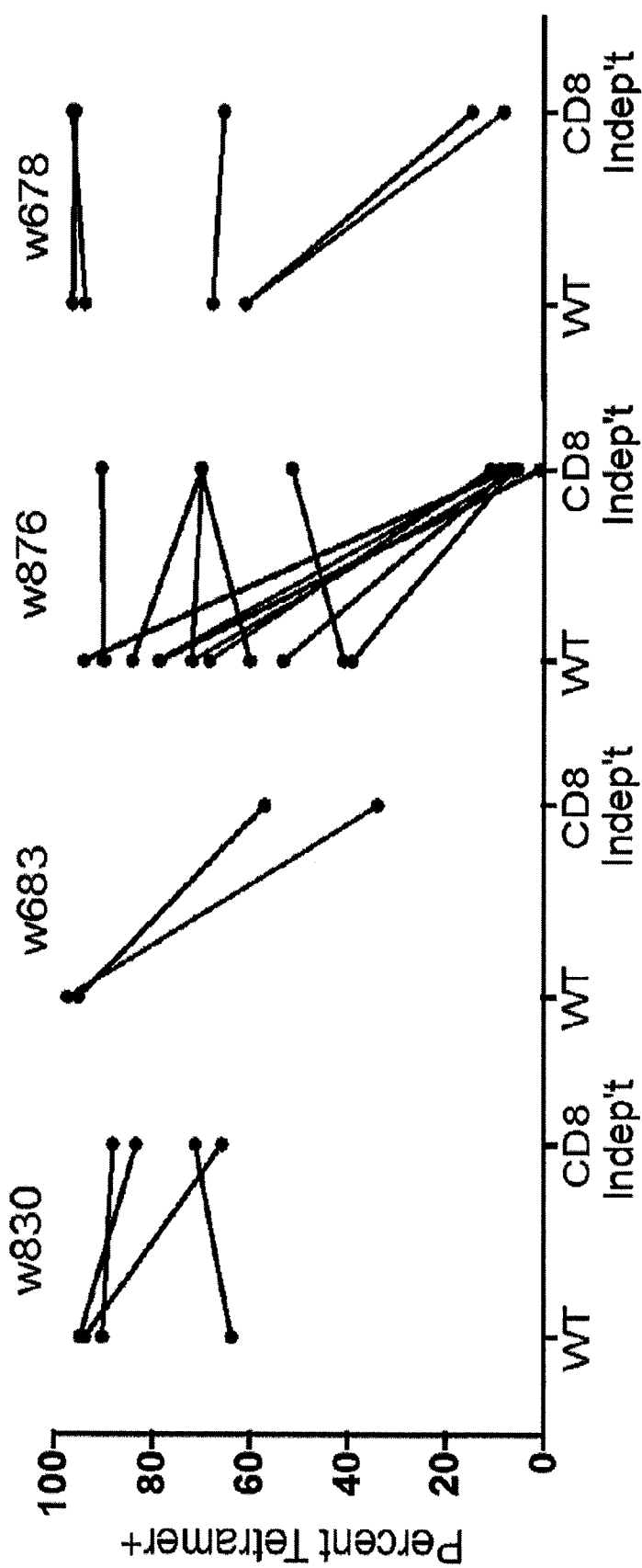

To investigate functional differences among MCPyV-specific T cell clones, secretion of a canonical Th1 effector cytokine, IFN-γ, ωασ measured after stimulation with T2 target cells pulsed with limiting dilution of an alanine-substituted variant of the peptide (KLLEIAPNA, SEQ ID NO:37; this peptide is antigenic but less susceptible to oxidation, allowing direct comparison of T cell clones to each other; see Methods for details). Clones displayed narrow ranges of intra-patient variability for functional avidity (Table 4, FIG. 5A). Concordant results were obtained in a separate, but analogous, assay using targets transfected with limiting dilution of plasmid encoding truncated Large T-Ag (FIG. 5B). Importantly, patients with improved MCC-specific survival had more functionally avid T cell clonotypes ($p<0.05$). To further interrogate the effector function of these clonotypes, the ability of 28 unique KLL-specific clonotypes to recognize the MCPyV+, HLA-A*02+ MCC cell lines (WaGa, MS-1 and MKL-2)+/−IFN-β treatment was tested. Five unique clonotypes secreted IFN-γ when incubated with MS-1; this response was generally lower than that to T2 cells pulsed with a maximal concentration of peptide. No clones recognized WaGa or MKL-2 (Table 4 and FIG. 5C). Reactive clones were derived from patient w678 who had the most functionally avid clonotypes in the IFN-γ release assay. The ability of KLL-specific clonotypes to bind was compared for both wild type and CD8-independent tetramers containing mutations in HLA-A*02:01 to abrogate CD8 stabilization of the TCR:pMHC interaction, which may select for more avid TCRs. While there was a trend that clonotypes that were more functionally avid in the IFN-γ assay (FIGS. 5A and 5B) bound both wild type (WT) and CD8-independent tetramers, other IFN-γ responsive clonotypes did not bind the CD8 independent tetramer well (Table 4 and FIG. 5D). Indeed, when clones from each patient were binned by whether they bound the CD8-independent tetramer 'equally' or 'lower', there was no significant difference between mean $EC_{50}$ amongst these two groups ($p=0.57$ for w678 by Mann-Whitney test, $p=0.30$ for w830, insufficient data for w830 and w683). No significant correlations between clonotype avidity and enrichment within tumors were identified.

Example 9

Codon Optimization and Functionality of Encoded KLL-Specific TCR

Figure 12A:
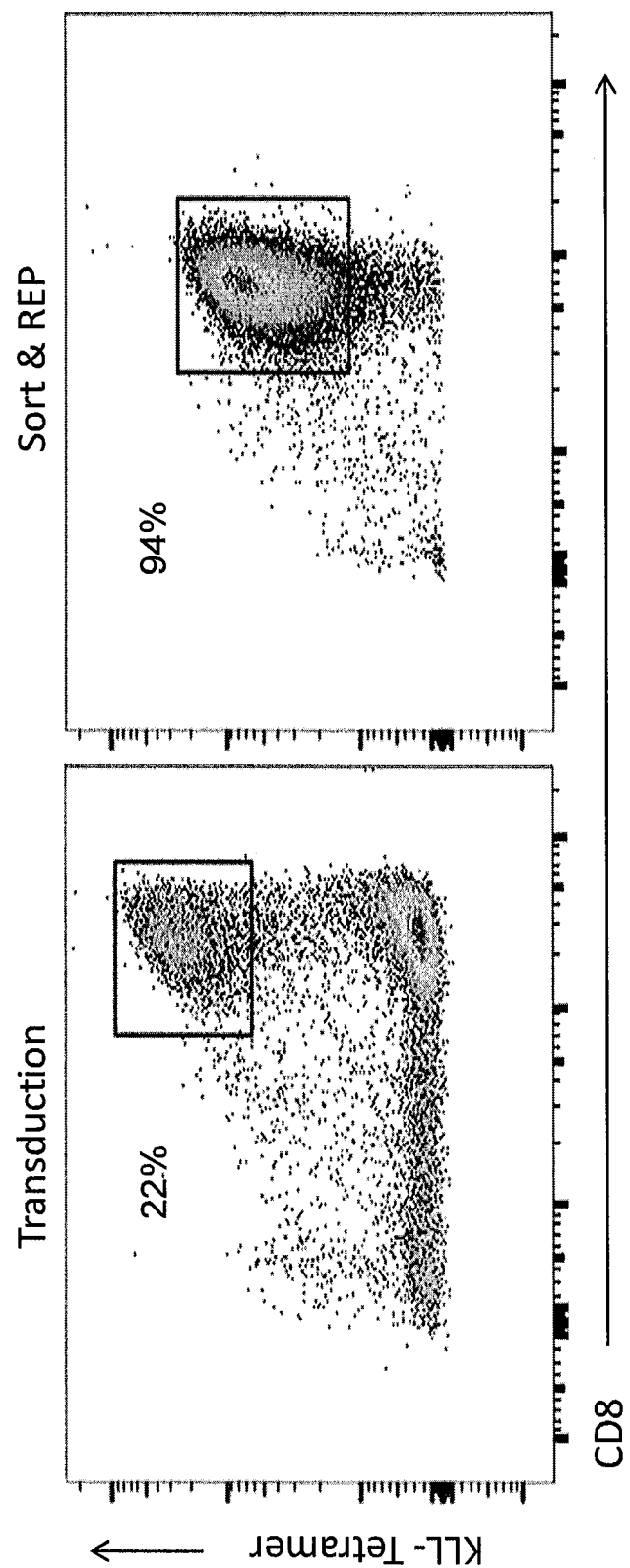
Figure 12B:
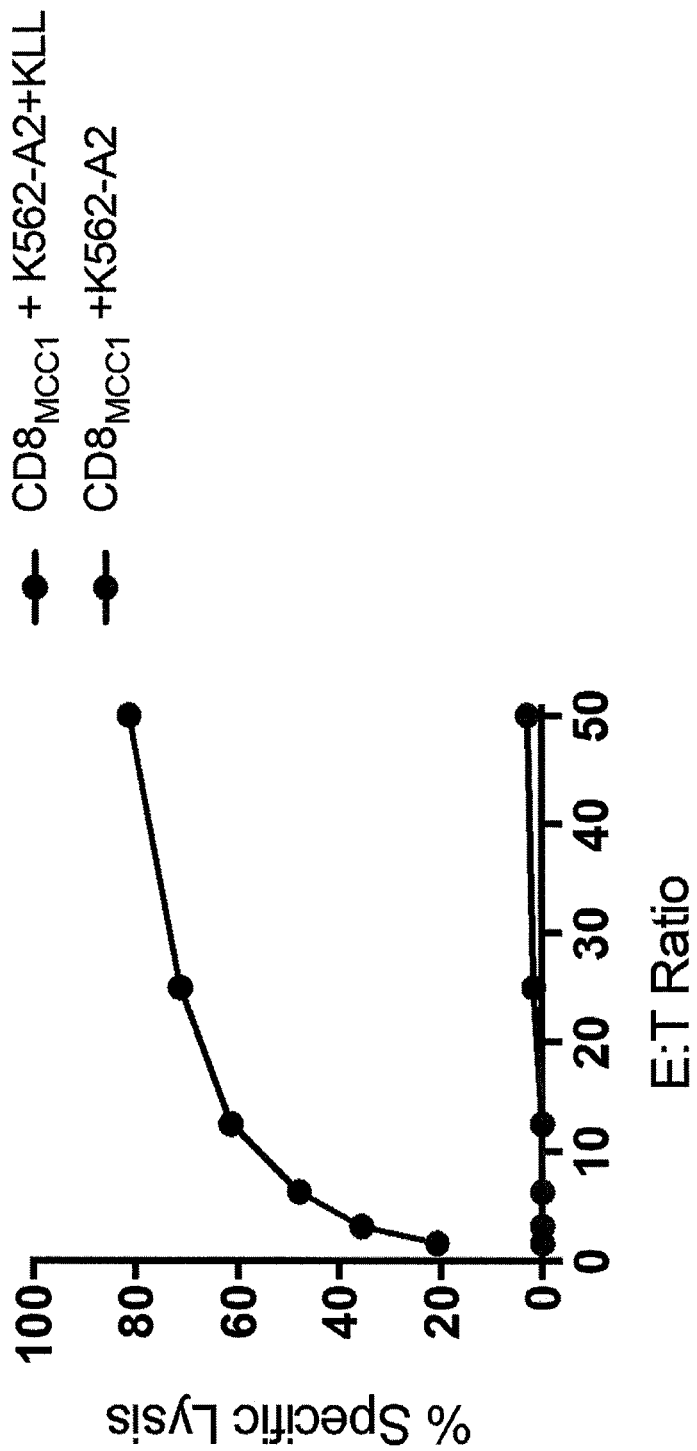
Figure 12C:
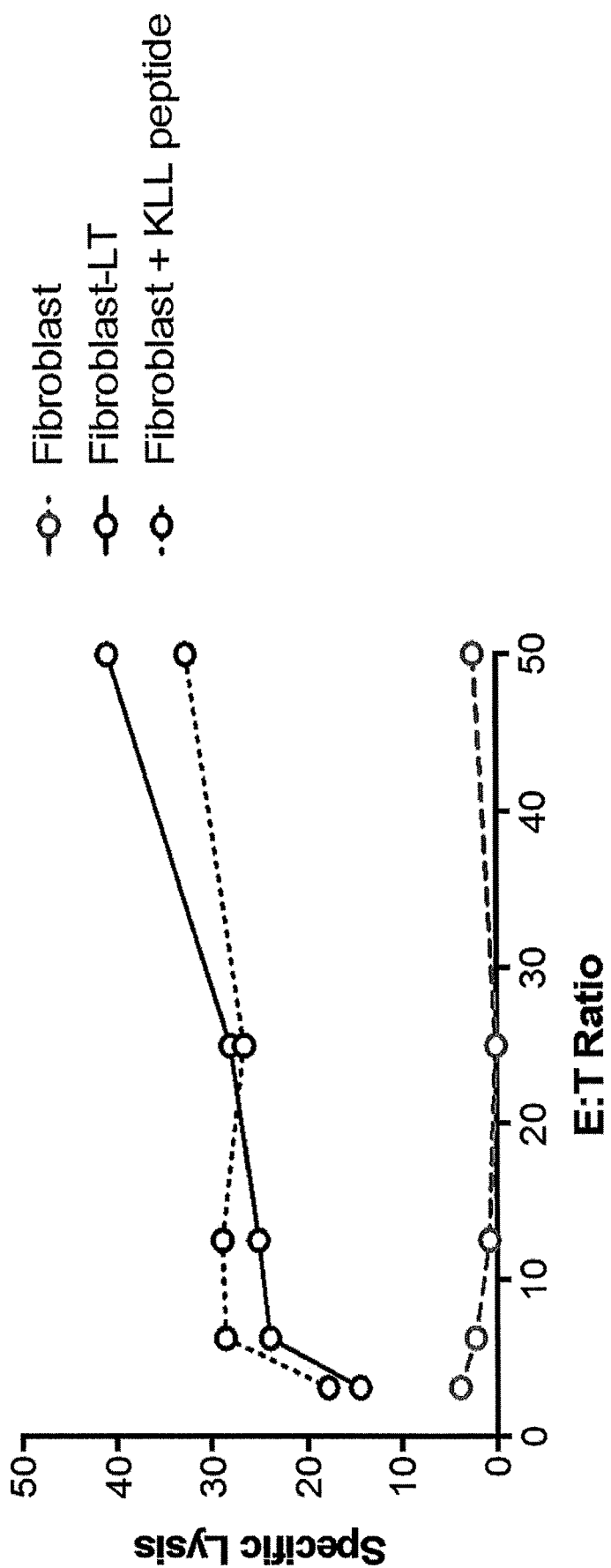
Figure 12D:
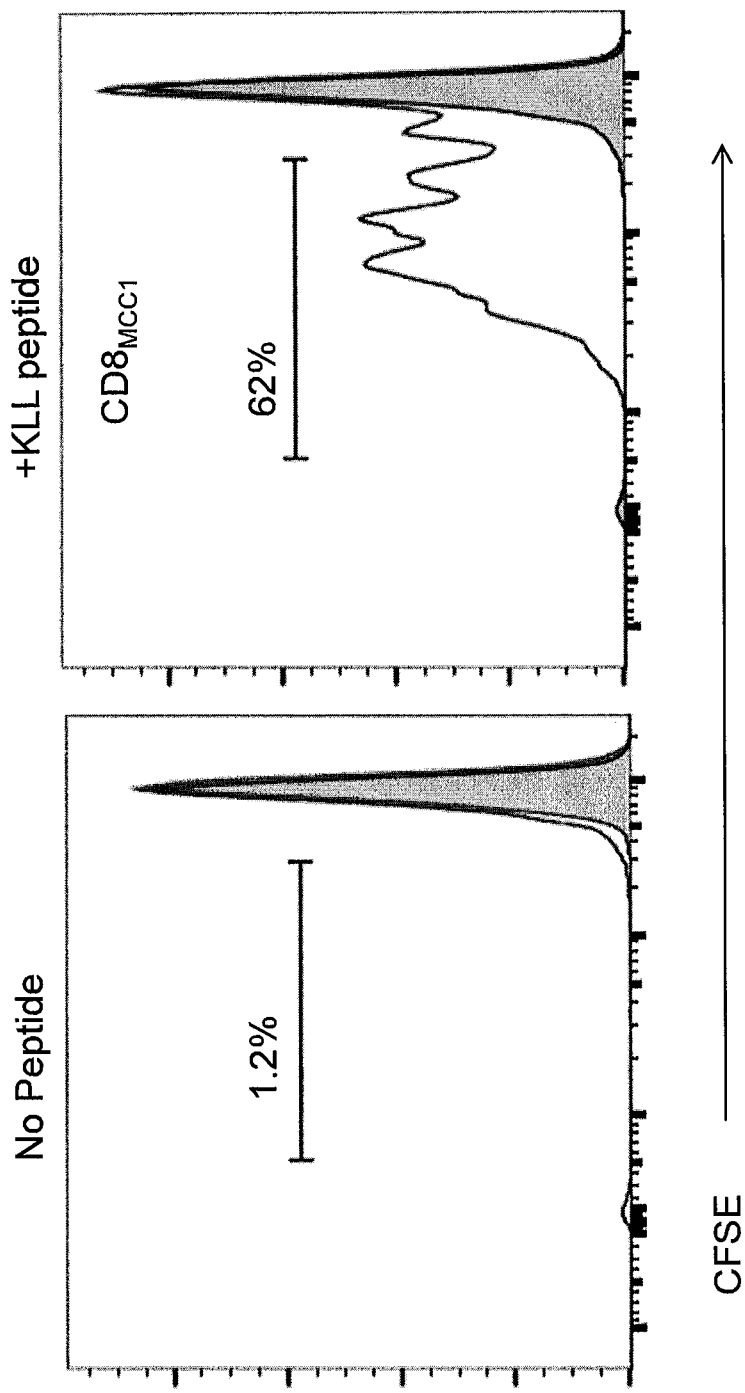
Figure 12E:
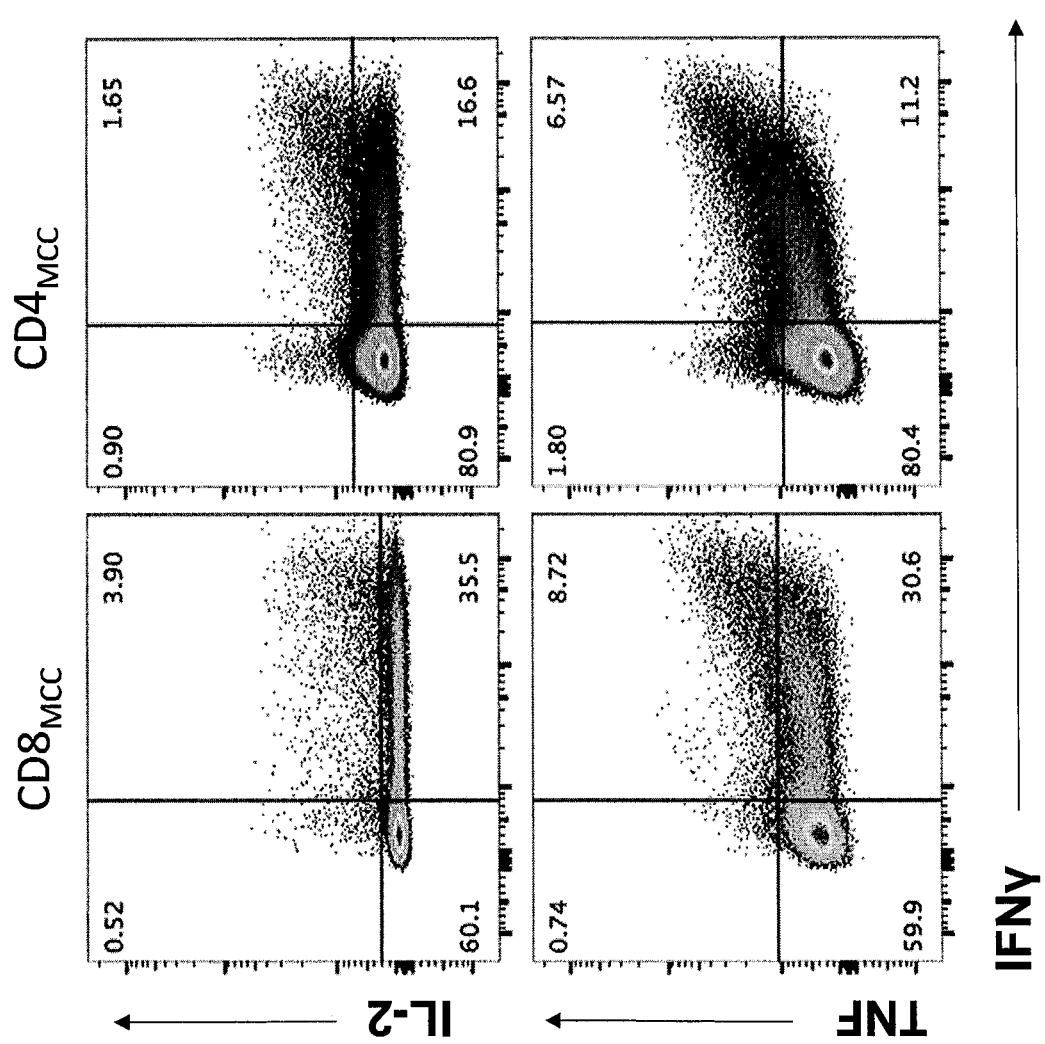
Figure 13:
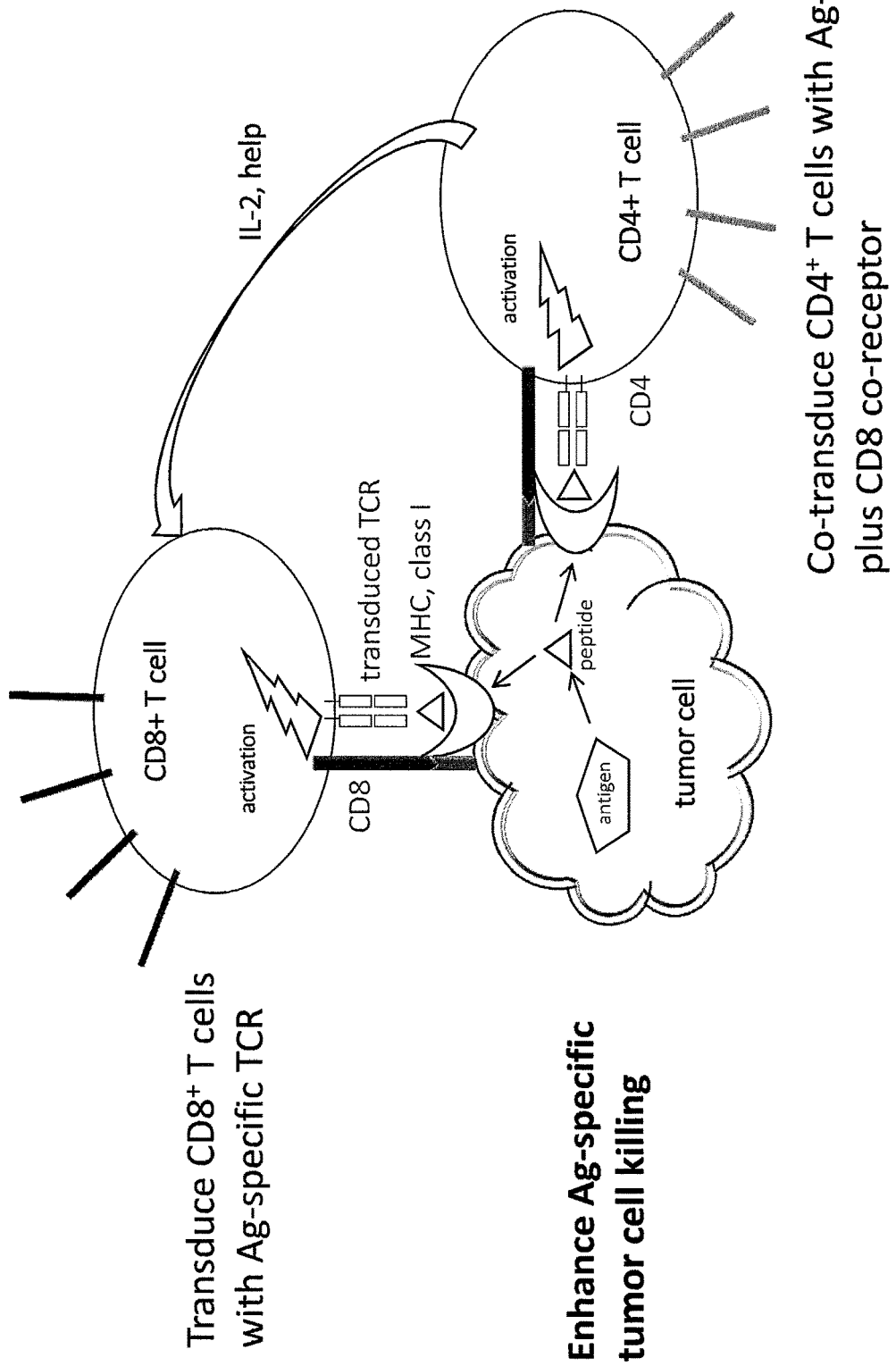
FIG. 13 illustrates an immunotherapy approach according to the present disclosure in which CD4+ T cells are transduced to express a TCR and a CD8 co-receptor, both from a CD8+ T cell that is specific for a peptide antigen. Activation of the transduced CD4+ T cell can augment or improve the antigenic response of CD8+ T cells, such as infused CTLs in an immunotherapy setting.
Figure 14:
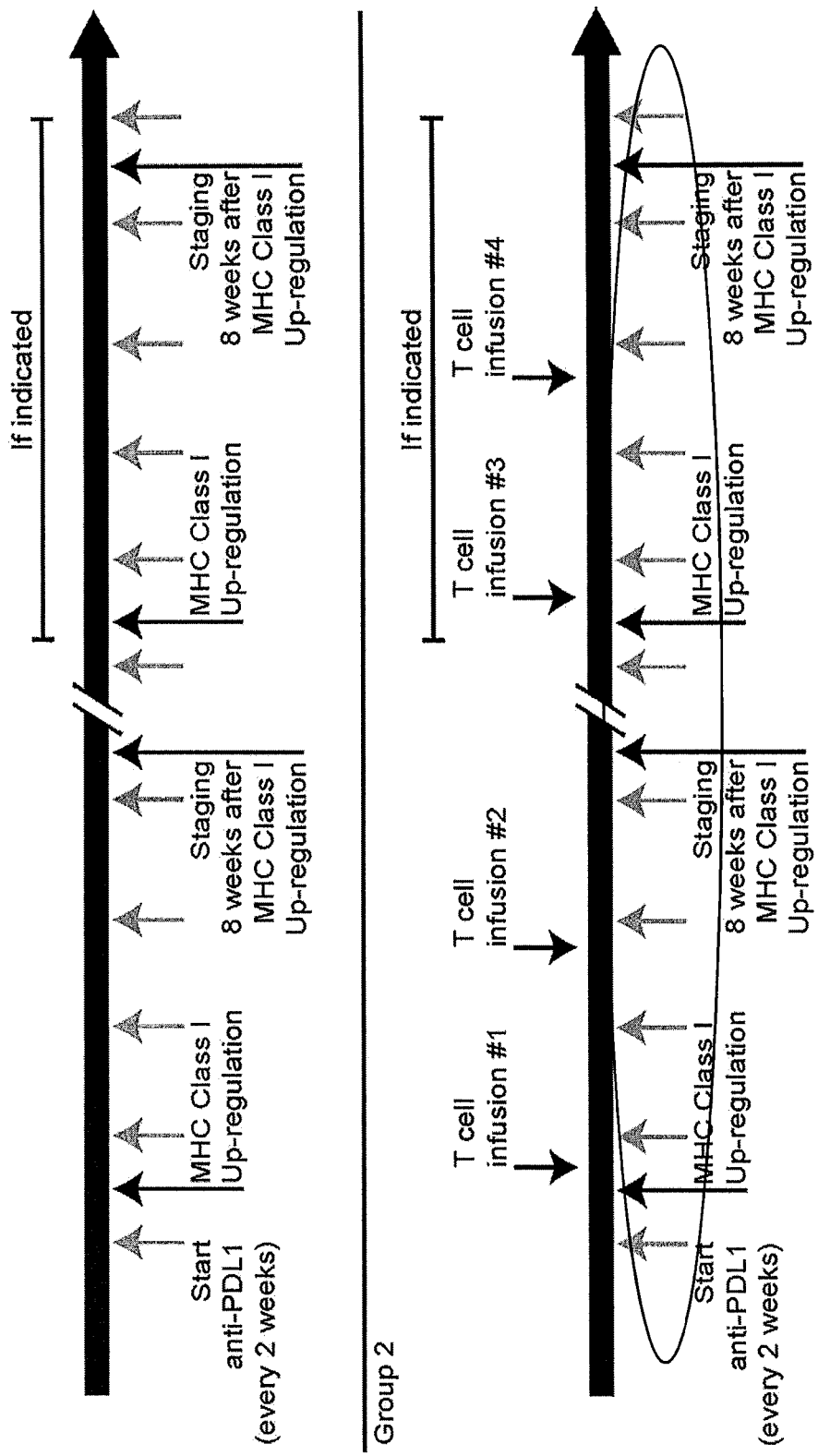
FIG. 14 shows a treatment schedule for a patient receiving T cell infusions of KLL-specific T cell receptors in combination therapy with anti-PDL1 and MHC Class I up-regulation.
Figure 15:
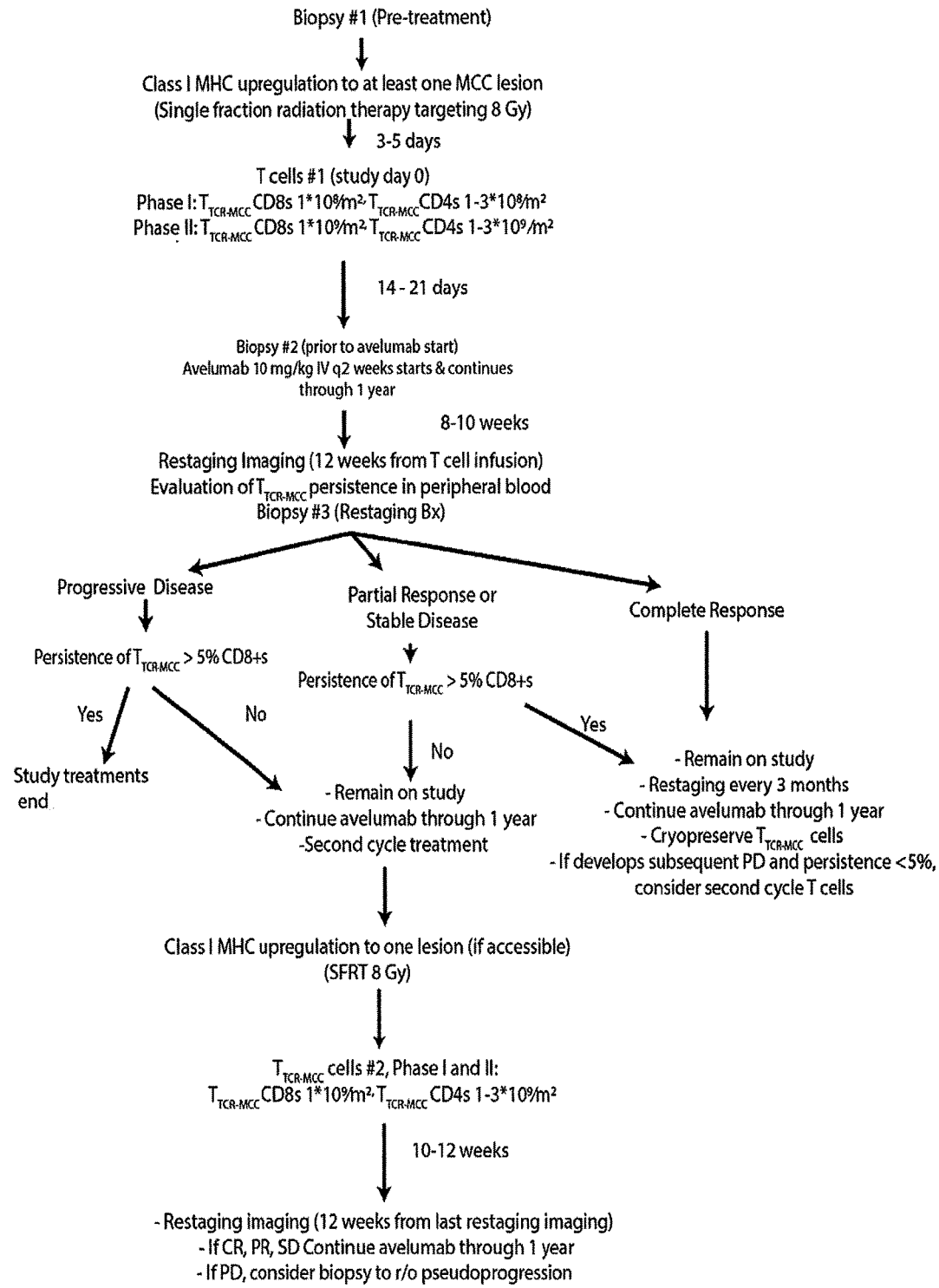
FIG. 15 shows a decision tree for a patient treated with MCPyV-specific HLA A*0201-restricted engineered T cells in combination therapy with anti-PDL1 (e.g., avelumab) and WIC Class I up-regulation.
Figure 16:
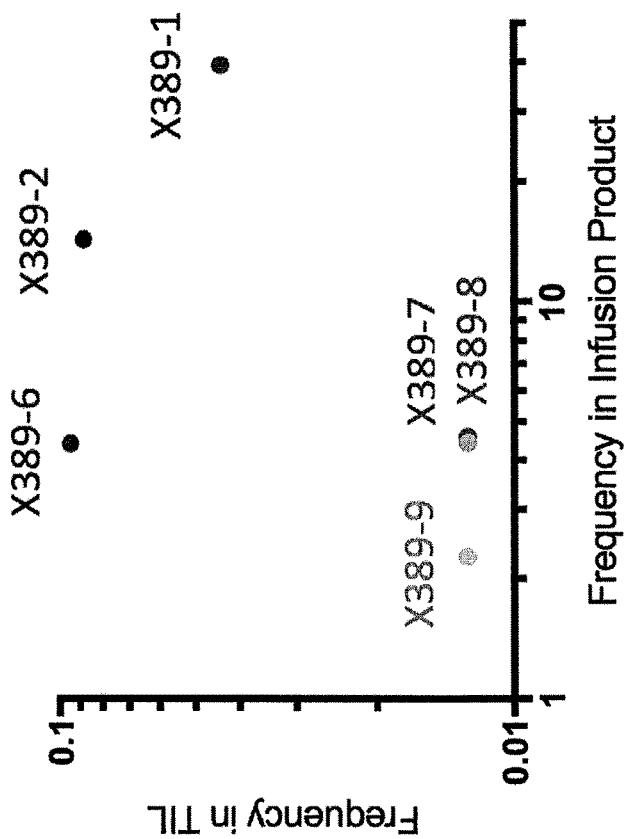
FIGS. 16A and 16B show the TRB CDR3 clonotype diversity among KLL tetramer+CD8+ cells from TILs in patient x389.
Figure 16:
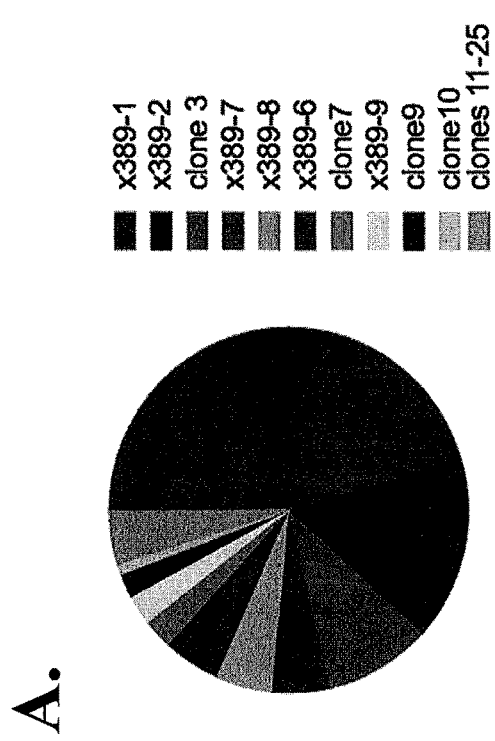
Figure 17:
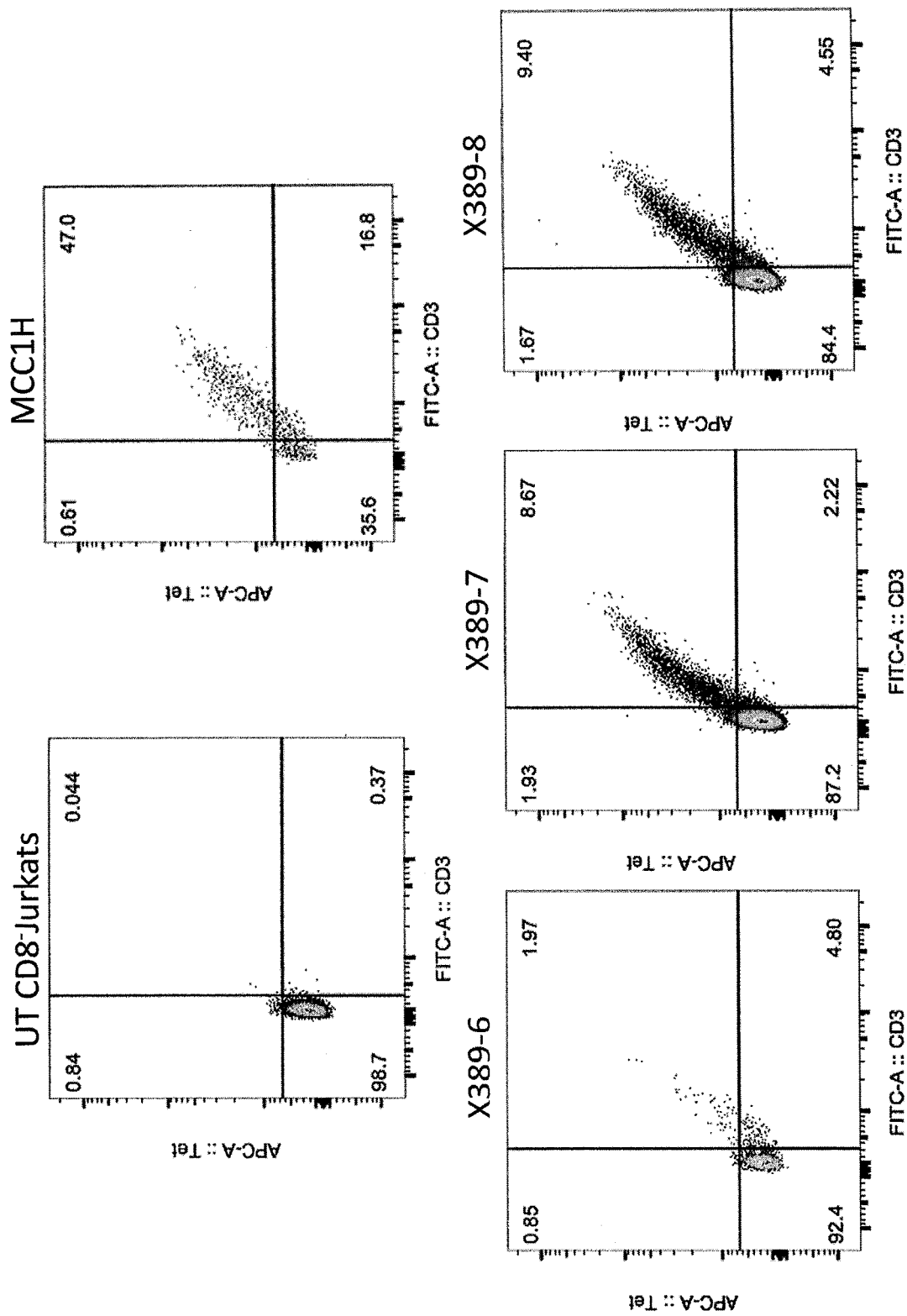
FIG. 17 shows that various additional class I MCPyV T antigen-specific TCRs (MCCH1, x389-6, x389-7, and x389-8) can bind independent of CD8 to cells presenting the KLL-epitope peptide.

The polynucleotide of one of the patient-derived class I high avidity TCR clones (MCC1) was codon optimized and transduced into CD8+ T and examined for their ability to activate CD4+ T cells. CD8+ and CD4+ T cells were successfully transduced with codon-optimized MCC-specific TCR (MCC1), and KLL-tetramer sorted cells were expanded in culture for two weeks and remained tetramer positive (FIG. 12A). In addition, CD8+ T cells transduced with KLL-specific TCR (MCC1) specifically killed only peptide loaded HLA-A*02:01 K562 cells (FIG. 12B) or HLA-A*02:01 fibroblast cell lines that had been transduced with MCPyV LT antigen, in a 4 hour chromium release assay (FIG. 12C), indicating that the MCPyV KLL-epitope is naturally processed and presented at levels high enough to trigger T cell function. Transduced CD8+ T cells readily proliferate over 72 hours (FIG. 12D) and make effector cytokines (FIG. 12E) in response to stimulation with peptide loaded HLA-A*02:01 K562 cells. CD4+ T cells transduced with MCC1 TCR have a reduced sensitivity to engage cytokine secretion (FIG. 12F), but the maximum percentage of transduced cells that secrete effector cytokines IFNγ, IL-2 and TNF at saturating levels of peptide (5 μg/mL) is similar between CD4+ and CD8+ T cells.

Example 10

Combination Therapy of MCPyV-Specific Cellular Therapy with a Checkpoint Inhibitor Several clinical trials have been performed using endogenous autologous MCPyV-specific cellular therapy for MCC and found response rates that were substantially higher (80% vs. 20%) when checkpoint inhibitors are combined with MCPyV-specific T cell therapy.

Briefly, a total of 5 patients were treated with MCPyV-specific T cells plus HLA-upregulation without checkpoint inhibitors (see, e.g., NCT01758458). Of these 5 patients, only 1 (20%) had an objective response, while the other 4 patients presented with progressive disease. Importantly, one of the patients who had progressive disease and had previously been pembrolizumab refractory was rechallenged with checkpoint inhibitors after T cell infusion (pembrolizumab and ipilimumab), and in this context developed a near-complete response lasting >20 months. The patient subsequently developed acquired resistance which was proven to be secondary to tumor downregulation of the specific HLA targeted by the infused MCPyV-specific T cells, confirming the therapeutic impact of MCPyV-specific T cells in the patient's remission. In contrast, a second clinical trial of 5 patients who received avelumab (anti-PDL-1 antibody) in addition to MCPyV-specific T cells and HLA-upregulation (see, e.g., NCT02584829), 4 out of 5 (80%) patients developed objective response, including 3 complete responses (CRs) lasting for >1 year. Two of those patients remain in CR as of this filing. Importantly, no increased toxicities were seen with the addition of avelumab. Overall, these data demonstrate that a combination therapy of a checkpoint inhibitor a with MCPyV-specific cellular immunetherapy provides an unexpected clinical response.

ADDITIONAL SEQUENCES

```
MCC1H-CDR3α [SEQ ID NO: 355]
CAVPNTGNQFYF

X389-1-CDR3α [SEQ ID NO: 356]
CAFTNTGKLIF

X389-2-CDR3α [SEQ ID NO: 357]
CAAKELGGATNKLIF
```

| ADDITIONAL SEQUENCES |
| --- |

X389-3-CDR3α [SEQ ID NO: 358]
CAVTTSGTYKYIF

X389-4-CDR3α [SEQ ID NO: 359]
CATDAGDTGFQKLVF

X389-5-CDR3α [SEQ ID NO: 360]
CAGANNYGQNFVF

X389-6-CDR3α [SEQ ID NO: 361]
CAWNTDKLIF

X389-7-CDR3α [SEQ ID NO: 362]
CVVRAAGNKLTF

X389-8-CDR3α [SEQ ID NO: 363]
CVVTGTGGFKTIF

X389-9-CDR3α [SEQ ID NO: 364]
CAVTRPSGGYNKLIF

MCC1H-CDR3β [SEQ ID NO: 365]
CASSLIAGLSYEQYF

X389-1-CDR3β [SEQ ID NO: 366]
CASALLEYSNQPQHF

X389-2-CDR3β [SEQ ID NO: 367]
CASSLGWGTTEAFF

X389-3-CDR3β [SEQ ID NO: 368]
CASSFSGSLGDTQYF

X389-4-CDR3β [SEQ ID NO: 369]
CASSPTLTSGGTDTQYF

X389-5-CDR3β [SEQ ID NO: 370]
CASSISLAGVHEQYF

X389-6-CDR3β [SEQ ID NO: 371]
CASSLAGDRSF

X389-7-CDR3β [SEQ ID NO: 372]
CASSVQGAPFPYEQYF

X389-8-CDR3β [SEQ ID NO: 373]
CASSSMSIAAGNTGELFF

X389-9-CDR3β [SEQ ID NO: 374
CASSFFGSETQYF

MCC1H Vα (wild-type) [SEQ ID NO: 375]
ATGGACAAGATCTTAGGAGCATCATTTTTAGTTCTGTGGCTTCAACTATGCT
GGGTGAGTGGCCAACAGAAGGAGAAAAGTGACCAGCAGCAGGTGAAACAA
AGTCCTCAATCTTTGATAGTCCAGAAAGGAGGGATTTCAATTATAAACTGTG
CTTATGAGAACACTGCGTTTGACTACTTTCCATGGTACCAACAATTCCCTGG
GAAAGGCCCTGCATTATTGATAGCCATACGTCCAGATGTGAGTGAAAAGAA
AGAAGGAAGATTCACAATCTCCTTCAATAAAAGTGCCAAGCAGTTCTCATT
GCATATCATGGATTCCCAGCCTGGAGACTCAGCCACCTACTTCTGTGCAGTC
CCGAACACCGGTAACCAGTTCTATTTTGGGACAGGGACAAGTTTGACGGTC
ATTCCA X389-1 Vα (wild-type) [SEQ ID NO: 376]
ATGACACGAGTTAGCTTGCTGTGGGCAGTCGTGGTCTCCACCTGTCTTGAAT
CCGGCATGGCCCAGACAGTCACTCAGTCTCAACCAGAGATGTCTGTGCAGG
AGGCAGAGACTGTGACCCTGAGTTGCACATATGACACCAGTGAGAATAATT
ATTATTTGTTCTGGTACAAGCAGCCTCCCAGCAGGCAGATGATTCTCGTTAT
TCGCCAAGAAGCTTATAAGCAACAGAATGCAACGGAGAATCGTTTCTCTGT
GAACTTCCAGAAAGCAGCCAAATCCTTCAGTCTCAAGATCTCAGACTCACA
GCTGGGGGACACTGCGATGTATTTCTGTGCTTTCACCAACACAGGCAAACT
AATCTTTGGGCAAGGGACAACTTTACAAGTAAAACCA X389-2 Vα (wild-type) [SEQ ID NO: 377]
ATGGCCATGCTCCTGGGGGCATCAGTGCTGATTCTGTGGCTTCAGCCAGACT
GGGTAAACAGTCAACAGAAGAATGATGACCAGCAAGTTAAGCAAAATTCA
CCATCCCTGAGCGTCCAGGAAGGAAGAATTTCTATTCTGAACTGTGACTATA
CTAACAGCATGTTTGATTATTTCCTATGGTACAAAAAATACCCTGCTGAAGG

| ADDITIONAL SEQUENCES |
| --- |
| TCCTACATTCCTGATATCTATAAGTTCCATTAAGGATAAAAATGAAGATGGA<br>AGATTCACTGTCTTCTTAAACAAAAGTGCCAAGCACCTCTCTCTGCACATTG<br>TGCCCTCCCAGCCTGGAGACTCTGCATGTGCAGCAAAGGAGTTAGGTGGTG<br>CTACAAACAAGCTCATCTTTGGAACTGGCACTCTGCTTGCTGTCCAGCCA |
| X389-3 Vα (wild-type) [SEQ ID NO: 378]<br>ATGGCCATGCTCCTGGGGGCATCAGTGCTGATTCTGTGGCTTCAGCCAGACT<br>GGGTAAACAGTCAACAGAAGAATGATGACCAGCAAGTTAAGCAAAATTCA<br>CCATCCCTGAGCGTCCAGGAAGGAAGAATTTCTATTCTGAACTGTGACTATA<br>CTAACAGCATGTTTGATTATTTCCTATGGTACAAAAAATACCCTGCTGAAGG<br>TCCTACATTCCTGATATCTATAAGTTCCATTAAGGATAAAAATGAAGATGGA<br>AGATTCACTGTCTTCTTAAACAAAAGTGCCAAGCACCTCTCTCTGCACATTG<br>TGCCCTCCCAGCCTGGAGACTCTGCAGTGTACTTCTGTGCAGTTACTACCTC<br>AGGAACCTACAAATACATCTTTGGAACAGGCACCAGGCTGAAGGTTTTAGC<br>A |
| X389-4 Vα (wild-type) [SEQ ID NO: 379]<br>ATGGAAACTCTCCTGGGAGTGTCTTTGGTGATTCTATGGCTTCAACTGGCTA<br>GGGTGAACAGTCAACAGGGAGAAGAGGATCCTCAGGCCTTGAGCATCCAG<br>GAGGGTGAAAATGCCACCATGAACTGCAGTTACAAAACTAGTATAAACAAT<br>TTACAGTGGTATAGACAAAATTCAGGTAGAGGCCTTGTCCACCTAATTTTAA<br>TACGTTCAAATGAAAGAGAGAAACACAGTGGAAGATTAAGAGTCACGCTTG<br>ACACTTCCAAGAAAAGCAGTTCCTTGTTGATCACGGCTTCCCGGGCAGCAG<br>ACACTGCTTCTTACTTCTGTGCTACGACGCGGGGGACACAGGCTTTCAGAA<br>ACTTGTATTTGGAACTGGCACCCGACTTCTGGTCAGT |
| X389-5 Vα (wild-type) [SEQ ID NO: 380]<br>ATGGTCCTGAAATTCTCCGTGTCCATTCTTTGGATTCAGTTGGCATGGGTGA<br>GCACCCAGCTGCTGGAGCAGAGCCCTCAGTTTCTAAGCATCCAAGAGGGAG<br>AAAATCTCACTGTGTACTGCAACTCCTCAAGTGTTTTTTCCAGCTTACAATG<br>GTACAGACAGGAGCCTGGGGAAGGTCCTGTCCTCCTGGTGACAGTAGTTAC<br>GGGTGGAGAAGTGAAGAAGCTGAAGAGACTAACCTTTCAGTTTGGTGATGC<br>AAGAAAGGACAGTTCTCTCCACATCACTGCAGCCCAGCCTGGTGATACAGG<br>CCTCTACTGTGCAGGAGCAAATAACTATGGTCAGAATTTTGTCTTTGGTCCC<br>GGAACCAGATTGTCCGTGCTGCCC |
| X389-6 Vα (wild-type) [SEQ ID NO: 381]<br>ATGGAGAAGAATCCTTTGGCAGCCCCATTACTAATCCTCTGGTTTCATCTTG<br>ACTGCGTGAGCAGCATACTGAACGTGGAACAAAGTCCTCAGTCACTGCATG<br>TTCAGGAGGGAGACAGCACCAATTTCACCTGCAGCTTCCCTTCCAGCAATTT<br>TTATGCCTTACACTGGTACAGATGGGAAACTGCAAAAAGCCCCGAGGCCTT<br>GTTTGTAATGACTTTAAATGGGGATGAAAAGAAGAAAGGACGAATAAGTGC<br>CACTCTTAATACCAAGGAGGGTTACAGCTATTTGTACATCAAAGGATCCCA<br>GCCTGAAGACTCAGCCACATACCTCTGTGCCTGGAACACCGACAAGCTCAT<br>CTTTGGGACTGGGACCAGATTACAAGTCTTTCCA |
| X389-7 Vα (wild-type) [SEQ ID NO: 382]<br>ATGATATCCTTGAGAGTTTTACTGGTGATCCTGTGGCTTCAGTTAAGCTGGG<br>TTTGGAGCCAACGGAAGGAGGTGGAGCAGGATCCTGGACCCTTCAATGTTC<br>CAGAGGGAGCCACTGTCGCTTTCAACTGTACTTACAGCAACAGTGCTTCTCA<br>GTCTTTCTTCTGGTACAGACAGGATTGCAGGAAAGAACCTAAGTTGCTGAT<br>GTCCGTATACTCCAGTGGTAATGAAGATGGAAGGTTTACAGCACAGCTCAA<br>TAGAGCCAGCCAGTATATTTCCCTGCTCATCAGAGACTCCAAGCTCAGTGAT<br>TCAGCCACCTACCTCTGTGTGGTGAGGGCTGCAGGCAACAAGCTAACTTTTG<br>GAGGAGGAACCAGGGTGCTAGTTAAACCA |
| X389-8 Vα (wild-type) [SEQ ID NO: 383]<br>ATGATATCCTTGAGAGTTTTACTGGTGATCCTGTGGCTTCAGTTAAGCTGGG<br>TTTGGAGCCAACGGAAGGAGGTGGAGCAGGATCCTGGACCCTTCAATGTTC<br>CAGAGGGAGCCACTGTCGCTTTCAACTGTACTTACAGCAACAGTGCTTCTCA<br>GTCTTTCTTCTGGTACAGACAGGATTGCAGGAAAGAACCTAAGTTGCTGAT<br>GTCCGTATACTCCAGTGGTAATGAAGATGGAAGGTTTACAGCACAGCTCAA<br>TAGAGCCAGCCAGTATATTTCCCTGCTCATCAGAGACTCCAAGCTCAGTGAT<br>TCAGCCACCTACCTCTGTGTGGTGACCGGAACTGGAGGCTTCAAAACTATCT<br>TTGGAGCAGGAACAAGACTATTTGTTAAAGCA |
| X389-9 Vα (wild-type) [SEQ ID NO: 384]<br>ATGAAGAGGATATTGGGAGCTCTGCTGGGGCTCTTGAGTGCCCAGGTTTGC<br>TGTGTGAGAGGAATACAAGTGGAGCAGAGTCCTCCAGACCTGATTCTCCAG<br>GAGGGAGCCAATTCCACGCTGCGGTGCAATTTTTCTGACTCTGTGAACAATT<br>TGCAGTGGTTTCATCAAAACCCTTGGGGACAGCTCATCAACCTGTTTTACAT<br>TCCCTCAGGGACAAAACAGAATGGAAGATTAAGCGCCACGACTGTCGCTAC<br>GGAACGCTACAGCTTATTGTACATTTCCTCTTCCCAGACCACAGACTCAGGC<br>GTTTATTTCTGTGCTGTCACACGCCCTTCTGGTGGCTACAATAAGCTGATTTT<br>TGGAGCAGGGACCAGGCTGGCTGTACACCCA |

ADDITIONAL SEQUENCES

MCC1H vβ (wild-type) [SEQ ID NO: 385]1
ATGGGCACCAGGCTCCTCTGCTGGGTGGTCCTGGGTTTCCTAGGGACAGATC
ACACAGGTGCTGGAGTCTCCCAGTCCCCTAGGTACAAAGTCGCAAAGAGAG
GACAGGATGTAGCTCTCAGGTGTGATCCAATTTCGGGTCATGTATCCCTTTT
TTGGTACCAACAGGCCCTGGGGCAGGGGCCAGAGTTTCTGACTTATTTCCA
GAATGAAGCTCAACTAGACAAATCGGGGCTGCCCAGTGATCGCTTCTTTGC
AGAAAGGCCTGAGGGATCCGTCTCCACTCTGAAGATCCAGCGCACACAGCA
GGAGGACTCCGCCGTGTATCTCTGTGCCAGCAGCTTAATAGCGGGGCTCTCC
TACGAGCAGTACTTCGGGCCGGGCACCAGGCTCACGGTCACA X389-1 vβ (wild-type) [SEQ ID NO: 386]
ATGAGCAACCAGGTGCTCTGCTGTGTGGTCCTTTGTTTCCTGGGAGCAAACA
CCGTGGATGGTGGAATCACTCAGTCCCCAAAGTACCTGTTCAGAAAGGAAG
GACAGAATGTGACCCTGAGTTGTGAACAGAATTTGAACCACGATGCCATGT
ACTGGTACCGACAGGACCCAGGGCAAGGGCTGAGATTGATCTACTACTCAC
AGATAGTAAATGACTTTCAGAAAGGAGATATAGCTGAAGGGTACAGCGTCT
CTCGGGAGAAGAAGGAATCCTTTCCTCTCACTGTGACATCGGCCCAAAAGA
ACCCGACAGCTTTCTATCTCTGTGCCAGTGCCCTTCTTGAATATAGCAATCA
GCCCCAGCATTTTGGTGATGGGACTCGACTCTCCATCCTG X389-2 vβ (wild-type) [SEQ ID NO: 387]
ATGGACTCCTGGACCTTCTGCTGTGTGTCCCTTTGCATCCTGGTAGCGAAGC
ATACAGATGCTGGAGTTATCCAGTCACCCCGCCATGAGGTGACAGAGATGG
GACAAGAAGTGACTCTGAGATGTAAACCAATTTCAGGCCACAACTCCCTTT
TCTGGTACAGACAGACCATGATGCGGGGACTGGAGTTGCTCATTTACTTTAA
CAACAACGTTCCGATAGATGATTCAGGGATGCCCGAGGATCGATTCTCAGC
TAAGATGCCTAATGCATCATTCTCCACTCTGAAGATCCAGCCCTCAGAACCC
AGGGACTCAGCTGTGTACTTCTGTGCCAGCAGTTTAGGGTGGGGGACCACT
GAAGCTTTCTTTGGACAAGGCACCAGACTCACAGTTGTG X389-3 vβ (wild-type) [SEQ ID NO: 388]
ATGGGCACCAGGCTCCTCTTCTGGGTGGCCTTCTGTCTCCTGGGGGCAGATC
ACACAGGAGCTGGAGTCTCCCAGTCCCCAGTAACAAGGTCACAGAGAAGG
GAAAGGATGTAGAGCTCAGGTGTGATCCAATTTCAGGTCATACTGCCCTTTA
CTGGTACCGACAGAGCCTGGGGCAGGGCCTGGAGTTTTTAATTTACTTCCAA
GGCAACAGTGCACCAGACAAATCAGGGCTGCCCAGTGATCGCTTCTCTGCA
GAGAGGACTGGGGGATCCGTCTCCACTCTGACGATCCAGCGCACACAGCAG
GAGGACTCGGCCGTGTATCTCTGTGCCAGCAGTTTTAGCGGGAGTCTCGGG
GATACGCAGTATTTTGGCCCAGGCACCCGGCTGACAGTGCTC X389-4 vβ (wild-type) [SEQ ID NO: 389]
ATGGGCTGCAGGCTGCTCTGCTGTGCGGTTCTCTGTCTCCTGGGAGCAGTTC
CCATAGACACTGAAGTTACCCAGACACCAAAACACCTGGTCATGGGAATGA
CAAATAAGAAGTCTTTGAAATGTGAACAACATATGGGGCACAGGGCTATGT
ATTGGTACAAGCAGAAAGCTAAGAAGCCACCGGAGCTCATGTTTGTCTACA
GCTATGAGAAACTCTCTATAAATGAAAGTGTGCCAAGTCGCTTCTCACCTGA
ATGCCCCAACAGCTCTCTCTTAAACCTTCACCTACACGCCCTGCAGCCAGAA
GACTCAGCCCTGTATCTCTGCGCCAGCAGCCCTACGCTTACTAGCGGGGGC
ACAGATACGCAGTATTTTGGCCCAGGCACCCGGCTGACAGTGCTC X389-5 vβ (wild-type) [SEQ ID NO: 390]
ATGAGCAACCAGGTGCTCTGCTGTGTGGTCCTTTGTTTCCTGGGAGCAAACA
CCGTGGATGGTGGAATCACTCAGTCCCCAAAGTACCTGTTCAGAAAGGAAG
GACAGAATGTGACCCTGAGTTGTGAACAGAATTTGAACCACGATGCCATGT
ACTGGTACCGACAGGACCCAGGGCAAGGGCTGAGATTGATCTACTACTCAC
AGATAGTAAATGACTTTCAGAAAGGAGATATAGCTGAAGGGTACAGCGTCT
CTCGGGAGAAGAAGGAATCCTTTCCTCTCACTGTGACATCGGCCCAAAAGA
ACCCGACAGCTTTCTATCTCTGTGCCAGTAGTATCTCCCTAGCGGGAGTCCA
CGAGCAGTACTTCGGGCCGGGCACCAGGCTCACGGTCACG X389-6 vβ (wild-type) [SEQ ID NO: 391]
ATGGACTCCTGGACCTTCTGCTGTGTGTCCCTTTGCATCCTGGTAGCGAAGC
ATACAGATGCTGGAGTTATCCAGTCACCCCGCCATGAGGTGACAGAGATGG
GACAAGAAGTGACTCTGAGATGTAAACCAATTTCAGGCCACAACTCCCTTT
TCTGGTACAGACAGACCATGATGCGGGGACTGGAGTTGCTCATTTACTTTAA
CAACAACGTTCCGATAGATGATTCAGGGATGCCCGAGGATCGATTCTCAGC
TAAGATGCCTAATGCATCATTCTCCACTCTGAAGATCCAGCCCTCAGAACCC
AGGGACTCAGCTGTGTACTTCTGTGCCAGCAGTTTAGCTGGGGACAGGAGC
TTCGGGCCGGGCACCAGGCTCACGGTCACA X389-7 vβ (wild-type) [SEQ ID NO: 392]
ATGGGCCCCGGGCTCCTCTGCTGGGCACTGCTTTGTCTCCTGGGAGCAGGCT
TAGTGGACGCTGGAGTCACCCAAAGTCCCACACACCTGATCAAAACGAGAG
GACAGCAAGTGACTCTGAGATGCTCTCCTAAGTCTGGGCATGACACTGTGT
CCTGGTACCAACAGGCCCTGGGTCAGGGGCCCCAGTTTATCTTTCAGTATTA
TGAGGAGGAAGAGAGACAGAGAGGCAACTTCCCTGATCGATTCTCAGGTCA

| ADDITIONAL SEQUENCES |
|---|
| CCAGTTCCCTAACTATAGCTCTGAGCTGAATGTGAACGCCTTGTTGCTGGGG<br>GACTCGGCCCTCTATCTCTGTGCCAGCAGCGTCCAGGGGGCACCGTTCCCCT<br>ACGAGCAGTACTTCGGGCCGGGCACCAGGCTCACGGTCACA<br><br>X389-8 vβ (wild-type) [SEQ ID NO: 393]<br>ATGAGCCCAATATTCACCTGCATCACAATCCTTTGTCTGCTGGCTGCAGGTT<br>CTCCTGGTGAAGAAGTCGCCCAGACTCCAAAACATCTTGTCAGAGGGGAAG<br>GACAGAAAGCAAAATTATATTGTGCCCCAATAAAAGGACACAGTTATGTTT<br>TTTGGTACCAACAGGTCCTGAAAAACGAGTTCAAGTTCTTGATTTCCTTCCA<br>GAATGAAAATGTCTTTGATGAAACAGGTATGCCCAAGGAAAGATTTTCAGC<br>TAAGTGCCTCCCAAATTCACCCTGTAGCCTTGAGATCCAGGCTACGAAGCTT<br>GAGGATTCAGCAGTGTATTTTTGTGCCAGCTCTTCGATGAGTATCGCCGCGG<br>GTAACACCGGGGAGCTGTTTTTTGGAGAAGGCTCTAGGCTGACCGTACTG<br><br>X389-9 vβ (wild-type) [SEQ ID NO: 394]<br>ATGGACTCCTGGACCTTCTGCTGTGTGTCCCTTTGCATCCTGGTAGCGAAGC<br>ATACAGATGCTGGAGTTATCCAGTCACCCCGCCATGAGGTGACAGAGATGG<br>GACAAGAAGTGACTCTGAGATGTAAACCAATTTCAGGCCACAACTCCCTTT<br>TCTGGTACAGACAGACCATGATGCGGGGACTGGAGTTGCTCATTTACTTTAA<br>CAACAACGTTCCGATAGATGATTCAGGGATGCCCGAGGATCGATTCTCAGC<br>TAAGATGCCTAATGCATCATTCTCCACTCTGAAGATCCAGCCCTCAGAACCC<br>AGGGACTCAGCTGTGTACTTCTGTGCCAGCAGTTTCTTTGGATCCGAGACCC<br>AGTACTTCGGGCCAGGCACGCGGCTCCTGGTGCTC<br><br>MCC1H Vα (codon optimized) [SEQ ID NO: 395]<br>ATGGACAAGATCCTGGGCGCCAGCTTTCTGGTGCTGTGGCTGCAACTGTGTT<br>GGGTGTCCGGCCAGCAGAAAGAGAAGTCCGACCAGCAGCAAGTGAAACAG<br>AGCCCTCAGAGCCTGATCGTGCAGAAAGGCGGCATCAGCATCATCAACTGC<br>GCCTACGAGAATACCGCCTTCGACTACTTCCCCTGGTATCAGCAGTTCCCCG<br>GCAAGGGACCTGCTCTGCTGATCGCCATTAGACCCGACGTGTCCGAGAAGA<br>AAGAGGGCAGATTCACCATCAGCTTCAACAAGAGCGCCAAGCAGTTCAGCC<br>TGCACATCATGGATAGCCAGCCTGGCGACAGCGCCACCTACTTTTGTGCCGT<br>GCCTAACACCGGCAACCAGTTCTACTTTGGCACCGGCACCAGCCTGACAGT<br>GATCCCT<br><br>X389-1 Vα (codon optimized) [SEQ ID NO: 396]<br>ATGACCAGAGTGTCTCTGCTGTGGGCCGTCGTGGTGTCCACATGTCTGGAAT<br>CTGGCATGGCCCAGACCGTGACACAGAGCCAGCCTGAGATGTCTGTGCAAG<br>AGGCCGAGACAGTGACCCTGAGCTGCACCTACGATACCAGCGAGAACAACT<br>ACTACCTGTTCTGGTACAAGCAGCCTCCTAGCCGGCAGATGATCCTGGTCAT<br>CAGACAAGAGGCCTATAAGCAGCAGAACGCCACCGAGAACAGATTCAGCG<br>TGAACTTCCAGAAGGCCGCCAAGAGCTTCAGCCTGAAGATCAGCGATAGCC<br>AGCTGGGCGACACCGCCATGTACTTTTGCGCCTTCACCAACACCGGCAAGC<br>TGATCTTTGGCCAGGGCACCACACTGCAAGTGAAGCCC<br><br>X389-2 Vα (codon optimized) [SEQ ID NO: 397]<br>ATGGCTATGCTGCTGGGCGCCTCTGTGCTGATTCTGTGGCTGCAACCCGACT<br>GGGTCAACAGCCAGCAGAAGAACGACGACCAGCAAGTGAAACAGAACAGC<br>CCCAGCCTGTCCGTGCAAGAAGGCAGGATCTCCATCCTGAACTGCGACTAC<br>ACCAACTCTATGTTCGACTACTTCCTGTGGTACAAGAAGTACCCCGCCGAGG<br>GACCCACCTTCCTGATCAGCATCAGCAGCATCAAGGACAAGAACGAGGACG<br>GCCGGTTCACCGTGTTTCTGAACAAGAGCGCCAAGCACCTGAGCCTGCACA<br>TCGTGCCTTCTCAGCCTGGCGATAGCGCCGTGTATTTCTGCGCCGCCAAAGA<br>ACTTGGCGGAGCCACCAACAAGCTGATTTTCGGCACCGGAACACTGCTGGC<br>CGTGCAGCCT<br><br>X389-3 Vα (codon optimized) [SEQ ID NO: 398]<br>ATGGCCATGTTGCTCGGCGCCAGCGTTCTGATCCTTTGGCTCCAGCCTGATT<br>GGGTCAACTCTCAGCAGAAAAATGATGATCAACAAGTCAAGCAGAACTCCC<br>CTAGCCTGAGTGTCCAAGAGGGCCGCATCAGCATTCTGAATTGTGATTACA<br>CGAATAGTATGTTTGATTACTTTCTCTGGTATAAGAAATATCCGGCTGAGGG<br>CCCTACCTTTCTGATTTCCATCAGCTCTATTAAGGATAAGAATGAGGATGGA<br>CGCTTTACGGTGTTCCTCAACAAATCCGCCAAACACCTGTCTCTGCATATTG<br>TGCCCAGCCAGCCAGGCGACTCTGCCGTCTATTTTTGTGCCGTGACCACCAG<br>CGGCACCTACAAGTACATCTTCGGCACAGGCACCCGGCTGAAGGTGCTGGC<br>T<br><br>X389-4 Vα (codon optimized) [SEQ ID NO: 399]<br>ATGGAAACACTGCTCGGAGTGTCCCTCGTCATCCTCTGGCTGCAGCTGGCCA<br>GAGTGAATTCCCAGCAGGGCGAAGAGGATCCCCAGGCTCTGTCTATTCAAG<br>AGGGCGAGAATGCCACCATGAACTGCAGCTACAAGACCAGCATCAACAAC<br>CTGCAGTGGTACAGGCAGAACAGCGGCAGAGGACTGGTGCACCTGATCCTG<br>ATCCGGTCCAACGAGAGAGAGAAGCACTCCGGCAGACTGCGCGTGACCCTG<br>GACACAAGCAAGAAGTCTAGCAGCCTGCTGATCACCGCCTCCAGAGCCGCT<br>GATACAGCCTCTTACTTCTGCGCCACCGACGCCGGCGATACCGGCTTTCAGA<br>AACTGGTGTTCGGAACCGGCACCAGGCTGCTGGTTTCT |

| ADDITIONAL SEQUENCES |
|---|
| X389-5 Vα (codon optimized) [SEQ ID NO: 4001]<br>ATGGTGCTGAAGTTCAGCGTGTCCATCCTGTGGATCCAGCTGGCCTGGGTTT<br>CCACACAGCTGCTGGAACAGAGCCCTCAGTTCCTGAGCATCCAAGAGGGCG<br>AGAACCTGACCGTGTACTGCAACAGCAGCAGCGTGTTCAGCTCCCTGCAGT<br>GGTACAGACAAGAGCCTGGCGAAGGACCTGTGCTGCTGGTCACAGTTGTGA<br>CAGGCGGCGAAGTGAAGAAGCTGAAGCGGCTGACCTTCCAGTTCGGCGACG<br>CCAGAAAGGATTCCAGCCTGCACATTACCGCTGCTCAGCCAGGCGATACCG<br>GCCTGTATCTTTGTGCCGGCGCTAACAACTACGGCCAGAACTTCGTGTTCGG<br>ACCCGGCACAAGACTGTCTGTGCTGCCC<br><br>X389-6 Vα (codon optimized) [SEQ ID NO: 4011]<br>ATGGAAAAGAACCCTCTGGCCGCTCCTCTGCTGATCCTGTGGTTTCACCTGG<br>ACTGCGTGTCCAGCATCCTGAACGTGGAACAGAGCCCTCAGAGCCTGCATG<br>TGCAAGAGGGCGACAGCACCAACTTCACCTGTAGCTTCCCCAGCAGCAACT<br>TCTACGCCCTGCACTGGTACAGATGGGAGACAGCCAAGTCTCCCGAGGCAC<br>TGTTCGTGATGACCCTGAACGGCGACGAGAAGAAGAAGGGCAGAATCAGC<br>GCCACACTGAACACCAAAGAGGGCTACTCCTACCTGTACATCAAGGGCAGC<br>CAGCCTGAGGACAGCGCCACTTATCTGTGCGCCTGGAACACCGACAAGCTG<br>ATCTTTGGCACCGGCACCAGACTCCAGGTGTTCCCT<br><br>X389-7 Vα (codon optimized) [SEQ ID NO: 4021]<br>ATGATCAGCCTGCGGGTGCTGCTGGTTATCCTGTGGCTGCAGCTGAGCTGGG<br>TCTGGTCCCAGAGAAAAGAGGTGGAACAGGACCCCGGACCTTTCAATGTGC<br>CTGAAGGCGCCACCGTGGCCTTCAACTGCACCTACAGCAATAGCGCCAGCC<br>AGAGCTTCTTTTGGTACAGACAGGACTGCCGGAAAGAACCCAAGCTGCTGA<br>TGAGCGTGTACAGCAGCGGCAACGAGGACGGCAGATTCACAGCCCAGCTG<br>AACAGGGCCAGCCAGTACATTAGCCTGCTGATCAGAGACAGCAAGCTGAGC<br>GACTCCGCCACCTACCTGTGTGTCGTTAGAGCCGCCGGAAACAAGCTGACA<br>TTTGGAGGCGGCACACGGGTGCTCGTGAAGCCT<br><br>X389-8 Vα (codon optimized) [SEQ ID NO: 4031]<br>ATGATTTCCCTGAGAGTGCTGCTCGTGATTCTCTGGCTCCAGCTCTCCTGGG<br>TTTGGAGCCAGCGGAAAGAGGTCGAGCAAGACCCTGGGCCTTTTAACGTTC<br>CAGAGGGCGCTACAGTGGCTTTTAATTGCACATACTCCAACAGCGCCTCAC<br>AGAGTTTTTTCTGGTATCGGCAGGACTGTAGAAAAGAACCGAAACTGCTCA<br>TGTCCGTGTATAGCTCCGGCAATGAGGATGGCCGGTTTACCGCTCAGCTGA<br>ATCGGGCCTCTCAGTACATCTCCCTGCTGATTCGGGACTCCAAGCTGTCCGA<br>TAGCGCAACATACCTGTGCGTGGTCACAGGCACCGGCGGCTTCAAGACAAT<br>CTTCGGAGCAGGCACCCGGCTGTTTGTGAAGGCT<br><br>X389-9 Vα (codon optimized) [SEQ ID NO: 4041]<br>ATGAAGAGAATCCTGGGCGCTCTGCTGGGACTGCTGTCTGCTCAAGTGTGCT<br>GTGTGCGGGGCATCCAGGTGGAACAGTCTCCACCAGACCTGATCCTGCAAG<br>AGGGCGCCAATAGCACCCTGCGGTGCAACTTTAGCGACAGCGTGAACAACC<br>TGCAGTGGTTCCACCAGAATCCTTGGGGCCAGCTGATCAACCTGTTCTACAT<br>CCCCAGCGGCACCAAGCAGAACGGCAGACTGTCTGCTACCACCGTGGCCAC<br>CGAGAGATACAGCCTGCTGTACATCAGCAGCAGCCAGACCACAGACAGCG<br>GCGTGTACTTCTGCGCCGTGACAAGACCTAGCGGCGGCTACAACAAGCTGA<br>TCTTCGGAGCCGGCACCAGACTGGCCGTGCATCCT<br><br>MCC1H Vβ (codon optimized) [SEQ ID NO: 405]<br>atgggcaccagactgctgtgctgggtcgtgctgggatttctgggcacagatcatacaggcgccggtgtcagccagtctcctag<br>atacaaggtggccaagcgcggacaggatgtggccctgagatgtgatcctatcagcggccacgtgtccctgttctggtatcaac<br>aggccctcggacagggccccgagttcctgacctactttcagaatgaggcccagctggacagagcggcctgcctagccata<br>gattcttcgccgaaagaccccgagggcagcgtgtccacactgaagatccagagaaccccagcaagaggacagcgccgtgtac<br>ctgtgtgcctcttctctgatcgccggcctgagctacgagcagtattttggccctggcacacggctgaccgtgacc<br><br>X389-1 Vβ (codon optimized) [SEQ ID NO: 406]<br>atgagcaaccaggtgctgtgctgcgtggtgctgtgtttcctgggagccaataccgtggacggcggcatcacacagtcccaa<br>agtacctgttccggaaagagggccagaacgtcaccctgtcctgcgagcagaacctgaaccacgacgccatgtattggtacag<br>acaggacccaggccagggcctgagactgatctactacagccagatcgtgaacgactttcagaagggcgacattgccgagg<br>gctacagcgtgtccagagagaagaaagagtcctttccactgaccgtgactagcgcccagaagaacccaccgccttctacct<br>gtgtgccagcgctctgctggaatactccaaccagcctcagcactttggcgacggcacaagactgagcatcctg<br><br>X389-2 Vβ (codon optimized) [SEQ ID NO: 407]<br>atggatagctggaccttctgctgcgtgtccctgtgcattctggtggccaagcacacagatgccggcgtgatccagtctcctaga<br>cacgaagtgaccgagatgggccaagaagtgacactgcgctgtaaacccatcagcggccacaacagccttttttggtatcgg<br>cagaccatgatgagaggcctggaactgctgatctatttcaacaacaacgtgcccatcgacgacagcggcatgcccgaggata<br>gattttccgccaagatgcccaacgccagcttcagcaccctgaaaatccagcctagcgagcccagagactccgctgtgtacttc<br>tgtgcctcttctctcggctggggaaccaccgaggcctttttggacaaggcaccagactgacagtggtt<br><br>X389-3 Vβ (codon optimized) [SEQ ID NO: 408]<br>atgggaaccagactgctgttctgggtcgccttttgtctgctgggagccgatcatacaggcgccggtgtttctcagagcccagc<br>aacaaagtgacagagaaaggcaaggacgtggaactgagatgcgaccccatctctggccacacagccctgtactggtatag<br>acagtctctcggccagggctcgagttcctcatctacttccaaggcaacagcgcccctgacaagtctggcctgcctagcgatag<br>attctctgccgaaagaaccggcggctccgtgtctacactgaccatccagagaaccccagcaagaggattccgccgtgtacctgt<br>gcgcctctagcttttctggctccctgggcgataccccagtacttcggccctggaacaaggctgaccgtgctc |

-continued

ADDITIONAL SEQUENCES

X389-4 Vβ (codon optimized) [SEQ ID NO: 409]
atgggctgcagactgctgtgttgtgccgtgctgtgtctgctggagccgtgcctatcgacaccgaagtgacccagacacctaa
gcacctggtcatgggcatgacaaacaagaaaagcctgaagtgcgagcagcacatgggccacagagccatgtactggtaca
agcagaaggccaagaaacctcctgagctgatgttcgtgtacagctacgagaagctgagcatcaacgagagcgtgcccagca
gattcagccctgagtgcccctaatagcagcctgctgaacctgcatctgcacgccctgcagcctgaagatagcgccctgtacctg
tgtgccagctctcctacactgacaagcggcggcaccgacacacagtattttggccctggcaccagactgaccgtgctg X389-5 Vβ (codon optimized) [SEQ ID NO: 410]
atgagcaatcaggtgctgtgctgcgttgtgctgtgtttcctgggcgccaataccgtggatggcggcatcacacagagccccaa
gtacctgttccggaaagagggacagaacgtcaccctgagctgcgagcagaacctgaaccacgacgctatgtattggtatcgg
caggaccctggacagggcctgagactgatctactacagccagatcgtgaacgacttccagaagggcgacattgccgaggg
ctactccgtgtccagagagaagaaagagtcctttccactgacagtgacaagcgcccagaagaacccaccgccttctatctgt
gtgcctccagcatttctctggccggcgtgcacgagcagtacttcggacctggaacaaggctgaccgtgacc X389-6 Vβ (codon optimized) [SEQ ID NO: 411]
atggacagctggaccttctgctgtgtgtccctgtgtatcctggtggccaagcacacagatgccggcgtgatccagtctcctaga
cacgaagtgaccgagatgggccaagaagtgaccctgcgctgcaagcctatcagcggccacaatagcctgttctggtacagg
cagaccatgatgagaggcctggaactgctgatctacttcaacaacaacgtgcccatcgacgacagcggcatgcccgaggat
agattcagcgccaagatgcccaacgccagcttcagcaccctgaagatccagcctagcgagcccagagatagcgccgtgtac
ttttgtgcctctagcctggccggcgacagatcttttggccccggaacaagactgaccgtgacc X389-7 Vβ (codon optimized) [SEQ ID NO: 412]
atgggacctggacttctgtgttgggccctgctgtgtctgcttggagctggacttgtggacgctggcgtcacacagtctcccaca
cacctgatcaagaccagaggccagcaagtgacactgagatgcagccctaagagcggccacgataccgtgtcttggtatcag
caagccctcggccagggacctcagttcatcttccagtactacgaggaagaggaacggcagcgggcaacttccctgataga
ttctccggccatcagttccccaactacagctccgagctgaacgtgaacgccctgctgctcggagactctgccctgtatctttgtg
ccagctctgtgcaaggcgcccccatttccttacgagcagtacttcggccctggcaccaggctgacagtgaca X389-8 Vβ (codon optimized) [SEQ ID NO: 413]
atgagccccatctttacctgcatcaccatcctgtgcctgctggccgctggatctcctggggaagaagtggcccagacacctaa
gcacctcgttagaggcgagggccagaaggccaagctgtattgcgccctcatcaagggccacagctatgtttttggtatcaac
aggtcctgaagaacgagttcaagttcctgatcagcttccagaacgagaacgtgttcgacgagacaggcatgcccaaagagc
ggttctccgccaagtgcctgcctaacagccctcgcagcctggaaatccaggccaccaagctggaagattccgccgtgtatttct
gcgccagcagcagcatgtctatcgccgctggaaataccggcgagctgttcttcggcgagggcagcagactgacagttctg X389-9 Vβ (codon optimized) [SEQ ID NO: 414]
atggatagctggaccttctgctgcgtgtccctgtgtatcctggtggctaagcacacagatgccggcgtgatccagtctcctaga
cacgaagtgaccgagatgggccaagaagtgaccctgcgctgtaaacccatcagcggccacaacagcctgttctggtacaga
cagaccatgatgagaggcctggaactgctgatctacttcaacaacaacgtgcccatcgacgacagcggcatgcccgaggat
agattcagcgccaagatgcccaacgccagcttcagcaccctgaagatccagcctagcgagcccagagattccgccgtgtact
tttgtgccagcagcttcttcggcagcgagacacagtattcggccctggcacaagactgctggtgctg cβ H1, 3-9 (codon optimized) [SEQ ID NO: 415]
GACCTGAAGAACGTGTTCCCCCCAGAGGTGGCCGTGTTCGAGCCTTCTGAG
GCCGAGATCAGCCACACCCAGAAAGCCACCCTCGTGTGTCTGGCCACCGGC
TTTTACCCCGACCACGTGGAACTGTCTTGGTGGGTCAACGGCAAAGAGGTG
CACTCCGGCGTGTGCACCGATCCCCAGCCTCTGAAAGAACAGCCCGCCCTG
AACGACAGCCGGTACTGCCTGTCCAGCAGACTGAGAGTGTCCGCCACCTTC
TGGCAGAACCCCCGGAACCACTTCAGATGCCAGGTGCAGTTCTACGGCCTG
AGCGAGAACGACGAGTGGACCCAGGACAGAGCCAAGCCCGTGACCCAGAT
CGTGTCTGCCGAAGCCTGGGGCAGAGCCGATTGCGGCTTTACCAGCGAGAG
CTACCAGCAGGGCGTGCTGTCTGCCACCATCCTGTACGAGATCCTGCTGGG
AAAGGCCACCCTGTACGCCGTGCTGGTGTCTGCCCTGGTGCTGATGGCCATG
GTCAAGCGGAAGGACAGCAGAGGC cβ 1, 2 (codon optimized) [SEQ ID NO: 416]
GAGGACCTGAACAAAGTGTTCCCCCCAGAGGTGGCCGTGTTCGAGCCTTCT
GAGGCCGAGATCAGCCACACCCAGAAAGCCACCCTCGTGTGCCTGGCCACC
GGCTTTTTCCCCGACCACGTGGAACTGTCTTGGTGGGTCAACGGCAAAGAG
GTGCACTCCGGCGTGTGCACCGATCCCCAGCCTCTGAAAGAACAGCCCGCC
CTGAACGACAGCCGGTACTGCCTGTCCAGCAGACTGAGAGTGTCCGCCACC
TTCTGGCAGAACCCCCGGAACCACTTCAGATGCCAGGTGCAGTTCTACGGC
CTGAGCGAGAACGACGAGTGGACCCAGGACAGAGCCAAGCCCGTGACACA
GATCGTGTCTGCCGAAGCCTGGGGCAGAGCCGATTGCGGCTTTACCTCCGT
GTCCTATCAGCAGGGCGTGCTGAGCGCCACCATCCTGTACGAGATCCTGCT
GGGCAAGGCCACACTGTACGCCGTGCTGGTGTCTGCCCTGGTGCTGATGGC
CATGGTCAAGCGGAAGGACTTC MCC1H (β chain-P2A-α chain)-(codon optimized) [SEQ ID NO: 417]
atgggcaccagactgctgtgctgggtcgtgctgggatttctgggcacagatcatacaggcgccggtgtcagccagtctcctag
atacaaggtggccaagcgcggacaggatgtggccctgagatgtgatcctatcagcggccacgtgtccctgttctggtatcaac
aggccctcggacagggccccgagttcctgacctactttcagaatgaggcccagcctggacaagagccgctgcctagcata
gattatcgccgaaagacccgagggcagcgtgtccacactgaagatccagagaaccccagcaagaggacagcgccgtgtac
ctgtgtgcctcttctctgatcgccggcctgagctacgagcagtattttggccctggcacacggctgaccgtgaccGACCT
GAAGAACGTGTTCCCCCCAGAGGTGGCCGTGTTCGAGCCTTCTGAGGCCGA
GATCAGCCACACCCAGAAAGCCACCCTCGTGTGTCTGGCCACCGGCTTTTAC

| ADDITIONAL SEQUENCES |
|---|
| CCCGACCACGTGGAACTGTCTTGGTGGGTCAACGGCAAAGAGGTGCACTCC<br>GGCGTGTGCACCGATCCCCAGCCTCTGAAAGAACAGCCCGCCCTGAACGAC<br>AGCCGGTACTGCCTGTCCAGCAGACTGAGAGTGTCCGCCACCTTCTGGCAG<br>AACCCCCGGAACCACTTCAGATGCCAGGTGCAGTTCTACGGCCTGAGCGAG<br>AACGACGAGTGGACCCAGGACAGAGCCAAGCCCGTGACCCAGATCGTGTCT<br>GCCGAAGCCTGGGGCAGAGCCGATTGCGGCTTTACCAGCGAGAGCTACCAG<br>CAGGGCGTGCTGTCTGCCACCATCCTGTACGAGATCCTGCTGGGAAAGGCC<br>ACCCTGTACGCCGTGCTGGTGTCTGCCCTGGTGCTGATGGCCATGGTCAAGC<br>GGAAGGACAGCAGAGGCggttccggagccacgaacttctctctgttaaagcaagcaggagacgtggaagaa<br>aaccccggtcccATGGACAAGATCCTGGGCGCCAGCTTTCTGGTGCTGTGGCTGCA<br>ACTGTGTTGGGTGTCCGGCCAGCAGAAAGAGAAGTCCGACCAGCAGCAAGT<br>GAAACAGAGCCCTCAGAGCCTGATCGTGCAGAAAGGCGGCATCAGCATCAT<br>CAACTGCGCCTACGAGAATACCGCCTTCGACTACTTCCCCTGGTATCAGCAG<br>TTCCCCGGCAAGGGACCTGCTCTGCTGATCGCCATTAGACCCGACGTGTCCG<br>AGAAGAAAGAGGGCAGATTCACCATCAGCTTCAACAAGAGCGCCAAGCAG<br>TTCAGCCTGCACATCATGGATAGCCAGCCTGGCGACAGCGCCACCTACTTTT<br>GTGCCGTGCCTAACACCGGCAACCAGTTCTACTTTGGCACCGGCACCAGCCT<br>GACAGTGATCCCTgacatccagaaccccgaccctgcagtgtaccagctgcgggacagcaagagcagcgacaa<br>gagcgtgtgcctgttcaccgacttcgacagccagaccaacgtgtcccagagcaaggacagcgacgtgtacatcaccgataa<br>gtgcgtgctggacatgcggagcatggacttcaagagcaacagcgccgtggcctggtccaacaagagcgacttcgcctgcgc<br>caacgccttcaacaacagcattatccccgaggacacattcttcccaagcccgagagcagctgcgacgtgaagctggtggaa<br>aagagatcgagacagacaccaacctgaacttccagaacctcagcgtgatcggcttccggatcctgctgctgaaggtggccg<br>gatcaacctgctgatgaccctgcggctgtggtccagctga<br><br>X389-1 (β chain-P2A-α chain)-(codon optimized) [SEQ ID NO: 418]<br>atgagcaaccaggtgctgtgctgcgtggtgctgtgtttcctgggagccaataccgtggacggcggcatcacacagtccccaa<br>agtacctgttccggaaagagggccagaacgtcaccctgtcctgcgagcagaacctgaaccacgacgccatgtattggtacag<br>acaggacccaggccagggcctgagactgatctactacagccagatcgtgaacgactttcagaagggcgacattgccgagg<br>gctacagcgtgtccagagagaagaaagagtcctttccactgaccgtgactagcgcccagaagaaccctaccgccttctacct<br>gtgtgccagcgctctgctggaatactccaaccagcctcagcactttggcgacggcacaagactgagcatcctgGAGGA<br>CCTGAACAAAGTGTTCCCCCCAGAGGTGGCCGTGTTCGAGCCTTCTGAGGC<br>CGAGATCAGCCACACCCAGAAAGCCACCCTCGTGTGCCTGGCCACCGGCTT<br>TTTCCCCGACCACGTGGAACTGTCTTGGTGGGTCAACGGCAAAGAGGTGCA<br>CTCCGGCGTGTGCACCGATCCCCAGCCTCTGAAAGAACAGCCCGCCCTGAA<br>CGACAGCCGGTACTGCCTGTCCAGCAGACTGAGAGTGTCCGCCACCTTCTG<br>GCAGAACCCCCGGAACCACTTCAGATGCCAGGTGCAGTTCTACGGCCTGAG<br>CGAGAACGACGAGTGGACCCAGGACAGAGCCAAGCCCGTGACACAGATCG<br>TGTCTGCCGAAGCCTGGGGCAGAGCCGATTGCGGCTTTACCTCCGTGTCCTA<br>TCAGCAGGGCGTGCTGAGCGCCACCATCCTGTACGAGATCCTGCTGGGCAA<br>GGCCACACTGTACGCCGTGCTGGTGTCTGCCCTGGTGCTGATGGCCATGGTC<br>AAGCGGAAGGACTTCggttccggagccacgaacttctctctgttaaagcaagcaggagacgtggaagaaaac<br>cccggtcccATGACCAGAGTGTCTCTGCTGTGGGCCGTCGTGGTGTCCACATGTC<br>TGGAATCTGGCATGGCCCAGACCGTGACACAGAGCCAGCCTGAGATGTCTG<br>TGCAAGAGGCCGAGACAGTGACCCTGAGCTGCACCTACGATACCAGCGAGA<br>ACAACTACTACCTGTTCTGGTACAAGCAGCCTCCTAGCCGGCAGATGATCCT<br>GGTCATCAGACAAGAGGCCTATAAGCAGCAGAACGCCACCGAGAACAGAT<br>TCAGCGTGAACTTCCAGAAGGCCGCCAAGAGCTTCAGCCTGAAGATCAGCG<br>ATAGCCAGCTGGGCGACACCGCCATGTACTTTTGCGCCTTCACCAACACCG<br>GCAAGCTGATCTTTGGCCAGGGCACCACACTGCAAGTGAAGCCCgacatccagaa<br>ccccgaccctgcagtgtaccagctgcgggacagcaagagcagcgacaagagcgtgtgcctgttcaccgacttcgacagcc<br>agaccaacgtgtcccagagcaaggacagcgacgtgtacatcaccgataagtgcgtgctggacatgcggagcatggacttca<br>agagcaacagcgccgtggcctggtccaacaagagcgacttcgcctgcgccaacgccttcaacaacagcattatccccgagg<br>acacattatcccaagcccgagagcagctgcgacgtgaagctggtggaaaagagcttcgagacagacaccaacctgaact<br>tccagaacctcagcgtgatcggcttccggatcctgctgctgaaggtggccggcttcaacctgctgatgaccctgcggctgtgg<br>tccagctga<br><br>X389-2 (β chain-P2A-α chain)-(codon optimized) [SEQ ID NO: 419]<br>atggatagctggaccttctgctgcgtgtccctgtgcattctggtggccaagcacacagatgccggcgtgatccagtctcctaga<br>cacgaagtgaccgagatgggccaagaagtgacactgcgctgtaaacccatcagcggccacaacagcctgttttggtatcgg<br>cagaccatgatgagaggcctggaactgctgatctatttcaacaacaacgtgccatcgacgacagcggcatgcccgaggata<br>gattttcgccaagatgccaacgccagatcagcaccctgaaaatccagcctagcgagcccagagactccgctgtgtacttc<br>tgtgcctatctctcggctggggaaccaccgaggccttttttggacaaggcaccagactgacagtggttGAGGACCTG<br>AACAAAGTGTTCCCCCCAGAGGTGGCCGTGTTCGAGCCTTCTGAGGCCGAG<br>ATCAGCCACACCCAGAAAGCCACCCTCGTGTGCCTGGCCACCGGCTTTTTCC<br>CCGACCACGTGGAACTGTCTTGGTGGGTCAACGGCAAAGAGGTGCACTCCG<br>GCGTGTGCACCGATCCCCAGCCTCTGAAAGAACAGCCCGCCCTGAACGACA<br>GCCGGTACTGCCTGTCCAGCAGACTGAGAGTGTCCGCCACCTTCTGGCAGA<br>ACCCCCGGAACCACTTCAGATGCCAGGTGCAGTTCTACGGCCTGAGCGAGA<br>ACGACGAGTGGACCCAGGACAGAGCCAAGCCCGTGACACAGATCGTGTCTG<br>CCGAAGCCTGGGGCAGAGCCGATTGCGGCTTTACCTCCGTGTCCTATCAGC<br>AGGGCGTGCTGAGCGCCACCATCCTGTACGAGATCCTGCTGGGCAAGGCCA<br>CACTGTACGCCGTGCTGGTGTCTGCCCTGGTGCTGATGGCCATGGTCAAGCG<br>GAAGGACTTCggttccggagccacgaacttctctctgttaaagcaagcaggagacgtggaagaaaacccggtcc<br>cATGGCTATGCTGCTGGGCGCCTCTGTGCTGATTCTGTGGCTGCAACCCGAC<br>TGGGTCAACAGCCAGCAGAAGAACGACGACCAGCAAGTGAAACAGAACAG<br>CCCCAGCCTGTCCGTGCAAGAAGGCAGGATCTCCATCCTGAACTGCGACTA<br>CACCAACTCTATGTTCGACTACTTCCTGTGGTACAAGAAGTACCCCGCCGAG |

-continued

| ADDITIONAL SEQUENCES |
|---|
| GGACCCACCTTCCTGATCAGCATCAGCAGCATCAAGGACAAGAACGAGGAC<br>GGCCGGTTCACCGTGTTTCTGAACAAGAGCGCCAAGCACCTGAGCCTGCAC<br>ATCGTGCCTTCTCAGCCTGGCGATAGCGCCGTGTATTTCTGCGCCGCCAAAG<br>AACTTGGCGGAGCCACCAACAAGCTGATTTTCGGCACCGGAACACTGCTGG<br>CCGTGCAGCCTgacatccagaaccccgaccctgcagtgtaccagctgcgggacagcaagagcagcgacaagag<br>cgtgtgcctgttcaccgacttcgacagccagaccaacgtgtcccagagcaaggacagcgacgtgtacatcaccgataagtgc<br>gtgctggacatgcggagcatggacttcaagagcaacagcgccgtggcctggtccaacaagagcgacttcgcctgcgccaa<br>cgccttcaacaacagcattatccccgaggacacattcttcccaagccccgagagcagctgcgacgtgaagctggtggaaaa<br>gagatcgagacagacaccaacctgaacttccagaacctcagcgtgatcggcttccggatcctgctgctgaaggtggccggc<br>ttcaacctgctgatgaccctgcggctgtggtccagctga |

X389-3 (β chain-P2A-α chain)-(codon optimized) [SEQ ID NO: 420]
atgggaaccagactgctgttctggtcgccttttgtctgctgggagccgatcatacaggcgccggtgtttctcagagccccagc
aacaaagtgacagagaaaggcaaggacgtggaactgagatgcgaccccatctctggccacacagccctgtactggtataga
cagtctctcggccaggggctcgagttcctcatctacttccaaggcaacagcgccctgacaagtctggcctgcctagcgatag
attctctgccgaaagaaccggcggctccgtgtctacactgaccatccagagaacccagcaagaggattccgccgtgtacctgt
gcgcctctagatttctggctccctgggcgataccagtacttcggccctggaacaaggctgaccgtgctcGACCTGAA
GAACGTGTTCCCCCCAGAGGTGGCCGTGTTCGAGCCTTCTGAGGCCGAGAT
CAGCCACACCCAGAAAGCCACCCTCGTGTGTCTGGCCACCGGCTTTTACCCC
GACCACGTGGAACTGTCTTGGTGGGTCAACGGCAAAGAGGTGCACTCCGGC
GTGTGCACCGATCCCCAGCCTCTGAAAGAACAGCCCGCCCTGAACGACAGC
CGGTACTGCCTGTCCAGCAGACTGAGAGTGTCCGCCACCTTCTGGCAGAAC
CCCCGGAACCACTTCAGATGCCAGGTGCAGTTCTACGGCCTGAGCGAGAAC
GACGAGTGGACCCAGGACAGAGCCAAGCCCGTGACCCAGATCGTGTCTGCC
GAAGCCTGGGGCAGAGCCGATTGCGGCTTTACCAGCGAGAGCTACCAGCAG
GGCGTGCTGTCTGCCACCATCCTGTACGAGATCCTGCTGGGAAAGGCCACC
CTGTACGCCGTGCTGGTGTCTGCCCTGGTGCTGATGGCCATGGTCAAGCGGA
AGGACAGCAGAGGCggttccggagccacgaacttctctctgttaaagcaagcaggagacgtggaagaaaacc
ccggtcccATGGCCATGTTGCTCGGCGCCAGCGTTCTGATCCTTTGGCTCCAGCC
TGATTGGGTCAACTCTCAGCAGAAAAATGATGATCAACAAGTCAAGCAGAA
CTCCCCTAGCCTGAGTGTCCAAGAGGGCCGCATCAGCATTCTGAATTGTGAT
TACACGAATAGTATGTTTGATTACTTTCTCTGGTATAAGAAATATCCGGCTG
AGGGCCCTACCTTTCTGATTTCCATCAGCTCTATTAAGGATAAGAATGAGGA
TGGACGCTTTACGGTGTTCCTCAACAAATCCGCCAAACACCTGTCTCTGCAT
ATTGTGCCCAGCCAGCCAGGCGACTCTGCCGTCTATTTTTGTGCCGTGACCA
CCAGCGGCACCTACAAGTACATCTTCGGCACAGGCACCCGGCTGAAGGTGC
TGGCTgacatccagaaccccgaccctgcagtgtaccagctgcgggacagcaagagcagcgacaagagcgtgtgcctg
ttcaccgacttcgacagccagaccaacgtgtcccagagcaaggacagcgacgtgtacatcaccgataagtgcgtgctggac
atgcggagcatggacttcaagagcaacagcgccgtggcctggtccaacaagagcgacttcgcctgcgccaacgccttcaac
aacagcattatccccgaggacacattcttcccaagccccgagagcagctgcgacgtgaagctggtggaaaagagcttcgag
acagacaccaacctgaacttccagaacctcagcgtgatcggatccggatcctgctgctgaaggtggccggcttcaacctgct
gatgaccctgcggctgtggtccagctga X389-4 (β chain-P2A-α chain)-(codon optimized) [SEQ ID NO: 421]
atgggctgcagactgctgtgttgtgccgtgctgtgtctgctgggagccgtgcctatcgacaccgaagtgacccagacacctaa
gcacctggtcatgggcatgacaaacaagaaaagcctgaagtgcgagcagcacatgggccacagagccatgtactggtaca
agcagaaggccaagaaacctcctgagctgatgttcgtgtacagctacgagaagctgagcatcaacgagagcgtgcccagca
gattcagccctgagtgccctaatagcagcctgctgaacctgcatctgcacgccctgcagcctgaagatagcgccctgtacctg
tgtgccagctctcctacactgacaagcggcggcaccgacacacagtattttggccctggcaccagactgaccgtgctgGA
CCTGAAGAACGTGTTCCCCCCAGAGGTGGCCGTGTTCGAGCCTTCTGAGGC
CGAGATCAGCCACACCCAGAAAGCCACCCTCGTGTGTCTGGCCACCGGCTT
TTACCCCGACCACGTGGAACTGTCTTGGTGGGTCAACGGCAAAGAGGTGCA
CTCCGGCGTGTGCACCGATCCCCAGCCTCTGAAAGAACAGCCCGCCCTGAA
CGACAGCCGGTACTGCCTGTCCAGCAGACTGAGAGTGTCCGCCACCTTCTG
GCAGAACCCCCGGAACCACTTCAGATGCCAGGTGCAGTTCTACGGCCTGAG
CGAGAACGACGAGTGGACCCAGGACAGAGCCAAGCCCGTGACCCAGATCG
TGTCTGCCGAAGCCTGGGGCAGAGCCGATTGCGGCTTTACCAGCGAGAGCT
ACCAGCAGGGCGTGCTGTCTGCCACCATCCTGTACGAGATCCTGCTGGGAA
AGGCCACCCTGTACGCCGTGCTGGTGTCTGCCCTGGTGCTGATGGCCATGGT
CAAGCGGAAGGACAGCAGAGGCggttccggagccacgaacttctctctgttaaagcaagcaggagacg
tggaagaaaaccccggtcccATGGAAACACTGCTCGGAGTGTCCCTCGTCATCCTCTGG
CTGCAGCTGGCCAGAGTGAATTCCCAGCAGGGCGAAGAGGATCCCCAGGCT
CTGTCTATTCAAGAGGGCGAGAATGCCACCATGAACTGCAGCTACAAGACC
AGCATCAACAACCTGCAGTGGTACAGGCAGAACAGCGGCAGAGGACTGGT
GCACCTGATCCTGATCCGGTCCAACGAGAGAGAGAAGCACTCCGGCAGACT
GCGCGTGACCCTGGACACAAGCAAGAAGTCTAGCAGCCTGCTGATCACCGC
CTCCAGAGCCGCTGATACAGCCTCTTACTTCTGCGCCACCGACGCCGGCGAT
ACCGGCTTTCAGAAACTGGTGTTCGGAACCGGCACCAGGCTGCTGGTTTCTg
acatccagaaccccgaccctgcagtgtaccagctgcgggacagcaagagcagcgacaagagcgtgtgcctgttcaccgac
ttcgacagccagaccaacgtgtcccagagcaaggacagcgacgtgtacatcaccgataagtgcgtgctggacatgcggagc
atggacttcaagagcaacagcgccgtggcctggtccaacaagagcgacttcgcctgcgccaacgccttcaacaacagcatta
tccccgaggacacattcccaagccccgagagcagctgcgacgtgaagctggtggaaaagagcttcgagacagacacc
aacctgaacttccagaacctcagcgtgatcggatccggatcctgctgctgaaggtggccggcttcaacctgctgatgaccct
gcggctgtggtccagctga -continued

ADDITIONAL SEQUENCES

X389-5 (β chain-P2A-α chain)-(codon optimized) [SEQ ID NO: 422]
atgagcaatcaggtgctgtgctgcgttgtgctgtgtttcctgggcgccaataccgtggatggcggcatcacacagagcccaa
gtacctgttccggaaagagggacagaacgtcaccctgagctgcgagcagaacctgaaccacgacgctatgtattggtatcgg
caggaccctggacagggcctgagactgatctactacagccagatcgtgaacgacttccagaagggcgacattgccgaggg
ctactccgtgtccagagagaagaaagagtcctttccactgacagtgacaagcgcccagaagaaccccaccgccttctatctgt
gtgcctccagcatttctctggccggcgtgcacgagcagtacttcggacctggaacaaggctgaccgtgaccGACCTGA
AGAACGTGTTCCCCCCAGAGGTGGCCGTGTTCGAGCCTTCTGAGGCCGAGA
TCAGCCACACCCAGAAAGCCACCCTCGTGTGTCTGGCCACCGGCTTTTACCC
CGACCACGTGGAACTGTCTTGGTGGGTCAACGGCAAAGAGGTGCACTCCGG
CGTGTGCACCGATCCCCAGCCTCTGAAAGAACAGCCCGCCCTGAACGACAG
CCGGTACTGCCTGTCCAGCAGACTGAGAGTGTCCGCCACCTTCTGGCAGAA
CCCCCGGAACCACTTCAGATGCCAGGTGCAGTTCTACGGCCTGAGCGAGAA
CGACGAGTGGACCCAGGACAGAGCCAAGCCCGTGACCCAGATCGTGTCTGC
CGAAGCCTGGGGCAGAGCCGATTGCGGCTTTACCAGCGAGAGCTACCAGCA
GGGCGTGCTGTCTGCCACCATCCTGTACGAGATCCTGCTGGGGAAAGGCCAC
CCTGTACGCCGTGCTGGTGTCTGCCCTGGTGCTGATGGCCATGGTCAAGCGG
AAGGACAGCAGAGGCggttccggagccacgaacttctctctgttaaagcaagcaggagacgtggaagaaaac
cccggtcccATGGTGCTGAAGTTCAGCGTGTCCATCCTGTGGATCCAGCTGGCCT
GGGTTTCCACACAGCTGCTGGAACAGAGCCCTCAGTTCCTGACCAAG
AGGGCGAGAACCTGACCGTGTACTGCAACAGCAGCAGCGTGTTCAGCTCCC
TGCAGTGGTACAGACAAGAGCCTGGCGAAGGACCTGTGCTGCTGGTCACAG
TTGTGACAGGCGGCGAAGTGAAGAAGCTGAAGCGGCTGACCTTCCAGTTCG
GCGACGCCAGAAAGGATTCCAGCCTGCACATTACCGCTGCTCAGCCAGGCG
ATACCGGCCTGTATCTTTGTGCCGGCGCTAACAACTACGGCCAGAACTTCGT
GTTCGGACCCGGCACAAGACTGTCTGTGCTGCCCgacatccagaacccccgaccctgcagtgt
accagctgcgggacagcaagagcagcgacaagagcgtgtgcctgttcaccgacttcgacagccagaccaacgtgtcccag
agcaaggacagcgacgtgtacatcaccgataagtgcgtgctggacatgcggagcatggacttcaagagcaacagcgccgt
ggcctggtccaacaagagcgacttcgcctgcgccaacgccttcaacaacagcattatccccgaggacacattcttcccaagc
cccgagagcagctgcgacgtgaagctggtggaaaagagcttcgagacagacaccaacctgaacttccagaacctcagcgt
gatcggatccggatcctgctgctgaaggtggccggcttcaacctgctgatgaccctgcgcgctgtggtccagctga X389-6 (β chain-P2A-α chain)-(codon optimized) [SEQ ID NO: 423]
atggacagctggaccttctgctgtgtgtccctgtgtatcctggtggccaagcacacagatgccggcgtgatccagtctcctaga
cacgaagtgaccgagatgggccaagaagtgaccctgcgctgcaagcctatcagcggccacaatagcctgttctggtacagg
cagaccatgatgagaggcctggaactgctgatctacttcaacaacaacgtgcccatcgacgacagcggcatgcccgaggat
agattcagcgccaagatgcccaacgccagatcagcaccctgaagatccagctagcgagcccagagatagcgccgtgtac
ttttgtgcctctagcctggccggcgacagatcttttggccccggaacaagactgaccgtgaccGACCTGAAGAAC
GTGTTCCCCCCAGAGGTGGCCGTGTTCGAGCCTTCTGAGGCCGAGATCAGC
CACACCCAGAAAGCCACCCTCGTGTGTCTGGCCACCGGCTTTTACCCCGACC
ACGTGGAACTGTCTTGGTGGGTCAACGGCAAAGAGGTGCACTCCGGCGTGT
GCACCGATCCCCAGCCTCTGAAAGAACAGCCCGCCCTGAACGACAGCCGGT
ACTGCCTGTCCAGCAGACTGAGAGTGTCCGCCACCTTCTGGCAGAACCCCC
GGAACCACTTCAGATGCCAGGTGCAGTTCTACGGCCTGAGCGAGAACGACG
AGTGGACCCAGGACAGAGCCAAGCCCGTGACCCAGATCGTGTCTGCCGAAG
CCTGGGGCAGAGCCGATTGCGGCTTTACCAGCGAGAGCTACCAGCAGGGCG
TGCTGTCTGCCACCATCCTGTACGAGATCCTGCTGGGAAAGGCCACCCTGTA
CGCCGTGCTGGTGTCTGCCCTGGTGCTGATGGCCATGGTCAAGCGGAAGGA
CAGCAGAGGCggttccggagccacgaacttctctctgttaaagcaagcaggagacgtggaagaaaacccccggtcc
cATGGAAAAGAACCCTCTGGCCGCTCCTCTGCTGATCCTGTGGTTTCACCTG
GACTGCGTGTCCAGCATCCTGAACGTGGAACAGAGCCCTCAGAGCCTGCAT
GTGCAAGAGGGCGACAGCACCAACTTCACCTGTAGCTTCCCCAGCAGCAAC
TTCTACGCCCTGCACTGGTACAGATGGGAGACAGCCAAGTCTCCCGAGGCA
CTGTTCGTGATGACCCTGAACGGCGACGAGAAGAAGAAGGGCAGAATCAG
CGCCACACTGAACACCAAAGAGGGCTACTCCTACCTGTACATCAAGGGCAG
CCAGCCTGAGGACAGCGCCACTTATCTGTGCGCCTGGAACACCGACAAGCT
GATCTTTGGCACCGGCACCAGACTCCAGGTGTTCCCTgacatccagaacccccgaccctgc
agtgtaccagctgcgggacagcaagagcagcgacaagagcgtgtgcctgttcaccgacttcgacagccagaccaacgtgtc
ccagagcaaggacagcgacgtgtacatcaccgataagtgcgtgctggacatgcggagcatggacttcaagagcaacagcg
ccgtggcctggtccaacaagagcgacttcgcctgcgccaacgccttcaacaacagcattatccccgaggacacattcttccca
agccccgagagcagctgcgacgtgaagctggtggaaaagagcttcgagacagacaccaacctgaacttccagaacctcag
cgtgatcggatccggatcctgctgctgaaggtggccggcttcaacctgctgatgaccctgcgcgctgtggtccagctga X389-7 (β chain-P2A-α chain)-(codon optimized) [SEQ ID NO: 424]
atgggacctggacttctgtgttgggccctgctgtgtctgcttggagctggacttgtggacgctggcgtcacacagtctcccaca
cacctgatcaagaccagaggccagcaagtgacactgagatgcagcccttaagagcggccacgataccgtgtatggtatcag
caagccctcggccagggacctcagttcatcttccagtactacggaggaagggaacggcagcggggcaacttccctgataga
ttctccggccatcagttccccaactacagctccgagctgaacgtgaacgccctgctgctcggagactctgccctgtatctttgtg
ccagctctgtgcaaggcgcccattcttacgagcagtacttcggccctggcaccaggctgacagtgacaGACCTGA
AGAACGTGTTCCCCCCAGAGGTGGCCGTGTTCGAGCCTTCTGAGGCCGAGA
TCAGCCACACCCAGAAAGCCACCCTCGTGTGTCTGGCCACCGGCTTTTACCC
CGACCACGTGGAACTGTCTTGGTGGGTCAACGGCAAAGAGGTGCACTCCGG
CGTGTGCACCGATCCCCAGCCTCTGAAAGAACAGCCCGCCCTGAACGACAG
CCGGTACTGCCTGTCCAGCAGACTGAGAGTGTCCGCCACCTTCTGGCAGAA
CCCCCGGAACCACTTCAGATGCCAGGTGCAGTTCTACGGCCTGAGCGAGAA
CGACGAGTGGACCCAGGACAGAGCCAAGCCCGTGACCCAGATCGTGTCTGC
CGAAGCCTGGGGCAGAGCCGATTGCGGCTTTACCAGCGAGAGCTACCAGCA

| ADDITIONAL SEQUENCES |
|---|
| GGGCGTGCTGTCTGCCACCATCCTGTACGAGATCCTGCTGGGAAAGGCCAC<br>CCTGTACGCCGTGCTGGTGTCTGCCCTGGTGCTGATGGCCATGGTCAAGCGG<br>AAGGACAGCAGAGGCggttccggagccacgaacttctctctgttaaagcaaggcaggagacgtggaagaaaac<br>cccggtcccATGATCAGCCTGCGGGTGCTGCTGGTTATCCTGTGTGGCTGCAGCTGA<br>GCTGGGTCTGGTCCCAGAGAAAAGAGGTGGAACAGGACCCCGGACCTTTCA<br>ATGTGCCTGAAGGCGCCACCGTGGCCTTCAACTGCACCTACAGCAATAGCG<br>CCAGCCAGAGCTTCTTTTGGTACAGACAGGACTGCCGGAAAGAACCCAAGC<br>TGCTGATGAGCGTGTACAGCAGCGGCAACGAGGACGGCAGATTCACAGCCC<br>AGCTGAACAGGGCCAGCCAGTACATTAGCCTGCTGATCAGAGACAGCAAGC<br>TGAGCGACTCCGCCACCTACCTGTGTGTCGTTAGAGCCGCCGGAAACAAGC<br>TGACATTTGGAGGCGGCACACGGGTGCTCGTGAAGCCTgacatccagaaccccgaccct<br>gcagtgtaccagctgcgggacagcaagagcagcgacaagagcgtgtgcctgttcaccgacttcgacagccagaccaacgt<br>gtcccagagcaaggacagcgacgtgtacatcaccgataagtgcgtgctggacatgcggagcatggacttcaagagcaaca<br>gcgccgtggcctggtccaacaagagcgacttcgcctgcgccaacgccttcaacaacagcattatccccgaggacacattctt<br>cccaagccccgagagcagctgcgacgtgaagctggtggaaaagagcttcgagacagacaccaacctgaacttccagaacc<br>tcagcgtgatcggcttccggatcctgctgctgaaggtggccggcttcaacctgctgatgaccctgcggctgtggtccagctga |

X389-8 (β chain-P2A-α chain)-(codon optimized) [SEQ ID NO: 425]
atgagccccatctttacctgcatcaccatcctgtgcctgctggccgctggatctcctggggaagaagtggcccagacacctaa
gcacctcgttagaggcgagggccagaaggccaagctgtattgcgccccctatcaagggccacagctatgttttttggtatcaac
aggtcctgaagaacgagttcaagttcctgatcagcttccagaacgagaacgtgttcgacgagacaggcatgcccaaagagc
ggttctccgccaagtgcctgcctaacagcccttgcagcctggaaatccaggccaccaagctggaagattccgccgtgtatttct
gcgccagcagcagcatgtctatcgccgctggaaataccggcgagctgttcttcggcgagggcagcagactgacagttctgG
ACCTGAAGAACGTGTTCCCCCCAGAGGTGGCCGTGTTCGAGCCTTCTGAGG
CCGAGATCAGCCACACCCAGAAAGCCACCCTCGTGTGTCTGGCCACCGGCT
TTTACCCCGACCACGTGGAACTGTCTTGGTGGGTCAACGGCAAAGAGGTGC
ACTCCGGCGTGTGCACCGATCCCCAGCCTCTGAAAGAACAGCCCGCCCTGA
ACGACAGCCGGTACTGCCTGTCCAGCAGACTGAGAGTGTCCGCCACCTTCT
GGCAGAACCCCCGGAACCACTTCAGATGCCAGGTGCAGTTCTACGGCCTGA
GCGAGAACGACGAGTGGACCCAGGACAGAGCCAAGCCCGTGACCCAGATC
GTGTCTGCCGAAGCCTGGGGCAGAGCCGATTGCGGCTTTACCAGCGAGAGC
TACCAGCAGGGCGTGCTGTCTGCCACCATCCTGTACGAGATCCTGCTGGGA
AAGGCCACCCTGTACGCCGTGCTGGTGTCTGCCCTGGTGCTGATGGCCATGG
TCAAGCGGAAGGACAGCAGAGGCggttccggagccacgaacttctctctgttaaagcaagcaggaga
cgtggaagaaaaccccggtcccATGATTTCCCTGAGAGTGCTGCTCGTGATTCTCTGGCT
CCAGCTCTCCTGGGTTTGGAGCCAGCGGAAAGAGGTCGAGCAAGACCCTGG
GCCTTTTAACGTTCCAGAGGGCGCTACAGTGGCTTTTAATTGCACATACTCC
AACAGCGCCTCACAGAGTTTTTTCTGGTATCGGCAGGACTGTAGAAAAGAA
CCGAAACTGCTCATGTCCGTGTATAGCTCCGGCAATGAGGATGGCCGGTTT
ACCGCTCAGCTGAATCGGGCCTCTCAGTACATCTCCCTGCTGATTCGGGACT
CCAAGCTGTCCGATAGCGCAACATACCTGTGCGTGGTCACAGGCACCGGCG
GCTTCAAGACAATCTTCGGAGCAGGCACCCGGCTGTTTGTGAAGGCTgacatcc
agaaccccgaccctgcagtgtaccagctgcgggacagcaagagcagcgacaagagcgtgtgcctgttcaccgacttcgac
agccagaccaacgtgtcccagagcaaggacagcgacgtgtacatcaccgataagtgcgtgctggacatgcggagcatgga
cttcaagagcaacagcgccgtggcctggtccaacaagagcgacttcgcctgcgccaacgccttcaacaacagcattatcccc
gaggacacattcttcccaagccccgagagcagctgcgacgtgaagctggtggaaaagagcttcgagacagacaccaacct
gaacttccagaacctcagcgtgatcggatccggatcctgctgctgaaggtggccggcttcaacctgctgatgaccctgcggc
tgtggtccagctga X389-9 (β chain-P2A-α chain)-(codon optimized) [SEQ ID NO: 426]
atggatagctggacctttctgctgcgtgtccctgtgtatcctggtggctaagcacacagatgccggcgtgatccagtctcctaga
cacgaagtgaccgagatgggccaagaagtgaccctgcgctgtaaacccatcagcggccacaacagcctgttctggtacaga
cagaccatgatgagaggcctggaactgctgatctacttcaacaacaacgtgcccatcgacgacagcggcatgccaggat
agattcagcgccaagatgcccaacgccagatcagcacccctgaagatccagcctagcgagcccagagattccgccgtgtact
tttgtgccagcagcttatcggcagcgagacacagtatttcggccctggcacaagactgctggtgctgGACCTGAAG
AACGTGTTCCCCCCAGAGGTGGCCGTGTTCGAGCCTTCTGAGGCCGAGATC
AGCCACACCCAGAAAGCCACCCTCGTGTGTCTGGCCACCGGCTTTTACCCCG
ACCACGTGGAACTGTCTTGGTGGGTCAACGGCAAAGAGGTGCACTCCGGCG
TGTGCACCGATCCCCAGCCTCTGAAAGAACAGCCCGCCCTGAACGACAGCC
GGTACTGCCTGTCCAGCAGACTGAGAGTGTCCGCCACCTTCTGGCAGAACC
CCCGGAACCACTTCAGATGCCAGGTGCAGTTCTACGGCCTGAGCGAGAACG
ACGAGTGGACCCAGGACAGAGCCAAGCCCGTGACCCAGATCGTGTCTGCCG
AAGCCTGGGGCAGAGCCGATTGCGGCTTTACCAGCGAGAGCTACCAGCAGG
GCGTGCTGTCTGCCACCATCCTGTACGAGATCCTGCTGGGAAAGGCCACCCT
GTACGCCGTGCTGGTGTCTGCCCTGGTGCTGATGGCCATGGTCAAGCGGAA
GGACAGCAGAGGCggttccggagccacgaacttctctctgttaaagcaagcaggagacgtggaagaaaacccc
ggtcccATGAAGAGAATCCTGGGCGCTCTGCTGGGACTGCTGTCTGCTCAAGTG
TGCTGTGTGCGGGGCATCCAGGTGGAACAGTCTCCACCAGACCTGATCCTG
CAAGAGGGCGCCAATAGCACCCTGCGGTGCAACTTTAGCGACAGCGTGAAC
AACCTGCAGTGGTTCCACCAGAATCCTTGGGGCCAGCTGATCAACCTGTTCT
ACATCCCCAGCGGCACCAAGCAGAACGGCAGACTGTCTGCTACCACCGTGG
CCACCGAGAGATACAGCCTGCTGTACATCAGCAGCAGCCAGACCACAGACA
GCGGCGTGTACTTCTGCGCCGTGACAAGACCTAGCGGCGGCTACAACAAGC
TGATCTTCGGAGCCGGCACCAGACTGGCCGTGCATCCTgacatccagaaccccgaccct
gcagtgtaccagctgcgggacagcaagagcagcgacaagagcgtgtgcctgttcaccgacttcgacagccagaccaacgt
gtcccagagcaaggacagcgacgtgtacatcaccgataagtgcgtgctggacatgcggagcatggacttcaagagcaaca
gcgccgtggcctggtccaacaagagcgacttcgcctgcgccaacgccttcaacaacagcattatccccgaggacacattctt -continued

| ADDITIONAL SEQUENCES |
|---|
| cccaagccccgagagcagctgcgacgtgaagctggtggaaaagagcttcgagacagacaccaacctgaacttccagaacc |
| tcagcgtgatcggcttccggatcctgctgctgaaggtggccggcttcaacctgctgatgaccctgcggctgtggtccagctga |

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, including U.S. Provisional Application No. 62/421,902, filed Nov. 14, 2016 and U.S. Provisional Application No. 62/480,247, filed Mar. 31, 2017, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. An expression vector comprising a polynucleotide encoding a binding protein, wherein the binding protein comprises:
   (a) a T cell receptor (TCR) α-chain variable (Vα) domain having a CDR3 amino acid sequence of any one of SEQ ID NOS.:13, 44 and 355-364; and
   (b) a TCR β-chain variable (Vβ) domain having a CDR3 amino acid sequence of any one of SEQ ID NOS.:14, 69 and 365-374.

2. The expression vector of claim 1, wherein the binding protein is capable of specifically binding to a Merkel cell polyomavirus T antigen peptide:HLA complex on a cell surface independent of CD8 or in the absence of CD8.

3. The expression vector according to claim 1, wherein the binding protein is capable of specifically binding to a KLLEIAPNC (SEQ ID NO.:17):human leukocyte antigen (HLA) complex or a KLLEIAPNA (SEQ ID NO.:37):human leukocyte antigen (HLA) complex with a $K_d$ less than or equal to about $10^{-8}$ M.

4. The expression vector according to claim 1, wherein the binding protein specifically binds to a KLLEIAPNC (SEQ ID NO.:17):HLA-A*02:01 complex or a KLLEIAPNA (SEQ ID NO.:37):HLA-A*02:01 complex.

5. The expression vector according to claim 1, wherein the Vα domain is at least about 90% identical to the Vα amino acid sequence set forth in
MDKILGASFLVLWLQLCWVSGQQKEKSDQQQVKQSPQSLIVQKGGISIINCAYENTAFDYFPWYQQFPGKGPALLIAIRPDVSEKKEGRFTISFNKSAKQFSLHIMDSQPGDSATYFCAVPNTGNQFYFGTGTSLTVIP (SEQ ID NO.: 428); and/or
the Vβ domain is at least about 90% identical to the Vβ amino acid sequence set forth in
MGTRLLCWVVLGFLGTDHTGAGVSQSPRYKVAKRGQDVALRCDPISGHVSLFW YQQALGQGPEFLTYFQNEAQLDKSGLPSDRFFAERPEGSVSTLKIQRTQQEDSAV YLCASSLIAGLSYEQYFGPGTRLTVT (SEQ ID NO.: 429).

6. The expression vector according to claim 1, wherein the Vα domain comprises the Vα amino acid sequence set forth in
MDKILGASFLVLWLQLCWVSGQQKEKSDQQQVKQSPQSLIVQKGGISIINCAYENTAFDYFPWYQQFPGKGPALLIAIRPDVSEKKEGRFTISFNKSAKQFSLHIMDSQPGDSATYFCAVPNTGNQFYFGTGTSLTVIP (SEQ ID NO.: 428); and/or
the Vβ domain comprises the Vβ amino acid sequence set forth in
MGTRLLCWVVLGFLGTDHTGAGVSQSPRYKVAKRGQDVALRCDPISGHVSLFW YQQALGQGPEFLTYFQNEAQLDKSGLPSDRFFAER-

PEGSVSTLKIQRTQQEDSAV YLCASSLIAG-
LSYEQYFGPGTRLTVT (SEQ ID NO.: 429).

7. The expression vector according claim 1, wherein the binding protein further comprises a TCR α-chain constant domain (Cα) having at least 90% sequence identity to the amino acid sequence of SEQ ID NO.:2, and/or wherein the binding protein further comprises a TCR β-chain constant domain (Cβ) having at least 90% sequence identity to the amino acid sequence of SEQ ID NO.:4.

8. The expression vector according claim 1, wherein:
the Vα domain comprises the Vα amino acid sequence set forth in
MDKILGASFLVLWLQLCWVSGQQKEKSDQQQV-
KQSPQSLIVQKGGISIINCAYENTAFD YFPWYQQ-
FPGKGPALLIAIRPDVSEKKEGRFTISFNKSAKQFSL-
HIMDSQPGDSATYFCA VPNTGNQFYFGTGTSLTVIP (SEQ ID NO.: 428); and
the Vβ domain comprises the Vβ amino acid sequence set forth in
MGTRLLCWVVLGFLGTDHTGAGVSQSPRYK-
VAKRGQDVALRCDPISGHVSLFWYQQA LGQGPE-
FLTYFQNEAQLDKSGLPSDRFFAERPEGSVSTL-
KIQRTQQEDSAVYLCASSLIA GLSYEQYFGP-
GTRLTVT (SEQ ID NO.: 429); and
wherein the binding protein further comprises a TCR α-chain constant domain (Cα) comprising the amino acid sequence of SEQ ID NO.:2; and a TCR β-chain constant domain (Cβ) comprising the amino acid sequence of SEQ ID NO.:4,
wherein the Vα and the Cα are comprised in a TCRα chain and wherein the Vβ and the Cβ are comprised in a TCRβ chain.

9. The expression vector according to claim 1, wherein the binding protein is a T cell receptor (TCR), an antigen-binding fragment of a TCR, or a chimeric antigen receptor.

10. The expression vector according to claim 9, wherein the TCR, the chimeric antigen receptor, or the antigen-binding fragment of the TCR is chimeric, humanized or human.

11. The expression vector according to claim 9, wherein the antigen-binding fragment of the TCR comprises a single chain TCR (scTCR).

12. A composition comprising the expression vector according to claim 1 and a pharmaceutically acceptable carrier, diluent, or excipient.

13. The expression vector of claim 1, wherein the polynucleotide is operably linked to an expression control sequence.

14. A genetically engineered host cell, comprising the expression vector of claim 1 and expressing the binding protein on its cell surface.

15. The genetically engineered host cell of claim 14, wherein:
(a) the host cell is a hematopoietic progenitor cell or a human immune system cell;
(b) the host cell is an immune system cell selected from the group consisting of: a CD4+ T cell, a CD8+ T cell, a CD4–CD8– double negative T cell, a γδ T cell, a natural killer cell, and a dendritic cell;
(c) the host cell is a T cell; or
(d) the host cell is a T cell selected from the group consisting of: a naïve T cell, a central memory T cell, and an effector memory T cell.

16. An adoptive immunotherapy method for treating a subject having a Merkel cell carcinoma, comprising administering to the subject an effective amount of a genetically engineered host cell according to claim 15.

17. A unit dose form comprising a genetically engineered host cell according to claim 15.

18. An adoptive immunotherapy method for treating a subject having a Merkel cell carcinoma, comprising administering to the subject an effective amount of a genetically engineered host cell according to claim 14.

19. A unit dose form comprising a genetically engineered host cell according to claim 14.

20. A host cell comprising a heterologous polynucleotide encoding a binding protein that is capable of specifically binding to a Merkel cell polyomavirus T antigen peptide:HLA complex, wherein the binding protein comprises:
(a) a T cell receptor (TCR) α chain variable (Vα) domain having a CDR3 amino acid sequence of any one of SEQ ID NOS.:13, 44, and 355-364, and
(b) a TCR β chain variable (Vβ) domain having a CDR3 amino acid sequence of any one of SEQ ID NOS.:14, 69, and 365-374.

21. The host cell of claim 20, wherein the host cell comprises a CD4+ T cell, a CD8+ T cell, a CD4–CD8– double negative T cell, a γδ T cell, a naïve T cell, a central memory T cell, an effector memory T cell, a natural killer cell, a dendritic cell, or any combination thereof.

22. A method of treating a Merkel cell carcinoma, comprising administering a therapeutically effective amount of the host cell according to claim 20 to a subject having or at risk of having Merkel cell carcinoma.

23. The host cell according to claim 20, wherein the binding protein comprises a TCR.

24. The host cell according to claim 20, wherein the host cell comprises a CD4+ T cell and further comprises a heterologous polynucleotide encoding a CD8 co-receptor molecule.

25. The host cell according to claim 20, wherein the binding protein is capable of specifically binding to a Merkel cell polyomavirus T antigen peptide:HLA complex on a cell surface independent of CD8 or in the absence of CD8.

26. The host cell according to claim 20, wherein the binding protein is capable of specifically binding to a KLLEIAPNC (SEQ ID NO.:17):human leukocyte antigen (HLA) complex and/or a KLLEIAPNA (SEQ ID NO.:37): human leukocyte antigen (HLA) complex, with a $K_d$ less than or equal to about $10^{-8}$ M.

27. The host cell according to claim 20, wherein the binding protein is capable of specifically binding to a KLLEIAPNC (SEQ ID NO.:17):HLA-A*02:01 complex and/or a KLLEIAPNA (SEQ ID NO.:37):HLA-A*02:01 complex.

28. The host cell according to claim 20, wherein
the $V_\alpha$ domain is at least about 90% identical to a $V_\alpha$ domain amino acid sequence set forth in
MDKILGASFLVLWLQLCWVSGQQKEKSD-
QQQVKQSPQSLIVQKGGISIINCAYE
NTAFDYFPWYQQFPGKGPALLIAIR-
PDVSEKKEGRFTISFNKSAKQFSLHIMDSQP
GDSATYFCAVPNTGNQFYFGTGTSLTVIP (SEQ ID NO.: 428); and/or
the $V_\beta$ domain is at least about 90% identical to a $V_\beta$ domain amino acid sequence set forth in
MGTRLLCWVVLGFLGTDHTGAGVSQSPRYK-
VAKRGQDVALRCDPISGHVSLFW YQQAL-
GQGPEFLTYFQNEAQLDKSGLPSDRFFAER-
PEGSVSTLKIQRTQQEDSAV YLCASSLIAG-
LSYEQYFGPGTRLTVT (SEQ ID NO.: 429).

29. The host cell according to claim 28, wherein
the $V_\alpha$ domain comprises an amino acid sequence set forth in MDKILGASFLVLWLQLCWVSGQQKEKS-
DQQQVKQSPQSLIVQKGGISIINCAYE
NTAFDYFPWYQQFPGKGPALLIAIR-
PDVSEKKEGRFTISFNKSAKQFSLHIMDSQP
GDSATYFCAVPNTGNQFYFGTGTSLTVIP (SEQ
ID NO.: 428); and/or
the $V_\beta$ domain comprises an amino acid sequence set forth in
MGTRLLCWVVLGFLGTDHTGAGVSQSPRYK-
VAKRGQDVALRCDPISGHVSLFW YQQAL-
GQGPEFLTYFQNEAQLDKSGLPSDRFFAER-
PEGSVSTLKIQRTQQEDSAV YLCASSLIA-
GLSYEQYFGPGTRLTVT (SEQ ID NO.: 429).

30. The host cell according to claim 29, wherein the binding protein further comprises a TCR α-chain constant domain having at least 90% sequence identity to the amino acid sequence set forth in SEQ ID NO.:2, and/or wherein the binding protein further comprises a TCR β-chain constant domain having at least 90% sequence identity to the amino acid sequence set forth in SEQ ID NO.:4.

31. The host cell according to claim 30, wherein the binding protein comprises a TCR comprising:

the $V_\alpha$ domain amino acid sequence set forth in
MDKILGASFLVLWLQLCWVSGQQKEKSDQQQV-
KQSPQSLIVQKGGISIINCAYENTAFD YFPWYQQ-
FPGKGPALLIAIRPDVSEKKEGRFTISFNKSAKQFSL-
HIMDSQPGDSATYFCA VPNTGNQFYFGTGTSLTVIP
(SEQ ID NO.: 428);

the α-chain constant domain amino acid sequence set forth in SEQ ID NO.:2;

the $V_\beta$ domain amino acid sequence set forth in
MGTRLLCWVVLGFLGTDHTGAGVSQSPRYKVAKR-
GQDVALRCDPISGHVSLFWYQQA LGQGPEFLTYF-
QNEAQLDKSGLPSDRFFAERPEGSVSTLKIQRTQQE-
DSAVYLCASSLIA GLSYEQYFGPGTRLTVT (SEQ ID
NO.: 429); and the β-chain constant domain amino acid sequence set forth in SEQ ID NO.:4.

32. The host cell according to claim 20, wherein the host cell comprises:
(i) a CD4+ T cell;
(ii) a CD8+ T cell;
(iii) a CD8+ CD62L+ T cell; or
(iv) any combination of (i)-(iii).

33. The host cell according to claim 20, wherein the host cell is a hematopoietic progenitor cell or a human immune system cell.

34. An isolated polynucleotide encoding a binding protein, wherein the binding protein comprises:
(a) a T cell receptor (TCR) α-chain variable (Vα) domain having a CDR3 amino acid sequence of any one of SEQ ID NOS.:13, 44 and 355-364; and
(b) a TCR β-chain variable (Vβ) domain having a CDR3 amino acid sequence of any one of SEQ ID NOS.:14, 69 and 365-374, wherein the polynucleotide comprises a Vα domain-encoding polynucleotide having at least 80% identity to the polynucleotide sequence of any one of SEQ ID NOs.:5, 6, 375-384 and 395-404, and a Vβ domain-encoding polynucleotide having at least 80% identity to the polynucleotide sequence of any one of SEQ ID NOs.: 9, 10, 385-394, and 405-414.

35. The isolated polynucleotide according to claim 34, wherein the TCR Vβ-encoding polynucleotide comprises or consists of the polynucleotide sequence set forth in SEQ ID NO.:405 and the TCR Vα-encoding the polynucleotide comprises or consists of the polynucleotide sequence set forth in SEQ ID NO.:395.

36. The isolated polynucleotide according to claim 35, wherein the binding protein further comprises a TCR beta chain constant domain (TCR Cβ) and/or a TCR alpha chain constant domain (TCR Cα), wherein the TCR Cβ-encoding polynucleotide comprises or consists of the polynucleotide sequence set forth in SEQ ID NO.:415 and the TCR Cα-encoding polynucleotide comprises or consists of the polynucleotide sequence set forth in SEQ ID NO.:8.

37. The isolated polynucleotide according to claim 35, comprising the polynucleotide sequence set forth in SEQ ID NO.:417.

* * * * *

SEQUENCE LISTING

```
<160> NUMBER OF SEQ ID NOS: 429

<210> SEQ ID NO 1
<211> LENGTH: 134
<212> TYPE: PRT
<213> ORGANISM: Artificial Sequence
<220> FEATURE:
<223> OTHER INFORMATION: Synthetic sequence MCC1 alpha chain variable
      domain

<400> SEQUENCE: 1

Met Ile Ser Leu Arg Val Leu Leu Val Ile Leu Trp Leu Gln Leu Ser
1               5                   10                  15

Trp Val Trp Ser Gln Arg Lys Glu Val Glu Gln Asp Pro Gly Pro Phe
                20                  25                  30

Asn Val Pro Glu Gly Ala Thr Val Ala Phe Asn Cys Thr Tyr Ser Asn
            35                  40                  45

Ser Ala Ser Gln Ser Phe Phe Trp Tyr Arg Gln Asp Cys Arg Lys Glu
        50                  55                  60

Pro Lys Leu Leu Met Ser Val Tyr Ser Ser Gly Asn Glu Asp Gly Arg
65                  70                  75                  80

Phe Thr Ala Gln Leu Asn Arg Ala Ser Gln Tyr Ile Ser Leu Leu Ile
                85                  90                  95

Arg Asp Ser Lys Leu Ser Asp Ser Ala Thr Tyr Leu Cys Val Val Ala
            100                 105                 110

Thr Tyr Ser Gly Gly Gly Ala Asp Gly Leu Thr Phe Gly Lys Gly Thr
        115                 120                 125

His Leu Ile Ile Gln Pro
    130

<210> SEQ ID NO 2
<211> LENGTH: 141
<212> TYPE: PRT
<213> ORGANISM: Artificial Sequence
<220> FEATURE:
<223> OTHER INFORMATION: Synthetic sequence MCC1 alpha chain constant
      domain

<400> SEQUENCE: 2

Asp Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
                20                  25                  30
```

```
Asn Val Ser Gln Ser Lys Asp Ser Asp Val Tyr Ile Thr Asp Lys Cys
            35                  40                  45

Val Leu Asp Met Arg Ser Met Asp Phe Lys Ser Asn Ser Ala Val Ala
        50                  55                  60

Trp Ser Asn Lys Ser Asp Phe Ala Cys Ala Asn Ala Phe Asn Asn Ser
 65                  70                  75                  80

Ile Ile Pro Glu Asp Thr Phe Phe Pro Ser Pro Glu Ser Ser Cys Asp
                    85                  90                  95

Val Lys Leu Val Glu Lys Ser Phe Glu Thr Asp Thr Asn Leu Asn Phe
                100                 105                 110

Gln Asn Leu Ser Val Ile Gly Phe Arg Ile Leu Leu Lys Val Ala
            115                 120                 125

Gly Phe Asn Leu Leu Met Thr Leu Arg Leu Trp Ser Ser
        130                 135                 140

<210> SEQ ID NO 3
<211> LENGTH: 133
<212> TYPE: PRT
<213> ORGANISM: Artificial Sequence
<220> FEATURE:
<223> OTHER INFORMATION: Synthetic sequence MCC1 beta chain variable
      domain

<400> SEQUENCE: 3

Met Gly Thr Arg Leu Phe Phe Tyr Val Ala Leu Cys Leu Leu Trp Ala
 1               5                  10                  15

Gly His Arg Asp Ala Gly Ile Thr Gln Ser Pro Arg Tyr Lys Ile Thr
                20                  25                  30

Glu Thr Gly Arg Gln Val Thr Leu Met Cys His Gln Thr Trp Ser His
            35                  40                  45

Ser Tyr Met Phe Trp Tyr Arg Gln Asp Leu Gly His Gly Leu Arg Leu
        50                  55                  60

Ile Tyr Tyr Ser Ala Ala Ala Asp Ile Thr Asp Lys Gly Glu Val Pro
 65                  70                  75                  80

Asp Gly Tyr Val Val Ser Arg Ser Lys Thr Glu Asn Phe Pro Leu Thr
                    85                  90                  95

Leu Glu Ser Ala Thr Arg Ser Gln Thr Ser Val Tyr Phe Cys Ala Ser
                100                 105                 110

Ser Ser Gly Asn Pro Ser Thr Asp Thr Gln Tyr Phe Gly Pro Gly Thr
            115                 120                 125

Arg Leu Thr Val Leu
        130

<210> SEQ ID NO 4
<211> LENGTH: 178
<212> TYPE: PRT
<213> ORGANISM: Artificial Sequence
<220> FEATURE:
<223> OTHER INFORMATION: Synthetic sequence MCC1 beta chain constant
      domain

<400> SEQUENCE: 4

Asp Leu Lys Asn Val Phe Pro Pro Glu Val Ala Val Phe Glu Pro Ser
 1               5                  10                  15

Glu Ala Glu Ile Ser His Thr Gln Lys Ala Thr Leu Val Cys Leu Ala
                20                  25                  30

Thr Gly Phe Tyr Pro Asp His Val Glu Leu Ser Trp Trp Val Asn Gly
            35                  40                  45
```

Lys Glu Val His Ser Gly Val Cys Thr Asp Pro Gln Pro Leu Lys Glu
            50                  55                  60

Gln Pro Ala Leu Asn Asp Ser Arg Tyr Cys Leu Ser Ser Arg Leu Arg
 65                  70                  75                  80

Val Ser Ala Thr Phe Trp Gln Asn Pro Arg Asn His Phe Arg Cys Gln
                 85                  90                  95

Val Gln Phe Tyr Gly Leu Ser Glu Asn Asp Glu Trp Thr Gln Asp Arg
                100                 105                 110

Ala Lys Pro Val Thr Gln Ile Val Ser Ala Glu Ala Trp Gly Arg Ala
            115                 120                 125

Asp Cys Gly Phe Thr Ser Glu Ser Tyr Gln Gln Gly Val Leu Ser Ala
            130                 135                 140

Thr Ile Leu Tyr Glu Ile Leu Leu Gly Lys Ala Thr Leu Tyr Ala Val
145                 150                 155                 160

Leu Val Ser Ala Leu Val Leu Met Ala Met Val Lys Arg Lys Asp Ser
                165                 170                 175

Arg Gly

<210> SEQ ID NO 5
<211> LENGTH: 402
<212> TYPE: DNA
<213> ORGANISM: Artificial Sequence
<220> FEATURE:
<223> OTHER INFORMATION: Synthetic sequence MCC1 alpha chain variable
      domain wild type

<400> SEQUENCE: 5
atgatatcct tgagagtttt actggtgatc ctgtggcttc agttaagctg ggtttggagc      60
caacggaagg aggtggagca ggatcctgga cccttcaatg ttccagaggg agccactgtc     120
gctttcaact gtacttacag caacagtgct tctcagtctt tcttctggta cagacaggat     180
tgcaggaaag aacctaagtt gctgatgtcc gtatactcca gtggtaatga agatggaagg     240
tttacagcac agctcaatag agccagccag tatatttccc tgctcatcag agactccaag     300
ctcagtgatt cagccaccta cctctgtgtg gtggcgacct attcaggagg aggtgctgac     360
ggactcacct ttggcaaagg gactcatcta atcatccagc cc                        402

<210> SEQ ID NO 6
<211> LENGTH: 402
<212> TYPE: DNA
<213> ORGANISM: Artificial Sequence
<220> FEATURE:
<223> OTHER INFORMATION: Synthetic sequence MCC1 alpha chain variable
      domain codon optimized

<400> SEQUENCE: 6
atgatcagcc tgcgggtgct gctcgtgatc ctgtggctgc agctgtcttg ggtgtggtcc      60
cagagaaaag aggtggaaca ggaccctggc cccttcaacg tgccagaggg cgccaccgtg     120
gccttcaatt gcacctacag caacagcgcc agccagagct cttctggta tcggcaggac     180 tgccggaaag aacccaagct gctgatgagc gtgtacagct ccggcaacga ggacggcaga     240
ttcaccgccc agctgaacag agcctcccag tacatctccc tgctgatccg ggacagcaag     300
ctgagcgaca gcgccaccta cctgtgcgtg gtggccacat attctggcgg cggagccgat     360
ggcctgacct ttggcaaggg cacccacctg atcatccagc cc                        402

<210> SEQ ID NO 7

-continued

```
<211> LENGTH: 426
<212> TYPE: DNA
<213> ORGANISM: Artificial Sequence
<220> FEATURE:
<223> OTHER INFORMATION: Synthetic sequence MCC1 alpha chain constant
      domain (wild type)

<400> SEQUENCE: 7
gatatccaga accctgaccc tgccgtgtac cagctgagag actctaaatc cagtgacaag      60
tctgtctgcc tattcaccga ttttgattct caaacaaatg tgtcacaaag taaggattct    120
gatgtgtata tcacagacaa atgtgtgcta gacatgaggt ctatggactt caagagcaac    180
agtgctgtgg cctggagcaa caaatctgac tttgcatgtg caaacgcctt caacaacagc    240
attattccag aagacacctt cttccccagc ccagaaagtt cctgtgatgt caagctggtc    300
gagaaaagct tgaaacaga tacgaaccta aactttcaaa acctgtcagt gattgggttc    360
cgaatcctcc tcctgaaagt ggccgggttt aatctgctca tgacgctgcg gctgtggtcc    420
agctga                                                                 426

<210> SEQ ID NO 8
<211> LENGTH: 426
<212> TYPE: DNA
<213> ORGANISM: Artificial Sequence
<220> FEATURE:
<223> OTHER INFORMATION: Synthetic sequence MCC1 alpha chain constant
      domain (codon optimized)

<400> SEQUENCE: 8
gacatccaga accccgaccc tgcagtgtac cagctgcggg acagcaagag cagcgacaag      60
agcgtgtgcc tgttcaccga cttcgacagc cagaccaacg tgtcccagag caaggacagc    120
gacgtgtaca tcaccgataa gtgcgtgctg gacatgcgga gcatggactt caagagcaac    180
agcgccgtgg cctggtccaa caagagcgac ttcgcctgcg ccaacgcctt caacaacagc    240 attatcccg aggacacatt cttcccaagc cccgagagca gctgcgacgt gaagctggtg    300
gaaaagagct tcgagacaga caccaacctg aacttccaga acctcagcgt gatcggcttc    360
cggatcctgc tgctgaaggt ggccggcttc aacctgctga tgaccctgcg gctgtggtcc    420
agctga                                                                 426

<210> SEQ ID NO 9
<211> LENGTH: 399
<212> TYPE: DNA
<213> ORGANISM: Artificial Sequence
<220> FEATURE:
<223> OTHER INFORMATION: Synthetic sequence MCC1 beta chain variable
      domain (wild-type)

<400> SEQUENCE: 9
atgggcacca ggctcttcct ctatgtggcc ctttgtctgc tgtgggcagg acacagggat      60
gctggaatca cccagagccc aagatacaag atcacagaa caggaaggca ggtgaccttg    120
atgtgtcacc agacttggag ccacagctat atgttctggt atcgacaaga cctgggacat    180
gggctgaggc tgatctatta ctcagcagct gctgatatta cagataaagg agaagtcccc    240
gatggctatg ttgtctccag atccaagaca gagaatttcc ccctcactct ggagtcagct    300
acccgctccc agacatctgt gtatttctgc gccagcagta gcggaaatcc tagcacagat    360
acgcagtatt ttggcccagg cacccggctg acagtgctc                            399

<210> SEQ ID NO 10
```

```
<211> LENGTH: 399
<212> TYPE: DNA
<213> ORGANISM: Artificial Sequence
<220> FEATURE:
<223> OTHER INFORMATION: Synthetic sequence MCC1 beta chain variable
      domain (codon optimized)

<400> SEQUENCE: 10
atgggcaccc ggctgttctt ttacgtggcc ctgtgcctgc tgtgggccgg acatagagat      60
gccggaatca cccagagccc ccggtacaag atcaccgaga caggcagaca agtgaccctg     120
atgtgccacc agacctggtc ccacagctac atgttctggt acagacagga cctgggccac     180
ggcctgcggc tgatctacta ttctgccgcc gctgacatca ccgacaaggg cgaagtgccc     240
gacggctacg tggtgtccag aagcaagacc gagaacttcc cactgaccct ggaaagcgcc     300
acccggtccc agaccagcgt gtacttttgt gccagcagca gcggcaaccc cagcaccgac     360
acccagtatt ttggccctgg caccagactg accgtgctg                            399

<210> SEQ ID NO 11
<211> LENGTH: 534
<212> TYPE: DNA
<213> ORGANISM: Artificial Sequence
<220> FEATURE:
<223> OTHER INFORMATION: Synthetic sequence MCC1 beta chain constant
      domain (wild type)

<400> SEQUENCE: 11
gacctgaaaa acgtgttccc acccgaggtc gctgtgtttg agccatcaga agcagagatc      60
tcccacaccc aaaaggccac actggtgtgc ctggccacag gcttctaccc cgaccacgtg     120
gagctgagct ggtgggtgaa tgggaaggag gtgcacagtg gggtctgcac agacccgcag     180 ccctcaagg agcagcccgc cctcaatgac tccagatact gcctgagcag ccgcctgagg     240
gtctcggcca ccttctggca gaaccccgc aaccacttcc gctgtcaagt ccagttctac     300
gggctctcgg agaatgacga gtggaccag gataggccca acctgtcac ccagatcgtc     360 agcgccgagg cctggggtag agcagactgt ggcttcacct ccgagtctta ccagcaaggg     420
gtcctgtctg ccaccatcct ctatgagatc ttgctaggga aggccacctt gtatgccgtg     480
ctggtcagtg ccctcgtgct gatggccatg gtcaagagaa aggattccag aggc           534

<210> SEQ ID NO 12
<211> LENGTH: 534
<212> TYPE: DNA
<213> ORGANISM: Artificial Sequence
<220> FEATURE:
<223> OTHER INFORMATION: Synthetic sequence MCC1 beta chain constant
      domain (codon optimized)

<400> SEQUENCE: 12
gacctgaaga acgtgttccc cccagaggtg gccgtgttcg agccttctga ggccgagatc      60
agccacaccc agaaagccac cctcgtgtgt ctggccaccg gcttctaccc cgaccacgtg     120
gaactgtctt ggtgggtcaa cggcaaagag gtgcactccg gcgtgtgcac cgatccccag     180
cctctgaaag agcagcccgc cctgaacgac agcaggtact gtctgagcag cagactgaga     240
gtgtccgcca ccttctggca gaaccccggg aaccacttca tgccaggt gcagttctac     300 ggcctgagcg agaacgacga gtggacccag gacagagcca gcccgtgac ccagatcgtg     360 tctgccgaag cctggggcag agccgattgc ggctttacca gcgagagcta ccagcagggc     420
gtgctgagcg ccaccatcct gtacgagatc ctgctgggca aggccaccct gtacgccgtg     480
```
ctggtgtctg ccctggtgct gatggccatg gtcaagcgga aggacagcag aggc                        534

<210> SEQ ID NO 13
<211> LENGTH: 16
<212> TYPE: PRT
<213> ORGANISM: Artificial Sequence
<220> FEATURE:
<223> OTHER INFORMATION: synthetic sequence MCC1 alpha chain CDR3

<400> SEQUENCE: 13

Cys Val Val Ala Thr Tyr Ser Gly Gly Gly Ala Asp Gly Leu Thr Phe
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: synthetic sequence MCC1 beta chain CDR3

<400> SEQUENCE: 14

Cys Ala Ser Ser Ser Gly Asn Pro Ser Thr Asp Thr Gln Tyr Phe
1               5                   10                  15

<210> SEQ ID NO 15
<211> LENGTH: 817
<212> TYPE: PRT
<213> ORGANISM: Merkel Cell Polyomavirus

<400> SEQUENCE: 15

Met Asp Leu Val Leu Asn Arg Lys Glu Arg Glu Ala Leu Cys Lys Leu
1               5                   10                  15

Leu Glu Ile Ala Pro Asn Cys Tyr Gly Asn Ile Pro Leu Met Lys Ala
                20                  25                  30

Ala Phe Lys Arg Ser Cys Leu Lys His His Pro Asp Lys Gly Gly Asn
            35                  40                  45

Pro Val Ile Met Met Glu Leu Asn Thr Leu Trp Ser Lys Phe Gln Gln
        50                  55                  60

Asn Ile His Lys Leu Arg Ser Asp Phe Ser Met Phe Asp Glu Val Asp
65                  70                  75                  80

Glu Ala Pro Ile Tyr Gly Thr Thr Lys Phe Lys Glu Trp Trp Arg Ser
                85                  90                  95

Gly Gly Phe Ser Phe Gly Lys Ala Tyr Glu Tyr Gly Pro Asn Pro His
            100                 105                 110

Gly Thr Asn Ser Arg Ser Arg Lys Pro Ser Ser Asn Ala Ser Arg Gly
        115                 120                 125

Ala Pro Ser Gly Ser Ser Pro Pro His Ser Gln Ser Ser Ser Ser Gly
    130                 135                 140

Tyr Gly Ser Phe Ser Ala Ser Gln Ala Ser Asp Ser Gln Ser Arg Gly
145                 150                 155                 160

Pro Asp Ile Pro Pro Glu His His Glu Glu Pro Thr Ser Ser Ser Gly
                165                 170                 175

Ser Ser Ser Arg Glu Glu Thr Thr Asn Ser Gly Arg Glu Ser Ser Thr
            180                 185                 190

Pro Asn Gly Thr Ser Val Pro Arg Asn Ser Ser Arg Thr Asp Gly Thr
        195                 200                 205

Trp Glu Asp Leu Phe Cys Asp Glu Ser Leu Ser Ser Pro Glu Pro Pro
    210                 215                 220

Ser Ser Ser Glu Glu Pro Glu Glu Pro Pro Ser Ser Arg Ser Ser Pro

```
            225                 230                 235                 240
Arg Gln Pro Pro Ser Ser Ala Glu Glu Ala Ser Ser Ser Gln Phe
                245                 250                 255
Thr Asp Glu Glu Tyr Arg Ser Ser Phe Thr Thr Pro Lys Thr Pro
                260                 265                 270
Pro Pro Phe Ser Arg Lys Arg Lys Phe Gly Gly Ser Arg Ser Ala
                275                 280                 285
Ser Ser Ala Ser Ser Ala Ser Phe Thr Ser Thr Pro Pro Lys Pro
                290                 295                 300
Lys Lys Asn Arg Glu Thr Pro Val Pro Thr Asp Phe Pro Ile Asp Leu Ser
305                 310                 315                 320
Asp Tyr Leu Ser His Ala Val Tyr Ser Asn Lys Thr Val Ser Cys Phe
                325                 330                 335
Ala Ile Tyr Thr Thr Ser Asp Lys Ala Ile Glu Leu Tyr Asp Lys Ile
                340                 345                 350
Glu Lys Phe Lys Val Asp Phe Lys Ser Arg His Ala Cys Glu Leu Gly
                355                 360                 365
Cys Ile Leu Leu Phe Ile Thr Leu Ser Lys His Arg Val Ser Ala Ile
                370                 375                 380
Lys Asn Phe Cys Ser Thr Phe Cys Thr Ile Ser Phe Leu Ile Cys Lys
385                 390                 395                 400
Gly Val Asn Lys Met Pro Glu Met Tyr Asn Asn Leu Cys Lys Pro Pro
                405                 410                 415
Tyr Lys Leu Leu Gln Glu Asn Lys Pro Leu Leu Asn Tyr Glu Phe Gln
                420                 425                 430
Glu Lys Glu Lys Glu Ala Ser Cys Asn Trp Asn Leu Val Ala Glu Phe
                435                 440                 445
Ala Cys Glu Tyr Glu Leu Asp Asp His Phe Ile Ile Leu Ala His Tyr
                450                 455                 460
Leu Asp Phe Ala Lys Pro Phe Pro Cys Gln Lys Cys Glu Asn Arg Ser
465                 470                 475                 480
Arg Leu Lys Pro His Lys Ala His Glu Ala His His Ser Asn Ala Lys
                485                 490                 495
Leu Phe Tyr Glu Ser Lys Ser Gln Lys Thr Ile Cys Gln Gln Ala Ala
                500                 505                 510
Asp Thr Val Leu Ala Lys Arg Arg Leu Glu Met Leu Glu Met Thr Arg
                515                 520                 525
Thr Glu Met Leu Cys Lys Lys Phe Lys Lys His Leu Glu Arg Leu Arg
                530                 535                 540
Asp Leu Asp Thr Ile Asp Leu Leu Tyr Tyr Met Gly Gly Val Ala Trp
545                 550                 555                 560
Tyr Cys Cys Leu Phe Glu Glu Phe Glu Lys Lys Leu Gln Lys Ile Ile
                565                 570                 575
Gln Leu Leu Thr Glu Asn Ile Pro Lys Tyr Arg Asn Ile Trp Phe Lys
                580                 585                 590
Gly Pro Ile Asn Ser Gly Lys Thr Ser Phe Ala Ala Ala Leu Ile Asp
                595                 600                 605
Leu Leu Glu Gly Lys Ala Leu Asn Ile Asn Cys Pro Ser Asp Lys Leu
                610                 615                 620
Pro Phe Glu Leu Gly Cys Ala Leu Asp Lys Phe Met Val Val Phe Glu
625                 630                 635                 640
Asp Val Lys Gly Gln Asn Ser Leu Asn Lys Asp Leu Gln Pro Gly Gln
                645                 650                 655
```

```
Gly Ile Asn Asn Leu Asp Asn Leu Arg Asp His Leu Asp Gly Ala Val
            660                 665                 670

Ala Val Ser Leu Glu Lys Lys His Val Asn Lys Lys His Gln Ile Phe
        675                 680                 685

Pro Pro Cys Ile Val Thr Ala Asn Asp Tyr Phe Ile Pro Lys Thr Leu
    690                 695                 700

Ile Ala Arg Phe Ser Tyr Thr Leu His Phe Ser Pro Lys Ala Asn Leu
705                 710                 715                 720

Arg Asp Ser Leu Asp Gln Asn Met Glu Ile Arg Lys Arg Arg Ile Leu
                725                 730                 735

Gln Ser Gly Thr Thr Leu Leu Leu Cys Leu Ile Trp Cys Leu Pro Asp
            740                 745                 750

Thr Thr Phe Lys Pro Cys Leu Gln Glu Glu Ile Lys Asn Trp Lys Gln
        755                 760                 765

Ile Leu Gln Ser Glu Ile Ser Tyr Gly Lys Phe Cys Gln Met Ile Glu
    770                 775                 780

Asn Val Glu Ala Gly Gln Asp Pro Leu Leu Asn Ile Leu Ile Glu Glu
785                 790                 795                 800

Glu Gly Pro Glu Glu Thr Glu Glu Thr Gln Asp Ser Gly Thr Phe Ser
                805                 810                 815

Gln

<210> SEQ ID NO 16
<211> LENGTH: 186
<212> TYPE: PRT
<213> ORGANISM: Merkel Cell Polyomavirus

<400> SEQUENCE: 16

Met Asp Leu Val Leu Asn Arg Lys Glu Arg Gly Ala Leu Cys Lys Leu
1               5                   10                  15

Leu Glu Ile Ala Pro Asn Cys Tyr Gly Asn Ile Pro Leu Met Lys Ala
            20                  25                  30

Ala Phe Lys Arg Ser Cys Leu Lys His His Pro Asp Lys Gly Gly Asn
        35                  40                  45

Pro Val Ile Met Met Glu Leu Asn Thr Leu Trp Ser Lys Phe Gln Gln
    50                  55                  60

Asn Ile His Lys Leu Arg Ser Asp Phe Ser Met Phe Asp Glu Val Ser
65                  70                  75                  80

Thr Lys Phe Pro Trp Glu Glu Tyr Gly Thr Leu Lys Asp Tyr Met Gln
                85                  90                  95

Ser Gly Tyr Asn Ala Arg Phe Cys Arg Gly Pro Gly Cys Met Leu Lys
            100                 105                 110

Gln Leu Arg Asp Ser Lys Cys Ala Cys Ile Ser Cys Lys Leu Ser Arg
        115                 120                 125

Gln His Cys Ser Leu Lys Thr Leu Lys Gln Lys Asn Cys Leu Thr Trp
    130                 135                 140

Gly Glu Cys Phe Cys Tyr Gln Cys Phe Ile Leu Trp Phe Gly Phe Pro
145                 150                 155                 160

Pro Thr Trp Glu Ser Phe Asp Trp Trp Gln Lys Thr Leu Glu Glu Thr
                165                 170                 175

Asp Tyr Cys Leu Leu His Leu His Leu Phe
            180                 185

<210> SEQ ID NO 17
```

```
<211> LENGTH: 9
<212> TYPE: PRT
<213> ORGANISM: Artificial Sequence
<220> FEATURE:
<223> OTHER INFORMATION: MCPyV T Antigen KLL synthetic peptide

<400> SEQUENCE: 17

Lys Leu Leu Glu Ile Ala Pro Asn Cys
1               5

<210> SEQ ID NO 18
<211> LENGTH: 66
<212> TYPE: DNA
<213> ORGANISM: Artificial Sequence
<220> FEATURE:
<223> OTHER INFORMATION: Porcine teschovirus-1 2A (P2A) synthetic
      sequence

<400> SEQUENCE: 18
ggaagcggag ctactaactt cagcctgctg aagcaggctg agacgtggga ggagaaccct      60
ggacct                                                                66

<210> SEQ ID NO 19
<211> LENGTH: 66
<212> TYPE: DNA
<213> ORGANISM: Artificial Sequence
<220> FEATURE:
<223> OTHER INFORMATION: Porcine teschovirus-1 2A (P2A) synthetic
      peptide (codon optimized)

<400> SEQUENCE: 19
ggttccggag ccacgaactt ctctctgtta aagcaagcag agacgtggga agaaaacccc      60
ggtccc                                                                66

<210> SEQ ID NO 20
<211> LENGTH: 63
<212> TYPE: DNA
<213> ORGANISM: Artificial Sequence
<220> FEATURE:
<223> OTHER INFORMATION: Thoseaasigna virus 2A (T2A) synthetic sequence

<400> SEQUENCE: 20
ggaagcggag agggcagagg aagtctgcta acatgcggtg acgtcgagga gaatcctgga      60
cct                                                                   63

<210> SEQ ID NO 21
<211> LENGTH: 69
<212> TYPE: DNA
<213> ORGANISM: Artificial Sequence
<220> FEATURE:
<223> OTHER INFORMATION: Equine rhinitis A virus (ERAV) 2A (E2A)
      synthetic sequence

<400> SEQUENCE: 21
ggaagcggac agtgtactaa ttatgctctc ttgaaattgg ctggagatgt tgagagcaac      60
cctggacct                                                             69

<210> SEQ ID NO 22
<211> LENGTH: 75
<212> TYPE: DNA
<213> ORGANISM: Artificial Sequence
<220> FEATURE:
<223> OTHER INFORMATION: Foot-and-Mouth disease virus 2A (F2A) synthetic
      sequence
```

```
<400> SEQUENCE: 22
ggaagcggag tgaaacagac tttgaatttt gaccttctca agttggcggg agacgtggag    60
tccaaccctg gacct                                                    75

<210> SEQ ID NO 23
<211> LENGTH: 20
<212> TYPE: PRT
<213> ORGANISM: Artificial Sequence
<220> FEATURE:
<223> OTHER INFORMATION: Equine rhinitis A virus (ERAV) 2A (E2A)
      synthetic peptide

<400> SEQUENCE: 23

Gln Cys Thr Asn Tyr Ala Leu Leu Lys Leu Ala Gly Asp Val Glu Ser
1               5                  10                  15

Asn Pro Gly Pro
            20

<210> SEQ ID NO 24
<211> LENGTH: 24
<212> TYPE: PRT
<213> ORGANISM: Artificial Sequence
<220> FEATURE:
<223> OTHER INFORMATION: Thoseaasigna virus 2A (T2A) synthetic peptide

<400> SEQUENCE: 24

Leu Glu Gly Gly Gly Glu Gly Arg Gly Ser Leu Leu Thr Cys Gly Asp
1               5                  10                  15

Val Glu Glu Asn Pro Gly Pro Arg
            20

<210> SEQ ID NO 25
<211> LENGTH: 22
<212> TYPE: PRT
<213> ORGANISM: Artificial Sequence
<220> FEATURE:
<223> OTHER INFORMATION: Porcine teschovirus-1 2A (P2A) synthetic
      peptide

<400> SEQUENCE: 25

Gly Ser Gly Ala Thr Asn Phe Ser Leu Leu Lys Gln Ala Gly Asp Val
1               5                  10                  15

Glu Glu Asn Pro Gly Pro
            20

<210> SEQ ID NO 26
<211> LENGTH: 25
<212> TYPE: PRT
<213> ORGANISM: Artificial sequence
<220> FEATURE:
<223> OTHER INFORMATION: Foot-and-Mouth disease virus (F2A) synthetic
      peptide

<400> SEQUENCE: 26

Gly Ser Gly Val Lys Gln Thr Leu Asn Phe Asp Leu Leu Lys Leu Ala
1               5                  10                  15

Gly Asp Val Glu Ser Asn Pro Gly Pro
            20                  25

<210> SEQ ID NO 27
<211> LENGTH: 15
<212> TYPE: DNA
<213> ORGANISM: Artificial Sequence
<220> FEATURE:
```

```
<223> OTHER INFORMATION: Glycine-Serine linker

<400> SEQUENCE: 27
ggggsggggs ggggs                                                  15

<210> SEQ ID NO 28
<211> LENGTH: 18
<212> TYPE: DNA
<213> ORGANISM: Artificial Sequence
<220> FEATURE:
<223> OTHER INFORMATION: Glycine-Serine linker

<400> SEQUENCE: 28
gstsgggsgg gsgggggss                                              18

<210> SEQ ID NO 29
<211> LENGTH: 25
<212> TYPE: DNA
<213> ORGANISM: Artificial Sequence
<220> FEATURE:
<223> OTHER INFORMATION: synthetic sequence TRAC_sgRNA_pLenti_F1

<400> SEQUENCE: 29
caccggagaa tcaaaatcgg tgaat                                       25

<210> SEQ ID NO 30
<211> LENGTH: 25
<212> TYPE: DNA
<213> ORGANISM: Artificial Sequence
<220> FEATURE:
<223> OTHER INFORMATION: synthetic sequence TRAC_sgRNA_pLenti_R1

<400> SEQUENCE: 30
aaacattcac cgattttgat tctcc                                       25

<210> SEQ ID NO 31
<211> LENGTH: 24
<212> TYPE: DNA
<213> ORGANISM: Artificial Sequence
<220> FEATURE:
<223> OTHER INFORMATION: synthetic sequence PD1_sgRNA_F1

<400> SEQUENCE: 31
caccgcagtt gtgtgacacg gaag                                        24

<210> SEQ ID NO 32
<211> LENGTH: 24
<212> TYPE: DNA
<213> ORGANISM: Artificial Sequence
<220> FEATURE:
<223> OTHER INFORMATION: synthetic sequence PD1_sgRNA_R1

<400> SEQUENCE: 32
aaaccttccg tgtcacacaa ctgc                                        24

<210> SEQ ID NO 33
<211> LENGTH: 25
<212> TYPE: DNA
<213> ORGANISM: Artificial Sequence
<220> FEATURE:
<223> OTHER INFORMATION: synthetic sequence CTLA4_sgRNA_F1

<400> SEQUENCE: 33
caccggcaaa ggtgagtgag acttt                                       25
```

```
<210> SEQ ID NO 34
<211> LENGTH: 25
<212> TYPE: DNA
<213> ORGANISM: Artificial Sequence
<220> FEATURE:
<223> OTHER INFORMATION: synthetic sequence CTLA4_sgRNA_R1

<400> SEQUENCE: 34
aaacaaagtc tcactcacct ttgcc                                            25

<210> SEQ ID NO 35
<211> LENGTH: 25
<212> TYPE: DNA
<213> ORGANISM: Artificial Sequence
<220> FEATURE:
<223> OTHER INFORMATION: synthetic sequence LAG3_sgRNA_F1

<400> SEQUENCE: 35
caccggtttc tgcagccgct ttggg                                            25

<210> SEQ ID NO 36
<211> LENGTH: 25
<212> TYPE: DNA
<213> ORGANISM: Artificial Sequence
<220> FEATURE:
<223> OTHER INFORMATION: synthetic sequence LAG3_sgRNA_R2

<400> SEQUENCE: 36 aaacccaaa gcggctgcag aaacc                                             25

<210> SEQ ID NO 37
<211> LENGTH: 9
<212> TYPE: PRT
<213> ORGANISM: Artificial Sequence
<220> FEATURE:
<223> OTHER INFORMATION: KLL Epitope homolog

<400> SEQUENCE: 37

Lys Leu Leu Glu Ile Ala Pro Asn Ala
1               5

<210> SEQ ID NO 38
<211> LENGTH: 10
<212> TYPE: PRT
<213> ORGANISM: Artificial Sequence
<220> FEATURE:
<223> OTHER INFORMATION: Synthetic sequence CDR3 region alpha chain

<400> SEQUENCE: 38

Cys Ala Phe Asn Thr Asp Lys Leu Ile Phe
1               5                   10

<210> SEQ ID NO 39
<211> LENGTH: 11
<212> TYPE: PRT
<213> ORGANISM: Artificial Sequence
<220> FEATURE:
<223> OTHER INFORMATION: Synthetic sequence CDR3 region alpha chain

<400> SEQUENCE: 39

Cys Ala Leu Thr Ser Gly Ser Arg Leu Thr Phe
1               5                   10

<210> SEQ ID NO 40
<211> LENGTH: 11
<212> TYPE: PRT
<213> ORGANISM: Artificial Sequence
```

-continued

```
<220> FEATURE:
<223> OTHER INFORMATION: Synthetic sequence CDR3 region alpha chain

<400> SEQUENCE: 40

Cys Ala Tyr Pro Ser Thr Asp Lys Leu Ile Phe
1               5                   10

<210> SEQ ID NO 41
<211> LENGTH: 10
<212> TYPE: PRT
<213> ORGANISM: Artificial Sequence
<220> FEATURE:
<223> OTHER INFORMATION: Synthetic sequence CDR3 region alpha chain

<400> SEQUENCE: 41

Cys Val Leu Asn Asn Asn Asp Met Arg Phe
1               5                   10

<210> SEQ ID NO 42
<211> LENGTH: 10
<212> TYPE: PRT
<213> ORGANISM: Artificial Sequence
<220> FEATURE:
<223> OTHER INFORMATION: Synthetic sequence CDR3 region alpha chain

<400> SEQUENCE: 42

Cys Val Val Asn Ala Asn Asp Met Arg Phe
1               5                   10

<210> SEQ ID NO 43
<211> LENGTH: 16
<212> TYPE: PRT
<213> ORGANISM: Artificial Sequence
<220> FEATURE:
<223> OTHER INFORMATION: Synthetic sequence CDR3 region alpha chain

<400> SEQUENCE: 43

Cys Val Val Ala Leu Tyr Ser Gly Gly Gly Ala Asp Gly Leu Thr Phe
1               5                   10                  15

<210> SEQ ID NO 44
<211> LENGTH: 11
<212> TYPE: PRT
<213> ORGANISM: Artificial Sequence
<220> FEATURE:
<223> OTHER INFORMATION: Synthetic sequence CDR3 region alpha chain

<400> SEQUENCE: 44

Cys Ala Phe Arg Val Ser His Asp Met Arg Phe
1               5                   10

<210> SEQ ID NO 45
<211> LENGTH: 16
<212> TYPE: PRT
<213> ORGANISM: Artificial Sequence
<220> FEATURE:
<223> OTHER INFORMATION: Synthetic sequence CDR3 region alpha chain

<400> SEQUENCE: 45

Cys Val Val Gly Glu Tyr Ser Gly Gly Gly Ala Asp Gly Leu Thr Phe
1               5                   10                  15

<210> SEQ ID NO 46
<211> LENGTH: 16
<212> TYPE: PRT
<213> ORGANISM: Artificial Sequence
<220> FEATURE:
```

```
<223> OTHER INFORMATION: Synthetic sequence CDR3 region alpha chain

<400> SEQUENCE: 46

Cys Val Val Thr Glu Tyr Ser Gly Gly Gly Ala Asp Gly Leu Thr Phe
1               5                   10                  15

<210> SEQ ID NO 47
<211> LENGTH: 17
<212> TYPE: PRT
<213> ORGANISM: Artificial Sequence
<220> FEATURE:
<223> OTHER INFORMATION: Synthetic sequence CDR3 region alpha chain

<400> SEQUENCE: 47

Cys Ala Leu Gly Gly Gly Thr Phe Thr Ser Gly Thr Tyr Lys Tyr Ile
1               5                   10                  15

Phe

<210> SEQ ID NO 48
<211> LENGTH: 17
<212> TYPE: PRT
<213> ORGANISM: Artificial Sequence
<220> FEATURE:
<223> OTHER INFORMATION: Synthetic sequence CDR3 region alpha chain

<400> SEQUENCE: 48

Cys Val Val Tyr Thr Gly Tyr Ser Gly Gly Ala Asp Gly Leu Thr
1               5                   10                  15

Phe

<210> SEQ ID NO 49
<211> LENGTH: 11
<212> TYPE: PRT
<213> ORGANISM: Artificial Sequence
<220> FEATURE:
<223> OTHER INFORMATION: Synthetic sequence CDR3 region alpha chain

<400> SEQUENCE: 49

Cys Ala Tyr Asn Gln Gly Gly Lys Leu Ile Phe
1               5                   10

<210> SEQ ID NO 50
<211> LENGTH: 14
<212> TYPE: PRT
<213> ORGANISM: Artificial Sequence
<220> FEATURE:
<223> OTHER INFORMATION: Synthetic sequence CDR3 region alpha chain

<400> SEQUENCE: 50

Cys Val Val Pro Leu Tyr Ser Ser Ala Ser Lys Ile Ile Phe
1               5                   10

<210> SEQ ID NO 51
<211> LENGTH: 9
<212> TYPE: PRT
<213> ORGANISM: Artificial Sequence
<220> FEATURE:
<223> OTHER INFORMATION: Synthetic sequence CDR3 region alpha chain

<400> SEQUENCE: 51

Cys Val Leu Asn Asn Asn Asp Arg Phe
1               5

<210> SEQ ID NO 52
<211> LENGTH: 10
```

```
<212> TYPE: PRT
<213> ORGANISM: Artificial Sequence
<220> FEATURE:
<223> OTHER INFORMATION: Synthetic sequence CDR3 region alpha chain

<400> SEQUENCE: 52

Cys Val Val Tyr Ala Ser Lys Ile Ile Phe
1               5                   10

<210> SEQ ID NO 53
<211> LENGTH: 10
<212> TYPE: PRT
<213> ORGANISM: Artificial Sequence
<220> FEATURE:
<223> OTHER INFORMATION: Synthetic sequence CDR3 region alpha chain

<400> SEQUENCE: 53

Cys Val Gly Asn Asn Asn Asp Met Arg Phe
1               5                   10

<210> SEQ ID NO 54
<211> LENGTH: 14
<212> TYPE: PRT
<213> ORGANISM: Artificial Sequence
<220> FEATURE:
<223> OTHER INFORMATION: Synthetic sequence CDR3 region alpha chain

<400> SEQUENCE: 54

Cys Val Val Tyr Gly Ser Ser Asn Thr Gly Lys Leu Ile Phe
1               5                   10

<210> SEQ ID NO 55
<211> LENGTH: 14
<212> TYPE: PRT
<213> ORGANISM: Artificial Sequence
<220> FEATURE:
<223> OTHER INFORMATION: Synthetic sequence CDR3 region alpha chain

<400> SEQUENCE: 55

Cys Ala Val Arg Asp Asn Ser Gly Thr Tyr Lys Tyr Ile Phe
1               5                   10

<210> SEQ ID NO 56
<211> LENGTH: 16
<212> TYPE: PRT
<213> ORGANISM: Artificial Sequence
<220> FEATURE:
<223> OTHER INFORMATION: Synthetic sequence CDR3 region alpha chain

<400> SEQUENCE: 56

Cys Val Val Thr Asp Thr Ser Gly Gly Gly Ala Asp Gly Leu Thr Phe
1               5                   10                  15

<210> SEQ ID NO 57
<211> LENGTH: 11
<212> TYPE: PRT
<213> ORGANISM: Artificial Sequence
<220> FEATURE:
<223> OTHER INFORMATION: Synthetic sequence CDR3 region alpha chain

<400> SEQUENCE: 57

Cys Val Val Pro Ser Ala Gly Lys Ser Thr Phe
1               5                   10

<210> SEQ ID NO 58
<211> LENGTH: 16
<212> TYPE: PRT
```

```
<213> ORGANISM: Artificial Sequence
<220> FEATURE:
<223> OTHER INFORMATION: Synthetic sequence CDR3 region alpha chain

<400> SEQUENCE: 58

Cys Ala Met Arg Glu Ala Gln Ser Gly Gly Tyr Gln Lys Val Thr Phe
1               5                   10                  15

<210> SEQ ID NO 59
<211> LENGTH: 15
<212> TYPE: PRT
<213> ORGANISM: Artificial Sequence
<220> FEATURE:
<223> OTHER INFORMATION: Synthetic sequence CDR3 region alpha chain

<400> SEQUENCE: 59

Cys Val Val Ser Ala Gly Ile Asn Gly Ala Asp Gly Leu Thr Phe
1               5                   10                  15

<210> SEQ ID NO 60
<211> LENGTH: 15
<212> TYPE: PRT
<213> ORGANISM: Artificial Sequence
<220> FEATURE:
<223> OTHER INFORMATION: Synthetic sequence CDR3 region alpha chain

<400> SEQUENCE: 60

Cys Ala Met Ser Val Ala Gln Gly Gly Ser Glu Lys Leu Val Phe
1               5                   10                  15

<210> SEQ ID NO 61
<211> LENGTH: 13
<212> TYPE: PRT
<213> ORGANISM: Artificial Sequence
<220> FEATURE:
<223> OTHER INFORMATION: Synthetic sequence CDR3 region alpha chain

<400> SEQUENCE: 61

Cys Ala Gly Asp Gln Gly Gly Ser Glu Lys Leu Val Phe
1               5                   10

<210> SEQ ID NO 62
<211> LENGTH: 11
<212> TYPE: PRT
<213> ORGANISM: Artificial Sequence
<220> FEATURE:
<223> OTHER INFORMATION: Synthetic sequence CDR3 region alpha chain

<400> SEQUENCE: 62

Cys Ala Leu Thr Gly Tyr Ser Thr Leu Thr Phe
1               5                   10

<210> SEQ ID NO 63
<211> LENGTH: 11
<212> TYPE: PRT
<213> ORGANISM: Artificial Sequence
<220> FEATURE:
<223> OTHER INFORMATION: synthetic sequence CDR3 region beta chain

<400> SEQUENCE: 63

Cys Ala Ser Ser Leu Ala Gly Phe Arg Phe Phe
1               5                   10

<210> SEQ ID NO 64
<211> LENGTH: 15
<212> TYPE: PRT
<213> ORGANISM: Artificial Sequence
```

-continued

```
<220> FEATURE:
<223> OTHER INFORMATION: synthetic sequence CDR3 region beta chain

<400> SEQUENCE: 64

Cys Ala Ser Ser Ile Met Leu Tyr Ser Asn Gln Pro Gln His Phe
1               5                   10                  15

<210> SEQ ID NO 65
<211> LENGTH: 15
<212> TYPE: PRT
<213> ORGANISM: Artificial Sequence
<220> FEATURE:
<223> OTHER INFORMATION: synthetic sequence CDR3 region beta chain

<400> SEQUENCE: 65

Cys Ala Ser Ser Ile Leu Gly Ala Ser Asn Gln Pro Gln His Phe
1               5                   10                  15

<210> SEQ ID NO 66
<211> LENGTH: 15
<212> TYPE: PRT
<213> ORGANISM: Artificial Sequence
<220> FEATURE:
<223> OTHER INFORMATION: synthetic sequence CDR3 region beta chain

<400> SEQUENCE: 66

Cys Ala Ile Arg Ala Arg Asp Gln Asn Thr Gly Glu Leu Phe Phe
1               5                   10                  15

<210> SEQ ID NO 67
<211> LENGTH: 13
<212> TYPE: PRT
<213> ORGANISM: Artificial Sequence
<220> FEATURE:
<223> OTHER INFORMATION: synthetic sequence CDR3 region beta chain

<400> SEQUENCE: 67

Cys Ala Ser Arg Ser Gln Asn Tyr Tyr Gly Tyr Thr Phe
1               5                   10

<210> SEQ ID NO 68
<211> LENGTH: 15
<212> TYPE: PRT
<213> ORGANISM: Artificial Sequence
<220> FEATURE:
<223> OTHER INFORMATION: synthetic sequence CDR3 region beta chain

<400> SEQUENCE: 68

Cys Ala Ile Arg Gln Phe Asp Ala Asn Thr Gly Glu Leu Phe Phe
1               5                   10                  15

<210> SEQ ID NO 69
<211> LENGTH: 16
<212> TYPE: PRT
<213> ORGANISM: Artificial Sequence
<220> FEATURE:
<223> OTHER INFORMATION: synthetic sequence CDR3 region beta chain

<400> SEQUENCE: 69

Cys Ala Ser Ser Ile Ile Ala Gly Ser Ser Tyr Asn Glu Gln Phe Phe
1               5                   10                  15

<210> SEQ ID NO 70
<211> LENGTH: 14
<212> TYPE: PRT
<213> ORGANISM: Artificial Sequence
<220> FEATURE:
```

<223> OTHER INFORMATION: synthetic sequence CDR3 region beta chain

<400> SEQUENCE: 70

Cys Ala Ile Arg Ala Gly Ala Ser Tyr Asn Glu Gln Phe Phe
1               5                   10

<210> SEQ ID NO 71
<211> LENGTH: 13
<212> TYPE: PRT
<213> ORGANISM: Artificial Sequence
<220> FEATURE:
<223> OTHER INFORMATION: synthetic sequence CDR3 region beta chain

<400> SEQUENCE: 71

Cys Ala Ser Arg Gly Gln Asn Thr Gly Glu Leu Phe Phe
1               5                   10

<210> SEQ ID NO 72
<211> LENGTH: 14
<212> TYPE: PRT
<213> ORGANISM: Artificial Sequence
<220> FEATURE:
<223> OTHER INFORMATION: synthetic sequence CDR3 region beta chain

<400> SEQUENCE: 72

Cys Ala Ser Ser Val Glu Asp Tyr Thr Gly Glu Leu Phe Phe
1               5                   10

<210> SEQ ID NO 73
<211> LENGTH: 13
<212> TYPE: PRT
<213> ORGANISM: Artificial Sequence
<220> FEATURE:
<223> OTHER INFORMATION: synthetic sequence CDR3 region beta chain

<400> SEQUENCE: 73

Cys Ala Ser Ser Val Leu Asn Thr Gly Glu Leu Phe Phe
1               5                   10

<210> SEQ ID NO 74
<211> LENGTH: 15
<212> TYPE: PRT
<213> ORGANISM: Artificial Sequence
<220> FEATURE:
<223> OTHER INFORMATION: synthetic sequence CDR3 region beta chain

<400> SEQUENCE: 74

Cys Ala Ser Ser Asp Thr Pro Asp Leu Asn Thr Glu Ala Phe Phe
1               5                   10                  15

<210> SEQ ID NO 75
<211> LENGTH: 15
<212> TYPE: PRT
<213> ORGANISM: Artificial Sequence
<220> FEATURE:
<223> OTHER INFORMATION: synthetic sequence CDR3 region beta chain

<400> SEQUENCE: 75

Cys Ala Ile Ser Ala Arg Asp Gln Asn Thr Gly Glu Leu Phe Phe
1               5                   10                  15

<210> SEQ ID NO 76
<211> LENGTH: 15
<212> TYPE: PRT
<213> ORGANISM: Artificial Sequence
<220> FEATURE:
<223> OTHER INFORMATION: synthetic sequence CDR3 region beta chain

<400> SEQUENCE: 76

Cys Ala Ile Arg Arg Gln Asp Gln Asn Thr Gly Glu Leu Phe Phe
1               5                   10                  15

<210> SEQ ID NO 77
<211> LENGTH: 15
<212> TYPE: PRT
<213> ORGANISM: Artificial Sequence
<220> FEATURE:
<223> OTHER INFORMATION: synthetic sequence CDR3 region beta chain

<400> SEQUENCE: 77

Cys Ala Ile His Glu Gly Asp Ser Asn Thr Gly Glu Leu Phe Phe
1               5                   10                  15

<210> SEQ ID NO 78
<211> LENGTH: 16
<212> TYPE: PRT
<213> ORGANISM: Artificial Sequence
<220> FEATURE:
<223> OTHER INFORMATION: synthetic sequence CDR3 region beta chain

<400> SEQUENCE: 78

Cys Ala Ser Ser Leu Ala Gly Leu Ala Gly Thr Asp Thr Gln Tyr Phe
1               5                   10                  15

<210> SEQ ID NO 79
<211> LENGTH: 14
<212> TYPE: PRT
<213> ORGANISM: Artificial Sequence
<220> FEATURE:
<223> OTHER INFORMATION: synthetic sequence CDR3 region beta chain

<400> SEQUENCE: 79

Cys Ala Ser Ser Glu Phe Ala Gly Gln Glu Thr Gln Tyr Phe
1               5                   10

<210> SEQ ID NO 80
<211> LENGTH: 13
<212> TYPE: PRT
<213> ORGANISM: Artificial Sequence
<220> FEATURE:
<223> OTHER INFORMATION: synthetic sequence CDR3 region beta chain

<400> SEQUENCE: 80

Cys Ala Ser Arg Ala Ser Asn Thr Tyr Gly Tyr Thr Phe
1               5                   10

<210> SEQ ID NO 81
<211> LENGTH: 15
<212> TYPE: PRT
<213> ORGANISM: Artificial Sequence
<220> FEATURE:
<223> OTHER INFORMATION: synthetic sequence CDR3 region beta chain

<400> SEQUENCE: 81

Cys Ala Ser Ser Thr Leu Ser Gly Thr His Asn Glu Gln Phe Phe
1               5                   10                  15

<210> SEQ ID NO 82
<211> LENGTH: 15
<212> TYPE: PRT
<213> ORGANISM: Artificial Sequence
<220> FEATURE:
<223> OTHER INFORMATION: synthetic sequence CDR3 region beta chain

```
<400> SEQUENCE: 82

Cys Ala Ser Ser Leu Ala Gly Leu Ala Asn Asn Glu Gln Phe Phe
1               5                   10                  15

<210> SEQ ID NO 83
<211> LENGTH: 15
<212> TYPE: PRT
<213> ORGANISM: Artificial Sequence
<220> FEATURE:
<223> OTHER INFORMATION: synthetic sequence CDR3 region beta chain

<400> SEQUENCE: 83

Cys Ala Ser Ser Phe Gly Ser Gly Thr Lys Asp Thr Gln Tyr Phe
1               5                   10                  15

<210> SEQ ID NO 84
<211> LENGTH: 13
<212> TYPE: PRT
<213> ORGANISM: Artificial Sequence
<220> FEATURE:
<223> OTHER INFORMATION: synthetic sequence CDR3 region beta chain

<400> SEQUENCE: 84

Cys Ala Ser Ser Gly Gln Asn Thr Gly Glu Leu Phe Phe
1               5                   10

<210> SEQ ID NO 85
<211> LENGTH: 11
<212> TYPE: PRT
<213> ORGANISM: Artificial Sequence
<220> FEATURE:
<223> OTHER INFORMATION: synthetic sequence CDR3 region beta chain

<400> SEQUENCE: 85

Cys Ala Ser Ser Pro Trp Asp Glu Gln Phe Phe
1               5                   10

<210> SEQ ID NO 86
<211> LENGTH: 18
<212> TYPE: PRT
<213> ORGANISM: Artificial Sequence
<220> FEATURE:
<223> OTHER INFORMATION: synthetic sequence CDR3 region beta chain

<400> SEQUENCE: 86

Cys Ala Ser Ser Ser Gly Thr Ser Gly Gly Leu Thr Tyr Asn Glu Gln
1               5                   10                  15

Phe Phe

<210> SEQ ID NO 87
<211> LENGTH: 14
<212> TYPE: PRT
<213> ORGANISM: Artificial Sequence
<220> FEATURE:
<223> OTHER INFORMATION: synthetic sequence CDR3 region beta chain

<400> SEQUENCE: 87

Cys Ala Ser Ser Ser Arg Thr Lys Ala Tyr Glu Gln Tyr Phe
1               5                   10

<210> SEQ ID NO 88
<211> LENGTH: 15
<212> TYPE: PRT
<213> ORGANISM: Artificial Sequence
<220> FEATURE:
<223> OTHER INFORMATION: synthetic sequence CDR3 region beta chain
```

```
<400> SEQUENCE: 88

Cys Ala Ser Ser Tyr Gln Ile Gly Leu Ser Tyr Glu Gln Tyr Phe
1               5                   10                  15

<210> SEQ ID NO 89
<211> LENGTH: 17
<212> TYPE: PRT
<213> ORGANISM: Artificial Sequence
<220> FEATURE:
<223> OTHER INFORMATION: synthetic sequence CDR3 region beta chain

<400> SEQUENCE: 89

Cys Ala Ser Ser Phe Asp Ser Lys Gly Ser Asn Thr Gly Glu Leu Phe
1               5                   10                  15

Phe

<210> SEQ ID NO 90
<211> LENGTH: 16
<212> TYPE: PRT
<213> ORGANISM: Artificial Sequence
<220> FEATURE:
<223> OTHER INFORMATION: synthetic sequence CDR3 region beta chain

<400> SEQUENCE: 90

Cys Ala Ser Ser Gln Leu Arg Thr Gly Asp Glu Tyr Glu Gln Tyr Phe
1               5                   10                  15

<210> SEQ ID NO 91
<211> LENGTH: 18
<212> TYPE: PRT
<213> ORGANISM: Artificial Sequence
<220> FEATURE:
<223> OTHER INFORMATION: synthetic sequence CDR3 region beta chain

<400> SEQUENCE: 91

Cys Ala Ser Ser Ser Gly Thr Ser Gly Gly Leu Asn Tyr Asn Glu Gln
1               5                   10                  15

Phe Phe

<210> SEQ ID NO 92
<211> LENGTH: 15
<212> TYPE: PRT
<213> ORGANISM: Artificial Sequence
<220> FEATURE:
<223> OTHER INFORMATION: synthetic sequence CDR3 region beta chain

<400> SEQUENCE: 92

Cys Ala Ser Arg Ser Gln Leu Ala Val Leu Asn Glu Gln Phe Phe
1               5                   10                  15

<210> SEQ ID NO 93
<211> LENGTH: 14
<212> TYPE: PRT
<213> ORGANISM: Artificial Sequence
<220> FEATURE:
<223> OTHER INFORMATION: synthetic sequence CDR3 region beta chain

<400> SEQUENCE: 93

Cys Ala Ser Arg Gly Gly Ser Ser Tyr Asn Glu Gln Phe Phe
1               5                   10

<210> SEQ ID NO 94
<211> LENGTH: 13
<212> TYPE: PRT
```

```
<213> ORGANISM: Artificial Sequence
<220> FEATURE:
<223> OTHER INFORMATION: synthetic sequence CDR3 region beta chain

<400> SEQUENCE: 94

Cys Ala Thr Arg Asp Ile Asn Thr Gly Glu Leu Phe Phe
1               5                   10

<210> SEQ ID NO 95
<211> LENGTH: 16
<212> TYPE: PRT
<213> ORGANISM: Artificial Sequence
<220> FEATURE:
<223> OTHER INFORMATION: Synthetic peptide

<400> SEQUENCE: 95

Cys Ala Ser Ser Gly Gly Leu Leu His Val Leu Asp Glu Gln Tyr Phe
1               5                   10                  15

<210> SEQ ID NO 96
<211> LENGTH: 13
<212> TYPE: PRT
<213> ORGANISM: Artificial Sequence
<220> FEATURE:
<223> OTHER INFORMATION: Synthetic peptide

<400> SEQUENCE: 96

Cys Ala Thr Thr Trp Arg Arg Tyr Tyr Glu Gln Tyr Phe
1               5                   10

<210> SEQ ID NO 97
<211> LENGTH: 18
<212> TYPE: PRT
<213> ORGANISM: Artificial Sequence
<220> FEATURE:
<223> OTHER INFORMATION: Synthetic peptide

<400> SEQUENCE: 97

Cys Ala Ser Ser Ile Leu Leu Val Pro Ile Ala Thr Asn Glu Lys Leu
1               5                   10                  15

Phe Phe

<210> SEQ ID NO 98
<211> LENGTH: 17
<212> TYPE: PRT
<213> ORGANISM: Artificial Sequence
<220> FEATURE:
<223> OTHER INFORMATION: Synthetic peptide

<400> SEQUENCE: 98

Cys Ala Ser Ser Arg Ala Leu Ala Thr Ala Arg Lys Asn Ile Gln Tyr
1               5                   10                  15

Phe

<210> SEQ ID NO 99
<211> LENGTH: 17
<212> TYPE: PRT
<213> ORGANISM: Artificial Sequence
<220> FEATURE:
<223> OTHER INFORMATION: Synthetic peptide

<400> SEQUENCE: 99

Cys Ala Ser Ser Leu Ser Met Leu Gln Gln Arg Lys Asn Ile Gln Tyr
1               5                   10                  15

Phe
```

<210> SEQ ID NO 100
<211> LENGTH: 13
<212> TYPE: PRT
<213> ORGANISM: Artificial Sequence
<220> FEATURE:
<223> OTHER INFORMATION: Synthetic peptide

<400> SEQUENCE: 100

Cys Ala Ser Ser Ser Gln Asn Tyr Tyr Gly Tyr Thr Phe
1               5                   10

<210> SEQ ID NO 101
<211> LENGTH: 17
<212> TYPE: PRT
<213> ORGANISM: Artificial Sequence
<220> FEATURE:
<223> OTHER INFORMATION: Synthetic peptide

<400> SEQUENCE: 101

Cys Ala Ser Ser Val Ala Leu Leu Gln His Ala Arg Asn Thr Ile Tyr
1               5                   10                  15

Phe

<210> SEQ ID NO 102
<211> LENGTH: 16
<212> TYPE: PRT
<213> ORGANISM: Artificial Sequence
<220> FEATURE:
<223> OTHER INFORMATION: Synthetic peptide

<400> SEQUENCE: 102

Cys Ala Ser Arg Ala Lys Leu Ala Thr Leu Arg Thr Glu Ala Phe Phe
1               5                   10                  15

<210> SEQ ID NO 103
<211> LENGTH: 13
<212> TYPE: PRT
<213> ORGANISM: Artificial Sequence
<220> FEATURE:
<223> OTHER INFORMATION: Synthetic peptide

<400> SEQUENCE: 103

Cys Ala Ser Lys Thr Gly Gly Arg Glu Lys Leu Phe Phe
1               5                   10

<210> SEQ ID NO 104
<211> LENGTH: 17
<212> TYPE: PRT
<213> ORGANISM: Artificial Sequence
<220> FEATURE:
<223> OTHER INFORMATION: Synthetic peptide

<400> SEQUENCE: 104

Cys Ala Ser Lys Lys Leu Asp Arg Pro Ala Pro Asn Ser Pro Leu His
1               5                   10                  15

Phe

<210> SEQ ID NO 105
<211> LENGTH: 16
<212> TYPE: PRT
<213> ORGANISM: Artificial Sequence
<220> FEATURE:
<223> OTHER INFORMATION: Synthetic peptide

<400> SEQUENCE: 105

```
Cys Ala Ser Ser Glu Phe Leu Arg Gly Ala Asp Tyr Gly Tyr Thr Phe
1               5                   10                  15
```

<210> SEQ ID NO 106
<211> LENGTH: 14
<212> TYPE: PRT
<213> ORGANISM: Artificial Sequence
<220> FEATURE:
<223> OTHER INFORMATION: Synthetic peptide

<400> SEQUENCE: 106

```
Cys Ala Ser Ser Leu Val Gly Gly Arg Asp Glu Gln Tyr Phe
1               5                   10
```

<210> SEQ ID NO 107
<211> LENGTH: 13
<212> TYPE: PRT
<213> ORGANISM: Artificial Sequence
<220> FEATURE:
<223> OTHER INFORMATION: Synthetic peptide

<400> SEQUENCE: 107

```
Cys Ala Ile Arg Asp Ser Asn Thr Gly Glu Leu Phe Phe
1               5                   10
```

<210> SEQ ID NO 108
<211> LENGTH: 17
<212> TYPE: PRT
<213> ORGANISM: Artificial Sequence
<220> FEATURE:
<223> OTHER INFORMATION: Synthetic peptide

<400> SEQUENCE: 108

```
Cys Ser Ala Arg Asp Leu Leu Ala Gly Thr Asn Thr Gly Glu Leu Phe
1               5                   10                  15

Phe
```

<210> SEQ ID NO 109
<211> LENGTH: 15
<212> TYPE: PRT
<213> ORGANISM: Artificial Sequence
<220> FEATURE:
<223> OTHER INFORMATION: Synthetic peptide

<400> SEQUENCE: 109

```
Cys Ala Ile Arg Leu Ala Asp Gln Asn Thr Gly Glu Leu Phe Phe
1               5                   10                  15
```

<210> SEQ ID NO 110
<211> LENGTH: 13
<212> TYPE: PRT
<213> ORGANISM: Artificial Sequence
<220> FEATURE:
<223> OTHER INFORMATION: Synthetic peptide

<400> SEQUENCE: 110

```
Cys Ala Ser Arg Asp Ile Gly Ser Gly Pro Gln His Phe
1               5                   10
```

<210> SEQ ID NO 111
<211> LENGTH: 13
<212> TYPE: PRT
<213> ORGANISM: Artificial Sequence
<220> FEATURE:
<223> OTHER INFORMATION: Synthetic peptide

<400> SEQUENCE: 111

Cys Ala Ser Arg Asp Gln Asn Thr Gly Glu Leu Phe Phe
1               5                   10

<210> SEQ ID NO 112
<211> LENGTH: 15
<212> TYPE: PRT
<213> ORGANISM: Artificial Sequence
<220> FEATURE:
<223> OTHER INFORMATION: Synthetic peptide

<400> SEQUENCE: 112

Cys Ala Ile Arg Ile Arg Asp Gln Asn Thr Gly Glu Leu Phe Phe
1               5                   10                  15

<210> SEQ ID NO 113
<211> LENGTH: 17
<212> TYPE: PRT
<213> ORGANISM: Artificial Sequence
<220> FEATURE:
<223> OTHER INFORMATION: Synthetic peptide

<400> SEQUENCE: 113

Cys Ala Ser Arg Thr Ile Phe Ala Thr Val Met Gln Asp Thr Gln Tyr
1               5                   10                  15

Phe

<210> SEQ ID NO 114
<211> LENGTH: 15
<212> TYPE: PRT
<213> ORGANISM: Artificial Sequence
<220> FEATURE:
<223> OTHER INFORMATION: Synthetic peptide

<400> SEQUENCE: 114

Cys Ala Ile Arg Thr Arg Asp Gln Asn Thr Gly Glu Leu Phe Phe
1               5                   10                  15

<210> SEQ ID NO 115
<211> LENGTH: 15
<212> TYPE: PRT
<213> ORGANISM: Artificial Sequence
<220> FEATURE:
<223> OTHER INFORMATION: Synthetic peptide

<400> SEQUENCE: 115

Cys Ala Ser Ser Arg Leu Gln Gln Arg Lys Asn Ile Gln Tyr Phe
1               5                   10                  15

<210> SEQ ID NO 116
<211> LENGTH: 15
<212> TYPE: PRT
<213> ORGANISM: Artificial Sequence
<220> FEATURE:
<223> OTHER INFORMATION: Synthetic peptide

<400> SEQUENCE: 116

Cys Ala Ser Ser Ile Met Val Tyr Ser Tyr Asn Glu Gln Phe Phe
1               5                   10                  15

<210> SEQ ID NO 117
<211> LENGTH: 15
<212> TYPE: PRT
<213> ORGANISM: Artificial Sequence
<220> FEATURE:
<223> OTHER INFORMATION: Synthetic peptide

```
<400> SEQUENCE: 117

Cys Ala Ile Arg Glu Gly Asp Gln Asn Thr Gly Glu Leu Phe Phe
1               5                   10                  15

<210> SEQ ID NO 118
<211> LENGTH: 15
<212> TYPE: PRT
<213> ORGANISM: Artificial Sequence
<220> FEATURE:
<223> OTHER INFORMATION: Synthetic peptide

<400> SEQUENCE: 118

Cys Ala Ser Ser Asp Phe Asn Pro Ser Thr Asp Thr Gln Tyr Phe
1               5                   10                  15

<210> SEQ ID NO 119
<211> LENGTH: 14
<212> TYPE: PRT
<213> ORGANISM: Artificial Sequence
<220> FEATURE:
<223> OTHER INFORMATION: Synthetic peptide

<400> SEQUENCE: 119

Cys Ala Ser Ser Arg Gly Ser Val Ser Asp Glu Gln Tyr Phe
1               5                   10

<210> SEQ ID NO 120
<211> LENGTH: 13
<212> TYPE: PRT
<213> ORGANISM: Artificial Sequence
<220> FEATURE:
<223> OTHER INFORMATION: Synthetic peptide

<400> SEQUENCE: 120

Cys Ala Ser Ser Asp Arg Asp Leu Tyr Gly Tyr Thr Phe
1               5                   10

<210> SEQ ID NO 121
<211> LENGTH: 15
<212> TYPE: PRT
<213> ORGANISM: Artificial Sequence
<220> FEATURE:
<223> OTHER INFORMATION: Synthetic peptide

<400> SEQUENCE: 121

Cys Ala Ser Ser Ile Ala Ala Gly Asp Ala Tyr Gly Tyr Thr Phe
1               5                   10                  15

<210> SEQ ID NO 122
<211> LENGTH: 13
<212> TYPE: PRT
<213> ORGANISM: Artificial Sequence
<220> FEATURE:
<223> OTHER INFORMATION: Synthetic peptide

<400> SEQUENCE: 122

Cys Ala Ser Ser Pro Arg Gly Asp Thr Glu Ala Phe Phe
1               5                   10

<210> SEQ ID NO 123
<211> LENGTH: 11
<212> TYPE: PRT
<213> ORGANISM: Artificial Sequence
<220> FEATURE:
<223> OTHER INFORMATION: Synthetic peptide
```

<400> SEQUENCE: 123

Cys Ala Ser Ser Phe Gly Ser Glu Gln Tyr Phe
1               5                   10

<210> SEQ ID NO 124
<211> LENGTH: 13
<212> TYPE: PRT
<213> ORGANISM: Artificial Sequence
<220> FEATURE:
<223> OTHER INFORMATION: Synthetic peptide

<400> SEQUENCE: 124

Cys Ala Ser Ser Trp Glu Leu Thr Asn Glu Gln Tyr Phe
1               5                   10

<210> SEQ ID NO 125
<211> LENGTH: 12
<212> TYPE: PRT
<213> ORGANISM: Artificial Sequence
<220> FEATURE:
<223> OTHER INFORMATION: Synthetic peptide

<400> SEQUENCE: 125

Cys Ala Ser Ser Trp Arg Val Gln Pro Gln His Phe
1               5                   10

<210> SEQ ID NO 126
<211> LENGTH: 15
<212> TYPE: PRT
<213> ORGANISM: Artificial Sequence
<220> FEATURE:
<223> OTHER INFORMATION: Synthetic peptide

<400> SEQUENCE: 126

Cys Ala Ser Ser Gln Ser Ile Ala Asp Asn Tyr Gly Tyr Thr Phe
1               5                   10                  15

<210> SEQ ID NO 127
<211> LENGTH: 12
<212> TYPE: PRT
<213> ORGANISM: Artificial Sequence
<220> FEATURE:
<223> OTHER INFORMATION: Synthetic peptide

<400> SEQUENCE: 127

Cys Ala Ser Ser Leu Ser Gly Gln Pro Gln His Phe
1               5                   10

<210> SEQ ID NO 128
<211> LENGTH: 15
<212> TYPE: PRT
<213> ORGANISM: Artificial Sequence
<220> FEATURE:
<223> OTHER INFORMATION: Synthetic peptide

<400> SEQUENCE: 128

Cys Ala Ser Ser Ile Leu Gly Tyr Ser Asn Gln Pro Gln His Phe
1               5                   10                  15

<210> SEQ ID NO 129
<211> LENGTH: 13
<212> TYPE: PRT
<213> ORGANISM: Artificial Sequence
<220> FEATURE:
<223> OTHER INFORMATION: Synthetic peptide

<400> SEQUENCE: 129

```
Cys Ala Ile Arg Asp Ser Asn Thr Gly Glu Leu Phe Phe
1               5                   10

<210> SEQ ID NO 130
<211> LENGTH: 15
<212> TYPE: PRT
<213> ORGANISM: Artificial Sequence
<220> FEATURE:
<223> OTHER INFORMATION: Synthetic peptide

<400> SEQUENCE: 130

Cys Ala Ile Arg Ala Gly Asp Ser Asn Thr Gly Glu Leu Phe Phe
1               5                   10                  15

<210> SEQ ID NO 131
<211> LENGTH: 14
<212> TYPE: PRT
<213> ORGANISM: Artificial Sequence
<220> FEATURE:
<223> OTHER INFORMATION: Synthetic peptide

<400> SEQUENCE: 131

Cys Ala Ser Arg Glu Gly Ala Ala Tyr Asn Glu Gln Phe Phe
1               5                   10

<210> SEQ ID NO 132
<211> LENGTH: 14
<212> TYPE: PRT
<213> ORGANISM: Artificial Sequence
<220> FEATURE:
<223> OTHER INFORMATION: Synthetic peptide

<400> SEQUENCE: 132

Cys Ala Ser Arg Glu Gly Ala Ala Tyr Asn Glu Gln Phe Phe
1               5                   10

<210> SEQ ID NO 133
<211> LENGTH: 15
<212> TYPE: PRT
<213> ORGANISM: Artificial Sequence
<220> FEATURE:
<223> OTHER INFORMATION: Synthetic peptide

<400> SEQUENCE: 133

Cys Ala Thr Ser Asp Pro Leu Ala Ala Ser Tyr Glu Gln Tyr Phe
1               5                   10                  15

<210> SEQ ID NO 134
<211> LENGTH: 14
<212> TYPE: PRT
<213> ORGANISM: Artificial Sequence
<220> FEATURE:
<223> OTHER INFORMATION: Synthetic peptide

<400> SEQUENCE: 134

Cys Ala Ser Ser Pro Pro Ser Ser Gly Asn Thr Ile Tyr Phe
1               5                   10

<210> SEQ ID NO 135
<211> LENGTH: 16
<212> TYPE: PRT
<213> ORGANISM: Artificial Sequence
<220> FEATURE:
<223> OTHER INFORMATION: Synthetic peptide

<400> SEQUENCE: 135
```

Cys Ala Ser Ser Val Arg Val Gln Gln Arg Lys Asn Ile Gln Tyr Phe
1               5                   10                  15

<210> SEQ ID NO 136
<211> LENGTH: 15
<212> TYPE: PRT
<213> ORGANISM: Artificial Sequence
<220> FEATURE:
<223> OTHER INFORMATION: Synthetic peptide

<400> SEQUENCE: 136

Cys Ala Ile Arg Thr Leu Asp Met Asn Thr Gly Glu Leu Phe Phe
1               5                   10                  15

<210> SEQ ID NO 137
<211> LENGTH: 16
<212> TYPE: PRT
<213> ORGANISM: Artificial Sequence
<220> FEATURE:
<223> OTHER INFORMATION: Synthetic peptide

<400> SEQUENCE: 137

Cys Ser Ala Arg Pro Gly Gln Gly Ala Tyr Asn Ser Pro Leu His Phe
1               5                   10                  15

<210> SEQ ID NO 138
<211> LENGTH: 13
<212> TYPE: PRT
<213> ORGANISM: Artificial Sequence
<220> FEATURE:
<223> OTHER INFORMATION: Synthetic peptide

<400> SEQUENCE: 138

Cys Ala Ser Ser Leu Tyr Arg Glu Glu Thr Gln Tyr Phe
1               5                   10

<210> SEQ ID NO 139
<211> LENGTH: 16
<212> TYPE: PRT
<213> ORGANISM: Artificial Sequence
<220> FEATURE:
<223> OTHER INFORMATION: Synthetic peptide

<400> SEQUENCE: 139

Cys Ala Ser Ser Leu Thr Gly Leu Ala Gly Thr Asp Thr Gln Tyr Phe
1               5                   10                  15

<210> SEQ ID NO 140
<211> LENGTH: 15
<212> TYPE: PRT
<213> ORGANISM: Artificial Sequence
<220> FEATURE:
<223> OTHER INFORMATION: Synthetic peptide

<400> SEQUENCE: 140

Cys Ala Ile Arg Lys Gln Asp Gln Asn Thr Gly Glu Leu Phe Phe
1               5                   10                  15

<210> SEQ ID NO 141
<211> LENGTH: 17
<212> TYPE: PRT
<213> ORGANISM: Artificial Sequence
<220> FEATURE:
<223> OTHER INFORMATION: Synthetic peptide

<400> SEQUENCE: 141

Cys Ala Ser Ser Phe Pro Gly Ala Gly Ser Asn Thr Gly Glu Leu Phe

<210> SEQ ID NO 142
<211> LENGTH: 17
<212> TYPE: PRT
<213> ORGANISM: Artificial Sequence
<220> FEATURE:
<223> OTHER INFORMATION: Synthetic peptide

<400> SEQUENCE: 142

Cys Ala Ser Ser Leu Val Ile Ala Thr Gln Ile Arg Thr Glu Ala Phe
1               5                   10                  15
Phe

<210> SEQ ID NO 143
<211> LENGTH: 18
<212> TYPE: PRT
<213> ORGANISM: Artificial Sequence
<220> FEATURE:
<223> OTHER INFORMATION: Synthetic peptide

<400> SEQUENCE: 143

Cys Ala Ser Arg Gly Leu Leu Ala Gln Gln Ser Arg Ala Asn Val Leu
1               5                   10                  15
Thr Phe

<210> SEQ ID NO 144
<211> LENGTH: 17
<212> TYPE: PRT
<213> ORGANISM: Artificial Sequence
<220> FEATURE:
<223> OTHER INFORMATION: Synthetic peptide

<400> SEQUENCE: 144

Cys Ala Ser Arg His Trp Leu Leu Gln His Ala Arg Asn Thr Ile Tyr
1               5                   10                  15
Phe

<210> SEQ ID NO 145
<211> LENGTH: 19
<212> TYPE: PRT
<213> ORGANISM: Artificial Sequence
<220> FEATURE:
<223> OTHER INFORMATION: Synthetic peptide

<400> SEQUENCE: 145

Cys Ala Ser Ser Asn Pro Gln Arg Ile Ala Gln Ser Arg Ala Asn Val
1               5                   10                  15
Leu Thr Phe

<210> SEQ ID NO 146
<211> LENGTH: 18
<212> TYPE: PRT
<213> ORGANISM: Artificial Sequence
<220> FEATURE:
<223> OTHER INFORMATION: Synthetic peptide

<400> SEQUENCE: 146

Cys Pro Gly Ser Arg Tyr Gly Ser Glu Gln Ser Arg Ala Asn Val Leu
1               5                   10                  15
Thr Phe

```
<210> SEQ ID NO 147
<211> LENGTH: 15
<212> TYPE: PRT
<213> ORGANISM: Artificial Sequence
<220> FEATURE:
<223> OTHER INFORMATION: Synthetic peptide

<400> SEQUENCE: 147

Cys Ala Ser Ser Ile Leu Leu Tyr Ser Asn Gln Pro Gln His Phe
1               5                   10                  15

<210> SEQ ID NO 148
<211> LENGTH: 17
<212> TYPE: PRT
<213> ORGANISM: Artificial Sequence
<220> FEATURE:
<223> OTHER INFORMATION: Synthetic peptide

<400> SEQUENCE: 148

Cys Ala Ser Ser Trp Ser Val Leu Gln His Ala Arg Asn Thr Ile Tyr
1               5                   10                  15

Phe

<210> SEQ ID NO 149
<211> LENGTH: 14
<212> TYPE: PRT
<213> ORGANISM: Artificial Sequence
<220> FEATURE:
<223> OTHER INFORMATION: Synthetic peptide

<400> SEQUENCE: 149

Cys Ala Ser Ser Leu Gly Trp Gly Asp Thr Glu Ala Phe Phe
1               5                   10

<210> SEQ ID NO 150
<211> LENGTH: 16
<212> TYPE: PRT
<213> ORGANISM: Artificial Sequence
<220> FEATURE:
<223> OTHER INFORMATION: Synthetic peptide

<400> SEQUENCE: 150

Cys Ala Ser Ser Leu Thr Gly Leu Ala Gly Thr Asp Thr Gln Tyr Phe
1               5                   10                  15

<210> SEQ ID NO 151
<211> LENGTH: 15
<212> TYPE: PRT
<213> ORGANISM: Artificial Sequence
<220> FEATURE:
<223> OTHER INFORMATION: Synthetic peptide

<400> SEQUENCE: 151

Cys Ala Ser Ser Ile Leu Ser Asn Ser Tyr Asn Glu Gln Phe Phe
1               5                   10                  15

<210> SEQ ID NO 152
<211> LENGTH: 17
<212> TYPE: PRT
<213> ORGANISM: Artificial Sequence
<220> FEATURE:
<223> OTHER INFORMATION: Synthetic peptide

<400> SEQUENCE: 152

Cys Ala Ser Arg Arg Ala Pro Gly Gly Gly Leu Tyr Asn Glu Gln Phe
1               5                   10                  15
```

Phe

```
<210> SEQ ID NO 153
<211> LENGTH: 15
<212> TYPE: PRT
<213> ORGANISM: Artificial Sequence
<220> FEATURE:
<223> OTHER INFORMATION: Synthetic peptide

<400> SEQUENCE: 153
```

Cys Ala Ile Arg Thr Leu Asp Met Asn Thr Gly Glu Leu Phe Phe
1               5                   10                  15

```
<210> SEQ ID NO 154
<211> LENGTH: 15
<212> TYPE: PRT
<213> ORGANISM: Artificial Sequence
<220> FEATURE:
<223> OTHER INFORMATION: Synthetic peptide

<400> SEQUENCE: 154
```

Cys Ala Ser Ser Leu Ser Arg Gly Leu Leu Asn Gly Tyr Thr Phe
1               5                   10                  15

```
<210> SEQ ID NO 155
<211> LENGTH: 14
<212> TYPE: PRT
<213> ORGANISM: Artificial Sequence
<220> FEATURE:
<223> OTHER INFORMATION: Synthetic peptide

<400> SEQUENCE: 155
```

Cys Ala Ser Ser Leu Val Gly Gly Arg Asp Gly Tyr Thr Phe
1               5                   10

```
<210> SEQ ID NO 156
<211> LENGTH: 16
<212> TYPE: PRT
<213> ORGANISM: Artificial Sequence
<220> FEATURE:
<223> OTHER INFORMATION: Synthetic peptide

<400> SEQUENCE: 156
```

Cys Ala Ser Ser Gln Phe Trp Ala Gly Gly Ile Tyr Glu Gln Tyr Phe
1               5                   10                  15

```
<210> SEQ ID NO 157
<211> LENGTH: 12
<212> TYPE: PRT
<213> ORGANISM: Artificial Sequence
<220> FEATURE:
<223> OTHER INFORMATION: Synthetic peptide

<400> SEQUENCE: 157
```

Cys Ala Ser Ser Gln Val Gly Glu Thr Gln Tyr Phe
1               5                   10

```
<210> SEQ ID NO 158
<211> LENGTH: 14
<212> TYPE: PRT
<213> ORGANISM: Artificial Sequence
<220> FEATURE:
<223> OTHER INFORMATION: Synthetic peptide

<400> SEQUENCE: 158
```

Cys Ala Ser Ser Tyr Gln Gly Glu Glu Glu Thr Gln Tyr Phe

<210> SEQ ID NO 159
<211> LENGTH: 16
<212> TYPE: PRT
<213> ORGANISM: Artificial Sequence
<220> FEATURE:
<223> OTHER INFORMATION: Synthetic peptide

<400> SEQUENCE: 159

Cys Ala Thr Ser Ser Asp Arg Gly Gly Leu Gln Glu Thr Gln Tyr Phe
1               5                   10                  15

<210> SEQ ID NO 160
<211> LENGTH: 17
<212> TYPE: PRT
<213> ORGANISM: Artificial Sequence
<220> FEATURE:
<223> OTHER INFORMATION: Synthetic peptide

<400> SEQUENCE: 160

Cys Ala Ser Arg His Asn Val Leu Gln His Ala Arg Asn Thr Ile Tyr
1               5                   10                  15

Phe

<210> SEQ ID NO 161
<211> LENGTH: 17
<212> TYPE: PRT
<213> ORGANISM: Artificial Sequence
<220> FEATURE:
<223> OTHER INFORMATION: Synthetic peptide

<400> SEQUENCE: 161

Cys Ala Ser Ser Gly Arg Leu Gln Gln Ser Arg Ala Asn Val Leu Thr
1               5                   10                  15

Phe

<210> SEQ ID NO 162
<211> LENGTH: 16
<212> TYPE: PRT
<213> ORGANISM: Artificial Sequence
<220> FEATURE:
<223> OTHER INFORMATION: Synthetic peptide

<400> SEQUENCE: 162

Cys Ala Ser Ser Tyr Pro Tyr Gly Gly Gly Gln Asn Glu Gln Phe Phe
1               5                   10                  15

<210> SEQ ID NO 163
<211> LENGTH: 11
<212> TYPE: PRT
<213> ORGANISM: Artificial Sequence
<220> FEATURE:
<223> OTHER INFORMATION: Synthetic peptide

<400> SEQUENCE: 163

Cys Ala Arg Gly Pro Thr Gly Gly Tyr Thr Phe
1               5                   10

<210> SEQ ID NO 164
<211> LENGTH: 15
<212> TYPE: PRT
<213> ORGANISM: Artificial Sequence
<220> FEATURE:
<223> OTHER INFORMATION: Synthetic peptide

```
<400> SEQUENCE: 164

Cys Ala Ser Ser Pro Arg Ala Gly Val Asp Tyr Gly Tyr Thr Phe
1               5                   10                  15

<210> SEQ ID NO 165
<211> LENGTH: 15
<212> TYPE: PRT
<213> ORGANISM: Artificial Sequence
<220> FEATURE:
<223> OTHER INFORMATION: Synthetic peptide

<400> SEQUENCE: 165

Cys Ala Ser Ser Leu Val Arg Asp Ser Tyr Asn Glu Gln Phe Phe
1               5                   10                  15

<210> SEQ ID NO 166
<211> LENGTH: 14
<212> TYPE: PRT
<213> ORGANISM: Artificial Sequence
<220> FEATURE:
<223> OTHER INFORMATION: Synthetic peptide

<400> SEQUENCE: 166

Cys Ala Ser Ser Gly Gly Arg Val Asn Glu Lys Leu Phe Phe
1               5                   10

<210> SEQ ID NO 167
<211> LENGTH: 14
<212> TYPE: PRT
<213> ORGANISM: Artificial Sequence
<220> FEATURE:
<223> OTHER INFORMATION: Synthetic peptide

<400> SEQUENCE: 167

Cys Ala Ser Ser Leu Gly Gly Asn Thr Gly Glu Leu Phe Phe
1               5                   10

<210> SEQ ID NO 168
<211> LENGTH: 14
<212> TYPE: PRT
<213> ORGANISM: Artificial Sequence
<220> FEATURE:
<223> OTHER INFORMATION: Synthetic peptide

<400> SEQUENCE: 168

Cys Ala Ser Ser Glu Trp Gly Gly Thr Gln Pro Gln His Phe
1               5                   10

<210> SEQ ID NO 169
<211> LENGTH: 14
<212> TYPE: PRT
<213> ORGANISM: Artificial Sequence
<220> FEATURE:
<223> OTHER INFORMATION: Synthetic peptide

<400> SEQUENCE: 169

Cys Ala Thr Ser Gly Thr Gly Arg Trp Glu Thr Gln Tyr Phe
1               5                   10

<210> SEQ ID NO 170
<211> LENGTH: 15
<212> TYPE: PRT
<213> ORGANISM: Artificial Sequence
<220> FEATURE:
<223> OTHER INFORMATION: Synthetic peptide

<400> SEQUENCE: 170
```

```
Cys Ala Ser Ser Leu Ala Arg Gly Pro Gly Asn Thr Ile Tyr Phe
1               5                   10                  15

<210> SEQ ID NO 171
<211> LENGTH: 13
<212> TYPE: PRT
<213> ORGANISM: Artificial Sequence
<220> FEATURE:
<223> OTHER INFORMATION: Synthetic peptide

<400> SEQUENCE: 171

Cys Ala Ser Arg Ile Thr Met Gly Gln Pro Gln His Phe
1               5                   10

<210> SEQ ID NO 172
<211> LENGTH: 14
<212> TYPE: PRT
<213> ORGANISM: Artificial Sequence
<220> FEATURE:
<223> OTHER INFORMATION: Synthetic peptide

<400> SEQUENCE: 172

Cys Ala Ser Ser Asp Arg Val Ala Gly Asn Glu Gln Phe Phe
1               5                   10

<210> SEQ ID NO 173
<211> LENGTH: 14
<212> TYPE: PRT
<213> ORGANISM: Artificial Sequence
<220> FEATURE:
<223> OTHER INFORMATION: Synthetic peptide

<400> SEQUENCE: 173

Cys Ala Ser Ser Leu Thr Ser Gly Val Thr Glu Ala Phe Phe
1               5                   10

<210> SEQ ID NO 174
<211> LENGTH: 14
<212> TYPE: PRT
<213> ORGANISM: Artificial Sequence
<220> FEATURE:
<223> OTHER INFORMATION: Synthetic peptide

<400> SEQUENCE: 174

Cys Ala Ser Ser Leu Ser Pro Glu Leu His Gly Tyr Thr Phe
1               5                   10

<210> SEQ ID NO 175
<211> LENGTH: 17
<212> TYPE: PRT
<213> ORGANISM: Artificial Sequence
<220> FEATURE:
<223> OTHER INFORMATION: Synthetic peptide

<400> SEQUENCE: 175

Cys Ala Thr Ser Arg Asp Ser Gly Gly Leu Asp Gly Asp Thr Gln Tyr
1               5                   10                  15

Phe

<210> SEQ ID NO 176
<211> LENGTH: 15
<212> TYPE: PRT
<213> ORGANISM: Artificial Sequence
<220> FEATURE:
<223> OTHER INFORMATION: Synthetic peptide
```

```
<400> SEQUENCE: 176

Cys Ala Ser Ser Pro Gly Glu Trp Gly Ser Glu Thr Gln Tyr Phe
1               5                   10                  15

<210> SEQ ID NO 177
<211> LENGTH: 14
<212> TYPE: PRT
<213> ORGANISM: Artificial Sequence
<220> FEATURE:
<223> OTHER INFORMATION: Synthetic peptide

<400> SEQUENCE: 177

Cys Ala Ser Ser Phe Gly Gly Gly Ala Asn Glu Gln Phe Phe
1               5                   10

<210> SEQ ID NO 178
<211> LENGTH: 15
<212> TYPE: PRT
<213> ORGANISM: Artificial Sequence
<220> FEATURE:
<223> OTHER INFORMATION: Synthetic peptide

<400> SEQUENCE: 178

Cys Ala Ser Thr Pro Gly Gly Leu Pro Lys Asn Ile Gln Tyr Phe
1               5                   10                  15

<210> SEQ ID NO 179
<211> LENGTH: 15
<212> TYPE: PRT
<213> ORGANISM: Artificial Sequence
<220> FEATURE:
<223> OTHER INFORMATION: Synthetic peptide

<400> SEQUENCE: 179

Cys Ala Ser Ser Ala Thr Gly Thr Gly Asp Leu Glu Gln Phe Phe
1               5                   10                  15

<210> SEQ ID NO 180
<211> LENGTH: 15
<212> TYPE: PRT
<213> ORGANISM: Artificial Sequence
<220> FEATURE:
<223> OTHER INFORMATION: Synthetic peptide

<400> SEQUENCE: 180

Cys Ala Ser Ser Trp Gly Tyr Asp Ser Tyr Asn Glu Gln Phe Phe
1               5                   10                  15

<210> SEQ ID NO 181
<211> LENGTH: 16
<212> TYPE: PRT
<213> ORGANISM: Artificial Sequence
<220> FEATURE:
<223> OTHER INFORMATION: Synthetic peptide

<400> SEQUENCE: 181

Cys Ala Ser Ser Gln Glu Thr Gly Glu Gly Asn Ser Pro Leu His Phe
1               5                   10                  15

<210> SEQ ID NO 182
<211> LENGTH: 17
<212> TYPE: PRT
<213> ORGANISM: Artificial Sequence
<220> FEATURE:
<223> OTHER INFORMATION: Synthetic peptide

<400> SEQUENCE: 182
```

```
Cys Ala Ser Arg Leu Thr Asp Arg Gly Arg Val Gly Glu Lys Leu Phe
1               5                   10                  15

Phe

<210> SEQ ID NO 183
<211> LENGTH: 15
<212> TYPE: PRT
<213> ORGANISM: Artificial Sequence
<220> FEATURE:
<223> OTHER INFORMATION: Synthetic peptide

<400> SEQUENCE: 183

Cys Ala Ser Ser Ile Leu Ser Asn Ser Tyr Asn Glu Gln Phe Phe
1               5                   10                  15

<210> SEQ ID NO 184
<211> LENGTH: 15
<212> TYPE: PRT
<213> ORGANISM: Artificial Sequence
<220> FEATURE:
<223> OTHER INFORMATION: Synthetic peptide

<400> SEQUENCE: 184

Cys Ala Ser Ser Ala Gly Thr Ala Ala Gly Asn Thr Ile Tyr Phe
1               5                   10                  15

<210> SEQ ID NO 185
<211> LENGTH: 19
<212> TYPE: PRT
<213> ORGANISM: Artificial Sequence
<220> FEATURE:
<223> OTHER INFORMATION: Synthetic peptide

<400> SEQUENCE: 185

Cys Ala Ser Ser Gly Val Lys Arg Ser His Lys Ser Arg Ala Asn Val
1               5                   10                  15

Leu Thr Phe

<210> SEQ ID NO 186
<211> LENGTH: 15
<212> TYPE: PRT
<213> ORGANISM: Artificial Sequence
<220> FEATURE:
<223> OTHER INFORMATION: Synthetic peptide

<400> SEQUENCE: 186

Cys Ala Ser Ser Gly Tyr His Asp Gly Phe Ser Glu Gln Tyr Phe
1               5                   10                  15

<210> SEQ ID NO 187
<211> LENGTH: 14
<212> TYPE: PRT
<213> ORGANISM: Artificial Sequence
<220> FEATURE:
<223> OTHER INFORMATION: Synthetic peptide

<400> SEQUENCE: 187

Cys Ala Ser Ser Leu Gln Gly Ala Gly Gln Pro Gln His Phe
1               5                   10

<210> SEQ ID NO 188
<211> LENGTH: 11
<212> TYPE: PRT
<213> ORGANISM: Artificial Sequence
<220> FEATURE:
```

<223> OTHER INFORMATION: Synthetic peptide

<400> SEQUENCE: 188

Cys Ala Asp Gly Arg Gly Asp Glu Gln Tyr Phe
1               5                   10

<210> SEQ ID NO 189
<211> LENGTH: 14
<212> TYPE: PRT
<213> ORGANISM: Artificial Sequence
<220> FEATURE:
<223> OTHER INFORMATION: Synthetic peptide

<400> SEQUENCE: 189

Cys Ala Ser Ser Pro Val Gly Gly Asp Gln Pro Gln His Phe
1               5                   10

<210> SEQ ID NO 190
<211> LENGTH: 14
<212> TYPE: PRT
<213> ORGANISM: Artificial Sequence
<220> FEATURE:
<223> OTHER INFORMATION: Synthetic peptide

<400> SEQUENCE: 190

Cys Ala Ser Ser Ile Gly Arg Thr Tyr Tyr Gly Tyr Thr Phe
1               5                   10

<210> SEQ ID NO 191
<211> LENGTH: 14
<212> TYPE: PRT
<213> ORGANISM: Artificial Sequence
<220> FEATURE:
<223> OTHER INFORMATION: Synthetic peptide

<400> SEQUENCE: 191

Cys Ala Tyr Gly Ala Gly Gly Pro Asn Thr Glu Ala Phe Phe
1               5                   10

<210> SEQ ID NO 192
<211> LENGTH: 12
<212> TYPE: PRT
<213> ORGANISM: Artificial Sequence
<220> FEATURE:
<223> OTHER INFORMATION: Synthetic peptide

<400> SEQUENCE: 192

Cys Ala Ser Asn Ile Tyr Ser Gln Pro Gln His Phe
1               5                   10

<210> SEQ ID NO 193
<211> LENGTH: 13
<212> TYPE: PRT
<213> ORGANISM: Artificial Sequence
<220> FEATURE:
<223> OTHER INFORMATION: Synthetic peptide

<400> SEQUENCE: 193

Cys Ala Ser Ser Leu Glu Gly Asp Thr Glu Ala Phe Phe
1               5                   10

<210> SEQ ID NO 194
<211> LENGTH: 16
<212> TYPE: PRT
<213> ORGANISM: Artificial Sequence
<220> FEATURE:
<223> OTHER INFORMATION: Synthetic peptide

<400> SEQUENCE: 194

Cys Ala Ser Ser Glu Thr Asp Arg Gly Leu Ala Tyr Glu Gln Tyr Val
1               5                   10                  15

<210> SEQ ID NO 195
<211> LENGTH: 13
<212> TYPE: PRT
<213> ORGANISM: Artificial Sequence
<220> FEATURE:
<223> OTHER INFORMATION: Synthetic peptide

<400> SEQUENCE: 195

Cys Ser Ala Arg Asp Arg Val Gly Asn Thr Ile Tyr Phe
1               5                   10

<210> SEQ ID NO 196
<211> LENGTH: 13
<212> TYPE: PRT
<213> ORGANISM: Artificial Sequence
<220> FEATURE:
<223> OTHER INFORMATION: Synthetic peptide

<400> SEQUENCE: 196

Cys Ala Ser Ser Tyr Phe Pro Gly Val Glu Ala Phe Phe
1               5                   10

<210> SEQ ID NO 197
<211> LENGTH: 14
<212> TYPE: PRT
<213> ORGANISM: Artificial Sequence
<220> FEATURE:
<223> OTHER INFORMATION: Synthetic peptide

<400> SEQUENCE: 197

Cys Ala Ser Ser Glu Gly Gln Gly Asn Ser Pro Leu His Phe
1               5                   10

<210> SEQ ID NO 198
<211> LENGTH: 13
<212> TYPE: PRT
<213> ORGANISM: Artificial Sequence
<220> FEATURE:
<223> OTHER INFORMATION: Synthetic peptide

<400> SEQUENCE: 198

Cys Ala Ser Gln Thr Gly Phe Tyr Asn Glu Gln Phe Phe
1               5                   10

<210> SEQ ID NO 199
<211> LENGTH: 14
<212> TYPE: PRT
<213> ORGANISM: Artificial Sequence
<220> FEATURE:
<223> OTHER INFORMATION: Synthetic peptide

<400> SEQUENCE: 199

Cys Ala Ser Lys Thr Ser Gly Phe Pro Asp Thr Gln Tyr Phe
1               5                   10

<210> SEQ ID NO 200
<211> LENGTH: 16
<212> TYPE: PRT
<213> ORGANISM: Artificial Sequence
<220> FEATURE:
<223> OTHER INFORMATION: Synthetic peptide

```
<400> SEQUENCE: 200

Cys Ala Ser Ser Leu Ser Arg Gly Asp Ser Asn Gln Pro Gln His Phe
1               5                   10                  15

<210> SEQ ID NO 201
<211> LENGTH: 12
<212> TYPE: PRT
<213> ORGANISM: Artificial Sequence
<220> FEATURE:
<223> OTHER INFORMATION: Synthetic peptide

<400> SEQUENCE: 201

Cys Ala Ser Arg Glu Ser Asn Thr Glu Ala Phe Phe
1               5                   10

<210> SEQ ID NO 202
<211> LENGTH: 13
<212> TYPE: PRT
<213> ORGANISM: Artificial Sequence
<220> FEATURE:
<223> OTHER INFORMATION: Synthetic peptide

<400> SEQUENCE: 202

Cys Ala Ser Ser Glu Gly Gln Ser Tyr Glu Gln Tyr Phe
1               5                   10

<210> SEQ ID NO 203

<400> SEQUENCE: 203

000

<210> SEQ ID NO 204
<211> LENGTH: 15
<212> TYPE: PRT
<213> ORGANISM: Artificial Sequence
<220> FEATURE:
<223> OTHER INFORMATION: Synthetic peptide

<400> SEQUENCE: 204

Cys Ala Ser Ser Ser Gly Thr Pro Ser Thr Asp Thr Gln Tyr Phe
1               5                   10                  15

<210> SEQ ID NO 205
<211> LENGTH: 15
<212> TYPE: PRT
<213> ORGANISM: Artificial Sequence
<220> FEATURE:
<223> OTHER INFORMATION: Synthetic peptide

<400> SEQUENCE: 205

Cys Ala Ser Arg Pro Asp Ile Pro Leu Gly Glu Thr Gln Tyr Phe
1               5                   10                  15

<210> SEQ ID NO 206
<211> LENGTH: 15
<212> TYPE: PRT
<213> ORGANISM: Artificial Sequence
<220> FEATURE:
<223> OTHER INFORMATION: Synthetic peptide

<400> SEQUENCE: 206

Cys Ala Ser Ser Ile Leu Ser Asn Ser Tyr Asn Glu Gln Phe Phe
1               5                   10                  15

<210> SEQ ID NO 207
```

```
<211> LENGTH: 17
<212> TYPE: PRT
<213> ORGANISM: Artificial Sequence
<220> FEATURE:
<223> OTHER INFORMATION: Synthetic peptide

<400> SEQUENCE: 207

Cys Ala Ser Lys Lys Leu Asp Arg Pro Ala Pro Asn Ser Pro Leu His
1               5                   10                  15
Phe

<210> SEQ ID NO 208
<211> LENGTH: 17
<212> TYPE: PRT
<213> ORGANISM: Artificial Sequence
<220> FEATURE:
<223> OTHER INFORMATION: Synthetic peptide

<400> SEQUENCE: 208

Cys Ala Ser Arg Arg Ala Pro Gly Gly Gly Leu Tyr Asn Glu Gln Phe
1               5                   10                  15
Ser

<210> SEQ ID NO 209
<211> LENGTH: 14
<212> TYPE: PRT
<213> ORGANISM: Artificial Sequence
<220> FEATURE:
<223> OTHER INFORMATION: Synthetic peptide

<400> SEQUENCE: 209

Cys Ala Ser Ser Tyr Gln Gly Glu Glu Glu Thr Gln Tyr Phe
1               5                   10

<210> SEQ ID NO 210
<211> LENGTH: 15
<212> TYPE: PRT
<213> ORGANISM: Artificial Sequence
<220> FEATURE:
<223> OTHER INFORMATION: Synthetic peptide

<400> SEQUENCE: 210

Cys Ala Ser Ser Ser Gly Thr Pro Ser Thr Asp Thr Gln Tyr Phe
1               5                   10                  15

<210> SEQ ID NO 211
<211> LENGTH: 15
<212> TYPE: PRT
<213> ORGANISM: Artificial Sequence
<220> FEATURE:
<223> OTHER INFORMATION: Synthetic peptide

<400> SEQUENCE: 211

Cys Ala Ile Asn Asn Arg Asp Gln Asn Thr Gly Glu Leu Phe Phe
1               5                   10                  15

<210> SEQ ID NO 212
<211> LENGTH: 13
<212> TYPE: PRT
<213> ORGANISM: Artificial Sequence
<220> FEATURE:
<223> OTHER INFORMATION: Synthetic peptide

<400> SEQUENCE: 212

Cys Ala Ser Thr Gln Ser Asn Thr Gly Glu Leu Phe Phe
1               5                   10
```

```
<210> SEQ ID NO 213
<211> LENGTH: 15
<212> TYPE: PRT
<213> ORGANISM: Artificial Sequence
<220> FEATURE:
<223> OTHER INFORMATION: Synthetic peptide

<400> SEQUENCE: 213

Cys Ala Ser Ser Glu Thr Pro Asp Met Asn Thr Glu Ala Phe Phe
1               5                   10                  15

<210> SEQ ID NO 214
<211> LENGTH: 15
<212> TYPE: PRT
<213> ORGANISM: Artificial Sequence
<220> FEATURE:
<223> OTHER INFORMATION: Synthetic peptide

<400> SEQUENCE: 214

Cys Ala Ser Ser Ser Gly Thr Pro Ser Thr Asp Thr Gln Tyr Phe
1               5                   10                  15

<210> SEQ ID NO 215
<211> LENGTH: 15
<212> TYPE: PRT
<213> ORGANISM: Artificial Sequence
<220> FEATURE:
<223> OTHER INFORMATION: Synthetic peptide

<400> SEQUENCE: 215

Cys Ala Ser Ser Ser Gly Thr Pro Ser Thr Asp Thr Gln Tyr Phe
1               5                   10                  15

<210> SEQ ID NO 216
<211> LENGTH: 13
<212> TYPE: PRT
<213> ORGANISM: Artificial Sequence
<220> FEATURE:
<223> OTHER INFORMATION: Synthetic peptide

<400> SEQUENCE: 216

Cys Ala Ser Thr Asp Ser Asn Thr Gly Glu Leu Phe Phe
1               5                   10

<210> SEQ ID NO 217
<211> LENGTH: 15
<212> TYPE: PRT
<213> ORGANISM: Artificial Sequence
<220> FEATURE:
<223> OTHER INFORMATION: Synthetic peptide

<400> SEQUENCE: 217

Cys Ala Ser Ser Ser Gly Thr Pro Ser Thr Asp Thr Gln Tyr Phe
1               5                   10                  15

<210> SEQ ID NO 218
<211> LENGTH: 15
<212> TYPE: PRT
<213> ORGANISM: Artificial Sequence
<220> FEATURE:
<223> OTHER INFORMATION: Synthetic peptide

<400> SEQUENCE: 218

Cys Ala Ser Ser Ser Gly Thr Pro Ser Thr Asp Thr Gln Tyr Phe
1               5                   10                  15
```

```
<210> SEQ ID NO 219
<211> LENGTH: 15
<212> TYPE: PRT
<213> ORGANISM: Artificial Sequence
<220> FEATURE:
<223> OTHER INFORMATION: Synthetic peptide

<400> SEQUENCE: 219

Cys Ala Ser Ser Gly Thr Pro Ser Thr Asp Thr Gln Tyr Phe
1               5                   10                  15

<210> SEQ ID NO 220
<211> LENGTH: 18
<212> TYPE: PRT
<213> ORGANISM: Artificial Sequence
<220> FEATURE:
<223> OTHER INFORMATION: Synthetic peptide

<400> SEQUENCE: 220

Cys Ala Ser Ser Leu Gly Val Ala Gly Gly Ser Ser Tyr Asn Glu Gln
1               5                   10                  15

Phe Phe

<210> SEQ ID NO 221
<211> LENGTH: 15
<212> TYPE: PRT
<213> ORGANISM: Artificial Sequence
<220> FEATURE:
<223> OTHER INFORMATION: Synthetic peptide

<400> SEQUENCE: 221

Cys Ala Ser Ser Tyr Ser Thr Gly Val Pro Glu Lys Leu Phe Phe
1               5                   10                  15

<210> SEQ ID NO 222
<211> LENGTH: 17
<212> TYPE: PRT
<213> ORGANISM: Artificial Sequence
<220> FEATURE:
<223> OTHER INFORMATION: Synthetic peptide

<400> SEQUENCE: 222

Cys Ala Ser Ser Trp Tyr Leu Ala Thr His Ser Asp Asn Glu Gln Phe
1               5                   10                  15

Phe

<210> SEQ ID NO 223
<211> LENGTH: 13
<212> TYPE: PRT
<213> ORGANISM: Artificial Sequence
<220> FEATURE:
<223> OTHER INFORMATION: Synthetic peptide

<400> SEQUENCE: 223

Cys Ala Ser Thr Gly Gly Leu Ala Asp Thr Gln Tyr Phe
1               5                   10

<210> SEQ ID NO 224
<211> LENGTH: 19
<212> TYPE: PRT
<213> ORGANISM: Artificial Sequence
<220> FEATURE:
<223> OTHER INFORMATION: Synthetic peptide

<400> SEQUENCE: 224
```

```
Cys Ala Ser Ser Ser Cys Met Asp Ile Tyr Lys Ser Arg Ala Asn Val
1               5                   10                  15

Leu Thr Phe

<210> SEQ ID NO 225
<211> LENGTH: 16
<212> TYPE: PRT
<213> ORGANISM: Artificial Sequence
<220> FEATURE:
<223> OTHER INFORMATION: Synthetic peptide

<400> SEQUENCE: 225

Cys Ala Ser Arg Arg Thr Ser Gly Gly Arg Thr Asp Thr Gln Tyr Phe
1               5                   10                  15

<210> SEQ ID NO 226
<211> LENGTH: 15
<212> TYPE: PRT
<213> ORGANISM: Artificial Sequence
<220> FEATURE:
<223> OTHER INFORMATION: Synthetic peptide

<400> SEQUENCE: 226

Cys Ala Ser Ser Ser Gly Thr Pro Ser Thr Asp Thr Gln Tyr Phe
1               5                   10                  15

<210> SEQ ID NO 227
<211> LENGTH: 15
<212> TYPE: PRT
<213> ORGANISM: Artificial Sequence
<220> FEATURE:
<223> OTHER INFORMATION: Synthetic peptide

<400> SEQUENCE: 227

Cys Ala Ser Ser Ser Gly Thr Pro Ser Thr Asp Thr Gln Tyr Phe
1               5                   10                  15

<210> SEQ ID NO 228
<211> LENGTH: 17
<212> TYPE: PRT
<213> ORGANISM: Artificial Sequence
<220> FEATURE:
<223> OTHER INFORMATION: Synthetic peptide

<400> SEQUENCE: 228

Cys Ala Ser Arg Gly Ser Ile Ala Thr Arg Tyr Asn Glu Lys Leu Phe
1               5                   10                  15

Phe

<210> SEQ ID NO 229
<211> LENGTH: 16
<212> TYPE: PRT
<213> ORGANISM: Artificial Sequence
<220> FEATURE:
<223> OTHER INFORMATION: Synthetic peptide

<400> SEQUENCE: 229

Cys Ala Arg Thr Glu Ser Arg Gln Ser Arg Ala Asn Val Leu Thr Phe
1               5                   10                  15

<210> SEQ ID NO 230
<211> LENGTH: 11
<212> TYPE: PRT
<213> ORGANISM: Artificial Sequence
<220> FEATURE:
<223> OTHER INFORMATION: Synthetic peptide
```

<400> SEQUENCE: 230

Cys Ala Ser Arg Asp Arg Arg Glu Gln Phe Phe
1               5                   10

<210> SEQ ID NO 231
<211> LENGTH: 17
<212> TYPE: PRT
<213> ORGANISM: Artificial Sequence
<220> FEATURE:
<223> OTHER INFORMATION: Synthetic peptide

<400> SEQUENCE: 231

Cys Ala Ser Arg Arg Val Leu Ala Tyr Arg Lys Thr Tyr Gly Tyr Thr
1               5                   10                  15

Phe

<210> SEQ ID NO 232
<211> LENGTH: 18
<212> TYPE: PRT
<213> ORGANISM: Artificial Sequence
<220> FEATURE:
<223> OTHER INFORMATION: Synthetic peptide

<400> SEQUENCE: 232

Cys Ala Ser Arg Arg Cys Ile Ala Thr His Thr His Asn Ser Pro Leu
1               5                   10                  15

His Phe

<210> SEQ ID NO 233
<211> LENGTH: 18
<212> TYPE: PRT
<213> ORGANISM: Artificial Sequence
<220> FEATURE:
<223> OTHER INFORMATION: Synthetic peptide

<400> SEQUENCE: 233

Cys Ala Ile Ser Ala Asp Asn Cys Ile Gln Ser Arg Ala Asn Val Leu
1               5                   10                  15

Thr Phe

<210> SEQ ID NO 234
<211> LENGTH: 17
<212> TYPE: PRT
<213> ORGANISM: Artificial Sequence
<220> FEATURE:
<223> OTHER INFORMATION: Synthetic peptide

<400> SEQUENCE: 234

Cys Ala Ser Arg Gly Asp Ile Gly Tyr Arg Lys Thr Tyr Gly Tyr Thr
1               5                   10                  15

Phe

<210> SEQ ID NO 235
<211> LENGTH: 15
<212> TYPE: PRT
<213> ORGANISM: Artificial Sequence
<220> FEATURE:
<223> OTHER INFORMATION: Synthetic peptide

<400> SEQUENCE: 235

Cys Ala Ser Ser Ile Leu Ser Ser Ser Asn Gln Pro Gln His Phe
1               5                   10                  15

<210> SEQ ID NO 236
<211> LENGTH: 15
<212> TYPE: PRT
<213> ORGANISM: Artificial Sequence
<220> FEATURE:
<223> OTHER INFORMATION: Synthetic peptide

<400> SEQUENCE: 236

Cys Ala Ser Thr Leu Gly Asn Pro Ser Thr Asp Thr Gln Tyr Phe
1               5                   10                  15

<210> SEQ ID NO 237
<211> LENGTH: 19
<212> TYPE: PRT
<213> ORGANISM: Artificial Sequence
<220> FEATURE:
<223> OTHER INFORMATION: Synthetic peptide

<400> SEQUENCE: 237

Cys Ala Ser Ser Ala Glu Val Thr Asn His Gln Ser Arg Ala Asn Val
1               5                   10                  15

Leu Thr Phe

<210> SEQ ID NO 238
<211> LENGTH: 15
<212> TYPE: PRT
<213> ORGANISM: Artificial Sequence
<220> FEATURE:
<223> OTHER INFORMATION: Synthetic peptide

<400> SEQUENCE: 238

Cys Ala Ser Ser Tyr Ser Thr Gly Val Pro Glu Lys Leu Phe Phe
1               5                   10                  15

<210> SEQ ID NO 239
<211> LENGTH: 15
<212> TYPE: PRT
<213> ORGANISM: Artificial Sequence
<220> FEATURE:
<223> OTHER INFORMATION: Synthetic peptide

<400> SEQUENCE: 239

Cys Ala Ile Arg Gly Gln Asp Gln Asn Thr Gly Glu Leu Phe Phe
1               5                   10                  15

<210> SEQ ID NO 240
<211> LENGTH: 14
<212> TYPE: PRT
<213> ORGANISM: Artificial Sequence
<220> FEATURE:
<223> OTHER INFORMATION: Synthetic peptide

<400> SEQUENCE: 240

Cys Ala Ser Ser Arg Thr Lys Ala Tyr Glu Gln Tyr Phe
1               5                   10

<210> SEQ ID NO 241
<211> LENGTH: 15
<212> TYPE: PRT
<213> ORGANISM: Artificial Sequence
<220> FEATURE:
<223> OTHER INFORMATION: Synthetic peptide

<400> SEQUENCE: 241

Cys Ala Ser Ser Leu Ile Ala Gly Leu Ser Tyr Glu Gln Tyr Phe
1               5                   10                  15

<210> SEQ ID NO 242
<211> LENGTH: 15
<212> TYPE: PRT
<213> ORGANISM: Artificial Sequence
<220> FEATURE:
<223> OTHER INFORMATION: Synthetic peptide

<400> SEQUENCE: 242

Cys Ala Ser Thr Leu Gly Asn Pro Ser Thr Asp Thr Gln Tyr Phe
1               5                   10                  15

<210> SEQ ID NO 243
<211> LENGTH: 15
<212> TYPE: PRT
<213> ORGANISM: Artificial Sequence
<220> FEATURE:
<223> OTHER INFORMATION: Synthetic peptide

<400> SEQUENCE: 243

Cys Ala Ser Ser Ile Gln Leu Phe Val Arg Thr Glu Ala Phe Phe
1               5                   10                  15

<210> SEQ ID NO 244
<211> LENGTH: 15
<212> TYPE: PRT
<213> ORGANISM: Artificial Sequence
<220> FEATURE:
<223> OTHER INFORMATION: Synthetic peptide

<400> SEQUENCE: 244

Cys Ala Ser Ser Ile Ile Ala Tyr Ser Asn Gln Pro Gln His Phe
1               5                   10                  15

<210> SEQ ID NO 245
<211> LENGTH: 15
<212> TYPE: PRT
<213> ORGANISM: Artificial Sequence
<220> FEATURE:
<223> OTHER INFORMATION: Synthetic peptide

<400> SEQUENCE: 245

Cys Ala Ser Ser Ile Leu Ser Ser Asn Gln Pro Gln His Phe
1               5                   10                  15

<210> SEQ ID NO 246
<211> LENGTH: 11
<212> TYPE: PRT
<213> ORGANISM: Artificial Sequence
<220> FEATURE:
<223> OTHER INFORMATION: Synthetic peptide

<400> SEQUENCE: 246

Cys Ala Ser Ser Leu Ala Gly Asp Arg Tyr Phe
1               5                   10

<210> SEQ ID NO 247
<211> LENGTH: 19
<212> TYPE: PRT
<213> ORGANISM: Artificial Sequence
<220> FEATURE:
<223> OTHER INFORMATION: Synthetic peptide

<400> SEQUENCE: 247

Cys Cys Ala Ser Ser Phe Gly Thr Ser Gly Gly Thr Thr Tyr Asn Glu
1               5                   10                  15

Gln Phe Phe

<210> SEQ ID NO 248
<211> LENGTH: 13
<212> TYPE: PRT
<213> ORGANISM: Artificial Sequence
<220> FEATURE:
<223> OTHER INFORMATION: Synthetic peptide

<400> SEQUENCE: 248

Cys Ala Ile Arg Gly Gln Asn Thr Gly Glu Leu Phe Phe
1               5                   10

<210> SEQ ID NO 249
<211> LENGTH: 15
<212> TYPE: PRT
<213> ORGANISM: Artificial Sequence
<220> FEATURE:
<223> OTHER INFORMATION: Synthetic peptide

<400> SEQUENCE: 249

Cys Ala Ser Thr Leu Gly Asn Pro Ser Thr Asp Thr Gln Tyr Phe
1               5                   10                  15

<210> SEQ ID NO 250
<211> LENGTH: 17
<212> TYPE: PRT
<213> ORGANISM: Artificial Sequence
<220> FEATURE:
<223> OTHER INFORMATION: Synthetic peptide

<400> SEQUENCE: 250

Cys Ala Ser Arg Thr Val Val Leu His Trp His His Gln Pro Gln His
1               5                   10                  15

Phe

<210> SEQ ID NO 251
<211> LENGTH: 14
<212> TYPE: PRT
<213> ORGANISM: Artificial Sequence
<220> FEATURE:
<223> OTHER INFORMATION: Synthetic peptide

<400> SEQUENCE: 251

Cys Ala Ile Arg Thr Gly Ser Ala Tyr Asn Glu Gln Phe Phe
1               5                   10

<210> SEQ ID NO 252
<211> LENGTH: 16
<212> TYPE: PRT
<213> ORGANISM: Artificial Sequence
<220> FEATURE:
<223> OTHER INFORMATION: Synthetic peptide

<400> SEQUENCE: 252

Cys Ser Ala Leu Pro Val Thr Gly Ala Phe Gln Glu Thr Gln Tyr Phe
1               5                   10                  15

<210> SEQ ID NO 253
<211> LENGTH: 15
<212> TYPE: PRT
<213> ORGANISM: Artificial Sequence
<220> FEATURE:
<223> OTHER INFORMATION: Synthetic peptide

<400> SEQUENCE: 253

Cys Ala Ile Arg Gly Gln Asp Gln Asn Thr Gly Glu Leu Phe Phe
1               5                   10                  15

<210> SEQ ID NO 254
<211> LENGTH: 13
<212> TYPE: PRT
<213> ORGANISM: Artificial Sequence
<220> FEATURE:
<223> OTHER INFORMATION: Synthetic peptide

<400> SEQUENCE: 254

Cys Ala Arg Ser Val Leu Asn Thr Gly Glu Leu Phe Phe
1               5                   10

<210> SEQ ID NO 255
<211> LENGTH: 15
<212> TYPE: PRT
<213> ORGANISM: Artificial Sequence
<220> FEATURE:
<223> OTHER INFORMATION: Synthetic peptide

<400> SEQUENCE: 255

Cys Ala Ser Ser Pro Thr Gly Ala Val Ser Tyr Glu Gln Tyr Phe
1               5                   10                  15

<210> SEQ ID NO 256
<211> LENGTH: 17
<212> TYPE: PRT
<213> ORGANISM: Artificial Sequence
<220> FEATURE:
<223> OTHER INFORMATION: Synthetic peptide

<400> SEQUENCE: 256

Cys Ser Ala Arg Ala Pro Thr Gly Thr Gly Asn Thr Gly Glu Leu Phe
1               5                   10                  15

Phe

<210> SEQ ID NO 257
<211> LENGTH: 15
<212> TYPE: PRT
<213> ORGANISM: Artificial Sequence
<220> FEATURE:
<223> OTHER INFORMATION: Synthetic peptide

<400> SEQUENCE: 257

Cys Ala Ile Arg Gly Gln Asp Gln Asn Thr Gly Glu Leu Phe Phe
1               5                   10                  15

<210> SEQ ID NO 258
<211> LENGTH: 15
<212> TYPE: PRT
<213> ORGANISM: Artificial Sequence
<220> FEATURE:
<223> OTHER INFORMATION: Synthetic peptide

<400> SEQUENCE: 258

Cys Ala Ile Arg Gly Gln Asp Gln Asn Thr Gly Glu Leu Phe Phe
1               5                   10                  15

<210> SEQ ID NO 259
<211> LENGTH: 15
<212> TYPE: PRT
<213> ORGANISM: Artificial Sequence
<220> FEATURE:
<223> OTHER INFORMATION: Synthetic peptide

<400> SEQUENCE: 259

```
Cys Ala Ser Thr Leu Gly Asn Pro Ser Thr Asp Thr Gln Tyr Phe
1               5                   10                  15

<210> SEQ ID NO 260
<211> LENGTH: 19
<212> TYPE: PRT
<213> ORGANISM: Artificial Sequence
<220> FEATURE:
<223> OTHER INFORMATION: Synthetic peptide

<400> SEQUENCE: 260

Cys Ala Ser Ser Asp Arg Pro Arg Ile Ala Gln Ser Arg Ala Asn Val
1               5                   10                  15

Leu Thr Phe

<210> SEQ ID NO 261
<211> LENGTH: 17
<212> TYPE: PRT
<213> ORGANISM: Artificial Sequence
<220> FEATURE:
<223> OTHER INFORMATION: Synthetic peptide

<400> SEQUENCE: 261

Cys Ala Ser Arg Arg Cys Ile Ala Thr Thr Ala Arg Asn Thr Ile Tyr
1               5                   10                  15

Phe

<210> SEQ ID NO 262
<211> LENGTH: 13
<212> TYPE: PRT
<213> ORGANISM: Artificial Sequence
<220> FEATURE:
<223> OTHER INFORMATION: Synthetic peptide

<400> SEQUENCE: 262

Cys Ala Ser Ser Glu Ser Asn Thr Leu Val Gly Phe Phe
1               5                   10

<210> SEQ ID NO 263
<211> LENGTH: 18
<212> TYPE: PRT
<213> ORGANISM: Artificial Sequence
<220> FEATURE:
<223> OTHER INFORMATION: Synthetic peptide

<400> SEQUENCE: 263

Cys Pro Gly Arg Arg Ala Arg Lys Arg Thr Ser Arg Ala Asn Val Leu
1               5                   10                  15

Thr Phe

<210> SEQ ID NO 264
<211> LENGTH: 13
<212> TYPE: PRT
<213> ORGANISM: Artificial Sequence
<220> FEATURE:
<223> OTHER INFORMATION: Synthetic peptide

<400> SEQUENCE: 264

Cys Ala Ser Ser Leu Phe Ser Val Tyr Thr Gln Phe Phe
1               5                   10

<210> SEQ ID NO 265
<211> LENGTH: 18
<212> TYPE: PRT
```

```
<213> ORGANISM: Artificial Sequence
<220> FEATURE:
<223> OTHER INFORMATION: Synthetic peptide

<400> SEQUENCE: 265

Cys Ala Ser Ser Leu Gly Val Ser Gly Gly Met Thr Tyr Asn Glu Gln
1               5                   10                  15

Phe Phe

<210> SEQ ID NO 266
<211> LENGTH: 18
<212> TYPE: PRT
<213> ORGANISM: Artificial Sequence
<220> FEATURE:
<223> OTHER INFORMATION: Synthetic peptide

<400> SEQUENCE: 266

Cys Pro Gly Ser Arg Leu Gly Ser Glu Gln Ser Arg Ala Asn Val Leu
1               5                   10                  15

Thr Phe

<210> SEQ ID NO 267
<211> LENGTH: 15
<212> TYPE: PRT
<213> ORGANISM: Artificial Sequence
<220> FEATURE:
<223> OTHER INFORMATION: Synthetic peptide

<400> SEQUENCE: 267

Cys Ala Ile Arg Gly Gln Asp Gln Asn Thr Gly Glu Leu Phe Phe
1               5                   10                  15

<210> SEQ ID NO 268
<211> LENGTH: 19
<212> TYPE: PRT
<213> ORGANISM: Artificial Sequence
<220> FEATURE:
<223> OTHER INFORMATION: Synthetic peptide

<400> SEQUENCE: 268

Cys Cys Ala Ser Ser Phe Gly Thr Ser Gly Gly Thr Thr Tyr Asn Glu
1               5                   10                  15

Gln Phe Phe

<210> SEQ ID NO 269
<211> LENGTH: 15
<212> TYPE: PRT
<213> ORGANISM: Artificial Sequence
<220> FEATURE:
<223> OTHER INFORMATION: Synthetic peptide

<400> SEQUENCE: 269

Cys Ala Ser Ser Ile Gln Leu Phe Val Arg Thr Glu Ala Phe Phe
1               5                   10                  15

<210> SEQ ID NO 270
<211> LENGTH: 15
<212> TYPE: PRT
<213> ORGANISM: Artificial Sequence
<220> FEATURE:
<223> OTHER INFORMATION: Synthetic peptide

<400> SEQUENCE: 270

Cys Ala Ser Ser Leu Ile Ala Gly Leu Ser Tyr Glu Gln Tyr Phe
1               5                   10                  15
```

<210> SEQ ID NO 271
<211> LENGTH: 14
<212> TYPE: PRT
<213> ORGANISM: Artificial Sequence
<220> FEATURE:
<223> OTHER INFORMATION: Synthetic peptide

<400> SEQUENCE: 271

Cys Ala Ser Ser Arg Tyr Gly Gln Gly Trp Glu Gln Tyr Phe
1               5                   10

<210> SEQ ID NO 272
<211> LENGTH: 14
<212> TYPE: PRT
<213> ORGANISM: Artificial Sequence
<220> FEATURE:
<223> OTHER INFORMATION: Synthetic peptide

<400> SEQUENCE: 272

Cys Ala Ser Arg Glu Gly Tyr Ser Asn Gln Pro Gln His Phe
1               5                   10

<210> SEQ ID NO 273
<211> LENGTH: 15
<212> TYPE: PRT
<213> ORGANISM: Artificial Sequence
<220> FEATURE:
<223> OTHER INFORMATION: Synthetic peptide

<400> SEQUENCE: 273

Cys Ala Ser Ser Gly Arg Asp Arg Gly Ser Glu Lys Leu Phe Phe
1               5                   10                  15

<210> SEQ ID NO 274
<211> LENGTH: 17
<212> TYPE: PRT
<213> ORGANISM: Artificial Sequence
<220> FEATURE:
<223> OTHER INFORMATION: Synthetic peptide

<400> SEQUENCE: 274

Cys Ala Ser Ser Gly Gln Val Ala Thr His Ala Arg Asn Thr Ile Tyr
1               5                   10                  15

Phe

<210> SEQ ID NO 275
<211> LENGTH: 14
<212> TYPE: PRT
<213> ORGANISM: Artificial Sequence
<220> FEATURE:
<223> OTHER INFORMATION: Synthetic peptide

<400> SEQUENCE: 275

Cys Ala Ser Ser His Gly Arg Leu Asn Glu Lys Leu Phe Phe
1               5                   10

<210> SEQ ID NO 276
<211> LENGTH: 14
<212> TYPE: PRT
<213> ORGANISM: Artificial Sequence
<220> FEATURE:
<223> OTHER INFORMATION: Synthetic peptide

<400> SEQUENCE: 276

Cys Ala Thr Ser His Ser Thr Val Gly Tyr Gly Tyr Thr Phe

<210> SEQ ID NO 277
<211> LENGTH: 16
<212> TYPE: PRT
<213> ORGANISM: Artificial Sequence
<220> FEATURE:
<223> OTHER INFORMATION: Synthetic peptide

<400> SEQUENCE: 277

Cys Ala Ser Ser Leu Ile Ile Gly Arg Asp Pro Tyr Glu Gln Tyr Phe
1               5                   10                  15

<210> SEQ ID NO 278
<211> LENGTH: 19
<212> TYPE: PRT
<213> ORGANISM: Artificial Sequence
<220> FEATURE:
<223> OTHER INFORMATION: Synthetic peptide

<400> SEQUENCE: 278

Cys Ala Ser Ser Leu Val Pro Ser Gly Ser Pro Val Ser Ala Gly Glu
1               5                   10                  15

Leu Phe Phe

<210> SEQ ID NO 279
<211> LENGTH: 15
<212> TYPE: PRT
<213> ORGANISM: Artificial Sequence
<220> FEATURE:
<223> OTHER INFORMATION: Synthetic peptide

<400> SEQUENCE: 279

Cys Ala Ser Ser Leu Trp Val Ala Gly Tyr Asn Glu Gln Phe Phe
1               5                   10                  15

<210> SEQ ID NO 280
<211> LENGTH: 13
<212> TYPE: PRT
<213> ORGANISM: Artificial Sequence
<220> FEATURE:
<223> OTHER INFORMATION: Synthetic peptide

<400> SEQUENCE: 280

Cys Ser Ala Arg Leu Ala Asn Ser Tyr Glu Gln Tyr Phe
1               5                   10

<210> SEQ ID NO 281
<211> LENGTH: 13
<212> TYPE: PRT
<213> ORGANISM: Artificial Sequence
<220> FEATURE:
<223> OTHER INFORMATION: Synthetic peptide

<400> SEQUENCE: 281

Cys Ala Ser Arg Asp Ile Asn Ser Gly Glu Leu Phe Phe
1               5                   10

<210> SEQ ID NO 282
<211> LENGTH: 15
<212> TYPE: PRT
<213> ORGANISM: Artificial Sequence
<220> FEATURE:
<223> OTHER INFORMATION: Synthetic peptide

<400> SEQUENCE: 282

```
Cys Ala Ser Thr Leu Gly Asn Pro Ser Thr Asp Thr Gln Tyr Phe
1               5                   10                  15
```

<210> SEQ ID NO 283
<211> LENGTH: 13
<212> TYPE: PRT
<213> ORGANISM: Artificial Sequence
<220> FEATURE:
<223> OTHER INFORMATION: Synthetic peptide

<400> SEQUENCE: 283

```
Cys Ala Cys Ser Val Leu Asn Thr Gly Glu Leu Phe Phe
1               5                   10
```

<210> SEQ ID NO 284
<211> LENGTH: 14
<212> TYPE: PRT
<213> ORGANISM: Artificial Sequence
<220> FEATURE:
<223> OTHER INFORMATION: Synthetic peptide

<400> SEQUENCE: 284

```
Cys Ala Ile Arg Ala Val Ala Ser Tyr Asn Glu Gln Phe Phe
1               5                   10
```

<210> SEQ ID NO 285
<211> LENGTH: 15
<212> TYPE: PRT
<213> ORGANISM: Artificial Sequence
<220> FEATURE:
<223> OTHER INFORMATION: Synthetic peptide

<400> SEQUENCE: 285

```
Cys Ala Ile Arg Gly Gln Asp Gln Asn Thr Gly Glu Leu Phe Phe
1               5                   10                  15
```

<210> SEQ ID NO 286
<211> LENGTH: 15
<212> TYPE: PRT
<213> ORGANISM: Artificial Sequence
<220> FEATURE:
<223> OTHER INFORMATION: Synthetic peptide

<400> SEQUENCE: 286

```
Cys Ala Ile Arg Arg Gln Asp His Asn Thr Gly Glu Leu Phe Phe
1               5                   10                  15
```

<210> SEQ ID NO 287
<211> LENGTH: 15
<212> TYPE: PRT
<213> ORGANISM: Artificial Sequence
<220> FEATURE:
<223> OTHER INFORMATION: Synthetic peptide

<400> SEQUENCE: 287

```
Cys Ala Ile Arg Arg Gln Asp Gln Asn Asn Gly Glu Leu Phe Phe
1               5                   10                  15
```

<210> SEQ ID NO 288
<211> LENGTH: 15
<212> TYPE: PRT
<213> ORGANISM: Artificial Sequence
<220> FEATURE:
<223> OTHER INFORMATION: Synthetic peptide

<400> SEQUENCE: 288

```
Cys Ala Ser Arg Gly Gln Asp Gln Asn Thr Gly Glu Leu Phe Phe
```

<210> SEQ ID NO 289
<211> LENGTH: 15
<212> TYPE: PRT
<213> ORGANISM: Artificial Sequence
<220> FEATURE:
<223> OTHER INFORMATION: Synthetic peptide

<400> SEQUENCE: 289

Cys Ala Ser Ser Leu Ile Ala Gly Leu Ser Tyr Glu Gln Tyr Phe
1               5                   10                  15

<210> SEQ ID NO 290
<211> LENGTH: 15
<212> TYPE: PRT
<213> ORGANISM: Artificial Sequence
<220> FEATURE:
<223> OTHER INFORMATION: Synthetic peptide

<400> SEQUENCE: 290

Cys Ala Ile Ser Asp Thr Pro Asp Leu Asn Thr Glu Ala Phe Phe
1               5                   10                  15

<210> SEQ ID NO 291
<211> LENGTH: 14
<212> TYPE: PRT
<213> ORGANISM: Artificial Sequence
<220> FEATURE:
<223> OTHER INFORMATION: Synthetic peptide

<400> SEQUENCE: 291

Cys Ala Asn Ser Ser Arg Thr Lys Ala Tyr Glu Gln Tyr Phe
1               5                   10

<210> SEQ ID NO 292
<211> LENGTH: 15
<212> TYPE: PRT
<213> ORGANISM: Artificial Sequence
<220> FEATURE:
<223> OTHER INFORMATION: Synthetic peptide

<400> SEQUENCE: 292

Cys Ala Ser Ser Leu Ile Ala Gly Leu Ser Tyr Glu Gln Tyr Phe
1               5                   10                  15

<210> SEQ ID NO 293
<211> LENGTH: 15
<212> TYPE: PRT
<213> ORGANISM: Artificial Sequence
<220> FEATURE:
<223> OTHER INFORMATION: Synthetic peptide

<400> SEQUENCE: 293

Cys Ala Ser Ser Leu Ile Ala Gly Leu Ser Tyr Glu Gln Tyr Phe
1               5                   10                  15

<210> SEQ ID NO 294
<211> LENGTH: 15
<212> TYPE: PRT
<213> ORGANISM: Artificial Sequence
<220> FEATURE:
<223> OTHER INFORMATION: Synthetic peptide

<400> SEQUENCE: 294

Cys Ala Ser Ser Leu Ile Ala Gly Leu Ser Tyr Glu Gln Tyr Phe
1               5                   10                  15

<210> SEQ ID NO 295
<211> LENGTH: 15
<212> TYPE: PRT
<213> ORGANISM: Artificial Sequence
<220> FEATURE:
<223> OTHER INFORMATION: Synthetic peptide

<400> SEQUENCE: 295

Cys Ala Ser Thr Leu Gly Asn Pro Ser Thr Asp Thr Gln Tyr Phe
1               5                   10                  15

<210> SEQ ID NO 296
<211> LENGTH: 14
<212> TYPE: PRT
<213> ORGANISM: Artificial Sequence
<220> FEATURE:
<223> OTHER INFORMATION: Synthetic peptide

<400> SEQUENCE: 296

Cys Ala Ser Arg Gly Gly Ala Ser Tyr Asn Glu Gln Phe Phe
1               5                   10

<210> SEQ ID NO 297
<211> LENGTH: 15
<212> TYPE: PRT
<213> ORGANISM: Artificial Sequence
<220> FEATURE:
<223> OTHER INFORMATION: Synthetic peptide

<400> SEQUENCE: 297

Cys Ala Ser Ser Ile Leu Leu Phe Ser Gly Asn Thr Ile Tyr Phe
1               5                   10                  15

<210> SEQ ID NO 298
<211> LENGTH: 15
<212> TYPE: PRT
<213> ORGANISM: Artificial Sequence
<220> FEATURE:
<223> OTHER INFORMATION: Synthetic peptide

<400> SEQUENCE: 298

Cys Ala Ile Arg Ser Arg Asp Gln Asn Thr Gly Glu Leu Phe Phe
1               5                   10                  15

<210> SEQ ID NO 299
<211> LENGTH: 16
<212> TYPE: PRT
<213> ORGANISM: Artificial Sequence
<220> FEATURE:
<223> OTHER INFORMATION: Synthetic peptide

<400> SEQUENCE: 299

Cys Ala Ser Ser Gln Asp Ala Arg Arg Ser Gly Asn Thr Ile Tyr Phe
1               5                   10                  15

<210> SEQ ID NO 300
<211> LENGTH: 14
<212> TYPE: PRT
<213> ORGANISM: Artificial Sequence
<220> FEATURE:
<223> OTHER INFORMATION: Synthetic peptide

<400> SEQUENCE: 300

Cys Ala Ser Ser Ile Gln Glu Gly Tyr Ser Glu Gln Tyr Phe
1               5                   10

<210> SEQ ID NO 301
<211> LENGTH: 18
<212> TYPE: PRT
<213> ORGANISM: Artificial Sequence
<220> FEATURE:
<223> OTHER INFORMATION: Synthetic peptide

<400> SEQUENCE: 301

Cys Ala Ser Ser Pro Ala Leu Ala Thr Thr Ser Arg Ala Asn Val Leu
1               5                   10                  15

Thr Phe

<210> SEQ ID NO 302
<211> LENGTH: 13
<212> TYPE: PRT
<213> ORGANISM: Artificial Sequence
<220> FEATURE:
<223> OTHER INFORMATION: Synthetic peptide

<400> SEQUENCE: 302

Cys Ala Ser Arg Thr Ser Asn Thr Tyr Gly Tyr Thr Phe
1               5                   10

<210> SEQ ID NO 303
<211> LENGTH: 15
<212> TYPE: PRT
<213> ORGANISM: Artificial Sequence
<220> FEATURE:
<223> OTHER INFORMATION: Synthetic peptide

<400> SEQUENCE: 303

Cys Ala Ile Arg Ala Ala Asp Gln Asn Thr Gly Glu Leu Phe Phe
1               5                   10                  15

<210> SEQ ID NO 304
<211> LENGTH: 17
<212> TYPE: PRT
<213> ORGANISM: Artificial Sequence
<220> FEATURE:
<223> OTHER INFORMATION: Synthetic peptide

<400> SEQUENCE: 304

Cys Ala Ser Arg Gln Phe Leu Ala Thr Pro Ser Asp Asn Glu Gln Phe
1               5                   10                  15

Phe

<210> SEQ ID NO 305
<211> LENGTH: 15
<212> TYPE: PRT
<213> ORGANISM: Artificial Sequence
<220> FEATURE:
<223> OTHER INFORMATION: Synthetic peptide

<400> SEQUENCE: 305

Cys Ala Ser Ser Leu Leu Arg Thr Ser Gln Glu Thr Gln Tyr Phe
1               5                   10                  15

<210> SEQ ID NO 306
<211> LENGTH: 14
<212> TYPE: PRT
<213> ORGANISM: Artificial Sequence
<220> FEATURE:
<223> OTHER INFORMATION: Synthetic peptide

<400> SEQUENCE: 306

```
Cys Ala Ser Ser Ile Gln Glu Gly Tyr Ser Glu Gln Tyr Phe
1               5                   10
```

<210> SEQ ID NO 307
<211> LENGTH: 18
<212> TYPE: PRT
<213> ORGANISM: Artificial Sequence
<220> FEATURE:
<223> OTHER INFORMATION: Synthetic peptide

<400> SEQUENCE: 307

```
Tyr Ala Ser Ser Asp Lys Ser Leu Gly Gly Val Asp Thr Gly Glu Leu
1               5                   10                  15

Phe Phe
```

<210> SEQ ID NO 308
<211> LENGTH: 14
<212> TYPE: PRT
<213> ORGANISM: Artificial Sequence
<220> FEATURE:
<223> OTHER INFORMATION: Synthetic peptide

<400> SEQUENCE: 308

```
Cys Ala Ser Arg Thr Gly Ser Ser Tyr Asn Glu Gln Phe Phe
1               5                   10
```

<210> SEQ ID NO 309
<211> LENGTH: 15
<212> TYPE: PRT
<213> ORGANISM: Artificial Sequence
<220> FEATURE:
<223> OTHER INFORMATION: Synthetic peptide

<400> SEQUENCE: 309

```
Cys Ala Ser Ser Thr Gly Glu Pro Gly Val Tyr Gly Tyr Thr Phe
1               5                   10                  15
```

<210> SEQ ID NO 310
<211> LENGTH: 15
<212> TYPE: PRT
<213> ORGANISM: Artificial Sequence
<220> FEATURE:
<223> OTHER INFORMATION: Synthetic peptide

<400> SEQUENCE: 310

```
Cys Ala Ser Thr Pro Gly Ala Gly Leu Lys Asn Glu Gln Phe Phe
1               5                   10                  15
```

<210> SEQ ID NO 311
<211> LENGTH: 15
<212> TYPE: PRT
<213> ORGANISM: Artificial Sequence
<220> FEATURE:
<223> OTHER INFORMATION: Synthetic peptide

<400> SEQUENCE: 311

```
Cys Ala Ser Ser Thr Gly Glu Pro Gly Val Tyr Gly Tyr Thr Phe
1               5                   10                  15
```

<210> SEQ ID NO 312
<211> LENGTH: 13
<212> TYPE: PRT
<213> ORGANISM: Artificial Sequence
<220> FEATURE:
<223> OTHER INFORMATION: Synthetic peptide

<400> SEQUENCE: 312

Cys Ala Ser Thr Thr Gly Glu Gly Tyr Glu Gln Tyr Phe
1               5                   10

<210> SEQ ID NO 313
<211> LENGTH: 15
<212> TYPE: PRT
<213> ORGANISM: Artificial Sequence
<220> FEATURE:
<223> OTHER INFORMATION: Synthetic peptide

<400> SEQUENCE: 313

Cys Ala Ser Ser Ser Gly Ala Ser Leu Leu Asn Glu Gln Phe Phe
1               5                   10                  15

<210> SEQ ID NO 314
<211> LENGTH: 12
<212> TYPE: PRT
<213> ORGANISM: Artificial Sequence
<220> FEATURE:
<223> OTHER INFORMATION: Synthetic peptide

<400> SEQUENCE: 314

Cys Ser Ala Arg Thr Gly Tyr Asn Glu Gln Phe Phe
1               5                   10

<210> SEQ ID NO 315
<211> LENGTH: 15
<212> TYPE: PRT
<213> ORGANISM: Artificial Sequence
<220> FEATURE:
<223> OTHER INFORMATION: Synthetic peptide

<400> SEQUENCE: 315

Cys Ala Ser Ile Leu Ile Ala Gly Gly Tyr Asn Glu Gln Phe Phe
1               5                   10                  15

<210> SEQ ID NO 316
<211> LENGTH: 15
<212> TYPE: PRT
<213> ORGANISM: Artificial Sequence
<220> FEATURE:
<223> OTHER INFORMATION: Synthetic peptide

<400> SEQUENCE: 316

Cys Ala Ser Ile Leu Ile Ala Gly Ala Tyr Asn Glu Gln Phe Phe
1               5                   10                  15

<210> SEQ ID NO 317
<211> LENGTH: 13
<212> TYPE: PRT
<213> ORGANISM: Artificial Sequence
<220> FEATURE:
<223> OTHER INFORMATION: Synthetic peptide

<400> SEQUENCE: 317

Cys Ala Ser Ser Pro Glu Gly Ser Gly Gly Tyr Thr Phe
1               5                   10

<210> SEQ ID NO 318
<211> LENGTH: 18
<212> TYPE: PRT
<213> ORGANISM: Artificial Sequence
<220> FEATURE:
<223> OTHER INFORMATION: Synthetic peptide

<400> SEQUENCE: 318

Cys Ala Ser Arg Cys Leu Val Leu Gln Gln Ser Arg Ala Asn Val Leu
1               5                   10                  15

Thr Phe

<210> SEQ ID NO 319
<211> LENGTH: 18
<212> TYPE: PRT
<213> ORGANISM: Artificial Sequence
<220> FEATURE:
<223> OTHER INFORMATION: Synthetic peptide

<400> SEQUENCE: 319

Cys Ala Ser Ser Ala Asp Arg Gly Gly Trp Ser Gly Asn Gln Pro Gln
1               5                   10                  15

His Phe

<210> SEQ ID NO 320
<211> LENGTH: 15
<212> TYPE: PRT
<213> ORGANISM: Artificial Sequence
<220> FEATURE:
<223> OTHER INFORMATION: Synthetic peptide

<400> SEQUENCE: 320

Cys Ala Ile Arg Thr Leu Asp Met Asn Thr Gly Glu Leu Phe Phe
1               5                   10                  15

<210> SEQ ID NO 321
<211> LENGTH: 17
<212> TYPE: PRT
<213> ORGANISM: Artificial Sequence
<220> FEATURE:
<223> OTHER INFORMATION: Synthetic peptide

<400> SEQUENCE: 321

Cys Ala Ser Ser Leu Asn Ile Ala His His Ser Asp Asn Glu Gln Phe
1               5                   10                  15

Phe

<210> SEQ ID NO 322
<211> LENGTH: 16
<212> TYPE: PRT
<213> ORGANISM: Artificial Sequence
<220> FEATURE:
<223> OTHER INFORMATION: Synthetic peptide

<400> SEQUENCE: 322

Cys Ala Ser Lys Arg Leu Ala Gly Glu Gly Thr Gly Glu Leu Phe Phe
1               5                   10                  15

<210> SEQ ID NO 323
<211> LENGTH: 15
<212> TYPE: PRT
<213> ORGANISM: Artificial Sequence
<220> FEATURE:
<223> OTHER INFORMATION: Synthetic peptide

<400> SEQUENCE: 323

Cys Ala Ile Ser Thr Leu Asp Met Asn Thr Gly Glu Leu Phe Phe
1               5                   10                  15

<210> SEQ ID NO 324
<211> LENGTH: 15
<212> TYPE: PRT
<213> ORGANISM: Artificial Sequence

```
<220> FEATURE:
<223> OTHER INFORMATION: Synthetic peptide

<400> SEQUENCE: 324

Cys Ala Ile Arg Thr Leu Asp Met Asn Thr Gly Glu Leu Phe Phe
1               5                   10                  15

<210> SEQ ID NO 325
<211> LENGTH: 14
<212> TYPE: PRT
<213> ORGANISM: Artificial Sequence
<220> FEATURE:
<223> OTHER INFORMATION: Synthetic peptide

<400> SEQUENCE: 325

Cys Ala Ser Ser Ser Ser Thr Glu Ile Leu Trp Leu His Leu
1               5                   10

<210> SEQ ID NO 326
<211> LENGTH: 15
<212> TYPE: PRT
<213> ORGANISM: Artificial Sequence
<220> FEATURE:
<223> OTHER INFORMATION: Synthetic peptide

<400> SEQUENCE: 326

Cys Ala Ile Arg Thr Leu Asp Met Asn Thr Gly Glu Leu Phe Phe
1               5                   10                  15

<210> SEQ ID NO 327
<211> LENGTH: 14
<212> TYPE: PRT
<213> ORGANISM: Artificial Sequence
<220> FEATURE:
<223> OTHER INFORMATION: Synthetic peptide

<400> SEQUENCE: 327

Cys Ala Ser Ser Gly Pro Asp Gly Asp Asn Glu Gln Phe Phe
1               5                   10

<210> SEQ ID NO 328
<211> LENGTH: 15
<212> TYPE: PRT
<213> ORGANISM: Artificial Sequence
<220> FEATURE:
<223> OTHER INFORMATION: Synthetic peptide

<400> SEQUENCE: 328

Cys Ala Ile Arg Thr Leu Asp Met Asn Thr Gly Glu Leu Phe Phe
1               5                   10                  15

<210> SEQ ID NO 329
<211> LENGTH: 13
<212> TYPE: PRT
<213> ORGANISM: Artificial Sequence
<220> FEATURE:
<223> OTHER INFORMATION: Synthetic peptide

<400> SEQUENCE: 329

Cys Ala Ser Ser Tyr Pro Asp Val Tyr Glu Gln Tyr Phe
1               5                   10

<210> SEQ ID NO 330
<211> LENGTH: 15
<212> TYPE: PRT
<213> ORGANISM: Artificial Sequence
<220> FEATURE:
```

<223> OTHER INFORMATION: Synthetic peptide

<400> SEQUENCE: 330

Cys Ala Ile Arg Thr Leu Asp Met Asn Thr Gly Glu Leu Phe Phe
1               5                   10                  15

<210> SEQ ID NO 331
<211> LENGTH: 15
<212> TYPE: PRT
<213> ORGANISM: Artificial Sequence
<220> FEATURE:
<223> OTHER INFORMATION: Synthetic peptide

<400> SEQUENCE: 331

Cys Ala Ile Arg Ile Arg Asp Gln Asn Thr Gly Glu Leu Phe Phe
1               5                   10                  15

<210> SEQ ID NO 332
<211> LENGTH: 15
<212> TYPE: PRT
<213> ORGANISM: Artificial Sequence
<220> FEATURE:
<223> OTHER INFORMATION: Synthetic peptide

<400> SEQUENCE: 332

Cys Ala Ile Arg Thr Leu Asp Met Asn Thr Gly Glu Leu Phe Phe
1               5                   10                  15

<210> SEQ ID NO 333
<211> LENGTH: 13
<212> TYPE: PRT
<213> ORGANISM: Artificial Sequence
<220> FEATURE:
<223> OTHER INFORMATION: Synthetic peptide

<400> SEQUENCE: 333

Cys Ala Ser Ser Tyr Pro Asp Val Tyr Glu Gln Tyr Phe
1               5                   10

<210> SEQ ID NO 334
<211> LENGTH: 19
<212> TYPE: PRT
<213> ORGANISM: Artificial Sequence
<220> FEATURE:
<223> OTHER INFORMATION: Synthetic peptide

<400> SEQUENCE: 334

Cys Ala Ser Ser Glu Gly Lys Thr Lys Ser Gln Ser Arg Ala Asn Val
1               5                   10                  15

Leu Thr Phe

<210> SEQ ID NO 335
<211> LENGTH: 12
<212> TYPE: PRT
<213> ORGANISM: Artificial Sequence
<220> FEATURE:
<223> OTHER INFORMATION: Synthetic peptide

<400> SEQUENCE: 335

Cys Ala Ser Ser Leu Gly Asn Thr Glu Ala Phe Phe
1               5                   10

<210> SEQ ID NO 336
<211> LENGTH: 14
<212> TYPE: PRT
<213> ORGANISM: Artificial Sequence

```
<220> FEATURE:
<223> OTHER INFORMATION: Synthetic peptide

<400> SEQUENCE: 336

Cys Ala Ser Ser Leu Val Ser Gly Gly Glu Ala Phe Phe
1               5                   10

<210> SEQ ID NO 337
<211> LENGTH: 15
<212> TYPE: PRT
<213> ORGANISM: Artificial Sequence
<220> FEATURE:
<223> OTHER INFORMATION: Synthetic peptide

<400> SEQUENCE: 337

Cys Ala Ile Arg Thr Leu Asp Met Asn Thr Gly Asp Leu Phe Phe
1               5                   10                  15

<210> SEQ ID NO 338
<211> LENGTH: 17
<212> TYPE: PRT
<213> ORGANISM: Artificial Sequence
<220> FEATURE:
<223> OTHER INFORMATION: Synthetic peptide

<400> SEQUENCE: 338

Cys Ala Ser Lys Lys Leu Asp Arg Pro Ala Pro Asn Ser Pro Leu His
1               5                   10                  15

Phe

<210> SEQ ID NO 339
<211> LENGTH: 14
<212> TYPE: PRT
<213> ORGANISM: Artificial Sequence
<220> FEATURE:
<223> OTHER INFORMATION: Synthetic peptide

<400> SEQUENCE: 339

Cys Ala Ser Ser Gly Pro Asp Gly Gly Asn Glu Gln Phe Phe
1               5                   10

<210> SEQ ID NO 340
<211> LENGTH: 14
<212> TYPE: PRT
<213> ORGANISM: Artificial Sequence
<220> FEATURE:
<223> OTHER INFORMATION: Synthetic peptide

<400> SEQUENCE: 340

Cys Ala Ser Ser Gly Pro Asp Gly Gly Asn Glu Gln Phe Phe
1               5                   10

<210> SEQ ID NO 341
<211> LENGTH: 14
<212> TYPE: PRT
<213> ORGANISM: Artificial Sequence
<220> FEATURE:
<223> OTHER INFORMATION: Synthetic peptide

<400> SEQUENCE: 341

Cys Ala Ser Ser Ser Gln Arg Lys Ser Tyr Gly Tyr Thr Phe
1               5                   10

<210> SEQ ID NO 342
<211> LENGTH: 14
<212> TYPE: PRT
```

```
<213> ORGANISM: Artificial Sequence
<220> FEATURE:
<223> OTHER INFORMATION: Synthetic peptide

<400> SEQUENCE: 342

Cys Ala Ser Ser Ser Ser Arg Lys Ser Tyr Gly Tyr Thr Phe
1               5                   10

<210> SEQ ID NO 343
<211> LENGTH: 14
<212> TYPE: PRT
<213> ORGANISM: Artificial Sequence
<220> FEATURE:
<223> OTHER INFORMATION: Synthetic peptide

<400> SEQUENCE: 343

Cys Ala Ser Ser Glu Thr Gly Thr Trp Asp Glu Gln Tyr Phe
1               5                   10

<210> SEQ ID NO 344
<211> LENGTH: 15
<212> TYPE: PRT
<213> ORGANISM: Artificial Sequence
<220> FEATURE:
<223> OTHER INFORMATION: Synthetic peptide

<400> SEQUENCE: 344

Cys Ala Ile Arg Thr Leu Asp Met Asn Thr Gly Glu Leu Phe Phe
1               5                   10                  15

<210> SEQ ID NO 345
<211> LENGTH: 15
<212> TYPE: PRT
<213> ORGANISM: Artificial Sequence
<220> FEATURE:
<223> OTHER INFORMATION: Synthetic peptide

<400> SEQUENCE: 345

Cys Ala Ile Arg Thr Leu Asp Met Asn Thr Gly Glu Leu Leu Phe
1               5                   10                  15

<210> SEQ ID NO 346
<211> LENGTH: 15
<212> TYPE: PRT
<213> ORGANISM: Artificial Sequence
<220> FEATURE:
<223> OTHER INFORMATION: Synthetic peptide

<400> SEQUENCE: 346

Cys Ala Ile Arg Thr Leu Asp Met Asn Thr Gly Glu Leu Phe Phe
1               5                   10                  15

<210> SEQ ID NO 347
<211> LENGTH: 14
<212> TYPE: PRT
<213> ORGANISM: Artificial Sequence
<220> FEATURE:
<223> OTHER INFORMATION: Synthetic peptide

<400> SEQUENCE: 347

Cys Ala Ser Ser Ser Ser Thr Glu Ser Tyr Gly Tyr Thr Phe
1               5                   10

<210> SEQ ID NO 348
<211> LENGTH: 15
<212> TYPE: PRT
<213> ORGANISM: Artificial Sequence
```

```
<220> FEATURE:
<223> OTHER INFORMATION: Synthetic peptide

<400> SEQUENCE: 348

Cys Ala Ile Arg Thr Leu Asp Met Asn Thr Gly Glu Leu Phe Phe
1               5                   10                  15

<210> SEQ ID NO 349
<211> LENGTH: 14
<212> TYPE: PRT
<213> ORGANISM: Artificial Sequence
<220> FEATURE:
<223> OTHER INFORMATION: Synthetic peptide

<400> SEQUENCE: 349

Cys Ala Ser Ser Gly Pro Asp Gly Asp Asn Glu Gln Phe Phe
1               5                   10

<210> SEQ ID NO 350
<211> LENGTH: 16
<212> TYPE: PRT
<213> ORGANISM: Artificial Sequence
<220> FEATURE:
<223> OTHER INFORMATION: Synthetic peptide

<400> SEQUENCE: 350

Cys Ala Ser Ser Glu Arg His Leu His Ala Arg Asn Thr Ile Tyr Phe
1               5                   10                  15

<210> SEQ ID NO 351
<211> LENGTH: 16
<212> TYPE: PRT
<213> ORGANISM: Artificial Sequence
<220> FEATURE:
<223> OTHER INFORMATION: Synthetic peptide

<400> SEQUENCE: 351

Cys Ala Ser Arg Ser Leu Ile Ala Thr Leu Leu Asp Glu Gln Tyr Phe
1               5                   10                  15

<210> SEQ ID NO 352
<211> LENGTH: 18
<212> TYPE: PRT
<213> ORGANISM: Artificial Sequence
<220> FEATURE:
<223> OTHER INFORMATION: Synthetic peptide

<400> SEQUENCE: 352

Cys Ala Ser Ser Ser Thr Leu Lys Ser Gln Ser Arg Ala Asn Val Leu
1               5                   10                  15

Thr Phe

<210> SEQ ID NO 353
<211> LENGTH: 12
<212> TYPE: PRT
<213> ORGANISM: Artificial Sequence
<220> FEATURE:
<223> OTHER INFORMATION: Synthetic peptide

<400> SEQUENCE: 353

Cys Ala Ile Ser Glu Pro Ser Gly Ala Gln His Phe
1               5                   10

<210> SEQ ID NO 354
<211> LENGTH: 15
<212> TYPE: PRT
```

```
<213> ORGANISM: Artificial Sequence
<220> FEATURE:
<223> OTHER INFORMATION: Synthetic peptide

<400> SEQUENCE: 354

Cys Ala Thr Ser Asp Pro Leu Ala Ala Ser Tyr Glu Gln Tyr Phe
1               5                   10                  15

<210> SEQ ID NO 355
<211> LENGTH: 12
<212> TYPE: PRT
<213> ORGANISM: Artificial Sequence
<220> FEATURE:
<223> OTHER INFORMATION: Synthetic peptide

<400> SEQUENCE: 355

Cys Ala Val Pro Asn Thr Gly Asn Gln Phe Tyr Phe
1               5                   10

<210> SEQ ID NO 356
<211> LENGTH: 11
<212> TYPE: PRT
<213> ORGANISM: Artificial Sequence
<220> FEATURE:
<223> OTHER INFORMATION: Synthetic peptide

<400> SEQUENCE: 356

Cys Ala Phe Thr Asn Thr Gly Lys Leu Ile Phe
1               5                   10

<210> SEQ ID NO 357
<211> LENGTH: 15
<212> TYPE: PRT
<213> ORGANISM: Artificial Sequence
<220> FEATURE:
<223> OTHER INFORMATION: Synthetic peptide

<400> SEQUENCE: 357

Cys Ala Ala Lys Glu Leu Gly Gly Ala Thr Asn Lys Leu Ile Phe
1               5                   10                  15

<210> SEQ ID NO 358
<211> LENGTH: 13
<212> TYPE: PRT
<213> ORGANISM: Artificial Sequence
<220> FEATURE:
<223> OTHER INFORMATION: Synthetic peptide

<400> SEQUENCE: 358

Cys Ala Val Thr Thr Ser Gly Thr Tyr Lys Tyr Ile Phe
1               5                   10

<210> SEQ ID NO 359
<211> LENGTH: 15
<212> TYPE: PRT
<213> ORGANISM: Artificial Sequence
<220> FEATURE:
<223> OTHER INFORMATION: Synthetic peptide

<400> SEQUENCE: 359

Cys Ala Thr Asp Ala Gly Asp Thr Gly Phe Gln Lys Leu Val Phe
1               5                   10                  15

<210> SEQ ID NO 360
<211> LENGTH: 13
<212> TYPE: PRT
<213> ORGANISM: Artificial Sequence
```

```
<220> FEATURE:
<223> OTHER INFORMATION: Synthetic peptide

<400> SEQUENCE: 360

Cys Ala Gly Ala Asn Asn Tyr Gly Gln Asn Phe Val Phe
1               5                   10

<210> SEQ ID NO 361
<211> LENGTH: 10
<212> TYPE: PRT
<213> ORGANISM: Artificial Sequence
<220> FEATURE:
<223> OTHER INFORMATION: Synthetic peptide

<400> SEQUENCE: 361

Cys Ala Trp Asn Thr Asp Lys Leu Ile Phe
1               5                   10

<210> SEQ ID NO 362
<211> LENGTH: 12
<212> TYPE: PRT
<213> ORGANISM: Artificial Sequence
<220> FEATURE:
<223> OTHER INFORMATION: Synthetic peptide

<400> SEQUENCE: 362

Cys Val Val Arg Ala Ala Gly Asn Lys Leu Thr Phe
1               5                   10

<210> SEQ ID NO 363
<211> LENGTH: 13
<212> TYPE: PRT
<213> ORGANISM: Artificial Sequence
<220> FEATURE:
<223> OTHER INFORMATION: Synthetic peptide

<400> SEQUENCE: 363

Cys Val Val Thr Gly Thr Gly Gly Phe Lys Thr Ile Phe
1               5                   10

<210> SEQ ID NO 364
<211> LENGTH: 15
<212> TYPE: PRT
<213> ORGANISM: Artificial Sequence
<220> FEATURE:
<223> OTHER INFORMATION: Synthetic peptide

<400> SEQUENCE: 364

Cys Ala Val Thr Arg Pro Ser Gly Gly Tyr Asn Lys Leu Ile Phe
1               5                   10                  15

<210> SEQ ID NO 365
<211> LENGTH: 15
<212> TYPE: PRT
<213> ORGANISM: Artificial Sequence
<220> FEATURE:
<223> OTHER INFORMATION: Synthetic peptide

<400> SEQUENCE: 365

Cys Ala Ser Ser Leu Ile Ala Gly Leu Ser Tyr Glu Gln Tyr Phe
1               5                   10                  15

<210> SEQ ID NO 366
<211> LENGTH: 15
<212> TYPE: PRT
<213> ORGANISM: Artificial Sequence
<220> FEATURE:
```

<223> OTHER INFORMATION: Synthetic peptide

<400> SEQUENCE: 366

Cys Ala Ser Ala Leu Leu Glu Tyr Ser Asn Gln Pro Gln His Phe
1               5                   10                  15

<210> SEQ ID NO 367
<211> LENGTH: 14
<212> TYPE: PRT
<213> ORGANISM: Artificial Sequence
<220> FEATURE:
<223> OTHER INFORMATION: Synthetic peptide

<400> SEQUENCE: 367

Cys Ala Ser Ser Leu Gly Trp Gly Thr Thr Glu Ala Phe Phe
1               5                   10

<210> SEQ ID NO 368
<211> LENGTH: 15
<212> TYPE: PRT
<213> ORGANISM: Artificial Sequence
<220> FEATURE:
<223> OTHER INFORMATION: Synthetic peptide

<400> SEQUENCE: 368

Cys Ala Ser Ser Phe Ser Gly Ser Leu Gly Asp Thr Gln Tyr Phe
1               5                   10                  15

<210> SEQ ID NO 369
<211> LENGTH: 17
<212> TYPE: PRT
<213> ORGANISM: Artificial Sequence
<220> FEATURE:
<223> OTHER INFORMATION: Synthetic peptide

<400> SEQUENCE: 369

Cys Ala Ser Ser Pro Thr Leu Thr Ser Gly Gly Thr Asp Thr Gln Tyr
1               5                   10                  15

Phe

<210> SEQ ID NO 370
<211> LENGTH: 15
<212> TYPE: PRT
<213> ORGANISM: Artificial Sequence
<220> FEATURE:
<223> OTHER INFORMATION: Synthetic peptide

<400> SEQUENCE: 370

Cys Ala Ser Ser Ile Ser Leu Ala Gly Val His Glu Gln Tyr Phe
1               5                   10                  15

<210> SEQ ID NO 371
<211> LENGTH: 11
<212> TYPE: PRT
<213> ORGANISM: Artificial Sequence
<220> FEATURE:
<223> OTHER INFORMATION: Synthetic peptide

<400> SEQUENCE: 371

Cys Ala Ser Ser Leu Ala Gly Asp Arg Ser Phe
1               5                   10

<210> SEQ ID NO 372
<211> LENGTH: 16
<212> TYPE: PRT
<213> ORGANISM: Artificial Sequence
<220> FEATURE:
<223> OTHER INFORMATION: Synthetic peptide

<400> SEQUENCE: 372

Cys Ala Ser Ser Val Gln Gly Ala Pro Phe Pro Tyr Glu Gln Tyr Phe
1               5                   10                  15

<210> SEQ ID NO 373
<211> LENGTH: 18
<212> TYPE: PRT
<213> ORGANISM: Artificial Sequence
<220> FEATURE:
<223> OTHER INFORMATION: Synthetic peptide

<400> SEQUENCE: 373

Cys Ala Ser Ser Ser Met Ser Ile Ala Ala Gly Asn Thr Gly Glu Leu
1               5                   10                  15

Phe Phe

<210> SEQ ID NO 374
<211> LENGTH: 13
<212> TYPE: PRT
<213> ORGANISM: Artificial Sequence
<220> FEATURE:
<223> OTHER INFORMATION: Synthetic peptide

<400> SEQUENCE: 374

Cys Ala Ser Ser Phe Phe Gly Ser Glu Thr Gln Tyr Phe
1               5                   10

<210> SEQ ID NO 375
<211> LENGTH: 417
<212> TYPE: DNA
<213> ORGANISM: Artificial Sequence
<220> FEATURE:
<223> OTHER INFORMATION: Synthetic sequence

<400> SEQUENCE: 375
atggacaaga tcttaggagc atcatttta gttctgtggc ttcaactatg ctgggtgagt      60
ggccaacaga aggagaaaag tgaccagcag caggtgaaac aaagtcctca atctttgata   120
gtccagaaag gagggatttc aattataaac tgtgcttatg agaacactgc gtttgactac   180
tttccatggt accaacaatt ccctgggaaa ggccctgcat tattgatagc atacgtcca    240 gatgtgagtg aaaagaaaga aggaagattc acaatctcct tcaataaaag tgccaagcag   300
ttctcattgc atatcatgga ttcccagcct ggagactcag ccacctactt ctgtgcagtc   360
ccgaacaccg gtaaccagtt ctattttggg acaggacaa gtttgacggt cattcca       417

<210> SEQ ID NO 376
<211> LENGTH: 396
<212> TYPE: DNA
<213> ORGANISM: Artificial Sequence
<220> FEATURE:
<223> OTHER INFORMATION: Synthetic sequence

<400> SEQUENCE: 376
atgacacgag ttagcttgct gtgggcagtc gtggtctcca cctgtcttga atccggcatg      60
gcccagacag tcactcagtc tcaaccagag atgtctgtgc aggaggcaga gactgtgacc   120
ctgagttgca catatgacac cagtgagaat aattattatt tgttctggta caagcagcct   180
cccagcaggc agatgattct cgttattcgc caagaagctt ataagcaaca gaatgcaacg   240
gagaatcgtt tctctgtgaa cttccagaaa gcagccaaat ccttcagtct caagatctca   300

```
gactcacagc tggggggacac tgcgatgtat ttctgtgctt tcaccaacac aggcaaacta    360
atctttgggc aagggacaac tttacaagta aaacca                              396

<210> SEQ ID NO 377
<211> LENGTH: 411
<212> TYPE: DNA
<213> ORGANISM: Artificial Sequence
<220> FEATURE:
<223> OTHER INFORMATION: Synthetic sequence

<400> SEQUENCE: 377
atggccatgc tcctgggggc atcagtgctg attctgtggc ttcagccaga ctgggtaaac     60
agtcaacaga agaatgatga ccagcaagtt aagcaaaatt caccatccct gagcgtccag    120
gaaggaagaa tttctattct gaactgtgac tatactaaca gcatgtttga ttatttccta    180
tggtacaaaa ataccctgc tgaaggtcct acattcctga tatctataag ttccattaag    240
gataaaaatg aagatggaag attcactgtc ttcttaaaca aaagtgccaa gcacctctct    300
ctgcacattg tgccctccca gcctggagac tctgcatgtg cagcaaagga gttaggtggt    360
gctacaaaca agctcatctt tggaactggc actctgcttg ctgtccagcc a             411

<210> SEQ ID NO 378
<211> LENGTH: 414
<212> TYPE: DNA
<213> ORGANISM: Artificial Sequence
<220> FEATURE:
<223> OTHER INFORMATION: Synthetic sequence

<400> SEQUENCE: 378
atggccatgc tcctgggggc atcagtgctg attctgtggc ttcagccaga ctgggtaaac     60
agtcaacaga agaatgatga ccagcaagtt aagcaaaatt caccatccct gagcgtccag    120
gaaggaagaa tttctattct gaactgtgac tatactaaca gcatgtttga ttatttccta    180
tggtacaaaa ataccctgc tgaaggtcct acattcctga tatctataag ttccattaag    240
gataaaaatg aagatggaag attcactgtc ttcttaaaca aaagtgccaa gcacctctct    300
ctgcacattg tgccctccca gcctggagac tctgcagtgt acttctgtgc agttactacc    360
tcaggaacct acaaatacat ctttggaaca ggcaccaggc tgaaggtttt agca          414

<210> SEQ ID NO 379
<211> LENGTH: 396
<212> TYPE: DNA
<213> ORGANISM: Artificial Sequence
<220> FEATURE:
<223> OTHER INFORMATION: Synthetic sequence

<400> SEQUENCE: 379
atggaaactc tcctgggagt gtctttggtg attctatggc ttcaactggc tagggtgaac     60
agtcaacagg agaagagga tcctcaggcc ttgagcatcc aggagggtga aaatgccacc    120
atgaactgca gttacaaaac tagtataaac aatttacagt ggtatagaca aaattcaggt    180
agaggccttg tccacctaat tttaatacgt tcaaatgaaa gagagaaaca cagtggaaga    240
ttaagagtca cgcttgacac ttccaagaaa agcagttcct tgttgatcac ggcttcccgg    300
gcagcagaca ctgcttctta cttctgtgct acggacgcgg gggacacagg ctttcagaaa    360
cttgtatttg gaactggcac ccgacttctg gtcagt                              396

<210> SEQ ID NO 380
```

```
<211> LENGTH: 384
<212> TYPE: DNA
<213> ORGANISM: Artificial Sequence
<220> FEATURE:
<223> OTHER INFORMATION: Synthetic sequence

<400> SEQUENCE: 380
atggtcctga aattctccgt gtccattctt tggattcagt tggcatgggt gagcacccag    60
ctgctggagc agagccctca gtttctaagc atccaagagg gagaaaatct cactgtgtac   120
tgcaactcct caagtgtttt ttccagctta caatggtaca gacaggagcc tggggaaggt   180
cctgtcctcc tggtgacagt agttacgggt ggagaagtga agaagctgaa gagactaacc   240
tttcagtttg gtgatgcaag aaaggacagt tctctccaca tcactgcagc ccagcctggt   300
gatacaggcc tctactgtgc aggagcaaat aactatggtc agaattttgt ctttggtccc   360
ggaaccagat tgtccgtgct gccc                                          384

<210> SEQ ID NO 381
<211> LENGTH: 393
<212> TYPE: DNA
<213> ORGANISM: Artificial Sequence
<220> FEATURE:
<223> OTHER INFORMATION: Synthetic sequence

<400> SEQUENCE: 381
atggagaaga tcctttggc agccccatta ctaatcctct ggtttcatct tgactgcgtg     60
agcagcatac tgaacgtgga acaaagtcct cagtcactgc atgttcagga gggagacagc   120
accaatttca cctgcagctt cccttccagc aattttatg ccttacactg gtacagatgg    180
gaaactgcaa aaagccccga ggccttgttt gtaatgactt aaatgggga tgaaaagaag    240
aaaggacgaa taagtgccac tcttaatacc aaggagggtt acagctattt gtacatcaaa   300
ggatcccagc ctgaagactc agccacatac ctctgtgcct ggaacaccga caagctcatc   360
tttgggactg ggaccagatt acaagtcttt cca                                393

<210> SEQ ID NO 382
<211> LENGTH: 390
<212> TYPE: DNA
<213> ORGANISM: Artificial Sequence
<220> FEATURE:
<223> OTHER INFORMATION: Synthetic sequence

<400> SEQUENCE: 382
atgatatcct tgagagtttt actggtgatc ctgtggcttc agttaagctg ggtttggagc    60
caacggaagg aggtggagca ggatcctgga cccttcaatg ttccagaggg agccactgtc   120
gctttcaact gtacttacag caacagtgct tctcagtctt tcttctggta cagacaggat   180
tgcaggaaag aacctaagtt gctgatgtcc gtatactcca gtggtaatga agatggaagg   240
tttacagcac agctcaatag agccagccag tatatttccc tgctcatcag agactccaag   300
ctcagtgatt cagccaccta cctctgtgtg gtgagggctg caggcaacaa gctaactttt   360
ggaggaggaa ccagggtgct agttaaacca                                    390

<210> SEQ ID NO 383
<211> LENGTH: 393
<212> TYPE: DNA
<213> ORGANISM: Artificial Sequence
<220> FEATURE:
<223> OTHER INFORMATION: Synthetic sequence

<400> SEQUENCE: 383
```

```
atgatatcct tgagagtttt actggtgatc ctgtggcttc agttaagctg ggtttggagc    60
caacggaagg aggtggagca ggatcctgga cccttcaatg ttccagaggg agccactgtc   120
gctttcaact gtacttacag caacagtgct tctcagtctt tcttctggta cagacaggat   180
tgcaggaaag aacctaagtt gctgatgtcc gtatactcca gtggtaatga agatggaagg   240
tttacagcac agctcaatag agccagccag tatatttccc tgctcatcag agactccaag   300
ctcagtgatt cagccaccta cctctgtgtg gtgaccggaa ctggaggctt caaaactatc   360
tttggagcag gaacaagact atttgttaaa gca                                393

<210> SEQ ID NO 384
<211> LENGTH: 393
<212> TYPE: DNA
<213> ORGANISM: Artificial Sequence
<220> FEATURE:
<223> OTHER INFORMATION: Synthetic sequence

<400> SEQUENCE: 384
atgaagagga tattgggagc tctgctgggg ctcttgagtg cccaggtttg ctgtgtgaga    60
ggaatacaag tggagcagag tcctccagac ctgattctcc aggagggagc caattccacg   120
ctgcggtgca ttttttctga ctctgtgaac aatttgcagt ggtttcatca aaacccttgg   180
ggacagctca tcaacctgtt ttacattccc tcagggacaa acagaatgg aagattaagc   240 gccacgactg tcgctacgga acgctacagc ttattgtaca tttcctcttc ccagaccaca   300
gactcaggcg tttatttctg tgctgtcaca cgcccttctg gtggctacaa taagctgatt   360
tttggagcag ggaccaggct ggctgtacac cca                                393

<210> SEQ ID NO 385
<211> LENGTH: 402
<212> TYPE: DNA
<213> ORGANISM: Artificial Sequence
<220> FEATURE:
<223> OTHER INFORMATION: Synthetic sequence

<400> SEQUENCE: 385
atgggcacca ggctcctctg ctgggtggtc ctgggtttcc tagggacaga tcacacaggt    60
gctggagtct cccagtcccc taggtacaaa gtcgcaaaga gaggacagga tgtagctctc   120
aggtgtgatc caatttcggg tcatgtatcc cttttttggt accaacaggc cctggggcag   180
gggccagagt ttctgactta tttccagaat gaagctcaac tagacaaatc ggggctgccc   240
agtgatcgct tctttgcaga aaggcctgag ggatccgtct ccactctgaa gatccagcgc   300
acacagcagg aggactccgc cgtgtatctc tgtgccagca gcttaatagc ggggctctcc   360
tacgagcagt acttcgggcc gggcaccagg ctcacggtca ca                      402

<210> SEQ ID NO 386
<211> LENGTH: 399
<212> TYPE: DNA
<213> ORGANISM: Artificial Sequence
<220> FEATURE:
<223> OTHER INFORMATION: Synthetic sequence

<400> SEQUENCE: 386
atgagcaacc aggtgctctg ctgtgtggtc ctttgtttcc tgggagcaaa caccgtggat    60
ggtggaatca ctcagtcccc aaagtacctg ttcagaaagg aaggacagaa tgtgaccctg   120
agttgtgaac agaatttgaa ccacgatgcc atgtactggt accgacagga cccagggcaa   180
```

```
gggctgagat tgatctacta ctcacagata gtaaatgact ttcagaaagg agatatagct    240
gaagggtaca gcgtctctcg ggagaagaag gaatcctttc ctctcactgt gacatcggcc    300
caaaagaacc cgacagcttt ctatctctgt gccagtgccc ttcttgaata tagcaatcag    360
ccccagcatt ttggtgatgg gactcgactc tccatcctg                           399

<210> SEQ ID NO 387
<211> LENGTH: 399
<212> TYPE: DNA
<213> ORGANISM: Artificial Sequence
<220> FEATURE:
<223> OTHER INFORMATION: Synthetic sequence

<400> SEQUENCE: 387
atggactcct ggaccttctg ctgtgtgtcc ctttgcatcc tggtagcgaa gcatacagat     60
gctggagtta tccagtcacc ccgccatgag gtgacagaga tgggacaaga agtgactctg    120
agatgtaaac caatttcagg ccacaactcc cttttctggt acagacagac catgatgcgg    180
ggactggagt tgctcattta ctttaacaac aacgttccga tagatgattc agggatgccc    240
gaggatcgat tctcagctaa gatgcctaat gcatcattct ccactctgaa gatccagccc    300
tcagaaccca gggactcagc tgtgtacttc tgtgccagca gtttagggtg ggggaccact    360
gaagctttct ttggacaagg caccagactc acagttgtg                           399

<210> SEQ ID NO 388
<211> LENGTH: 402
<212> TYPE: DNA
<213> ORGANISM: Artificial Sequence
<220> FEATURE:
<223> OTHER INFORMATION: Synthetic sequence

<400> SEQUENCE: 388
atgggcacca ggctcctctt ctgggtggcc ttctgtctcc tggggcagat cacacagga     60 gctggagtct cccagtcccc cagtaacaag gtcacagaga agggaaagga tgtagagctc    120
aggtgtgatc caatttcagg tcatactgcc ctttactggt accgacagag cctggggcag    180
ggcctggagt ttttaattta cttccaaggc aacagtgcac cagacaaatc agggctgccc    240
agtgatcgct tctctgcaga gaggactggg gatccgtctc ccactctgac gatccagcgc    300
acacagcagg aggactcggc cgtgtatctc tgtgccagca gttttagcgg gagtctcggg    360
gatacgcagt attttggccc aggcacccgg ctgacagtgc tc                       402

<210> SEQ ID NO 389
<211> LENGTH: 405
<212> TYPE: DNA
<213> ORGANISM: Artificial Sequence
<220> FEATURE:
<223> OTHER INFORMATION: Synthetic sequence

<400> SEQUENCE: 389
atgggctgca ggctgctctg ctgtgcggtt ctctgtctcc tgggagcagt tcccatagac     60
actgaagtta cccagacacc aaaacacctg gtcatgggaa tgacaaataa gaagtctttg    120
aaatgtgaac aacatatggg gcacagggct atgtattggt acaagcagaa agctaagaag    180
ccaccggagc tcatgtttgt ctacagctat gagaaactct ctataaatga aagtgtgcca    240
agtcgcttct cacctgaatg ccccaacagc tctctcttaa accttcacct acacgccctg    300
cagccagaag actcagccct gtatctctgc gccagcagcc tacgcttac tagcgggggc    360 acagatacgc agtattttgg cccaggcacc cggctgacag tgctc                    405
```

<210> SEQ ID NO 390
<211> LENGTH: 399
<212> TYPE: DNA
<213> ORGANISM: Artificial Sequence
<220> FEATURE:
<223> OTHER INFORMATION: Synthetic sequence

<400> SEQUENCE: 390

```
atgagcaacc aggtgctctg ctgtgtggtc ctttgtttcc tgggagcaaa caccgtggat      60
ggtggaatca ctcagtcccc aaagtacctg ttcagaaagg aaggacagaa tgtgaccctg     120
agttgtgaac agaatttgaa ccacgatgcc atgtactggt accgacagga cccagggcaa     180
gggctgagat tgatctacta ctcacagata gtaaatgact ttcagaaagg agatatagct     240
gaagggtaca gcgtctctcg ggagaagaag gaatcctttc ctctcactgt gacatcggcc     300
caaaagaacc cgacagcttt ctatctctgt gccagtagta tctccctagc gggagtccac     360
gagcagtact cgggccgggg caccaggctc acggtcacg                            399
```

<210> SEQ ID NO 391
<211> LENGTH: 390
<212> TYPE: DNA
<213> ORGANISM: Artificial Sequence
<220> FEATURE:
<223> OTHER INFORMATION: Synthetic sequence

<400> SEQUENCE: 391

```
atggactcct ggaccttctg ctgtgtgtcc ctttgcatcc tggtagcgaa gcatacagat      60
gctggagtta tccagtcacc ccgccatgag gtgacagaga tgggacaaga agtgactctg     120
agatgtaaac caatttcagg ccacaactcc cttttctggt acagacagac catgatgcgg     180
ggactggagt tgctcattta ctttaacaac aacgttccga tagatgattc agggatgccc     240
gaggatcgat tctcagctaa gatgcctaat gcatcattct ccactctgaa gatccagccc     300
tcagaaccca gggactcagc tgtgtacttc tgtgccagca gtttagctgg ggacaggagc     360
ttcgggccgg gcaccaggct cacggtcaca                                      390
```

<210> SEQ ID NO 392
<211> LENGTH: 402
<212> TYPE: DNA
<213> ORGANISM: Artificial Sequence
<220> FEATURE:
<223> OTHER INFORMATION: Synthetic sequence

<400> SEQUENCE: 392

```
atgggccccg ggctcctctg ctgggcactg ctttgtctcc tgggagcagg cttagtggac      60
gctggagtca cccaaagtcc cacacacctg atcaaaacga gaggacagca agtgactctg     120
agatgctctc ctaagtctgg gcatgacact gtgtcctggt accaacaggc cctgggtcag     180 gggcccagt ttatctttca gtattatgag gaggaagaga gacagagagg caacttccct     240
gatcgattct caggtcacca gttccctaac tatagctctg agctgaatgt gaacgccttg     300
ttgctggggg actcggccct ctatctctgt gccagcagcg tccagggggc accgttcccc     360
tacgagcagt acttcgggcc gggcaccagg ctcacggtca ca                        402
```

<210> SEQ ID NO 393
<211> LENGTH: 411
<212> TYPE: DNA
<213> ORGANISM: Artificial Sequence
<220> FEATURE:

<223> OTHER INFORMATION: Synthetic sequence

<400> SEQUENCE: 393

| | |
|---|---|
| atgagcccaa tattcacctg catcacaatc ctttgtctgc tggctgcagg ttctcctggt | 60 |
| gaagaagtcg cccagactcc aaaacatctt gtcagagggg aaggacagaa agcaaaatta | 120 |
| tattgtgccc aataaaagg acacagttat gttttttggt accaacaggt cctgaaaaac | 180 |
| gagttcaagt tcttgatttc cttccagaat gaaaatgtct ttgatgaaac aggtatgccc | 240 |
| aaggaaagat tttcagctaa gtgcctccca aattcaccct gtagccttga gatccaggct | 300 |
| acgaagcttg aggattcagc agtgtatttt tgtgccagct cttcgatgag tatcgccgcg | 360 |
| ggtaacaccg gggagctgtt ttttggagaa ggctctaggc tgaccgtact g | 411 |

<210> SEQ ID NO 394
<211> LENGTH: 396
<212> TYPE: DNA
<213> ORGANISM: Artificial Sequence
<220> FEATURE:
<223> OTHER INFORMATION: Synthetic sequence

<400> SEQUENCE: 394

| | |
|---|---|
| atggactcct ggaccttctg ctgtgtgtcc ctttgcatcc tggtagcgaa gcatacagat | 60 |
| gctggagtta ccagtcacc ccgccatgag gtgacagaga tgggacaaga agtgactctg | 120 |
| agatgtaaac caatttcagg ccacaactcc cttttctggt acagacagac catgatgcgg | 180 |
| ggactggagt tgctcattta ctttaacaac aacgttccga tagatgattc agggatgccc | 240 |
| gaggatcgat tctcagctaa gatgcctaat gcatcattct ccactctgaa gatccagccc | 300 |
| tcagaaccca gggactcagc tgtgtacttc tgtgccagca gtttctttgg atccgagacc | 360 |
| cagtacttcg ggccaggcac gcggctcctg gtgctc | 396 |

<210> SEQ ID NO 395
<211> LENGTH: 417
<212> TYPE: DNA
<213> ORGANISM: Artificial Sequence
<220> FEATURE:
<223> OTHER INFORMATION: Synthetic sequence

<400> SEQUENCE: 395

| | |
|---|---|
| atggacaaga tcctgggcgc cagctttctg gtgctgtggc tgcaactgtg ttgggtgtcc | 60 |
| ggccagcaga aagagaagtc cgaccagcag caagtgaaac agagccctca gagcctgatc | 120 |
| gtgcagaaag gcggcatcag catcatcaac tgcgcctacg agaataccgc cttcgactac | 180 |
| ttcccctggt atcagcagtt ccccggcaag ggacctgctc tgctgatcgc cattagaccc | 240 |
| gacgtgtccg agaagaaga gggcagattc accatcagct caacaagag cgccaagcag | 300 |
| ttcagcctgc acatcatgga tagccagcct ggcgacagcg ccacctactt tgtgccgtg | 360 |
| cctaacaccg gcaaccagtt ctactttggc accggcacca gcctgacagt gatccct | 417 |

<210> SEQ ID NO 396
<211> LENGTH: 396
<212> TYPE: DNA
<213> ORGANISM: Artificial Sequence
<220> FEATURE:
<223> OTHER INFORMATION: Synthetic sequence

<400> SEQUENCE: 396

| | |
|---|---|
| atgaccagag tgtctctgct gtgggccgtc gtggtgtcca catgtctgga atctggcatg | 60 |
| gcccagaccg tgacacagag ccagcctgag atgtctgtgc aagaggccga cagtgacc | 120 |

```
ctgagctgca cctacgatac cagcgagaac aactactacc tgttctggta caagcagcct    180
cctagccggc agatgatcct ggtcatcaga caagaggcct ataagcagca gaacgccacc    240
gagaacagat tcagcgtgaa cttccagaag gccgccaaga gcttcagcct gaagatcagc    300
gatagccagc tgggcgacac cgccatgtac ttttgcgcct tcaccaacac cggcaagctg    360
atctttggcc agggcaccac actgcaagtg aagccc                             396

<210> SEQ ID NO 397
<211> LENGTH: 420
<212> TYPE: DNA
<213> ORGANISM: Artificial Sequence
<220> FEATURE:
<223> OTHER INFORMATION: Synthetic sequence

<400> SEQUENCE: 397
atggctatgc tgctgggcgc ctctgtgctg attctgtggc tgcaacccga ctgggtcaac     60
agccagcaga agaacgacga ccagcaagtg aaacagaaca gccccagcct gtccgtgcaa    120
gaaggcagga tctccatcct gaactgcgac tacaccaact ctatgttcga ctacttcctg    180
tggtacaaga agtaccccgc cgagggaccc accttcctga tcagcatcag cagcatcaag    240
gacaagaacg aggacggccg gttcaccgtg tttctgaaca gagcgccaa gcacctgagc    300 ctgcacatcg tgccttctca gcctggcgat agcgccgtgt atttctgcgc cgccaaagaa    360
cttggcggag ccaccaacaa gctgattttc ggcaccggaa cactgctggc cgtgcagcct    420

<210> SEQ ID NO 398
<211> LENGTH: 414
<212> TYPE: DNA
<213> ORGANISM: Artificial Sequence
<220> FEATURE:
<223> OTHER INFORMATION: Synthetic sequence

<400> SEQUENCE: 398
atggccatgt tgctcggcgc cagcgttctg atcctttggc tccagcctga ttgggtcaac     60
tctcagcaga aaaatgatga tcaacaagtc aagcagaact cccctagcct gagtgtccaa    120
gagggccgca tcagcattct gaattgtgat tacacgaata gtatgtttga ttactttctc    180
tggtataaga aatatccggc tgagggccct acctttctga tttccatcag ctctattaag    240
gataagaatg aggatggacg ctttacggtg ttcctcaaca aatccgccaa acacctgtct    300
ctgcatattg tgcccagcca gccaggcgac tctgccgtct attttgtgc cgtgaccacc    360 agcggcacct acaagtacat cttcggcaca ggcacccggc tgaaggtgct ggct         414

<210> SEQ ID NO 399
<211> LENGTH: 396
<212> TYPE: DNA
<213> ORGANISM: Artificial Sequence
<220> FEATURE:
<223> OTHER INFORMATION: Synthetic sequence

<400> SEQUENCE: 399
atggaaacac tgctcggagt gtccctcgtc atcctctggc tgcagctggc cagagtgaat     60
tcccagcagg gcgaagagga tccccaggct ctgtctattc aagagggcga gaatgccacc    120
atgaactgca gctacaagac cagcatcaac aacctgcagt ggtacaggca gaacagcggc    180
agaggactgg tgcacctgat cctgatccgg tccaacgaga gagaagca ctccggcaga     240 ctgcgcgtga ccctggacac aagcaagaag tctagcagcc tgctgatcac cgcctccaga    300
```

```
gccgctgata cagcctctta cttctgcgcc accgacgccg gcgataccgg ctttcagaaa    360
ctggtgttcg gaaccggcac caggctgctg gtttct                              396
```

<210> SEQ ID NO 400
<211> LENGTH: 387
<212> TYPE: DNA
<213> ORGANISM: Artificial Sequence
<220> FEATURE:
<223> OTHER INFORMATION: Synthetic sequence

<400> SEQUENCE: 400

```
atggtgctga agttcagcgt gtccatcctg tggatccagc tggcctgggt ttccacacag     60
ctgctggaac agagccctca gttcctgagc atccaagagg gcgagaacct gaccgtgtac    120
tgcaacagca gcagcgtgtt cagctccctg cagtggtaca gcaagagcc tggcgaagga    180 cctgtgctgc tggtcacagt tgtgacaggc ggcgaagtga agaagctgaa gcggctgacc    240
ttccagttcg cgacgccag aaaggattcc agcctgcaca ttaccgctgc tcagccaggc    300
gataccggcc tgtatctttg tgccggcgct aacaactacg ccagaacttc gtgttcgga    360 cccggcacaa gactgtctgt gctgccc                                       387
```

<210> SEQ ID NO 401
<211> LENGTH: 393
<212> TYPE: DNA
<213> ORGANISM: Artificial Sequence
<220> FEATURE:
<223> OTHER INFORMATION: Synthetic sequence

<400> SEQUENCE: 401

```
atggaaaaga accctctggc cgctcctctg ctgatcctgt ggtttcacct ggactgcgtg     60
tccagcatcc tgaacgtgga acagagccct cagagcctgc atgtgcaaga gggcgacagc    120
accaacttca cctgtagctt ccccagcagc aacttctacg ccctgcactg gtacagatgg    180
gagacagcca gtctcccga ggcactgttc gtgatgaccc tgaacggcga cgagaagaag    240
aagggcagaa tcagcgccac actgaacacc aaagagggct actcctacct gtacatcaag    300
ggcagccagc tgaggacag cgccacttat ctgtgcgcct ggaacaccga caagctgatc    360
tttggcaccg gcaccagact ccaggtgttc cct                                 393
```

<210> SEQ ID NO 402
<211> LENGTH: 390
<212> TYPE: DNA
<213> ORGANISM: Artificial Sequence
<220> FEATURE:
<223> OTHER INFORMATION: Synthetic sequence

<400> SEQUENCE: 402

```
atgatcagcc tgcgggtgct gctggttatc ctgtggctgc agctgagctg gtctggtcc     60 cagagaaaag aggtggaaca ggaccccgga cctttcaatg tgcctgaagg cgccaccgtg    120
gccttcaact gcacctacag caatagcgcc agccagagct ctttttggta cagacaggac    180
tgccggaaag aacccaagct gctgatgagc gtgtacagca gcggcaacga ggacggcaga    240
ttcacagccc agctgaacag ggccagccag tacattagcc tgctgatcag agacagcaag    300
ctgagcgact ccgccaccta cctgtgtgtc gttagagccg ccggaaacaa gctgacattt    360
ggaggcggca cacgggtgct cgtgaagcct                                     390
```

<210> SEQ ID NO 403
<211> LENGTH: 393

<212> TYPE: DNA
<213> ORGANISM: Artificial Sequence
<220> FEATURE:
<223> OTHER INFORMATION: Synthetic sequence

<400> SEQUENCE: 403

```
atgatttccc tgagagtgct gctcgtgatt ctctggctcc agctctcctg ggtttggagc    60
cagcggaaag aggtcgagca agaccctggg cctttaacg ttccagaggg cgctacagtg   120
gcttttaatt gcacatactc caacagcgcc tcacagagtt ttttctggta tcggcaggac   180
tgtagaaaag aaccgaaact gctcatgtcc gtgtatagct ccggcaatga ggatggccgg   240
tttaccgctc agctgaatcg ggcctctcag tacatctccc tgctgattcg ggactccaag   300
ctgtccgata gcgcaacata cctgtgcgtg gtcacaggca ccggcggctt caagacaatc   360
ttcggagcag gcacccggct gtttgtgaag gct                                393
```

<210> SEQ ID NO 404
<211> LENGTH: 393
<212> TYPE: DNA
<213> ORGANISM: Artificial Sequence
<220> FEATURE:
<223> OTHER INFORMATION: Synthetic sequence

<400> SEQUENCE: 404

```
atgaagagaa tcctgggcgc tctgctggga ctgctgtctg ctcaagtgtg ctgtgtgcgg    60
ggcatccagg tggaacagtc tccaccagac ctgatcctgc aagagggcgc caatagcacc   120
ctgcggtgca actttagcga cagcgtgaac aacctgcagt ggttccacca gaatccttgg   180
ggccagctga tcaacctgtt ctacatcccc agcggcacca gcagaacgg cagactgtct   240
gctaccaccg tggccaccga gatacagc ctgctgtaca tcagcagcag ccagaccaca   300
gacagcggcg tgtacttctg cgccgtgaca agacctagcg gcggctacaa caagctgatc   360
ttcggagccg gcaccagact ggccgtgcat cct                                393
```

<210> SEQ ID NO 405
<211> LENGTH: 402
<212> TYPE: DNA
<213> ORGANISM: Artificial Sequence
<220> FEATURE:
<223> OTHER INFORMATION: Synthetic sequence

<400> SEQUENCE: 405

```
atgggcacca gactgctgtg ctgggtcgtg ctgggatttc tgggcacaga tcatacaggc    60
gccggtgtca gccagtctcc tagatacaag gtggccaagc gcggacagga tgtggccctg   120
agatgtgatc ctatcagcgg ccacgtgtcc ctgttctggt atcaacaggc cctcggacag   180
ggccccgagt tcctgaccta ctttcagaat gaggcccagc tggacaagag cggcctgcct   240
agcgatagat tcttcgccga aagacccgag ggcagcgtgt ccacactgaa gatccagaga   300
acccagcaag aggacagcgc cgtgtacctg tgtgcctctt ctctgatcgc cggcctgagc   360
tacgagcagt atttggccc tggcacacgg ctgaccgtga cc                       402
```

<210> SEQ ID NO 406
<211> LENGTH: 399
<212> TYPE: DNA
<213> ORGANISM: Artificial Sequence
<220> FEATURE:
<223> OTHER INFORMATION: Synthetic sequence

<400> SEQUENCE: 406

```
atgagcaacc aggtgctgtg ctgcgtggtg ctgtgtttcc tgggagccaa taccgtggac    60
ggcggcatca cacagtcccc aaagtacctg ttccggaaag agggccagaa cgtcaccctg   120
tcctgcgagc agaacctgaa ccacgacgcc atgtattggt acagacagga cccaggccag   180
ggcctgagac tgatctacta cagccagatc gtgaacgact tcagaaggg cgacattgcc    240 gagggctaca gcgtgtccag agagaagaaa gagtcctttc cactgaccgt gactagcgcc   300
cagaagaacc ctaccgcctt ctacctgtgt gccagcgctc tgctggaata ctccaaccag   360
cctcagcact ttggcgacgg cacaagactg agcatcctg                          399
```

<210> SEQ ID NO 407
<211> LENGTH: 399
<212> TYPE: DNA
<213> ORGANISM: Artificial Sequence
<220> FEATURE:
<223> OTHER INFORMATION: Synthetic sequence

<400> SEQUENCE: 407

```
atggatagct ggaccttctg ctgcgtgtcc ctgtgcattc tggtggccaa gcacacagat    60
gccggcgtga tccagtctcc tagacacgaa gtgaccgaga tgggccaaga agtgacactg   120
cgctgtaaac ccatcagcgg ccacaacagc ctgttttggt atcggcagac catgatgaga   180
ggcctggaac tgctgatcta tttcaacaac aacgtgccca tcgacgacag cggcatgccc   240
gaggatagat tttccgccaa gatgcccaac gccagcttca gcaccctgaa aatccagcct   300
agcgagccca gagactccgc tgtgtacttc tgtgcctctt ctctcggctg ggaaccacc    360 gaggcctttt ttggacaagg caccagactg acagtggtt                          399
```

<210> SEQ ID NO 408
<211> LENGTH: 402
<212> TYPE: DNA
<213> ORGANISM: Artificial Sequence
<220> FEATURE:
<223> OTHER INFORMATION: Synthetic sequence

<400> SEQUENCE: 408

```
atgggaacca gactgctgtt ctgggtcgcc ttttgtctgc tgggagccga tcatacaggc    60
gccggtgttt ctcagagccc cagcaacaaa gtgacagaga aaggcaagga cgtggaactg   120
agatgcgacc ccatctctgg ccacacagcc ctgtactggt atagacagtc tctcggccag   180
gggctcgagt tcctcatcta cttccaaggc aacagcgccc tgacaagtc tggcctgcct   240 agcgatagat tctctgccga aaagaaccggc ggctccgtgt ctacactgac catccagaga   300
acccagcaag aggattccgc cgtgtacctg tgcgcctcta gcttttctgg ctccctgggc   360 gataccagt acttcggccc tggaacaagg ctgaccgtgc tc                       402
```

<210> SEQ ID NO 409
<211> LENGTH: 405
<212> TYPE: DNA
<213> ORGANISM: Artificial Sequence
<220> FEATURE:
<223> OTHER INFORMATION: Synthetic sequence

<400> SEQUENCE: 409

```
atgggctgca gactgctgtg ttgtgccgtg ctgtgtctgc tgggagccgt gcctatcgac    60
accgaagtga cccagacacc taagcacctg gtcatgggca tgacaaacaa gaaaagcctg   120
aagtgcgagc agcacatggg ccacagagcc atgtactggt acaagcagaa ggccaagaaa   180
cctcctgagc tgatgttcgt gtacagctac gagaagctga gcatcaacga gagcgtgccc   240
```

```
agcagattca gccctgagtg ccctaatagc agcctgctga acctgcatct gcacgccctg    300
cagcctgaag atagcgccct gtacctgtgt gccagctctc ctacactgac aagcggcggc    360
accgacacac agtattttgg ccctggcacc agactgaccg tgctg                    405
```

<210> SEQ ID NO 410
<211> LENGTH: 399
<212> TYPE: DNA
<213> ORGANISM: Artificial Sequence
<220> FEATURE:
<223> OTHER INFORMATION: Synthetic sequence

<400> SEQUENCE: 410

```
atgagcaatc aggtgctgtg ctgcgttgtg ctgtgtttcc tgggcgccaa taccgtggat     60
ggcggcatca cacagagccc caagtacctg ttccggaaag agggacagaa cgtcaccctg    120
agctgcgagc agaacctgaa ccacgacgct atgtattggt atcgcaggga ccctggacag    180
ggcctgagac tgatctacta cagccagatc gtgaacgact ccagaagggg cgacattgcc    240
gagggctact ccgtgtccag agagaagaaa gagtcctttc cactgacagt gacaagcgcc    300
cagaagaacc ccaccgcctt ctatctgtgt gcctccagca tttctctggc cggcgtgcac    360
gagcagtact tcggacctgg aacaaggctg accgtgacc                          399
```

<210> SEQ ID NO 411
<211> LENGTH: 390
<212> TYPE: DNA
<213> ORGANISM: Artificial Sequence
<220> FEATURE:
<223> OTHER INFORMATION: Synthetic sequence

<400> SEQUENCE: 411

```
atggacagct ggaccttctg ctgtgtgtcc ctgtgtatcc tggtggccaa gcacacagat     60
gccggcgtga tccagtctcc tagacacgaa gtgaccgaga tgggccaaga agtgaccctg    120
cgctgcaagc ctatcagcgg ccacaatagc ctgttctggt acaggcagac catgatgaga    180
ggcctggaac tgctgatcta cttcaacaac aacgtgccca tcgacgacag cggcatgccc    240
gaggatagat tcagcgccaa gatgcccaac gccagcttca gcaccctgaa gatccagcct    300
agcgagccca gagatagcgc cgtgtacttt tgtgcctcta gcctggccgg cgacagatct    360
tttggccccg aacaagact gaccgtgacc                                     390
```

<210> SEQ ID NO 412
<211> LENGTH: 402
<212> TYPE: DNA
<213> ORGANISM: Artificial Sequence
<220> FEATURE:
<223> OTHER INFORMATION: Synthetic sequence

<400> SEQUENCE: 412

```
atgggacctg gacttctgtg ttgggccctg ctgtgtctgc ttggagctgg acttgtggac     60
gctggcgtca cacagtctcc cacacacctg atcaagacca gaggccagca agtgacactg    120
agatgcagcc ctaagagcgg ccacgatacc gtgtcttggt atcagcaagc cctcggccag    180
ggacctcagt tcatcttcca gtactacgag gaagaggaac ggcagcgggg caacttccct    240
gatagattct ccggccatca gttccccaac tacagctccg agctgaacgt gaacgccctg    300
ctgctcggag actctgccct gtatctttgt gccagctctg tgcaaggcgc cccatttcct    360
tacgagcagt acttcggccc tggcaccagg ctgacagtga ca                      402
```

<210> SEQ ID NO 413
<211> LENGTH: 411
<212> TYPE: DNA
<213> ORGANISM: Artificial Sequence
<220> FEATURE:
<223> OTHER INFORMATION: Synthetic sequence

<400> SEQUENCE: 413

```
atgagcccca tctttacctg catcaccatc ctgtgcctgc tggccgctgg atctcctggg      60
gaagaagtgg cccagacacc taagcacctc gttagaggcg agggccagaa ggccaagctg     120
tattgcgccc ctatcaaggg ccacagctat gttttttggt atcaacaggt cctgaagaac     180
gagttcaagt tcctgatcag cttccagaac gagaacgtgt cgacgagac aggcatgccc      240
aaagagcggt tctccgccaa gtgcctgcct aacagccctt gcagcctgga atccaggcc      300
accaagctgg aagattccgc cgtgtatttc tgcgccagca gcagcatgtc tatcgccgct     360
ggaaataccg cgagctgtt cttcggcgag ggcagcagac tgacagttct g               411
```

<210> SEQ ID NO 414
<211> LENGTH: 396
<212> TYPE: DNA
<213> ORGANISM: Artificial Sequence
<220> FEATURE:
<223> OTHER INFORMATION: Synthetic sequence

<400> SEQUENCE: 414

```
atggatagct ggaccttctg ctgcgtgtcc ctgtgtatcc tggtggctaa gcacacagat      60
gccggcgtga tccagtctcc tagacacgaa gtgaccgaga tgggccaaga agtgaccctg     120
cgctgtaaac ccatcagcgg ccacaacagc ctgttctggt acagacagac catgatgaga     180
ggcctggaac tgctgatcta cttcaacaac aacgtgccca tcgacgacag cggcatgccc     240
gaggatagat tcagcgccaa gatgcccaac gccagcttca gcaccctgaa gatccagcct     300
agcgagccca gagattccgc cgtgtacttt tgtgccagca gcttcttcgg cagcgagaca     360
cagtatttcg gccctggcac aagactgctg gtgctg                                396
```

<210> SEQ ID NO 415
<211> LENGTH: 534
<212> TYPE: DNA
<213> ORGANISM: Artificial Sequence
<220> FEATURE:
<223> OTHER INFORMATION: Synthetic sequence

<400> SEQUENCE: 415

```
gacctgaaga acgtgttccc cccagaggtg gccgtgttcg agccttctga ggccgagatc      60
agccacaccc agaaagccac cctcgtgtgt ctggccaccg gcttttaccc cgaccacgtg     120
gaactgtctt ggtgggtcaa cggcaaagag gtgcactccg gcgtgtgcac cgatccccag     180
cctctgaaag aacagcccgc cctgaacgac agccggtact gcctgtccag cagactgaga     240
gtgtccgcca ccttctggca gaaccccgg aaccacttca gatgccaggt gcagttctac     300
ggcctgagcg agaacgacga gtggacccag gacagagcca gcccgtgac ccagatcgtg     360
tctgccgaag cctggggcag agccgattgc ggctttacca gcgagagcta ccagcagggc     420
gtgctgtctg ccaccatcct gtacgagatc ctgctgggaa aggccaccct gtacgccgtg     480
ctggtgtctg ccctggtgct gatggccatg gtcaagcgga aggacagcag aggc           534
```

<210> SEQ ID NO 416
<211> LENGTH: 531

<212> TYPE: DNA
<213> ORGANISM: Artificial Sequence
<220> FEATURE:
<223> OTHER INFORMATION: Synthetic sequence

<400> SEQUENCE: 416

```
gaggacctga acaaagtgtt cccccagag gtggccgtgt tcgagccttc tgaggccgag      60
atcagccaca cccagaaagc caccctcgtg tgcctggcca ccggctttta ccccgaccac   120
gtggaactgt cttggtgggt caacggcaaa gaggtgcact ccggcgtgtg caccgatccc   180
cagcctctga agaacagcc cgccctgaac gacagccggt actgcctgtc agcagactg    240
agagtgtccg ccaccttctg gcagaacccc cggaaccact cagatgccag gtgcagttc   300
tacggcctga gcgagaacga cgagtggacc caggacagag ccaagcccgt gacacagatc   360
gtgtctgccg aagcctgggg cagagccgat tgcggcttta cctccgtgtc ctatcagcag   420
ggcgtgctga gcgccaccat cctgtacgag atcctgctgg gcaaggccac actgtacgcc   480
gtgctggtgt ctgccctggt gctgatggcc atggtcaagc ggaaggactt c            531
```

<210> SEQ ID NO 417
<211> LENGTH: 1845
<212> TYPE: DNA
<213> ORGANISM: Artificial Sequence
<220> FEATURE:
<223> OTHER INFORMATION: Synthetic sequence

<400> SEQUENCE: 417

```
atgggcacca gactgctgtg ctgggtcgtg ctgggattc tgggcacaga tcatacaggc       60
gccggtgtca gccagtctcc tagatacaag gtggccaagc gcggacagga tgtggccctg    120
agatgtgatc ctatcagcgg ccacgtgtcc ctgttctggt atcaacaggc cctcggacag    180
ggccccgagt tcctgaccta cttcagaat gaggcccagc tggacaagag cggcctgcct     240
agcgatagat tcttcgccga aagacccgag ggcagcgtgt ccacactgaa gatccagaga    300
acccagcaag aggacagcgc cgtgtacctg tgtgcctctt ctctgatcgc cggcctgagc    360
tacgagcagt attttggccc tggcacacgg ctgaccgtga ccgacctgaa gaacgtgttc    420
cccccagagg tggccgtgtt cgagccttct gaggccgaga tcagccacac ccagaaagcc   480
accctcgtgt gtctggccac cggcttttac cccgaccacg tggaactgtc ttggtgggtc   540
aacggcaaag aggtgcactc cggcgtgtgc accgatcccc agcctctgaa gaacagccc    600
gccctgaacg acagccggta ctgcctgtcc agcagactga gagtgtccgc caccttctgg   660
cagaaccccc ggaaccactt cagatgccag gtgcagttct acggcctgag cgagaacgac   720
gagtggaccc aggacagagc caagcccgtg acccagatcg tgtctgccga agcctggggc   780
agagccgatt gcggctttac cagcgagagc taccagcagg gcgtgctgtc tgccaccatc   840
ctgtacgaga tcctgctggg aaaggccacc ctgtacgccg tgctggtgtc tgccctggtg   900
ctgatggcca tggtcaagcg gaaggacagc agaggcggtt ccggagccac gaacttctct   960
ctgttaaagc aagcaggaga cgtggaagaa acccccggtc catggacaa gatcctgggc   1020
gccagctttc tggtgctgtg gctgcaactg tgttgggtgt ccggccagca gaaagagaag   1080
tccgaccagc agcaagtgaa acagagccct cagagcctga tcgtgcagaa aggcggcatc   1140
agcatcatca actgcgccta cgagaatacc gccttcgact acttcccctg gtatcagcag   1200
ttccccggca agggacctgc tctgctgatc gccattagac ccgacgtgtc cgagaagaaa   1260
gagggcagat tcaccatcag cttcaacaag agcgccaagc agttcagcct gcacatcatg   1320
```

```
gatagccagc ctggcgacag cgccacctac ttttgtgccg tgcctaacac cggcaaccag   1380
ttctactttg gcaccggcac cagcctgaca gtgatccctg acatccagaa ccccgaccct   1440
gcagtgtacc agctgcggga cagcaagagc agcgacaaga gcgtgtgcct gttcaccgac   1500
ttcgacagcc agaccaacgt gtcccagagc aaggacagcg acgtgtacat caccgataag   1560
tgcgtgctgg acatgcggag catggacttc aagagcaaca cgccgtggc ctggtccaac   1620 aagagcgact cgcctgcgc caacgccttc aacaacagca ttatccccga ggacacattc   1680
ttcccaagcc ccgagagcag ctgcgacgtg aagctggtgg aaaagagctt cgagacagac   1740
accaacctga acttccagaa cctcagcgtg atcggcttcc ggatcctgct gctgaaggtg   1800
gccggcttca acctgctgat gaccctgcgg ctgtggtcca gctga              1845
```

<210> SEQ ID NO 418
<211> LENGTH: 1818
<212> TYPE: DNA
<213> ORGANISM: Artificial Sequence
<220> FEATURE:
<223> OTHER INFORMATION: Synthetic sequence

<400> SEQUENCE: 418

```
atgagcaacc aggtgctgtg ctgcgtggtg ctgtgtttcc tgggagccaa taccgtggac     60
ggcggcatca cacagtcccc aaagtacctg ttccggaaag agggccagaa cgtcaccctg    120
tcctgcgagc agaacctgaa ccacgacgcc atgtattggt acagacagga cccaggccag    180
ggcctgagac tgatctacta cagccagatc gtgaacgact tcagaaggg cgacattgcc    240 gagggctaca gcgtgtccag agagaagaaa gagtcctttc cactgaccgt gactagcgcc    300
cagaagaacc ctaccgcctt ctacctgtgt gccagcgctc tgctggaata ctccaaccag    360
cctcagcact ttggcgacgg cacaagactg agcatcctgg aggacctgaa caaagtgttc    420 ccccagagg tggccgtgtt cgagccttct gaggccgaga tcagccacac ccagaaagcc    480
accctcgtgt gcctggccac cggctttttc cccgaccacg tgaactgtc ttggtgggtc    540 aacggcaaag aggtgcactc cggcgtgtgc accgatcccc agcctctgaa agaacagccc    600
gccctgaacg acagccggta ctgcctgtcc agcagactga gagtgtccgc caccttctgg    660 cagaacccccc ggaaccactt cagatgccag gtgcagttct acggcctgag cgagaacgac    720
gagtggaccc aggacagagc caagcccgtg acacagatcg tgtctgccga agcctggggc    780
agagccgatt gcggctttac ctccgtgtcc tatcagcagg gcgtgctgag cgccaccatc    840
ctgtacgaga tcctgctggg caaggccaca ctgtacgccg tgctggtgtc tgccctggtg    900
ctgatggcca tggtcaagcg gaaggacttc ggttccggag ccacgaactt ctctctgtta    960
aagcaagcag gagacgtgga agaaaacccc ggtcccatga ccagagtgtc tctgctgtgg    1020
gccgtcgtgg tgtccacatg tctggaatct ggcatggccc agaccgtgac acagagccag    1080
cctgagatgt ctgtgcaaga ggccgagaca gtgaccctga gctgcaccta cgataccagc    1140
gagaacaact actacctgtt ctggtacaag cagcctccta ccggcagat gatcctggtc    1200 atcagacaag aggcctataa gcagcagaac gccaccgaga acagattcag cgtgaacttc    1260
cagaaggccg ccaagagctt cagcctgaag atcagcgata gccagctggg cgacaccgcc    1320
atgtactttt gcgccttcac caacaccggc aagctgatct ttggccaggg caccacactg    1380
caagtgaagc ccgacatcca gaaccccgac cctgcagtgt accagctgcg ggacagcaag    1440
agcagcgaca gagcgtgtg cctgttcacc gacttcgaca gccagaccaa cgtgtcccag    1500
agcaaggaca gcgacgtgta catcaccgat aagtgcgtgc tggacatgcg gagcatggac    1560
```

```
ttcaagagca acagcgccgt ggcctggtcc aacaagagcg acttcgcctg cgccaacgcc    1620
ttcaacaaca gcattatccc cgaggacaca ttcttcccaa gccccgagag cagctgcgac    1680
gtgaagctgg tggaaaagag cttcgagaca gacaccaacc tgaacttcca gaacctcagc    1740
gtgatcggct ccggatcct gctgctgaag gtggccggct tcaacctgct gatgaccctg    1800
cggctgtggt ccagctga                                                 1818
```

<210> SEQ ID NO 419
<211> LENGTH: 1842
<212> TYPE: DNA
<213> ORGANISM: Artificial Sequence
<220> FEATURE:
<223> OTHER INFORMATION: Synthetic sequence

<400> SEQUENCE: 419

```
atggatagct ggaccttctg ctgcgtgtcc ctgtgcattc tggtggccaa gcacacagat     60
gccggcgtga tccagtctcc tagacacgaa gtgaccgaga tgggccaaga agtgacactg    120
cgctgtaaac ccatcagcgg ccacaacagc ctgttttggt atcggcagac catgatgaga    180
ggcctggaac tgctgatcta tttcaacaac aacgtgccca tcgacgacag cggcatgccc    240
gaggatagat tttccgccaa gatgcccaac gccagcttca gcaccctgaa aatccagcct    300
agcgagccca gagactccgc tgtgtacttc tgtgcctctt ctctcggctg gggaaccacc    360
gaggcctttt ttggacaagg caccagactg acagtggttg aggacctgaa caaagtgttc    420
cccccagagg tggccgtgtt cgagccttct gaggccgaga tcagccacac ccagaaagcc    480
accctcgtgt gcctggccac cggcttttc cccgaccacg tggaactgtc ttggtgggtc    540
aacggcaaag aggtgcactc cggcgtgtgc accgatcccc agcctctgaa agaacagccc    600
gccctgaacg acagccggta ctgcctgtcc agcagactga gagtgtccgc caccttctgg    660
cagaaccccc ggaaccactt cagatgccag gtgcagttct acggcctgag cgagaacgac    720
gagtggaccc aggacagagc caagcccgtg acacagatcg tgtctgccga gcctggggc    780 agagccgatt gcggctttac ctccgtgtcc tatcagcagg gcgtgctgag cgccaccatc    840
ctgtacgaga tcctgctggg caaggccaca ctgtacgccg tgctggtgtc tgccctggtg    900
ctgatggcca tggtcaagcg gaaggacttc ggttccggag ccacgaactt ctctctgtta    960
aagcaagcag gagacgtgga agaaaacccc ggtcccatgg ctatgctgct gggcgcctct   1020
gtgctgattc tgtggctgca acccgactgg gtcaacagcc agcagaagaa cgacgaccag   1080
caagtgaaac agaacagccc cagcctgtcc gtgcaagaag caggatctc catcctgaac   1140 tgcgactaca ccaactctat gttcgactac ttcctgtggt acaagaagta ccccgccgag   1200
ggacccacct tcctgatcag catcagcagc atcaaggaca gaacgagga cggccggttc   1260 accgtgtttc tgaacaagag cgccaagcac ctgagcctgc acatcgtgcc ttctcagcct   1320
ggcgatagcg ccgtgtattt ctgcgccgcc aaagaacttg gcgagccac caacaagctg   1380 attttcggca ccggaacact gctggccgtg cagcctgaca tccagaaccc cgaccctgca   1440
gtgtaccagc tgcgggacag caagagcagc gacaagagcg tgtgcctgtt caccgacttc   1500
gacagccaga ccaacgtgtc ccagagcaag gacagcgacg tgtacatcac cgataagtgc   1560
gtgctggaca tgcggagcat ggacttcaag agcaacagcg ccgtggcctg gtccaacaag   1620
agcgacttcg cctgcgccaa cgccttcaac aacagcatta tccccgagga cacattcttc   1680
ccaagccccg agagcagctg cgacgtgaag ctggtggaaa agagcttcga gacagacacc   1740
```
aacctgaact tccagaacct cagcgtgatc ggcttccgga tcctgctgct gaaggtggcc    1800
ggcttcaacc tgctgatgac cctgcggctg tggtccagct ga                      1842

<210> SEQ ID NO 420
<211> LENGTH: 1842
<212> TYPE: DNA
<213> ORGANISM: Artificial Sequence
<220> FEATURE:
<223> OTHER INFORMATION: Synthetic sequence

<400> SEQUENCE: 420
atgggaacca gactgctgtt ctgggtcgcc ttttgtctgc tgggagccga tcatacaggc      60
gccggtgttt ctcagagccc cagcaacaaa gtgacagaga aggcaagga cgtggaactg     120 agatgcgacc ccatctctgg ccacacagcc ctgtactggt atagacagtc tctcggccag    180
gggctcgagt tcctcatcta cttccaaggc aacagcgccc tgacaagtc tggcctgcct    240 agcgatagat tctctgccga aaaccggg ggctccgtgt ctacactgac catccagaga     300
acccagcaag aggattccgc cgtgtacctg tgcgcctcta gcttttctgg ctccctgggc    360 gataccagt acttcggccc tggaacaagg ctgaccgtgc tcgacctgaa gaacgtgttc    420
cccccagagg tggccgtgtt cgagccttct gaggccgaga tcagccacac ccagaaagcc    480
accctcgtgt gtctggccac cggcttttac cccgaccacg tggaactgtc ttggtgggtc    540
aacggcaaag aggtgcactc cggcgtgtgc accgatcccc agcctctgaa agaacagccc    600
gccctgaacg acagccggta ctgcctgtcc agcagactga gagtgtccgc caccttctgg    660
cagaaccccc ggaaccactt cagatgccag gtgcagttct acggcctgag cgagaacgac    720
gagtggaccc aggacagagc caagcccgtg acccagatcg tgtctgccga agcctggggc    780
agagccgatt gcggctttac cagcgagagc taccagcagg gcgtgctgtc tgccaccatc    840
ctgtacgaga tcctgctggg aaaggccacc ctgtacgccg tgctggtgtc tgccctggtg    900
ctgatggcca tggtcaagcg gaaggacagc agaggcggtt ccggagccac gaacttctct    960
ctgttaaagc aagcaggaga cgtggaagaa accccggtc ccatggccat gttgctcggc   1020
gccagcgttc tgatcctttg gctccagcct gattgggtca actctcagca gaaaaatgat   1080
gatcaacaag tcaagcagaa ctcccctagc ctgagtgtcc aagagggccg catcagcatt   1140
ctgaattgtg attacacgaa tagtatgttt gattactttc tctggtataa gaaatatccg   1200
gctgagggcc ctacctttct gatttccatc agctctatta aggataagaa tgaggatgga   1260
cgctttacgg tgttcctcaa caatccgcc aaacacctgt ctctgcatat tgtgcccagc   1320
cagccaggcg actctgccgt ctattttgt gccgtgacca ccagcggcac ctacaagtac   1380
atcttcggca caggcacccg gctgaaggtg ctggctgaca tccagaaccc cgaccctgca   1440
gtgtaccagc tgcgggacag caagagcagc gacaagagcg tgtgcctgtt caccgacttc   1500
gacagccaga ccaacgtgtc ccagagcaag gacagcgacg tgtacatcac cgataagtgc   1560
gtgctggaca tgcggagcat ggacttcaag agcaacagcc ccgtggcctg gtccaacaag   1620
agcgacttcg cctgcgccaa cgccttcaac aacagcatta tccccgagga cacattcttc   1680
ccaagccccg agagcagctg cgacgtgaag ctggtggaaa agagcttcga cagacacacc   1740
aacctgaact tccagaacct cagcgtgatc ggcttccgga tcctgctgct gaaggtggcc   1800
ggcttcaacc tgctgatgac cctgcggctg tggtccagct ga                      1842

<210> SEQ ID NO 421
<211> LENGTH: 1827

```
<212> TYPE: DNA
<213> ORGANISM: Artificial Sequence
<220> FEATURE:
<223> OTHER INFORMATION: Synthetic sequence

<400> SEQUENCE: 421
atgggctgca gactgctgtg ttgtgccgtg ctgtgtctgc tgggagccgt gcctatcgac      60
accgaagtga cccagacacc taagcacctg gtcatgggca tgacaaacaa gaaaagcctg     120
aagtgcgagc agcacatggg ccacagagcc atgtactggt acaagcagaa ggccaagaaa     180
cctcctgagc tgatgttcgt gtacagctac gagaagctga gcatcaacga gagcgtgccc     240
agcagattca gccctgagtg ccctaatagc agcctgctga acctgcatct gcacgccctg     300
cagcctgaag atagcgccct gtacctgtgt gccagctctc ctacactgac aagcggcggc     360
accgacacac agtattttgg ccctggcacc agactgaccg tgctggacct gaagaacgtg     420
ttccccccag aggtggccgt gttcgagcct tctgaggccg agatcagcca cacccagaaa     480
gccaccctcg tgtgtctggc caccggcttt tacccagacc acgtggaact gtcttggtgg     540
gtcaacggca agaggtgcac tccggcgtg tgcaccgatc cccagcctct gaaagaacag     600
cccgccctga cgacagccg gtactgcctg tccagcagac tgagagtgtc cgccaccttc     660
tggcagaacc cccggaacca cttcagatgc caggtgcagt tctacggcct gagcgagaac     720
gacgagtgga cccaggacag agccaagccc gtgacccaga tcgtgtctgc cgaagcctgg     780
ggcagagccg attgcggctt taccagcgag agctaccagc agggcgtgct gtctgccacc     840
atcctgtacg agatcctgct gggaaaggcc accctgtacg ccgtgctggt gtctgccctg     900
gtgctgatgg ccatggtcaa gcggaaggac agcagaggcg gttccggagc cacgaacttc     960
tctctgttaa gcaagcagg agacgtggaa gaaaacccg gtcccatgga aacactgctc    1020
ggagtgtccc tcgtcatcct ctggctgcag ctggccagag tgaattccca gcagggcgaa    1080
gaggatcccc aggctctgtc tattcaagag ggcgagaatg ccaccatgaa ctgcagctac    1140
aagaccagca tcaacaacct gcagtggtac aggcagaaca gcggcagagg actggtgcac    1200
ctgatcctga tccggtccaa cgagagagag aagcactccg gcagactgcg cgtgaccctg    1260
gacacaagca agaagtctag cagcctgctg atcaccgcct ccagagccgc tgatacagcc    1320
tcttacttct gcgccaccga cgccggcgat accggctttc agaaactggt gttcggaacc    1380
ggcaccaggc tgctggtttc tgacatccag aaccccgacc ctgcagtgta ccagctgcgg    1440
gacagcaaga gcagcgacaa gagcgtgtgc ctgttcaccg acttcgacag ccagaccaac    1500
gtgtcccaga gcaaggacag cgacgtgtac atcaccgata gtgcgtgct ggacatgcgg    1560 agcatggact tcaagagcaa cagcgccgtg gcctggtcca acaagagcga cttcgcctgc    1620
gccaacgcct tcaacaacag cattatcccc gaggacacat tcttcccaag ccccgagagc    1680
agctgcgacg tgaagctggt ggaaaagagc ttcgagacag acaccaacct gaacttccag    1740
aacctcagcg tgatcggctt ccggatcctg ctgctgaagg tggccggctt caacctgctg    1800
atgaccctgc ggctgtggtc cagctga                                        1827

<210> SEQ ID NO 422
<211> LENGTH: 1812
<212> TYPE: DNA
<213> ORGANISM: Artificial Sequence
<220> FEATURE:
<223> OTHER INFORMATION: Synthetic sequence

<400> SEQUENCE: 422
```

| | |
|---|---|
| atgagcaatc aggtgctgtg ctgcgttgtg ctgtgtttcc tgggcgccaa taccgtggat | 60 |
| ggcggcatca cacagagccc caagtacctg ttccggaaag agggacagaa cgtcaccctg | 120 |
| agctgcgagc agaacctgaa ccacgacgct atgtattggt atcggcagga ccctggacag | 180 |
| ggcctgagac tgatctacta cagccagatc gtgaacgact tccagaaggg cgacattgcc | 240 |
| gagggctact ccgtgtccag agagaagaaa gagtcctttc cactgacagt gacaagcgcc | 300 |
| cagaagaacc ccaccgcctt ctatctgtgt gcctccagca tttctctggc cggcgtgcac | 360 |
| gagcagtact tcggacctgg aacaaggctg accgtgaccg acctgaagaa cgtgttcccc | 420 |
| ccagaggtgg ccgtgttcga gccttctgag gccgagatca gccacaccca gaaagccacc | 480 |
| ctcgtgtgtc tggccaccgg cttttacccc gaccacgtgg aactgtcttg gtgggtcaac | 540 |
| ggcaaagagg tgcactccgg cgtgtgcacc gatccccagc ctctgaaaga cagcccgcc | 600 |
| ctgaacgaca gccggtactg cctgtccagc agactgagag tgtccgccac cttctggcag | 660 |
| aaccccgga accacttcag atgccaggtg cagttctacg gcctgagcga aacgacgag | 720 |
| tggacccagg acagagccaa gcccgtgacc cagatcgtgt ctgccgaagc ctggggcaga | 780 |
| gccgattgcg gctttaccag cgagagctac cagcagggcg tgctgtctgc caccatcctg | 840 |
| tacgagatcc tgctgggaaa ggccaccctg tacgccgtgc tggtgtctgc cctggtgctg | 900 |
| atggccatgg tcaagcggaa ggacagcaga ggcggttccg gagccacgaa cttctctctg | 960 |
| ttaaagcaag caggagacgt ggaagaaaac cccggtccca tggtgctgaa gttcagcgtg | 1020 |
| tccatcctgt ggatccagct ggcctgggtt ccacacagc tgctggaaca gagccctcag | 1080 |
| ttcctgagca tccaagaggg cgagaacctg accgtgtact gcaacagcag cagcgtgttc | 1140 |
| agctccctgc agtggtacag acaagagcct ggcgaaggac ctgtgctgct ggtcacagtt | 1200 |
| gtgacaggcg gcgaagtgaa gaagctgaag cggctgacct tccagttcgg cgacgccaga | 1260 |
| aaggattcca gcctgcacat taccgctgct cagccaggcg ataccggcct gtatctttgt | 1320 |
| gccggcgcta caactacgg ccagaacttc gtgttcggac ccggcacaag actgtctgtg | 1380 |
| ctgcccgaca tccagaaccc cgaccctgca gtgtaccagc tgcgggacag caagagcagc | 1440 |
| gacaagagcg tgtgcctgtt caccgacttc gacagccaga ccaacgtgtc ccagagcaag | 1500 |
| gacagcgacg tgtacatcac cgataagtgc gtgctggaca tgcggagcat ggacttcaag | 1560 |
| agcaacagcg ccgtggcctg gtccaacaag agcgcgacttcg cctgcgccaa cgccttcaac | 1620 |
| aacagcatta tccccgagga cacattcttc ccaagccccg agagcagctg cgacgtgaag | 1680 |
| ctggtggaaa agagcttcga gacagacacc aacctgaact tccagaacct cagcgtgatc | 1740 |
| ggcttccgga tcctgctgct gaaggtggcc ggcttcaacc tgctgatgac cctgcggctg | 1800 |
| tggtccagct ga | 1812 |

<210> SEQ ID NO 423
<211> LENGTH: 1809
<212> TYPE: DNA
<213> ORGANISM: Artificial Sequence
<220> FEATURE:
<223> OTHER INFORMATION: Synthetic sequence

<400> SEQUENCE: 423

| | |
|---|---|
| atggacagct ggaccttctg ctgtgtgtcc ctgtgtatcc tggtggccaa gcacacagat | 60 |
| gccggcgtga tccagtctcc tagacacgaa gtgaccgaga tgggccaaga agtgaccctg | 120 |
| cgctgcaagc ctatcagcgg ccacaatagc ctgttctggt acaggcagac catgatgaga | 180 |
| ggcctggaac tgctgatcta cttcaacaac aacgtgccca tcgacgacag cggcatgccc | 240 |

```
gaggatagat tcagcgccaa gatgcccaac gccagcttca gcaccctgaa gatccagcct    300
agcgagccca gagatagcgc cgtgtacttt tgtgcctcta gcctggccgg cgacagatct    360
tttggccccg aacaagact gaccgtgacc gacctgaaga acgtgttccc cccagaggtg    420
gccgtgttcg agccttctga ggccgagatc agccacaccc agaaagccac cctcgtgtgt    480
ctggccaccg gcttttaccc cgaccacgtg gaactgtctt ggtgggtcaa cggcaaagag    540
gtgcactccg gcgtgtgcac cgatccccag cctctgaaag aacagccgc cctgaacgac    600 agccggtact gcctgtccag cagactgaga gtgtccgcca ccttctggca gaaccccgg    660 aaccacttca gatgccaggt gcagttctac ggcctgagcg agaacgacga gtggacccag    720
gacagagcca agcccgtgac ccagatcgtg tctgccgaag cctggggcag agccgattgc    780
ggctttacca gcgagagcta ccagcagggc gtgctgtctg ccaccatcct gtacgagatc    840
ctgctgggaa aggccaccct gtacgccgtg ctggtgtctg ccctggtgct gatggccatg    900
gtcaagcgga aggacagcag aggcggttcc ggagccacga acttctctct gttaaagcaa    960
gcaggagacg tggaagaaaa ccccggtccc atggaaaaga accctctggc cgctcctctg    1020
ctgatcctgt ggtttcacct ggactgcgtg tccagcatcc tgaacgtgga acagagccct    1080
cagagcctgc atgtgcaaga gggcgacagc accaacttca cctgtagctt ccccagcagc    1140
aacttctacg ccctgcactg gtacagatgg gagacagcca gtctcccga ggcactgttc    1200 gtgatgaccc tgaacggcga cgagaagaag aagggcagaa tcagcgccac actgaacacc    1260
aaagagggct actcctacct gtacatcaag ggcagcagc ctgaggacag cgccactttat    1320 ctgtgcgcct ggaacaccga caagctgatc tttggcaccg gcaccagact ccaggtgttc    1380
cctgacatcc agaaccccga ccctgcagtg taccagctgc gggacagcaa gagcagcgac    1440
aagagcgtgt gcctgttcac cgacttcgac agccagacca acgtgtccca gagcaaggac    1500
agcgacgtgt acatcaccga taagtgcgtg ctggacatgc ggagcatgga cttcaagagc    1560
aacagcgccg tggcctggtc caacaagagc gacttcgcct gcgccaacgc cttcaacaac    1620
agcattatcc ccgaggacac attcttccca agccccgaga gcagctgcga cgtgaagctg    1680
gtggaaaaga gcttcgagac agacaccaac ctgaacttcc agaacctcag cgtgatcggc    1740
ttccggatcc tgctgctgaa ggtggccggc ttcaacctgc tgatgaccct gcggctgtgg    1800
tccagctga                                                            1809
```

<210> SEQ ID NO 424
<211> LENGTH: 1818
<212> TYPE: DNA
<213> ORGANISM: Artificial Sequence
<220> FEATURE:
<223> OTHER INFORMATION: Synthetic sequence

<400> SEQUENCE: 424

```
atgggacctg gacttctgtg ttgggccctg ctgtgtctgc ttggagctgg acttgtggac    60
gctggcgtca cacagtctcc cacacacctg atcaagacca gaggccagca agtgacactg    120
agatgcagcc ctaagagcgg ccacgatacc gtgtcttggt atcagcaagc cctcggccag    180
ggacctcagt tcatcttcca gtactacgag gaagaggaac ggcagcgggg caacttccct    240
gatagattct ccggccatca gttccccaac tacagctccg agctgaacgt gaacgccctg    300
ctgctcggag actctgccct gtatctttgt gccagctctg tgcaaggcgc ccatttcct    360 tacgagcagt acttcggccc tggcaccagg ctgacagtga cagacctgaa gaacgtgttc    420
```

| | |
|---|---|
| cccccagagg tggccgtgtt cgagccttct gaggccgaga tcagccacac ccagaaagcc | 480 |
| accctcgtgt gtctggccac cggcttttac cccgaccacg tggaactgtc ttggtgggtc | 540 |
| aacggcaaag aggtgcactc cggcgtgtgc accgatcccc agcctctgaa agaacagccc | 600 |
| gccctgaacg acagccggta ctgcctgtcc agcagactga gagtgtccgc caccttctgg | 660 |
| cagaaccccc ggaaccactt cagatgccag gtgcagttct acggcctgag cgagaacgac | 720 |
| gagtggaccc aggacagagc caagcccgtg acccagatcg tgtctgccga agcctggggc | 780 |
| agagccgatt gcggctttac cagcgagagc taccagcagg gcgtgctgtc tgccaccatc | 840 |
| ctgtacgaga tcctgctggg aaaggccacc ctgtacgccg tgctggtgtc tgccctggtg | 900 |
| ctgatggcca tggtcaagcg gaaggacagc agaggcggtt ccggagccac gaacttctct | 960 |
| ctgttaaagc aagcaggaga cgtggaagaa accccggtc ccatgatcag cctgcgggtg | 1020 |
| ctgctggtta tcctgtggct gcagctgagc tgggtctggt cccagagaaa agaggtggaa | 1080 |
| caggaccccg gacctttcaa tgtgcctgaa ggcgccaccg tggccttcaa ctgcacctac | 1140 |
| agcaatagcg ccagccagag cttcttttgg tacagacagg actgccggaa agaacccaag | 1200 |
| ctgctgatga gcgtgtacag cagcggcaac gaggacggca gattcacagc ccagctgaac | 1260 |
| agggccagcc agtacattag cctgctgatc agagacagca agctgagcga ctccgccacc | 1320 |
| tacctgtgtg tcgttagagc cgccggaaac aagctgacat ttggaggcgg cacacgggtg | 1380 |
| ctcgtgaagc ctgacatcca gaaccccgac cctgcagtgt accagctgcg ggacagcaag | 1440 |
| agcagcgaca agagcgtgtg cctgttcacc gacttcgaca gccagaccaa cgtgtcccag | 1500 |
| agcaaggaca gcgacgtgta catcaccgat aagtgcgtgc tggacatgcg gagcatggac | 1560 |
| ttcaagagca acagcgccgt ggcctggtcc aacaagagcg acttcgcctg cgccaacgcc | 1620 |
| ttcaacaaca gcattatccc cgaggacaca ttcttcccaa gccccgagag cagctgcgac | 1680 |
| gtgaagctgg tggaaaagag cttcgagaca gacaccaacc tgaacttcca gaacctcagc | 1740 |
| gtgatcggct ccggatcct gctgctgaag gtggccggct tcaacctgct gatgaccctg | 1800 |
| cggctgtggt ccagctga | 1818 |

<210> SEQ ID NO 425
<211> LENGTH: 1830
<212> TYPE: DNA
<213> ORGANISM: Artificial Sequence
<220> FEATURE:
<223> OTHER INFORMATION: Synthetic sequence

<400> SEQUENCE: 425

| | |
|---|---|
| atgagcccca tctttacctg catcaccatc ctgtgcctgc tggccgctgg atctcctggg | 60 |
| gaagaagtgg cccagacacc taagcacctc gttagaggcg agggccagaa ggccaagctg | 120 |
| tattgcgccc ctatcaaggg ccacagctat gttttttggt atcaacaggt cctgaagaac | 180 |
| gagttcaagt tcctgatcag cttccagaac gagaacgtgt cgacgagac aggcatgccc | 240 |
| aaagagcggt tctccgccaa gtgcctgcct aacagccctt gcagcctgga atccaggcc | 300 |
| accaagctgg aagattccgc cgtgtatttc tgcgccagca gcagcatgtc tatcgccgct | 360 |
| ggaaataccg cgagctgtt cttcggcgag gcagcagac tgcagttct ggacctgaag | 420 |
| aacgtgttcc ccccagaggt ggccgtgttc gagccttctg aggccgagat cagccacacc | 480 |
| cagaaagcca ccctcgtgtg tctggccacc ggcttttacc ccgaccacgt ggaactgtct | 540 |
| tggtgggtca acggcaaaga ggtgcactcc ggcgtgtgca ccgatcccca gcctctgaaa | 600 |
| gaacagcccg ccctgaacga cagccggtac tgcctgtcca gcagactgag agtgtccgcc | 660 |

```
accttctggc agaaccccg gaaccactc agatgccagg tgcagttcta cggcctgagc    720
gagaacgacg agtggaccca ggacagagcc aagcccgtga cccagatcgt gtctgccgaa    780
gcctggggca gagccgattg cggctttacc agcgagagct accagcaggg cgtgctgtct    840
gccaccatcc tgtacgagat cctgctggga aaggccaccc tgtacgccgt gctggtgtct    900
gccctggtgc tgatggccat ggtcaagcgg aaggacagca gaggcggttc cggagccacg    960
aacttctctc tgttaaagca agcaggagac gtggaagaaa accccggtcc catgatttcc   1020
ctgagagtgc tgctcgtgat tctctggctc cagctctcct gggtttggag ccagcggaaa   1080
gaggtcgagc aagaccctgg gccttttaac gttccagagg cgctacagt ggcttttaat   1140
tgcacatact ccaacagcgc ctcacagagt tttttctggt atcggcagga ctgtagaaaa   1200
gaaccgaaac tgctcatgtc cgtgtatagc tccggcaatg aggatggccg gtttaccgct   1260
cagctgaatc gggcctctca gtacatctcc ctgctgattc gggactccaa gctgtccgat   1320
agcgcaacat acctgtgcgt ggtcacaggc accggcggct tcaagacaat cttcggagca   1380
ggcacccggc tgtttgtgaa ggctgacatc cagaaccccg accctgcagt gtaccagctg   1440
cgggacagca gagcagcga caagagcgtg tgcctgttca ccgacttcga cagccagacc   1500
aacgtgtccc agagcaagga cagcgacgtg tacatcaccg ataagtgcgt gctggacatg   1560
cggagcatgg acttcaagag caacagcgcc gtggcctggt ccaacaagag cgacttcgcc   1620
tgcgccaacg ccttcaacaa cagcattatc cccgaggaca cattcttccc aagccccgag   1680
agcagctgcg acgtgaagct ggtggaaaag agcttcgaga cagacaccaa cctgaacttc   1740
cagaacctca gcgtgatcgg cttccggatc ctgctgctga aggtggccgg cttcaacctg   1800
ctgatgaccc tgcggctgtg gtccagctga                                    1830
```

<210> SEQ ID NO 426
<211> LENGTH: 1815
<212> TYPE: DNA
<213> ORGANISM: Artificial Sequence
<220> FEATURE:
<223> OTHER INFORMATION: Synthetic sequence

<400> SEQUENCE: 426

```
atggatagct ggaccttctg ctgcgtgtcc ctgtgtatcc tggtggctaa gcacacagat     60
gccggcgtga tccagtctcc tagacacgaa gtgaccgaga tgggccaaga agtgaccctg    120
cgctgtaaac ccatcagcgg ccacaacagc ctgttctggt acagacagac catgatgaga    180
ggcctggaac tgctgatcta cttcaacaac aacgtgccca tcgacgacag cggcatgccc    240
gaggatagat tcagcgccaa gatgcccaac gccagcttca gcaccctgaa gatccagcct    300
agcgagccca gagattccgc cgtgtacttt tgtgccagca gcttcttcgg cagcgagaca    360
cagtatttcg gcctggcac aagactgctg gtgctggacc tgaagaacgt gttcccccca    420
gaggtggccg tgttcgagcc ttctgaggcc gagatcagcc acacccagaa agccaccctc    480
gtgtgtctgg ccaccggctt ttaccccgac cacgtggaac tgtcttggtg ggtcaacggc    540
aaagaggtgc actccggcgt gtgcaccgat ccccagcctc tgaaagaaca gcccgccctg    600
aacgacagcc ggtactgcct gtccagcaga ctgagagtgt ccgccacctt ctggcagaac    660
ccccggaacc acttcagatg ccaggtgcag ttctacggcc tgagcgagaa cgacgagtgg    720
acccaggaca gagccaagcc cgtgacccag atcgtgtctg ccgaagcctg ggcagagcc    780
gattgcggct taccagcga gagctaccag cagggcgtgc tgtctgccac catcctgtac    840
```

```
gagatcctgc tgggaaaggc caccctgtac gccgtgctgg tgtctgccct ggtgctgatg      900
gccatggtca gcggaagga cagcagaggc ggttccggag ccacgaactt ctctctgtta      960
aagcaagcag gagacgtgga agaaaacccc ggtcccatga agagaatcct gggcgctctg     1020
ctgggactgc tgtctgctca agtgtgctgt gtgcggggca tccaggtgga acagtctcca     1080
ccagacctga tcctgcaaga gggcgccaat agcaccctgc ggtgcaactt tagcgacagc     1140
gtgaacaacc tgcagtggtt ccaccagaat ccttggggcc agctgatcaa cctgttctac     1200
atccccagcg gcaccaagca gaacggcaga ctgtctgcta ccaccgtggc caccgagaga     1260
tacagcctgc tgtacatcag cagcagccag accacagaca gcggcgtgta cttctgcgcc     1320
gtgacaagac ctagcggcgg ctacaacaag ctgatcttcg gagccggcac cagactggcc     1380
gtgcatcctg acatccagaa ccccgaccct gcagtgtacc agctgcggga cagcaagagc     1440
agcgacaaga gcgtgtgcct gttcaccgac ttcgacagcc agaccaacgt gtcccagagc     1500
aaggacagcg acgtgtacat caccgataag tgcgtgctgg acatgcggag catggacttc     1560
aagagcaaca gcgccgtggc ctggtccaac aagagcgact tcgcctgcgc caacgccttc     1620
aacaacagca ttatccccga ggacacattc ttcccaagcc ccgagagcag ctgcgacgtg     1680
aagctggtgg aaaagagctt cgagacagac accaacctga acttccagaa cctcagcgtg     1740
atcggcttcc ggatcctgct gctgaaggtg gccggcttca acctgctgat gaccctgcgg     1800
ctgtggtcca gctga                                                     1815

<210> SEQ ID NO 427
<211> LENGTH: 17
<212> TYPE: PRT
<213> ORGANISM: Artificial Sequence
<220> FEATURE:
<223> OTHER INFORMATION: Synthetic peptide

<400> SEQUENCE: 427

Cys Ala Ser Asn Arg Gly Ser Thr Gln Ser Arg Ala Asn Val Leu Thr
1               5                   10                  15

Phe

<210> SEQ ID NO 428
<211> LENGTH: 139
<212> TYPE: PRT
<213> ORGANISM: Artificial Sequence
<220> FEATURE:
<223> OTHER INFORMATION: Synthetic sequence - MCC1H V alpha

<400> SEQUENCE: 428

Met Asp Lys Ile Leu Gly Ala Ser Phe Leu Val Leu Trp Leu Gln Leu
1               5                   10                  15

Cys Trp Val Ser Gly Gln Gln Lys Glu Lys Ser Asp Gln Gln Gln Val
                20                  25                  30

Lys Gln Ser Pro Gln Ser Leu Ile Val Gln Lys Gly Gly Ile Ser Ile
            35                  40                  45

Ile Asn Cys Ala Tyr Glu Asn Thr Ala Phe Asp Tyr Phe Pro Trp Tyr
        50                  55                  60

Gln Gln Phe Pro Gly Lys Gly Pro Ala Leu Leu Ile Ala Ile Arg Pro
65                  70                  75                  80

Asp Val Ser Glu Lys Lys Glu Gly Arg Phe Thr Ile Ser Phe Asn Lys
                85                  90                  95

Ser Ala Lys Gln Phe Ser Leu His Ile Met Asp Ser Gln Pro Gly Asp
            100                 105                 110
```

```
Ser Ala Thr Tyr Phe Cys Ala Val Pro Asn Thr Gly Asn Gln Phe Tyr
        115                 120                 125

Phe Gly Thr Gly Thr Ser Leu Thr Val Ile Pro
    130                 135

<210> SEQ ID NO 429
<211> LENGTH: 134
<212> TYPE: PRT
<213> ORGANISM: Artificial Sequence
<220> FEATURE:
<223> OTHER INFORMATION: Synthetic sequence - MCC1H V beta

<400> SEQUENCE: 429

Met Gly Thr Arg Leu Leu Cys Trp Val Val Leu Gly Phe Leu Gly Thr
1               5                   10                  15

Asp His Thr Gly Ala Gly Val Ser Gln Ser Pro Arg Tyr Lys Val Ala
            20                  25                  30

Lys Arg Gly Gln Asp Val Ala Leu Arg Cys Asp Pro Ile Ser Gly His
        35                  40                  45

Val Ser Leu Phe Trp Tyr Gln Gln Ala Leu Gly Gln Gly Pro Glu Phe
    50                  55                  60

Leu Thr Tyr Phe Gln Asn Glu Ala Gln Leu Asp Lys Ser Gly Leu Pro
65                  70                  75                  80

Ser Asp Arg Phe Phe Ala Glu Arg Pro Glu Gly Ser Val Ser Thr Leu
                85                  90                  95

Lys Ile Gln Arg Thr Gln Gln Glu Asp Ser Ala Val Tyr Leu Cys Ala
            100                 105                 110

Ser Ser Leu Ile Ala Gly Leu Ser Tyr Glu Gln Tyr Phe Gly Pro Gly
        115                 120                 125

Thr Arg Leu Thr Val Thr
    130
```